US012618054B2

(12) United States Patent
Behlke et al.

(10) Patent No.: US 12,618,054 B2
(45) **Date of Patent: \*May 5, 2026**

(54) CRISPR/Cpf1 SYSTEMS AND METHODS

(71) Applicant: Integrated DNA Technologies, Inc., Coralville, IA (US)

(72) Inventors: Mark Aaron Behlke, Coralville, IA (US); Michael Allen Collingwood, North Liberty, IA (US); Rolf Turk, Iowa City, IA (US); Christopher Anthony Vakulskas, North Liberty, IA (US)

(73) Assignee: Integrated DNA Technologies, Inc., Coralville, IA (US)

( * ) Notice: Subject to any disclaimer, the term of this patent is extended or adjusted under 35 U.S.C. 154(b) by 1078 days.

This patent is subject to a terminal disclaimer.

(21) Appl. No.: 17/469,578

(22) Filed: Sep. 8, 2021

(65) Prior Publication Data

US 2022/0002693 A1     Jan. 6, 2022

Related U.S. Application Data

(63) Continuation of application No. 15/821,736, filed on Nov. 22, 2017, now Pat. No. 11,136,567.

(60) Provisional application No. 62/425,307, filed on Nov. 22, 2016, provisional application No. 62/482,896, filed on Apr. 7, 2017.

(51) Int. Cl.

| | |
|---|---|
| *C12N 9/22* | (2006.01) |
| *C12N 15/10* | (2006.01) |
| *C12N 15/11* | (2006.01) |
| *C12N 15/113* | (2010.01) |
| *C12N 15/63* | (2006.01) |
| *C12N 15/85* | (2006.01) |
| *C12N 15/90* | (2006.01) |

(52) U.S. Cl.

CPC ............ *C12N 9/22* (2013.01); *C12N 15/102* (2013.01); *C12N 15/111* (2013.01); *C12N 15/113* (2013.01); *C12N 15/63* (2013.01); *C12N 15/8509* (2013.01); *C12N 15/90* (2013.01); *C12N 2310/20* (2017.05); *C12Y 301/30* (2013.01)

(58) Field of Classification Search

CPC ...... C12N 9/22; C12N 15/102; C12N 15/111; C12N 15/113; C12N 15/63; C12N 15/8509; C12N 15/90; C12N 2310/20; C12Y 301/30

See application file for complete search history.

(56) References Cited

U.S. PATENT DOCUMENTS

| | | | |
|---|---|---|---|
| 2016/0208241 A1* | 7/2016 | Tsai | C12Q 1/6869 |
| 2016/0208243 A1 | 7/2016 | Zhang et al. | |
| 2016/0215300 A1* | 7/2016 | May | C12N 15/63 |

FOREIGN PATENT DOCUMENTS

| | | |
|---|---|---|
| CN | 106244591 A | 12/2016 |
| WO | 2016115179 A1 | 7/2016 |
| WO | 2016161207 A1 | 10/2016 |
| WO | 2017184768 A1 | 10/2017 |
| WO | 2017184786 A1 | 10/2017 |
| WO | 2017189308 A1 | 11/2017 |
| WO | 2017190664 A1 | 11/2017 |
| WO | 2022003188 A2 | 1/2022 |

OTHER PUBLICATIONS

Zetsche et al. "Cpf1 is a single RNA-guided endonuclease of a class 2 CRISPR-Cas system" Cell. Oct. 22, 2015;163(3):759-71. (Year: 2015).*

Kleinstiver et al. "Genome-wide specificities of CRISPR-Cas Cpf1 nucleases in human cells." Nat Biotechnol. Aug. 2016;34(8):869-74. (Year: 2016).*

EP Communication pursuant to Article 94(3) EPC dated Mar. 11, 2025 issued in EP Pat Appln No. 23199206.6.

International Preliminary Report on Patentability issued in PCT Patent Application No. PCT/US17/63161, dated May 28, 2019.

International Search Report and Written Opinion issued in PCT Patent Application No. PCT/US17/63161, dated Apr. 24, 2018.

Office Action for Canadian Patent Application No. 3,044,101 issued on Feb. 21, 2025.

Examination Report for Australian Patent Application No. 2024204029 mailed on Aug. 26, 2025.

Latoree, A. et al., "Modified RNAs in CRISPR/Cas9: An Old Trick Works Again" Angew Chem Int. Ed., 2016, vol. 55, pp. 3548-3550.

* cited by examiner

*Primary Examiner* — Titilayo Moloye

(74) *Attorney, Agent, or Firm* — Potomac Law Group, PLLC; Reza Mollaaghababa; Joseph F. Murphy

(57) ABSTRACT

This invention pertains to recombinant AsCpf1 and LbCpf1 nucleic acids and polypeptides for use in CRISPR/Cpf1 endonuclease systems and mammalian cell lines encoding recombinant AsCpf1 or LbCpf1 polypeptides. The invention includes recombinant ribonucleoprotein complexes and CRSPR/Cpf1 endonuclease systems having a suitable AsCpf1 crRNA is selected from a length-truncated AsCpf1 crRNA, a chemically-modified AsCpf1 crRNA, or an AsCpf1 crRNA comprising both length truncations and chemical modifications. Methods of performing gene editing using these systems and reagents are also provided.

8 Claims, 9 Drawing Sheets

Specification includes a Sequence Listing.

Universal Loop Domain    Target-specific Protospacer Domain

X-uaauuucuacucuuguaguunnnnnnnnnnnnnnnnnnnn-X

U*a*auuucuacucuuguaguunnnnnnnnnnnnnnnnnnnnN*N*N

U*a*a*uUUCUACuCUUgUAGAunnnnnnnnnnnnnnnnnnnn*n*n*n

U*a*auUUCUACuCUUgUAGAunnnnnnnnnnnnnnnnnnnn*n*n

X-UaauUUCUACuCUUgUAGAunnnnnnnnnnnnnnnnnnnnnn-X

FIG. 8

CRISPR/Cpf1 SYSTEMS AND METHODS

CROSS-REFERENCE TO RELATED APPLICATIONS

This application is a continuation application of U.S. patent application Ser. No. 15/821,736, filed Nov. 22, 2017 and entitled "CRISPR/CPF1 SYSTEMS AND METH-ODS," which claims benefit of priority under 35 U.S.C. 119 to U.S. Provisional Patent Application Ser. No. 62/425,307, filed Nov. 22, 2016 and entitled "CPF1 CRISPR SYSTEMS AND METHODS," and U.S. Provisional Patent Application Ser. No. 62/482,896, filed Apr. 7, 2017 and entitled "HEK293 CELL LINE WITH STABLE EXPRESSION OF *Acidaminococcus* SP. BV3L6 CPF1," the contents of which are herein incorporated by reference in their entirety.

SEQUENCE LISTING

The instant application contains a Sequence Listing that has been submitted in ASCII format via EFS-Web and is hereby incorporated by reference in its entirety. The ASCII copy, created on Sep. 8, 2021, is named IDT01-010-US-CON ST25.txt, and is 263,473 bytes in size.

FIELD OF THE INVENTION

This invention pertains to Cpf1-based CRISPR genes, polypeptides encoded by the same, mammalian cell lines that stably express Cpf1, crRNAs and the use of these materials in compositions of CRISPR-Cpf1 systems and methods.

BACKGROUND OF THE INVENTION

The use of clustered regularly interspaced short palindro-mic repeats (CRISPR) and associated Cas proteins (CRISPR-Cas system) for site-specific DNA cleavage has shown great potential for a number of biological applica-tions. CRISPR is used for genome editing; the genome-scale-specific targeting of transcriptional repressors (CRIS-PRi) and activators (CRISPRa) to endogenous genes; and other applications of RNA-directed DNA targeting with Cas enzymes.

CRISPR-Cas systems are native to bacteria and Archaea and provide adaptive immunity against viruses and plas-mids. Three classes of CRISPR-Cas systems could poten-tially be adapted for research and therapeutic reagents. Type-II CRISPR systems have a desirable characteristic in utilizing a single CRISPR associated (Cas) nuclease (spe-cifically Cas9) in a complex with the appropriate guide RNAs (gRNAs). In bacteria or Archaea, Cas9 guide RNAs comprise 2 separate RNA species. A target-specific CRISPR-activating RNA (crRNA) directs the Cas9/gRNA complex to bind and target a specific DNA sequence. The crRNA has 2 functional domains, a 5'-domain that is target specific and a 3'-domain that directs binding of the crRNA to the transactivating crRNA (tracrRNA). The tracrRNA is a longer, universal RNA that binds the crRNA and mediates binding of the gRNA complex to Cas9. Binding of the tracrRNA induces an alteration of Cas9 structure, shifting from an inactive to an active conformation. The gRNA function can also be provided as an artificial single guide RNA (sgRNA), where the crRNA and tracrRNA are fused into a single species (see Jinek, M., et al., Science 337 p 816-21, 2012). The sgRNA format permits transcription of a functional gRNA from a single transcription unit that can be provided by a double-stranded DNA (dsDNA) cassette containing a transcription promoter and the sgRNA sequence. In mammalian systems, these RNAs have been introduced by transfection of DNA cassettes containing RNA Pol III promoters (such as U6 or H1) driving RNA transcription, viral vectors, and single-stranded RNA fol-lowing in vitro transcription (see Xu, T., et al., Appl Environ Microbiol, 2014. 80(5): p. 1544-52). In bacterial systems, these RNAs are expressed as part of a primitive immune system, or can be artificially expressed from a plasmid that is introduced by transformation (see Fonfara, I., et al., Nature, 2016. 532(7600): p. 517-21).

In the CRISPR-Cas system, using the system present in *Streptococcus pyogenes* as an example (S.py. or Spy), native crRNAs are about 42 bases long and contain a 5'-region of about 20 bases in length that is complementary to a target sequence (also referred to as a protospacer sequence or protospacer domain of the crRNA) and a 3' region typically of about 22 bases in length that is complementary to a region of the tracrRNA sequence and mediates binding of the crRNA to the tracrRNA. A crRNA:tracrRNA complex com-prises a functional gRNA capable of directing Cas9 cleavage of a complementary target DNA. The native tracrRNAs are about 85-90 bases long and have a 5'-region containing the region complementary to the crRNA. The remaining 3' region of the tracrRNA includes secondary structure motifs (herein referred to as the "tracrRNA 3'-tail") that mediate binding of the crRNA:tracrRNA complex to Cas9.

Jinek et al. extensively investigated the physical domains of the crRNA and tracrRNA that are required for proper functioning of the CRISPR-Cas system (Science, 2012. 337(6096): p. 816-21). They devised a truncated crRNA: tracrRNA fragment that could still function in CRISPR-Cas wherein the crRNA was the wild type 42 nucleotides and the tracrRNA was truncated to 75 nucleotides. They also devel-oped an embodiment wherein the crRNA and tracrRNA are attached with a linker loop, forming a single guide RNA (sgRNA), which varies between 99-123 nucleotides in dif-ferent embodiments.

At least three groups have elucidated the crystal structure of *Streptococcus pyogenes* Cas9 (SpyCas9). In Jinek, M., et al., the structure did not show the nuclease in complex with either a guide RNA or target DNA. They carried out molecu-lar modeling experiments to reveal predictive interactions between the protein in complex with RNA and DNA (Sci-ence, 2014. 343, p. 1215, DOI: 10.1126/science/1247997).

In Nishimasu, H., et al., the crystal structure of Spy Cas9 is shown in complex with sgRNA and its target DNA at 2.5 angstrom resolution (Cell, 2014. 156(5): p. 935-49, incor-porated herein in its entirety). The crystal structure identified two lobes to the Cas9 enzyme: a recognition lobe (REC) and a nuclease lobe (NUC). The sgRNA:target DNA heterodu-plex (negatively charged) sits in the positively charged groove between the two lobes. The REC lobe, which shows no structural similarity with known proteins and therefore likely a Cas9-specific functional domain, interacts with the portions of the crRNA and tracrRNA that are complemen-tary to each other.

Another group, Briner et al. (Mol Cell, 2014. 56(2): p. 333-9, incorporated herein in its entirety), identified and characterized the six conserved modules within native crR-NA:tracrRNA duplexes and sgRNA. Anders et al. (Nature, 2014, 513(7519) p. 569-73) elucidated the structural basis for DNA sequence recognition of protospacer associate motif (PAM) sequences by Cas9 in association with an sgRNA guide.

The CRISPR-Cas endonuclease system is utilized in genomic engineering as follows: the gRNA complex (either a crRNA:tracrRNA complex or an sgRNA) binds to Cas9, inducing a conformational change that activates Cas9 and opens the DNA binding cleft, the protospacer domain of the crRNA (or sgRNA) aligns with the complementary target DNA and Cas9 binds the PAM sequence, initiating unwinding of the target DNA followed by annealing of the protospacer domain to the target, after which cleavage of the target DNA occurs. The Cas9 contains two domains, homologous to endonucleases HNH and RuvC respectively, wherein the HNH domain cleaves the DNA strand complementary to the crRNA and the RuvC-like domain cleaves the non-complementary strand. This results in a double-stranded break in the genomic DNA. When repaired by non-homologous end joining (NHEJ) the break is typically repaired in an imprecise fashion, resulting in the DNA sequence being shifted by 1 or more bases, leading to disruption of the natural DNA sequence and, in many cases, leading to a frameshift mutation if the event occurs in a coding exon of a protein-encoding gene. The break may also be repaired by homology directed recombination (HDR), which permits insertion of new genetic material based upon exogenous DNA introduced into the cell with the Cas9/gRNA complex, which is introduced into the cut site created by Cas9 cleavage.

While SpyCas9 is the protein being most widely used, it does hold some barriers to its effectiveness. SpyCas9 recognizes targeted sequences in the genome that are immediately followed by a GG dinucleotide sequence, and this system is therefore limited to GC-rich regions of the genome. AT-rich species or genomic regions are therefore often not targetable with the SpyCas9 system. Furthermore, the fact that the Cas9 system includes a gRNA having both a crRNA and a tracrRNA moiety that comprise over 100 bases means that more RNA must be optimized and synthesized for sequence-specific targeting. As such, a shorter simpler gRNA would be desirable.

A second class 2 CRISPR system, assigned to type V, has been identified. This type V CRISPR-associated system contains Cpf1, which is a ~1300 amino acid protein— slightly smaller than Cas9 from *S. pyogenes*. The PAM recognition sequence of Cpf1 from *Acidaminococcus* sp. BV3L6 or *Lachnospiraceae bacterium* ND2006 is TTTN, in contrast to the NGG PAM recognition domain of *S. pyogenes* Cas9 (FIG. 1). Having the ability to target AT-rich areas of the genome will be greatly beneficial to manipulate and study gene targets in regions that are lacking GG dinucleotide motifs. The Cpf1 system is also remarkably simple in that it does not utilize a separate tracrRNA, and only requires a single short crRNA of 40-45 base length that both specifies target DNA sequence and directs binding of the RNA to the Cpf1 nuclease.

In contrast to Cas9 which produces blunt-ended cleavage products, Cpf1 facilitates double stranded breaks with 4-5 nucleotide overhangs. The advantage of this is that it may ensure proper orientation as well as providing microhomology during non-homologous end joining (NHEJ). This could also be advantageous in non-dividing cell types that tend to be resistant to homology-directed repair (HDR). Furthermore, when Cpf1 cleaves, it does so further away from PAM than Cas9, which is also further away from the target site. As a result, the protospacer, and especially the seed sequence of the protospacer, are less likely to be edited, thereby leaving open the potential for a second round of cleavage if the desired repair event doesn't happen the first time.

The Cpf1 protein forms a complex with a single stranded RNA oligonucleotide to mediate targeted DNA cleavage. The single strand guide RNA oligonucleotide consists of a constant region of 20 nt and a target region of 21-24 nt for an overall length of 41-44 nt. There are many known orthologs of Cpf1 from a variety of different bacterial and Archaea sources that differ with respect to activity and target preference and may be candidates for use in genome editing applications. For the purposes of this invention, we primarily studied, as representative examples, the Cpf1 nucleases from A.s. (*Acidaminococcus* sp. BV3L6) Cpf1 and L.b. (*Lachnospiraceae bacterium* ND2006), both of which have already been shown to be active in mammalian cells as a tool for genome editing. Of note, the PAM recognition sequence is TTTN. The structure of the Cpf1 crRNA and relationship of RNA binding to the PAM site in genomic DNA is shown in FIG. 1.

Since the discovery of Cpf1 as another CRISPR pathway with potential utility for genome editing in mammalian cells, several publications have confirmed that the system works in mammals, can be used for embryo engineering, and the crystal structure and mechanism of PAM site recognition have been described. This system has also shown utility for screening purposes in genetically-tractable bacterial species such as *E. coli*. The system therefore has proven utility and developing optimized reagents to perform genome editing using Cpf1 would be beneficial.

Previous work done on the SpyCas9 crRNA and tracrRNA demonstrated that significant shortening of the naturally occurring crRNA and tracrRNA species could be done for RNAs made by chemical synthesis and that such shortened RNAs were 1) higher quality, 2) less costly to manufacture, and 3) showed improved performance in mammalian genome editing compared with the wild-type (WT) RNAs. See Collingwood, M. A., Jacobi, A. M., Rettig, G. R., Schubert, M. S., and Behlke, M. A., "CRISPR-BASED COMPOSITIONS AND METHOD OF USE," U.S. patent application Ser. No. 14/975,709, filed Dec. 18, 2015, published now as U.S. Patent Application Publication No. US2016/0177304A1 on Jun. 23, 2016 and issued as U.S. Pat. No. 9,840,702 on Dec. 12, 2017.

Prior work demonstrated that reducing the length of the FnCpf1 crRNA from 22 to 18 base length with deletions from the 3'-end supported cleavage of target DNA but that lengths of 17 or shorter showed reduced activity. Deletions or mutations that disrupted base-pairing in the universal loop domain disrupted activity. See Zetsche, B., Gootenberg, J. S., Abudayyeh, O. O., Slaymaker, I. M., Makarova, K. S., Essletzbichler, P., Volz, S. E., Joung, J., van der Oost, J., Regev, A., Koonin, E. V., and Zhang, F. (2015) Cpf1 is a single RNA-guided endonuclease of a class 2 CRISPR-Cas system. *Cell* 163:1-13. The FnCpf1 nuclease, however, does not work in mammalian cells to perform genome editing. It is unknown if the same length rules apply to the AsCpf1 crRNA as were observed for the FnCpf1 crRNA. We establish herein the shortest version of AsCpf1 crRNAs having full activity in mammalian genome editing applications. We also establish chemical modification patterns that maintain or improve functioning of synthetic Cpf1 crRNAs when used in mammalian or prokaryotic cells.

BRIEF SUMMARY OF THE INVENTION

This invention pertains to Cpf1-based CRISPR genes, polypeptides encoded by the same, mammalian cell lines that stably express Cpf1, and chemically synthesized Cpf1 crRNAs and their use in compositions of CRISPR-Cpf1 systems and methods. Examples are shown employing the Cpf1 systems from *Acidaminococcus* sp. BV3L6 and *Lachnospiraceae bacterium* ND2006, however this is not intended to limit scope, which extends to Cpf1 homologs or orthologs isolated from other species.

In a first aspect, an isolated nucleic acid is provided. The isolated nucleic acid encodes an As Cpf1 polypeptide codon optimized for expression in *H. sapiens* as seen in SEQ ID NO:8, SEQ ID NO:15 and SEQ ID NO:22 which includes the use of nuclear localization signals as well as an epitope tag. The isolated nucleic acid also encodes as As Cpf1 polypeptide codon optimized for expression in *E. coli* which comprises SEQ ID NO:5 and may be fused or linked to a nuclear localization signal, multiple nuclear localization signals, or sequences encoding an epitope tag enabling detection by antibodies or other methods, and/or an affinity tag that enables simple purification of recombinants proteins expressed from the nucleic acid, such as a His-Tag as seen in SEQ ID NO:12 and SEQ ID NO:19.

In a second aspect, an isolated polypeptide encoding a wild-type As Cpf1 protein is provided. In a first respect, the isolated polypeptide comprises SEQ ID NO:2. The protein may be fused or linked to a nuclear localization signal, multiple nuclear localization signals, or sequences encoding an epitope tag enabling detection by antibodies or other methods, and/or an affinity tag that enables simple purification of recombinants proteins expressed from the nucleic acid, such as a His-Tag as seen in SEQ ID NO:12, SEQ ID NO:16 and SEQ ID NO:19.

In a third aspect, an isolated nucleic acid is provided. The isolated nucleic acid encodes an Lb Cpf1 polypeptide codon optimized for expression in *H. sapiens* as seen in SEQ ID NO:9 and SEQ ID NO:17, which includes the use of nuclear localization signals as well as an epitope tag. The isolated nucleic acid also encodes as Lb Cpf1 polypeptide codon optimized for expression in *E. coli* which comprises SEQ ID NO:6 and may be fused or linked to a nuclear localization signal, multiple nuclear localization signals, or sequences encoding an epitope tag enabling detection by antibodies or other methods, and/or an affinity tag that enables simple purification of recombinants proteins expressed from the nucleic acid, such as a His-Tag as seen in SEQ ID NO:13.

In a fourth aspect, an isolated polypeptide encoding a wild-type Lb Cpf1 protein is provided. In a first respect, the isolated polypeptide comprises SEQ ID NO:7 and SEQ ID NO:10. The protein may be fused or linked to a nuclear localization signal, multiple nuclear localization signals, or sequences encoding an epitope tag enabling detection by antibodies or other methods, and/or an affinity tag that enables simple purification of recombinants proteins expressed from the nucleic acid, such as a His-Tag as seen in SEQ ID NO:14.

In a fifth aspect, an isolated expression vector encoding SEQ ID NO:11, SEQ ID NO:13, SEQ ID NO:15 and SEQ ID NO:17 is provided. The isolated expression vectors include a transcriptional initiator element, such as a promoter and enhancer, operably-linked to SEQ ID NO:11, SEQ ID NO:13, SEQ ID NO:15 or SEQ ID NO:17 to permit expression of the polypeptide encoded by SEQ ID NO:12, SEQ ID NO:14 or SEQ ID NO:16.

In a sixth aspect, a host cell including an isolated expression vector encoding SEQ ID NO:11, SEQ ID NO:13, SEQ ID NO:15 and SEQ ID NO:17 is provided. The isolated expression vector encoding SEQ ID NO:11, SEQ ID NO:13, SEQ ID NO:15 or SEQ ID NO:17 is operably linked to a suitable promoter and other genetic elements (as necessary)

to permit expression of a polypeptide comprising SEQ ID NO:12, SEQ ID NO:14 or SEQ ID NO:16.

In a seventh aspect, an isolated CRISPR/Cpf1 endonuclease system is provided. The system includes an AsCpf1 polypeptide and a suitable AsCpf1 crRNA.

In an eighth aspect, an isolated CRISPR/Cpf1 endonuclease system is provided. The system includes a human cell line expressing a AsCpf1 polypeptide and a suitable AsCpf1 crRNA.

In a ninth aspect, an isolated AsCpf1 crRNA is provided. The isolated AsCpf1 crRNA is active in a Clustered Regularly Interspaced Short Palindromic Repeats (CRISPR)/CRISPR-associated protein endonuclease system. Different variants of the crRNA are provided including species optimized for performance in mammalian cells and species optimized for performance in bacteria.

In a tenth aspect, a method of performing gene editing is provided. The method includes the step of contacting a candidate editing target site locus with an active CRISPR/Cpf1 endonuclease system having a wild-type AsCpf1 polypeptide and a suitable AsCpf1 crRNA.

BRIEF DESCRIPTION OF THE DRAWINGS

FIG. 8 depicts exemplary modified variants AsCpf1 crR-NAs that are active in genome editing applications in mammalian cells at multiple target sites and therefore are not site-specific. The sequence of the universal 5'-loop domain is shown (5'-3' orientation) and indicated with underline. The sequence of the variable 3'-target specific protospacer domain is indicated as "N" bases, as this sequence varies for every target. 2'OMe RNA modifications are indicated in uppercase and RNA residues are indicated in lowercase. "X" indicates a terminal non-base modifier, such as a C3 spacer (propanediol) or ZEN (napthyl-azo) group. "*" indicates a phosphorothioate (PS) internucleotide linkage.

DETAILED DESCRIPTION OF THE INVENTION

Figure 1:
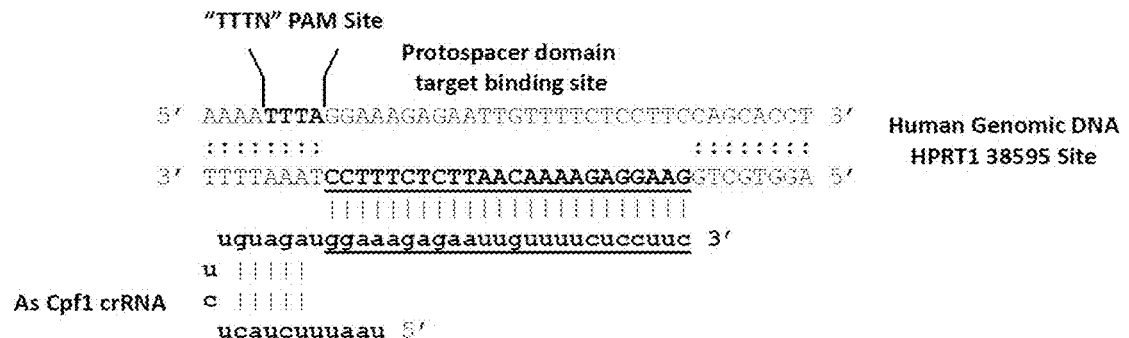
FIG. 1 is a graphical representation of Cpf1 PAM recognition sites and alignment of guide crRNA to target DNA. Genomic DNA sequence of the human HPRT1 gene is shown at site '38595'. The "TTTN" PAM site that identifies As Cpf1 sites is highlighted and the sequence of the guide-binding site is underlined. DNA is shown in uppercase and RNA is shown in lowercase. In the Cpf1 crRNA, the protospacer target-specific domain s underlined and comprises the 3'-domain. The universal hairpin RNA sequence that mediates binding to Cpf1 protein comprises the 5'-domain.

The methods and compositions of the invention described herein provide wild-type AsCpf1 nucleic acids and polypep-tides for use in a CRISPR/Cpf1 system. The present inven-tion describes an HEK293 cell line that has stable, low levels of expression of AsCpf1 in HEK293 and can be used as a platform for investigation and optimization of the nucleic acid components of the system. AsCpf1 provides a useful complement to SpyCas9 by expanding the range of PAM sequences that can be targeted from GC-rich areas (Cas9) to AT-rich areas of the genome (Cpf1), thereby expanding the range of sequences that can be modified using CRISPR genome engineering methods. In addition to having a T-rich PAM site, another advantage of the AsCpf1 system com-pared with Cas9 is the use of a single, short RNA molecule. However, unlike Cas9 that shows activity at most sites in the human genome, AsCpf1 shows little to no activity at half of TTTN PAM sites. Thus, exploiting the full potential of the AsCpf1 CRISPR system will be enhanced by the availability of suitable predictive software that enriches for high activity sites based on sequence context. The use of a stable consti-tutive Cpf1-expressing cell line makes the development of an algorithm easier to develop with reduced effort and cost as compared to using alternative methods, such as electropo-ration of ribonucleoprotein protein (RNP) complexes. HEK293 cells are an immortalized cell line that are easily cultured, passaged and cryogenically preserved. We estab-lished clonal cell lines that constitutively express SpyCas9 and AsCpf1 as suitable test vehicles for algorithm develop-ment or rapid testing/optimization of the chemical structure of guide RNAs. The present invention describes length and chemical modification of length-optimized variants of the AsCpf1 and LbCpf1 crRNAs that improve function in genome editing.

AsCpf1-Encoded Genes, Polypeptides, Expression Vectors and Host Cells

The term "wild-type AsCpf1 protein" ("WT-AsCpf1" or "WT-AsCpf1 protein") encompasses a protein having the identical amino acid sequence of the naturally-occurring *Acidaminococcus* sp. BV3L6 Cpf1 (e.g., SEQ ID NO:2) and that has biochemical and biological activity when combined with a suitable crRNA to form an active CRISPR/Cpf1 endonuclease system.

The term "wild-type LbCpf1 protein" ("WT-LbCpf1" or "WT-LbCpf1 protein") encompasses a protein having the identical amino acid sequence of the naturally-occurring *Lachnospiraceae bacterium* ND2006 Cpf1 (e.g., SEQ ID NO:4) and that has biochemical and biological activity when combined with a suitable crRNA to form an active CRISPR/ Cpf1 endonuclease system.

The term "wild-type CRISPR/Cpf1 endonuclease system" refers to a CRISPR/Cpf1 endonuclease system that includes wild-type AsCpf1 protein and a suitable AsCpf1 crRNA as a guide RNA.

The term "polypeptide" refers to any linear or branched peptide comprising more than one amino acid. Polypeptide includes protein or fragment thereof or fusion thereof, provided such protein, fragment or fusion retains a useful biochemical or biological activity.

Fusion proteins typically include extra amino acid infor-mation that is not native to the protein to which the extra amino acid information is covalently attached. Such extra amino acid information may include tags that enable puri-fication or identification of the fusion protein. Such extra amino acid information may include peptides that enable the fusion proteins to be transported into cells and/or transported to specific locations within cells. Examples of tags for these purposes include the following: AviTag, which is a peptide allowing biotinylation by the enzyme BirA so the protein can be isolated by streptavidin (GLNDIFEAQKIEWHE); Calmodulin-tag, which is a peptide bound by the protein calmodulin (KRRWKKNFIAVSAANRFKKISSSGAL); polyglutamate tag, which is a peptide binding efficiently to anion-exchange resin such as Mono-Q (EEEEEE); E-tag, which is a peptide recognized by an antibody (GAPVPYPDPLEPR); FLAG-tag, which is a peptide rec-ognized by an antibody (DYKDDDDK); HA-tag, which is a peptide from hemagglutinin recognized by an antibody (YPYDVPDYA); His-tag, which is typically 5-10 histidines and can direct binding to a nickel or cobalt chelate (HHHHHH); Myc-tag, which is a peptide derived from c-myc recognized by an antibody (EQKLISEEDL); NE-tag, which is a novel 18-amino-acid synthetic peptide (TKEN-PRSNQEESYDDNES) recognized by a monoclonal IgG1 antibody, which is useful in a wide spectrum of applications including Western blotting, ELISA, flow cytometry, immu-nocytochemistry, immunoprecipitation, and affinity purifi-cation of recombinant proteins; S-tag, which is a peptide derived from Ribonuclease A (KETAAAKFERQHMDS); SBP-tag, which is a peptide which binds to streptavidin; (MDEKTTGWRGGHVVEGLAGELEQLRAR-LEHHPQGQREP); Softag 1, which is intended for mam-malian expression (SLAELLNAGLGGS); Softag 3, which is intended for prokaryotic expression (TQDPSRVG); Strep-tag, which is a peptide which binds to streptavidin or the modified streptavidin called streptactin (Strep-tag II: WSHPQFEK); TC tag, which is a tetracysteine tag that is recognized by FlAsH and ReAsH biarsenical compounds (CCPGCC)V5 tag, which is a peptide recognized by an antibody (GKPIPNPLLGLDST); VSV-tag, a peptide recog-nized by an antibody (YTDIEMNRLGK); Xpress tag (DLYDDDDK); Isopeptag, which is a peptide which binds covalently to pilin-C protein (TDKDMTITFTNKKDAE); SpyTag, which is a peptide which binds covalently to SpyCatcher protein (AHIVMVDAYKPTK); SnoopTag, a peptide which binds covalently to SnoopCatcher protein (KLGDIEFIKVNK); BCCP (Biotin Carboxyl Carrier Protein), which is a protein domain biotinylated by BirA to enable recognition by streptavidin; Glutathione-S-transferase-tag, which is a protein that binds to immobilized glutathione; Green fluorescent protein-tag, which is a protein which is spontaneously fluorescent and can be bound by antibodies; HaloTag, which is a mutated bacterial haloalkane dehalogenase that covalently attaches to a reactive haloalkane substrate to allow attachment to a wide variety of substrates; Maltose binding protein-tag, a protein which binds to amylose agarose; Nus-tag; Thioredoxin-tag; and Fc-tag, derived from immunoglobulin Fc domain, which allows dimerization and solubilization and can be used for purification on Protein-A Sepharose.

Nuclear localization signals (NLS), such as those obtained from SV40, allow for proteins to be transported to the nucleus immediately upon entering the cell. Given that the native AsCpf1 protein is bacterial in origin and therefore does not naturally comprise a NLS motif, addition of one or more NLS motifs to the recombinant AsCpf1 protein is expected to show improved genome editing activity when used in eukaryotic cells where the target genomic DNA substrate resides in the nucleus. Functional testing in HEK293 cells revealed that using a bipartite NLS (nucleoplasmin) increased editing in comparison to the current commercial design (3 SV40 NLS) and the use of single or dual OpT NLS that showed promise in the Cpf1 protein. Additional combinations of NLS elements including the bipartite are envisioned. Of note, the nucleoplasmin functions best in mammalian cells while the SV40 NLS appears to function in almost any nucleated cell. The bipartite SV40 NLS is functional in both Cas9 and Cpf1. Having two different NLS domains may expand effectiveness across a broad spectrum of species.

One skilled in the art would appreciate these various fusion tag technologies, as well as how to make and use fusion proteins that include them.

The term "isolated nucleic acid" include DNA, RNA, cDNA, and vectors encoding the same, where the DNA, RNA, cDNA and vectors are free of other biological materials from which they may be derived or associated, such as cellular components. Typically, an isolated nucleic acid will be purified from other biological materials from which they may be derived or associated, such as cellular components.

The term "isolated wild-type AsCpf1 nucleic acid" is an isolated nucleic acid that encodes a wild-type AsCpf1 protein. Examples of an isolated wild-type AsCpf1 nucleic acid include SEQ ID NO:1.

The term "isolated wild-type LbCpf1 nucleic acid" is an isolated nucleic acid that encodes a wild-type LbCpf1 protein. Examples of an isolated wild-type LbCpf1 nucleic acid include SEQ ID NO:3.

In a first aspect, an isolated nucleic acid is provided. The isolated nucleic acid encodes an As Cpf1 polypeptide codon optimized for expression in *H. sapiens*. In a first respect, the isolated nucleic acid comprises SEQ ID NO:8, SEQ ID NO:15 and SEQ ID NO:22 which includes the use of nuclear localization signals as well as an epitope tag. The isolated nucleic acid also encodes as As Cpf1 polypeptide codon optimized for expression in *E. coli* which comprises SEQ ID NO:5 and may be fused or linked to a nuclear localization signal, multiple nuclear localization signals, or sequences encoding an epitope tag enabling detection by antibodies or other methods, and/or an affinity tag that enables simple purification of recombinants proteins expressed from the nucleic acid, such as a His-Tag as seen in SEQ ID NO:12 and SEQ ID NO:19.

In a second aspect, an isolated polypeptide encoding a wild-type As Cpf1 protein is provided. In a first respect, the isolated polypeptide comprises SEQ ID NO:2, SEQ ID NO:12, SEQ ID NO:16 or SEQ ID NO:19.

In a third aspect, an isolated expression vector encoding SEQ ID NO:15 is provided. The isolated expression vector includes transcriptional initiator elements, such as a promoter and enhancer, operably-linked to SEQ ID NO:15 to permit expression of the polypeptide encoded by SEQ ID NO:16. The isolated expression vector may additionally include transcriptional termination elements, posttranscriptional processing elements (for example, splicing donor and acceptor sequences and/or polyadenylation signaling sequences), mRNA stability elements and mRNA translational enhancer elements. Such genetic elements are understood and used by those having ordinary skill in the art.

In a fourth aspect, a host cell comprising an isolated expression vector encoding SEQ ID NO:15 is provided. The isolated expression vector encoding SEQ ID NO:15 is operably linked to a suitable promoter and other genetic elements (as necessary) to permit expression of a polypeptide comprising SEQ ID NO:16. In a first respect, the host cell includes a human cell. In a second respect, the human cell comprises an immortalized cell line. In a third respect, the immortalized cell line is a HEK293 cell line. As a further elaboration of this third respect, the immortalized cell line comprises an isolated AsCpf1 crRNA capable of forming a ribonucleoprotein complex with the polypeptide comprising SEQ ID NO:2 to form a wild-type CRISPR/Cpf1 endonuclease.

Length- and Chemical Structure-Optimized AsCpf1 crRNAs

The term "length-modified," as that term modifies RNA, refers to a shortened or truncated form of a reference RNA lacking nucleotide sequences or an elongated form of a reference RNA including additional nucleotide sequences.

The term "chemically-modified," as that term modifies RNA, refers to a form of a reference RNA containing a chemically-modified nucleotide or a non-nucleotide chemical group covalently linked to the RNA. Chemically-modified RNA, as described herein, generally refers to synthetic RNA prepared using oligonucleotide synthesis procedures wherein modified nucleotides are incorporated during synthesis of an RNA oligonucleotide.

However, chemically-modified RNA also includes synthetic RNA oligonucleotides modified with suitable modifying agents post-synthesis.

A competent CRISPR/Cpf1 endonuclease system includes a ribonucleoprotein (RNP) complex formed with isolated AsCpf1 protein and a guide RNA consisting of an isolated AsCpf1 crRNA. In some embodiments, an isolated length-modified and/or chemically-modified form of AsCpf1 crRNA is combined with purified AsCpf1 protein, an isolated mRNA encoding AsCpf1 protein or a gene encoding AsCpf1 protein in an expression vector. In certain assays, an isolated length-modified and/or chemically-modified form of AsCpf1 crRNA can be introduced into cell lines that stably express AsCpf1 protein from an endogenous expression cassette encoding the AsCpf1 gene.

It is desirable for synthesis of synthetic RNAs that sequences are shortened of unnecessary bases but not so shortened that loss of function results. The 5'-constant regions that mediates binding of the crRNA to the Cpf1 nuclease shows loss of activity if truncated below 20 residues. The 3'-variable domain that comprises the protospacer guide region which confers target sequence specificity to the crRNA naturally occurs as long as 25 bases. This domain can be shortened to around 20-21 bases with no loss of functional activity. The optimized length of the Cpf1 crRNA is therefore 40-41 bases, comprising a 20 base 5'-constant domain and a 20-21 base 3'-variable domain.

The present invention provides suitable guide RNAs for triggering DNA nuclease activity of the AsCpf1 nuclease. These optimized reagents, both in terms of length-modified and/or chemically-modified forms of crRNA's, provide for improved genome editing in any application with AsCpf1. The applications of CRISPR-based tools include, but are not limited to: plant gene editing, yeast gene editing, rapid generation of knockout/knockin animal lines, generating an animal model of disease state, correcting a disease state, inserting reporter genes, and whole genome functional screening. The "tool-kit" could be further expanded by including nickase versions and a dead mutant of AsCpf1 as a fusion protein with transcriptional activators CRISPRa) and repressors (CRISPRi).

RNA-guided DNA cleavage by AsCpf1 is primarily useful for its ability to target AT-rich gene regions (as compared with the GC-rich targeting by SpyCas9). The newly-discovered AsCpf1 crRNA truncation and modification variants will be suitable to promote AsCpf1-mediated staggered cutting and beneficial in gene silencing, homology directed repair or exon excision. The present invention defines the shortest AsCpf1 guide RNA that has full potency to direct gene editing by the CRISPR/Cpf1 endonuclease. This is useful for manufacturing to synthesize the shortest compound that fully functions, leading to higher quality, lower cost, while maximizing functionality.

Unlike Spy. Cas9 which requires a complex of 2 RNAs to recognize and cleave a target DNA sequence (comprising a hybridized crRNA:tracrRNA pair) or a long synthetic single-guide sgRNA, the Cpf1 nuclease only requires a short, single crRNA species to direct target recognition. This RNA comprises 2 domains, a 5'-domain of 20 RNA residues that is universal and mediates binding of the RNA species to the Cpf1 protein and a 3' domain of 21-24 RNA residues which is target specific and mediates binding of the RNP complex to a precise DNA sequence. A functional nuclease complex comprises a single crRNA (41-44 bases in length) and isolated Cpf1 protein, which combine in a 1:1 molar ratio to form an active complex. The guide crRNA species can be expressed in mammalian cells from expression plasmids or viral vectors. The crRNA can also be made as an in vitro transcript (IVT) and isolated as a pure enzymatic RNA species. More preferably, the crRNAs can be manufactured as a synthetic chemical RNA oligonucleotide. Chemical manufacturing enables use of modified residues, which have many advantages as will be outlined below.

Synthetic nucleic acids are attacked by cellular nucleases and rapidly degrade in mammalian cells or in serum. Chemical modification can confer relative nuclease resistance to the synthetic nucleic acids and prolong their half-lives, thereby dramatically improving functional performance and potency. As a further complication, synthetic nucleic acids are often recognized by the antiviral surveillance machinery in mammalian cells that are part of the innate immune system and lead to interferon response pathway activation, which can lead to cell death. Chemical modification can reduce or eliminate unwanted immune responses to synthetic RNAs. It is therefore useful to establish methods to chemically modify synthetic RNA oligonucleotides intended for use in live cells. Nucleic acid species that have specific interactions with protein factors, however, cannot be blindly modified as chemical modification will change tertiary structure of the nucleic acid and can block critical contact points between the nucleic acid and amino-acid residues. For example, the 2'-O-methyl RNA modification (2'OMe) will block the 2'-oxygen of RNA from interaction with amino-acid residues that in turn can disrupt functional interaction between a modified RNA and a protein. Likewise, a phosphorothioate modification can disrupt protein binding along the phosphate backbone of a nucleic acid through substitution of a non-bridging oxygen at the phosphate.

The 2'OMe modification is particularly useful in this setting as it has previously been shown to increase nuclease stability of antisense oligonucleotides (ASOs) and siRNAs and at the same kind can also reduce the risk that a chemically-synthesized RNA will trigger an innate immune response when introduced into mammalian cells. Specific modification patterns have been established that permit incorporation of this modified residue into an ASO or siRNA and retain function. Likewise, we have recently developed chemical modification patterns that improved the stability of the crRNA and tracrRNA that serve as guide RNA in the SpyCas9 system. Use of 2'OMe-modified residues in a CRISPR guide RNA improves RNA stability to nucleases and boosts the overall efficiency of editing in nuclease-rich environments while at the same time reduces cell death and toxicity associated with immunogenic triggers (such as is seen with long, unmodified RNAs).

The present invention relates to defining chemical modification patterns for the AsCpf1 crRNA that retain function in forming an active RNP complex capable of use in genome editing in mammalian cells. Modification 'walks' were performed where a single 2'OMe residue was place sequentially at every position with the Cpf1 crRNA. Sites that reduced or killed function of the RNP complex in genome editing were identified. Chemical modification patterns were defined that were compatible with high efficiency genome editing. The utility of 2'-fluoro (2'F) and locked nucleic acid (LNA) modifications at 'modification competent' position in the crRNA were also demonstrated. The use of phosphorothioate internucleotide linkages to modify select sites to reduce nuclease susceptibility was shown, as well as successful use of non-base modifiers as end blocks to reduce exonuclease attack on the synthetic RNAs. Taken together, these studies provide a 'map' of sites in the Cpf1 crRNA amenable to chemical modification along with a suite of modification chemistries demonstrated to function in the intended application in mammalian cells.

Specific examples of modification patterns are shown in the examples below. The 20-base 5'-constant domain could be heavily modified and retain function. In particular, using a 20-base 5'-constant region and counting from the 5'-end, RNA residues at position 1, 5, 6, 7, 8, 9, 10, 12, 13, 14, 16, 17, 18, and 19 can all be substituted with 2'OMe RNA residues with no loss of activity. Such substitutions can be made single, multiply, or all 14 residues modified, such that 14/20 residues have been changed in this domain from RNA to 2'OMe RNA. Maximum modification patterns that are tolerated in the 21-base 3'-variable domain vary with sequence of the domain. Within this domain, residues 21, 22, 23, 28, 29, 30, 32, 34, 35, 39, 40, and 41 (counting from the first base of the 5'-constant region) can be substituted with 2'OMe residues with no loss of activity.

Figure 7:
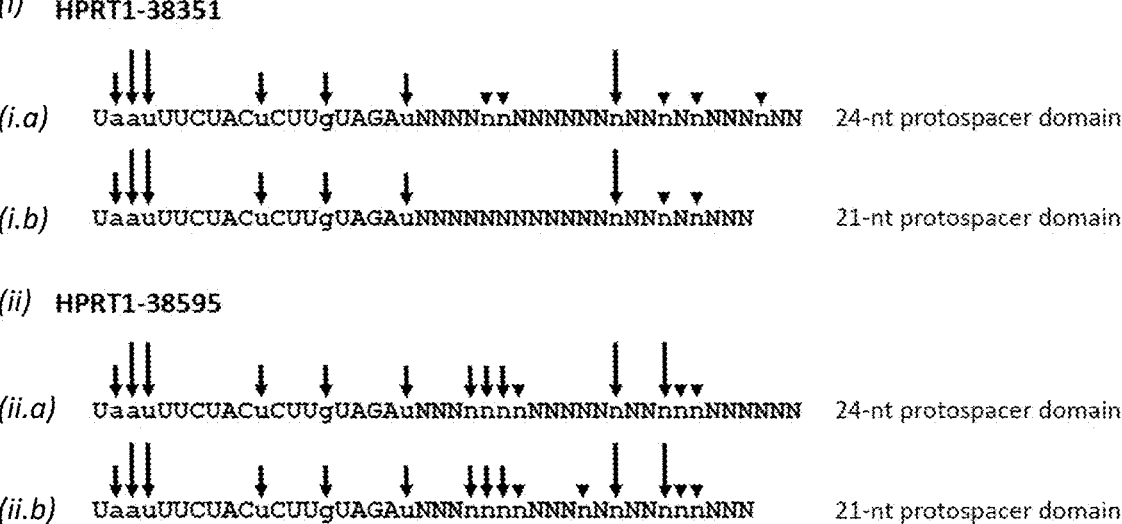
FIG. 7 depicts a modification tolerance map of AsCpf1 crRNAs at 2 sequence target sites, HPRT1-38351 (panel (i)) and HPRT1-38595 (panel (ii)), wherein the sequence of the universal 5'-loop domain is shown (5'-3' orientation) for both the 24-nt protospacer domains (panels (i.a) and (ii.a)) and the 21-nt protospacer domains (panels (i.b) and (ii.b)). The sequence of the variable 3'-target specific protospacer domain is indicated as "N" bases, as this sequence varies for every target. Positions that did not suffer loss of activity when modified as a 2'OMe RNA residue in the single base walk are indicated in upper case whereas positions that showed loss of activity with modification are indicated in lower case. Above the lower case residues an arrow is shown that indicates the relative magnitude of the loss of activity, wherein a large arrow represents a large loss of activity, a mid-sized arrow represents a medium loss of activity, and a small arrow represents a minor loss of activity when the respective RNA residues are changed to 2'OMe RNA.

Only select positions within the 21-24-base 3'-target specific domain can be modified without compromising activity. Based on the crystal structure of Cpf1, there are many protein contact points within the constant region as well as the target region. For constant region modification, there is no obvious correlation that emerges when comparing the Cpf1 crystal structure contact points with the identified functional positions that can be modified—meaning that a good modification pattern cannot be predicted from the crystal structure. Likewise, empirical testing was needed to determine target region modification patterns. Based on the early 2'OMe modification testing, selected areas within the Cpf1 crRNA were modified using 2'OMe as an attempt to narrow down an area that will tolerate modification. The position of single residues within the Cpf1 crRNA that are sensitive to 2'OMe modification are shown in FIG. 7. Higher-level modification patterns that are potent triggers of Cpf1-mediated genome editing are shown in FIG. 8. 2'F modifications can be positioned at any residue that is tolerant to 2'OMe modification. Further, the 3'-variable domain is more tolerate of large blocks of 2'F modification than large blocks of 2'OMe modification. Hence a highly modified version of the Cpf1 crRNA comprises 2'OMe modification in the 3'-domain and 2'F modification in the 5'-domain. For medium or light modification patterns, either 2'OMe or 2'F (or both) modifications can be used in both domains. Also, LNA residues can be incorporated into the crRNA without compromising function, as defined in the examples below.

As an alternative to extensive use of 2'OMe or other modified sugar approaches, blocking exonuclease attack with non-base modifiers at the 3'-end and 5'-end are compatible with crRNA function and improve function in cells. Small C3 spacer (propanediol) or large ZEN groups work equally well for this approach. Further, phosphorothioate internucleotide linkages can be placed at select sites, such as between the terminal 2-3 bases on each end of the crRNA, but complete PS modification of the crRNA or complete modification of either the loop domain or the protospacer domain show reduced activity.

Guide RNAs are required in RNA-directed dsDNA cleavage by AsCpf1, which initiate the subsequent repair events that are involved in most CRISPR applications in mammalian cells. The use of modified synthetic AsCpf1 crRNAs as guides for AsCpf1 genome editing is provided. The utility of 2'OMe-modified AsCpf1 crRNAs, 2'F-modified AsCpf1 crRNAs, LNA modified AsCpf1 crRNAs, and end-blocked AsCpf1 crRNAs for CRISPR/Cpf1 applications in mammalian cells is demonstrated. Those with skill in the art will recognize and appreciate additional chemical modifications are possible based upon this disclosure. It is expected that many of these base modifying groups will likewise function according to the patterns taught in the present invention. Heretofore, all crRNAs used with Cpf1 for genome editing were unmodified RNA. In the present invention, functional modification patterns that improve properties of the AsCpf1 crRNA and lower risk of toxicity are provided.

AsCpf1 crRNAs can be made in cells from RNA transcription vectors, as in vitro transcripts (IVTs), or by chemical synthesis. Synthetic RNA oligonucleotides offer a distinct advantage because they alone allow for precise insertion of modified bases at specific sites in the molecule. The present invention provides a map of positions amenable to chemical modification that can be used to improve AsCpf1 crRNA performance in cells. For some applications, "minimal modification" approaches will be sufficient. In higher nuclease environments or for use in cells with particularly high innate immune reactivity, "high modification" approaches may work better. The present invention provides methods for low, medium, or high modification needs.

The applications of AsCpf1-based tools are many and varied. They include, but are not limited to: bacterial gene editing, plant gene editing, yeast gene editing, mammalian gene editing, editing of cells in the organs of live animals, editing of embryos, rapid generation of knockout/knock-in animal lines, generating an animal model of disease state, correcting a disease state, inserting a reporter gene, and whole genome functional screening.

In a fifth aspect, an isolated CRISPR/Cpf1 endonuclease system is provided. The system includes an AsCpf1 polypeptide and a suitable AsCpf1 crRNA. In a first respect, the AsCpf1 polypeptide comprises SEQ ID NO:2. In a second respect, the suitable AsCpf1 crRNA is selected from a length-truncated AsCpf1 crRNA or a chemically-modified AsCpf1 crRNA, or an AsCpf1 crRNA containing both length truncations and chemical modifications.

In a sixth aspect, an isolated CRISPR/Cpf1 endonuclease system is provided. The system includes a human cell line expressing an AsCpf1 polypeptide and a suitable AsCpf1 crRNA. In a first respect, the AsCpf1 polypeptide comprises at least one member selected from the group consisting of SEQ ID NO:2, SEQ ID NO:12, SEQ ID NO:16 and SEQ ID NO:19. In a second respect, the suitable AsCpf1 crRNA is selected from a length-truncated AsCpf1 crRNA or a chemically-modified AsCpf1 crRNA, or an AsCpf1 crRNA containing both length truncations and chemical modifications.

In a seventh aspect, an isolated AsCpf1 crRNA is provided. The isolated AsCpf1 crRNA is active in a Clustered Regularly Interspaced Short Palindromic Repeats (CRISPR)/CRISPR-associated protein endonuclease system. In a first respect, the isolated AsCpf1 crRNA is selected from length-truncated AsCpf1 crRNA, a chemically-modified AsCpf1 crRNA, or an AsCpf1 crRNA containing both length truncations and chemical modifications.

In an eighth aspect, a method of performing gene editing is provided. The method includes the step of contacting a candidate editing target site locus with an active CRISPR/Cpf1 endonuclease system having a wild-type AsCpf1 polypeptide and a suitable AsCpf1 crRNA. In a first respect, the wild-type AsCpf1 polypeptide comprises at least one member selected from the group consisting of SEQ ID NO:2, SEQ ID NO:12, SEQ ID NO:16 and SEQ ID NO:19. In a second respect, the suitable AsCpf1 crRNA is selected from a length-truncated AsCpf1 crRNA, a chemically-modified AsCpf1 crRNA, or an AsCpf1 crRNA containing both length truncations and chemical modifications.

In another aspect, an isolated nucleic acid encoding an Lb Cpf1 polypeptide codon optimized for expression in *H. sapiens* is provided. In a first respect the isolated nucleic acid comprises SEQ ID NO:17 or SEQ ID NO:396.

In another aspect, an isolated polypeptide encoding a wild-type Lp Cpf1 protein is provided. In a first respect, the isolated polypeptide comprises SEQ ID NO:14 or SEQ ID NO:24.

In another aspect, an isolated expression vector encoding SEQ ID NO:17 or SEQ ID NO:396 is provided.

In another aspect, a host cell including an isolated expression vector encoding SEQ ID NO:17 or SEQ ID NO:396 is provided. The isolated expression vector encoding SEQ ID NO:17 or SEQ ID NO:396 is operably linked to a suitable promoter to permit expression of a polypeptide comprising SEQ ID NO:14 or SEQ ID NO:24, respectively. In a first respect, the host cell comprises a human cell. In a second respect, the human cell comprises an immortalized cell line. In a third respect, the immortalized cell line is a HEK293 cell line. In a further elaboration of this respect, the host cell includes an isolated Lb Cpf1 crRNA capable of forming a ribonucleoprotein complex with the polypeptide selected from the group consisting of SEQ ID NO:4, SEQ ID NO:14, SEQ ID NO:20 and SEQ ID NO:24 to form a wild-type CRISPR/Cpf1 endonuclease.

In another aspect, an isolated CRISPR/Cpf1 endonuclease system having an Lb Cpf1 polypeptide and a suitable Cpf1 crRNA is provided. In a first respect, the CRISPR/Cpf1 endonuclease system includes a Lb Cpf1 polypeptide in the form of SEQ ID NO:14. In a second respect, the isolated CRISPR/Cpf1 endonuclease system includes a suitable Cpf1 crRNA selected from a length-truncated Cpf1 crRNA or a chemically-modified Cpf1 crRNA, or a Cpf1 crRNA comprising both length truncations and chemical modifications.

In another aspect, an isolated CRISPR/Cpf1 endonuclease system having a human cell line expressing an Lb Cpf1 polypeptide and a suitable Cpf1 crRNA is provided. In a first respect, the Lb Cpf1 polypeptide is SEQ ID NO:14 or SEQ ID NO:24. In a second respect, the suitable Cpf1 crRNA is selected from a length-truncated Cpf1 crRNA or a chemically-modified Cpf1 crRNA, or a Cpf1 crRNA comprising both length truncations and chemical modifications.

In another respect, a method of performing gene editing is provided. The method includes the steps of contacting a candidate editing target site locus with an active CRISPR/Cpf1 endonuclease system having a wild-type Lb Cpf1 polypeptide and a suitable Cpf1 crRNA. In a first respect, the method includes a wild-type Lb Cpf1 polypeptide selected from the group consisting of SEQ ID NO:4, SEQ ID NO:14, SEQ ID NO:20 and SEQ ID NO:24. In a second respect, the suitable Cpf1 crRNA is selected from a length-truncated Cpf1 crRNA, a chemically-modified Cpf1 crRNA, or a Cpf1 crRNA comprising both length truncations and chemical modifications.

In another respect, a CRISPR endonuclease system having a recombinant Cpf1 fusion protein and a suitable crRNA is provided. In a first respect, the recombinant Cpf1 fusion protein is an isolated, purified protein. In a second respect, the recombinant Cpf1 fusion protein includes an N-terminal NLS, a C-terminal NLS and a plurality of affinity tags located at either the N-terminal or C-terminal ends. In one preferred embodiment, the recombinant Cpf1 fusion protein includes an N-terminal NLS, a C-terminal NLS and 3 N-terminal FLAG tags and a C-terminal 6×His tag. In a third respect, the recombinant Cpf1 fusion protein and a suitable crRNA is provided in a 1:1 stoichiometric ratio (that is, in equimolar amounts).

Example 1

DNA and Amino Acid Sequences of Wild Type as Cpf1 Polypeptide, as Encoded in Isolated Nucleic Acid Vectors The list below shows wild type (WT) As Cpf1 nucleases expressed as a polypeptide fusion protein described in the present invention. It will be appreciated by one with skill in the art that many different DNA sequences can encode/express the same amino acid (AA) sequence since in many cases more than one codon can encode for the same amino acid. The DNA sequences shown below only serve as example and other DNA sequences that encode the same protein (e.g., same amino acid sequence) are contemplated. It is further appreciated that additional features, elements or tags may be added to said sequences, such as NLS domains and the like. Examples are shown for WT AsCpf1 showing amino acid and DNA sequences for those proteins as Cpf1 alone and Cpf1 fused to both C-terminal and N-terminal SV40 NLS domains and a HIS-tag. Amino acid sequences that represent NLS sequences, domain linkers, or purification tags are indicated in bold font.

```
AsCpf1 Native Nucleotide Sequence
                                          SEQ ID NO: 1
ATGACCCAATTTGAAGGTTTTACCAATTTATACCAAGTTTCGAAGACCCTTCGTTTTGAACTGATTC

CCCAAGGAAAAACACTCAAACATATCCAGGAGCAAGGGTTCATTGAGGAGGATAAAGCTCGCAATGA

CCATTACAAAGAGTTAAAACCAATCATTGACCGCATCTATAAGACTTATGCTGATCAATGTCTCCAA

CTGGTACAGCTTGACTGGGAGAATCTATCTGCAGCCATAGACTCCTATCGTAAGGAAAAAACCGAAG

AAACACGAAATGCGCTGATTGAGGAGCAAGCAACATATAGAAATGCGATTCATGACTACTTTATAGG

TCGGACGGATAATCTGACAGATGCCATAAATAAGCGCCATGCTGAAATCTATAAAGGACTTTTTAAA

GCTGAACTTTTCAATGGAAAAGTTTTAAAGCAATTAGGGACCGTAACCACGACAGAACATGAAAATG

CTCTACTCCGTTCGTTTGACAAATTTACGACCTATTTTTCCGGCTTTTATGAAAACCGAAAAAATGT

CTTTAGCGCTGAAGATATCAGCACGGCAATTCCCCATCGAATCGTCCAGGACAATTTCCCTAAATTT

AAGGAAAACTGCCATATTTTTACAAGATTGATAACCGCAGTTCCTTCTTTGCGGGAGCATTTTGAAA

ATGTCAAAAAGGCCATTGGAATCTTTGTTAGTACGTCTATTGAAGAAGTCTTTTCCTTTCCCTTTTA

TAATCAACTTCTAACCCAAACGCAAATTGATCTTTATAATCAACTTCTCGGCGGCATATCTAGGGAA

GCAGGCACAGAAAAAATCAAGGGACTTAATGAAGTTCTCAATCTGGCTATCCAAAAAAATGATGAAA

CAGCCCATATAATCGCGTCCCTGCCGCATCGTTTTATTCCTCTTTTTAAACAAATTCTTTCCGATCG

AAATACGTTATCCTTTATTTTGGAAGAATTCAAAAGCGATGAGGAAGTCATCCAATCCTTCTGCAAA

TATAAAACCCTCTTGAGAAACGAAAATGTACTGGAGACTGCAGAAGCCCTTTTCAATGAATTAAATT

CCATTGATTTGACTCATATCTTTATTTCCCATAAAAAGTTAGAAACCATCTCTTCAGCGCTTTGTGA

CCATTGGGATACCTTGCGCAATGCACTTTACGAAAGACGGATTTCTGAACTCACTGGCAAAATAACA
```

-continued

```
AAAAGTGCCAAAGAAAAAGTTCAAAGGTCATTAAAACATGAGGATATAAATCTCCAAGAAATTATTT

CTGCTGCAGGAAAAGAACTATCAGAAGCATTCAAACAAAAAACAAGTGAAATTCTTTCCCATGCCCA

TGCTGCACTTGACCAGCCTCTTCCCACAACATTAAAAAAACAGGAAGAAAAAGAAATCCTCAAATCA

CAGCTCGATTCGCTTTTAGGCCTTTATCATCTTCTTGATTGGTTTGCTGTCGATGAAAGCAATGAAG

TCGACCCAGAATTCTCAGCACGGCTGACAGGCATTAAACTAGAAATGGAACCAAGCCTTTCGTTTTA

TAATAAAGCAAGAAATTATGCGACAAAAAAGCCCTATTCGGTGGAAAAATTTAAATTGAATTTTCAA

ATGCCAACCCTTGCCTCTGGTTGGGATGTCAATAAAGAAAAAAATAATGGAGCTATTTTATTCGTAA

AAAATGGTCTCTATTACCTTGGTATCATGCCTAAACAGAAGGGGCGCTATAAAGCCCTGTCTTTTGA

GCCGACAGAAAAAACATCAGAAGGATTCGATAAGATGTACTATGACTACTTCCCAGATGCCGCAAAA

ATGATTCCTAAGTGTTCCACTCAGCTAAAGGCTGTAACCGCTCATTTTCAAACTCATACCACCCCCA

TTCTTCTCTCAAATAATTTCATTGAACCTCTTGAAATCACAAAAGAAATTTATGACCTGAACAATCC

TGAAAAGGAGCCTAAAAAGTTTCAAACGGCTTATGCAAAGAAGACAGGCGATCAAAAAGGCTATAGA

GAAGCGCTTTGCAAATGGATTGACTTTACGCGGGATTTTCTCTCTAAATATACGAAAACAACTTCAA

TCGATTTATCTTCACTCCGCCCTTCTTCGCAATATAAAGATTTAGGGGAATATTACGCCGAACTGAA

TCCGCTTCTCTATCATATCTCCTTCCAACGAATTGCTGAAAAGGAAATCATGGATGCTGTAGAAACG

GGAAAATTGTATCTGTTCCAAATCTACAATAAGGATTTTGCGAAGGGCCATCACGGGAAACCAAATC

TCCACACCCTGTATTGGACAGGTCTCTTCAGTCCTGAAAACCTTGCGAAAACCAGCATCAAACTTAA

TGGTCAAGCAGAATTGTTCTATCGACCTAAAAGCCGCATGAAGCGGATGGCCCATCGTCTTGGGGAA

AAAATGCTGAACAAAAAACTAAAGGACCAGAAGACACCGATTCCAGATACCCTCTACCAAGAACTGT

ACGATTATGTCAACCACCGGCTAAGCCATGATCTTTCCGATGAAGCAAGGGCCCTGCTTCCAAATGT

TATCACCAAAGAAGTCTCCCATGAAATTATAAAGGATCGGCGGTTTACTTCCGATAAATTTTTCTTC

CATGTTCCCATTACACTGAATTATCAAGCAGCCAATAGTCCCAGTAAATTCAACCAGCGTGTCAATG

CCTACCTTAAGGAGCATCCGGAAACGCCCATCATTGGTATCGATCGTGGAGAACGCAATCTAATCTA

TATTACCGTCATTGACAGTACTGGGAAAATTTTGGAGCAGCGTTCCCTGAATACCATCCAGCAATTT

GACTACCAAAAAAAATTGGACAACAGGGAAAAAGAGCGTGTTGCCGCCCGTCAAGCCTGGTCCGTCG

TCGGAACGATCAAAGACCTTAAACAAGGCTACTTGTCACAGGTCATCCATGAAATTGTAGACCTGAT

GATTCATTACCAAGCTGTTGTCGTCCTTGAAAACCTCAACTTCGGATTTAAATCAAAACGGACAGGC

ATTGCCGAAAAAGCAGTCTACCAACAATTTGAAAAGATGCTAATAGATAAACTCAACTGTTTGGTTC

TCAAAGATTATCCTGCTGAGAAAGTGGGAGGCGTCTTAAACCCGTATCAACTTACAGATCAGTTCAC

GAGCTTTGCAAAAATGGGCACGCAAAGCGGCTTCCTTTTCTATGTACCGGCCCCTTATACCTCAAAG

ATTGATCCCCTGACTGGTTTTGTCGATCCCTTTGTATGGAAGACCATTAAAAATCATGAAAGTCGGA

AGCATTTCCTAGAAGGATTTGATTTCCTGCATTATGATGTCAAAACAGGTGATTTTATCCTCCATTT

TAAAATGAATCGGAATCTCTCTTTCCAGAGAGGGCTTCCTGGCTTCATGCCAGCTTGGGATATTGTT

TTCGAAAAGAATGAAACCCAATTTGATGCAAAAGGGACGCCCTTCATTGCAGGAAAACGAATTGTTC

CTGTAATCGAAAATCATCGTTTTACGGGTCGTTACAGAGACCTCTATCCCGCTAATGAACTCATTGC

CCTTCTGGAAGAAAAAGGCATTGTCTTTAGAGACGGAAGTAATATATTACCCAAACTTTTAGAAAAT

GATGATTCTCATGCAATTGATACGATGGTCGCCTTGATTCGCAGTGTACTCCAAATGAGAAACAGCA

ATGCCGCAACGGGGGAAGACTACATCAACTCTCCCGTTAGGGATCTGAACGGGGTGTGTTTCGACAG

TCGATTCCAAAATCCAGAATGGCCAATGGATGCGGATGCCAACGGAGCTTATCATATTGCCTTAAAA

GGGCAGCTTCTTCTGAACCACCTCAAAGAAAGCAAAGATCTGAAATTACAAAACGGCATCAGCAACC

AAGATTGGCTGGCCTACATTCAGGAACTGAGAAACTGA
```

-continued

AsCpf1 Native Protein Sequence

SEQ ID NO: 2

MTQFEGFTNLYQVSKTLRFELIPQGKTLKHIQEQGFIEEDKARNDHYKELKPIIDRIYKTYADQCLQ

LVQLDWENLSAAIDSYRKEKTEETRNALIEEQATYRNAIHDYFIGRTDNLTDAINKRHAEIYKGLFK

AELFNGKVLKQLGTVTTTEHENALLRSFDKFTTYFSGFYENRKNVFSAEDISTAIPHRIVQDNFPKF

KENCHIFTRLITAVPSLREHFENVKKAIGIFVSTSIEEVFSFPFYNQLLTQTQIDLYNQLLGGISRE

AGTEKIKGLNEVLNLAIQKNDETAHIIASLPHRFIPLFKQILSDRNTLSFILEEFKSDEEVIQSFCK

YKTLLRNENVLETAEALFNELNSIDLTHIFISHKKLETISSALCDHWDTLRNALYERRISELTGKIT

KSAKEKVQRSLKHEDINLQEIISAAGKELSEAFKQKTSEILSHAHAALDQPLPTTLKKQEEKEILKS

QLDSLLGLYHLLDWFAVDESNEVDPEFSARLTGIKLEMEPSLSFYNKARNYATKKPYSVEKFKLNFQ

MPTLASGWDVNKEKNNGAILFVKNGLYYLGIMPKQKGRYKALSFEPTEKTSEGFDKMYYDYFPDAAK

MIPKCSTQLKAVTAHFQTHTTPILLSNNFIEPLEITKEIYDLNNPEKEPKKFQTAYAKKTGDQKGYR

EALCKWIDFTRDFLSKYTKTTSIDLSSLRPSSQYKDLGEYYAELNPLLYHISFQRIAEKEIMDAVET

GKLYLFQTYNKDFAKGHHGKPNLHTLYWTGLFSPENLAKTSIKLNGQAELFYRPKSRMKRMAHRLGE

KMLNKKLKDQKTPIPDTLYQELYDYVNHRLSHDLSDEARALLPNVITKEVSHEIIKDRRFTSDKFFF

HVPITLNYQAANSPSKFNQRVNAYLKEHPETPIIGIDRGERNLIYITVIDSTGKILEQRSLNTIQQF

DYQKKLDNREKERVAARQAWSVVGTIKDLKQGYLSQVIHEIVDLMIHYQAVVVLENLNFGFKSKRTG

IAEKAVYQQFEKMLIDKLNCLVLKDYPAEKVGGVLNPYQLTDQFTSFAKMGTQSGFLFYVPAPYTSK

IDPLTGFVDPFVWKTIKNHESRKHFLEGFDFLHYDVKTGDFILHFKMNRNLSFQRGLPGFMPAWDIV

FEKNETQFDAKGTPFIAGKRIVPVIENHRFTGRYRDLYPANELIALLEEKGIVERDGSNILPKLLEN

DDSHAIDTMVALIRSVLQMRNSNAATGEDYINSPVRDLNGVCFDSRFQNPEWPMDADANGAYHIALK

GQLLLNHLKESKDLKLQNGISNQDWLAYIQELRN

*E. coli* optimized AsCpf1 DNA

SEQ ID NO: 5

ATGACCCAGTTTGAAGGTTTCACCAATCTGTATCAGGTTAGCAAAACCCTGCGTTTTGAACTGATTC

CGCAGGGTAAAACCCTGAAACATATTCAAGAACAGGGCTTCATCGAAGAGGATAAAGCACGTAACGA

TCACTACAAAGAACTGAAACCGATTATCGACCGCATCTATAAAACCTATGCAGATCAGTGTCTGCAG

CTGGTTCAGCTGGATTGGGAAAATCTGAGCGCAGCAATTGATAGTTATCGCAAAGAAAAAACCGAAG

AAACCCGTAATGCACTGATTGAAGAACAGGCAACCTATCGTAATGCCATCCATGATTATTTCATTGG

TCGTACCGATAATCTGACCGATGCAATTAACAAACGTCACGCCGAAATCTATAAAGGCCTGTTTAAA

GCCGAACTGTTTAATGGCAAAGTTCTGAAACAGCTGGGCACCGTTACCACCACCGAACATGAAAATG

CACTGCTGCGTAGCTTTGATAAATTCACCACCTATTTCAGCGGCTTTTATGAGAATCGCAAAAACGT

GTTTAGCGCAGAAGATATTAGCACCGCAATTCCGCATCGTATTGTGCAGGATAATTTCCCGAAATTC

AAAGAGAACTGCCACATTTTTACCCGTCTGATTACCGCAGTTCCGAGCCTGCGTGAACATTTTGAAA

ACGTTAAAAAAGCCATCGGCATCTTTGTTAGCACCAGCATTGAAGAAGTTTTTAGCTTCCCGTTTTA

CAATCAGCTGCTGACCCAGACCCAGATTGATCTGTATAACCAACTGCTGGGTGGTATTAGCCGTGAA

GCAGGCACCGAAAAAAATCAAAGGTCTGAATGAAGTGCTGAATCTGGCCATTCAGAAAAATGATGAAA

CCGCACATATTATTGCAAGCCTGCCGCATCGTTTTATTCCGCTGTTCAAACAAATTCTGAGCGATCG

TAATACCCTGAGCTTTATTCTGGAAGAATTCAAATCCGATGAAGAGGTGATTCAGAGCTTTTGCAAA

TACAAAACGCTGCTGCGCAATGAAAATGTTCTGGAAACTGCCGAAGCACTGTTTAACGAACTGAATA

GCATTGATCTGACCCACATCTTTATCAGCCACAAAAAACTGGAAACCATTTCAAGCGCACTGTGTGA

TCATTGGGATACCCTGCGTAATGCCCTGTATGAACGTCGTATTAGCGAACTGACCGGTAAAATTACC

-continued

```
AAAAGCGCGAAAGAAAAAGTTCAGCGCAGTCTGAAACATGAGGATATTAATCTGCAAGAGATTATTA

GCGCAGCCGGTAAAGAACTGTCAGAAGCATTTAAACAGAAAACCAGCGAAATTCTGTCACATGCACA

TGCAGCACTGGATCAGCCGCTGCCGACCACCCTGAAAAAACAAGAAGAAAAAGAAATCCTGAAAAGC

CAGCTGGATAGCCTGCTGGGTCTGTATCATCTGCTGGACTGGTTTGCAGTTGATGAAAGCAATGAAG

TTGATCCGGAATTTAGCGCACGTCTGACCGGCATTAAACTGGAAATGGAACCGAGCCTGAGCTTTTA

TAACAAAGCCCGTAATTATGCCACCAAAAAACCGTATAGCGTCGAAAAATTCAAACTGAACTTTCAG

ATGCCGACCCTGGCAAGCGGTTGGGATGTTAATAAAGAAAAAAACAACGGTGCCATCCTGTTCGTGA

AAAATGGCCTGTATTATCTGGGTATTATGCCGAAACAGAAAGGTCGTTATAAAGCGCTGAGCTTTGA

ACCGACGGAAAAAACCAGTGAAGGTTTTGATAAAATGTACTACGACTATTTTCCGGATGCAGCCAAA

ATGATTCCGAAATGTAGCACCCAGCTGAAAGCAGTTACCGCACATTTTCAGACCCATACCACCCCGA

TTCTGCTGAGCAATAACTTTATTGAACCGCTGGAAATCACCAAAGAGATCTACGATCTGAATAACCC

GGAAAAAGAGCCGAAAAAATTCCAGACCGCATATGCAAAAAAAACCGGTGATCAGAAAGGTTATCGT

GAAGCGCTGTGTAAATGGATTGATTTCACCCGTGATTTTCTGAGCAAATACACCAAAACCACCAGTA

TCGATCTGAGCAGCCTGCGTCCGAGCAGCCAGTATAAAGATCTGGGCGAATATTATGCAGAACTGAA

TCCGCTGCTGTATCATATTAGCTTTCAGCGTATTGCCGAGAAAGAAATCATGGACGCAGTTGAAACC

GGTAAACTGTACCTGTTCCAGATCTACAATAAAGATTTTGCCAAAGGCCATCATGGCAAACCGAATC

TGCATACCCTGTATTGGACCGGTCTGTTTAGCCCTGAAAATCTGGCAAAAACCTCGATTAAACTGAA

TGGTCAGGCGGAACTGTTTTATCGTCCGAAAAGCCGTATGAAACGTATGGCACATCGTCTGGGTGAA

AAAATGCTGAACAAAAAACTGAAAGACCAGAAAACCCCGATCCCGGATACACTGTATCAAGAACTGT

ATGATTATGTGAACCATCGTCTGAGCCATGATCTGAGTGATGAAGCACGTGCCCTGCTGCCGAATGT

TATTACCAAAGAAGTTAGCCACGAGATCATTAAAGATCGTCGTTTTACCAGCGACAAATTCTTTTTT

CATGTGCCGATTACCCTGAATTATCAGGCAGCAAATAGCCCGAGCAAATTTAACCAGCGTGTTAATG

CATATCTGAAAGAACATCCAGAAACGCCGATTATTGGTATTGATCGTGGTGAACGTAACCTGATTTA

TATCACCGTTATTGATAGCACCGGCAAAATCCTGGAACAGCGTAGCCTGAATACCATTCAGCAGTTT

GATTACCAGAAAAAACTGGATAATCGCGAGAAAGAACGTGTTGCAGCACGTCAGGCATGGTCAGTTG

TTGGTACAATTAAAGACCTGAAACAGGGTTATCTGAGCCAGGTTATTCATGAAATTGTGGATCTGAT

GATTCACTATCAGGCCGTTGTTGTGCTGGAAAACCTGAATTTTGGCTTTAAAAGCAAACGTACCGGC

ATTGCAGAAAAAGCAGTTTATCAGCAGTTCGAGAAAATGCTGATTGACAAACTGAATTGCCTGGTGC

TGAAAGATTATCCGGCTGAAAAAGTTGGTGGTGTTCTGAATCCGTATCAGCTGACCGATCAGTTTAC

CAGCTTTGCAAAAATGGGCACCCAGAGCGGATTTCTGTTTTATGTTCCGGCACCGTATACGAGCAAA

ATTGATCCGCTGACCGGTTTTGTTGATCCGTTTGTTTGGAAAACCATCAAAAACCATGAAAGCCGCA

AACATTTTCTGGAAGGTTTCGATTTTCTGCATTACGACGTTAAAACGGGTGATTTCATCCTGCACTT

TAAAATGAATCGCAATCTGAGTTTTCAGCGTGGCCTGCCTGGTTTTATGCCTGCATGGGATATTGTG

TTTGAGAAAAACGAAACACAGTTCGATGCAAAAGGCACCCCGTTTATTGCAGGTAAACGTATTGTTC

CGGTGATTGAAAATCATCGTTTCACCGGTCGTTATCGCGATCTGTATCCGGCAAATGAACTGATCGC

ACTGCTGGAAGAGAAAGGTATTGTTTTTCGTGATGGCTCAAACATTCTGCCGAAACTGCTGGAAAAT

GATGATAGCCATGCAATTGATACCATGGTTGCACTGATTCGTAGCGTTCTGCAGATGCGTAATAGCA

ATGCAGCAACCGGTGAAGATTACATTAATAGTCCGGTTCGTGATCTGAATGGTGTTTGTTTTGATAG

CCGTTTTCAGAATCCGGAATGGCCGATGGATGCAGATGCAAATGGTGCATATCATATTGCACTGAAA

GGACAGCTGCTGCTGAACCACCTGAAAGAAAGCAAAGATCTGAAACTGCAAAACGGCATTAGCAATC

AGGATTGGCTGGCATATATCCAAGAACTGCGTAACTGA
```

-continued

AsCpf1 Human Codon Optimized Nucleotide Sequence

SEQ ID NO: 8

ATGACCCAGTTCGAGGGCTTCACCAACCTGTACCAGGTGTCCAAGACCCTGAGATTCGAGCTGATCC

CCCAGGGCAAGACACTGAAGCACATCCAGGAACAGGGCTTCATCGAAGAGGACAAGGCCCGGAACGA

CCACTACAAAGAGCTGAAGCCCATCATCGACCGGATCTACAAGACCTACGCCGACCAGTGCCTGCAG

CTGGTGCAGCTGGACTGGGAGAATCTGAGCGCCGCCATCGACAGCTACCGGAAAGAGAAAACCGAGG

AAACCCGGAACGCCCTGATCGAGGAACAGGCCACCTACAGAAACGCCATCCACGACTACTTCATCGG

CCGGACCGACAACCTGACCGACGCCATCAACAAGCGGCACGCCGAGATCTATAAGGGCCTGTTCAAG

GCCGAGCTGTTCAACGGCAAGGTGCTGAAGCAGCTGGGCACCGTGACCACCACCGAGCACGAAAACG

CCCTGCTGCGGAGCTTCGACAAGTTCACCACCTACTTCAGCGGCTTCTACGAGAACCGGAAGAACGT

GTTCAGCGCCGAGGACATCAGCACCGCCATCCCCCACAGAATCGTGCAGGACAACTTCCCCAAGTTC

AAAGAGAACTGCCACATCTTCACCCGGCTGATCACCGCCGTGCCCAGCCTGAGAGAACACTTCGAGA

ACGTGAAGAAGGCCATCGGCATCTTCGTGTCCACCAGCATCGAGGAAGTGTTCAGCTTCCCCATTCTA

CAACCAGCTGCTGACCCAGACCCAGATCGACCTGTATAATCAGCTGCTGGGCGGCATCAGCAGAGAG

GCCGGCACCGAGAAGATCAAGGGCCTGAACGAAGTGCTGAACCTGGCCATCCAGAAGAACGACGAGA

CAGCCCACATCATTGCCAGCCTGCCCCACCGGTTCATCCCTCTGTTCAAGCAGATCCTGAGCGACAG

AAACACCCTGAGCTTCATCCTGGAAGAGTTCAAGTCCGATGAGGAAGTGATCCAGAGCTTCTGCAAG

TATAAGACCCTGCTGAGGAACGAGAATGTGCTGGAAACCGCCGAGGCCCTGTTCAATGAGCTGAACA

GCATCGACCTGACCCACATCTTTATCAGCCACAAGAAGCTGGAAACAATCAGCAGCGCCCTGTGCGA

CCACTGGGACACACTGCGGAATGCCCTGTACGAGCGGCGGATCTCTGAGCTGACCGGCAAGATCACC

AAGAGCGCCAAAGAAAAGGTGCAGCGGAGCCTGAAGCACGAGGATATCAACCTGCAGGAAATCATCA

GCGCCGCTGGCAAAGAACTGAGCGAGGCCTTTAAGCAGAAAACCAGCGAGATCCTGTCCCACGCCCA

CGCCGCACTGGATCAGCCTCTGCCTACCACCCTGAAGAAGCAGGAAGAGAAAGAGATCCTGAAGTCC

CAGCTGGACAGCCTGCTGGGCCTGTACCATCTGCTGGATTGGTTCGCCGTGGACGAGAGCAACGAGG

TGGACCCCGAGTTCTCCGCCAGACTGACAGGCATCAAACTGGAAATGGAACCCAGCCTGTCCTTCTA

CAACAAGGCCAGAAACTACGCCACCAAGAAACCCTACAGCGTGGAAAAGTTTAAGCTGAACTTCCAG

ATGCCCACCCTGGCCAGCGGCTGGGACGTGAACAAAGAGAAGAACAACGGCGCCATCCTGTTCGTGA

AGAACGGACTGTACTACCTGGGCATCATGCCTAAGCAGAAGGGCAGATACAAGGCCCTGTCCTTTGA

GCCCACCGAAAAGACCAGCGAGGGCTTTGACAAGATGTACTACGATTACTTCCCCGACGCCGCCAAG

ATGATCCCCAAGTGCAGCACCCAGCTGAAGGCCGTGACCGCCCACTTTCAGACCCACACCACCCCCA

TCCTGCTGAGCAACAACTTCATCGAGCCCCTGGAAATCACCAAAGAGATCTACGACCTGAACAACCC

CGAGAAAGAGCCCAAGAAGTTCCAGACCGCCTACGCCAAGAAAACCGGCGACCAGAAGGGCTACCGC

GAGGCTCTGTGCAAGTGGATCGACTTTACCCGGGACTTCCTGAGCAAGTACACCAAGACCACCTCCA

TCGATCTGAGCAGCCTGCGGCCCAGCTCCCAGTACAAGGATCTGGGCGAGTACTACGCCGAGCTGAA

CCCTCTGCTGTACCACATCAGCTTCCAGCGGATCGCCGAAAAAGAAATCATGGACGCCGTGGAAACC

GGCAAGCTGTACCTGTTCCAGATCTATAACAAGGACTTCGCCAAGGGCCACCACGGCAAGCCCAATC

TGCACACCCTGTACTGGACCGGCCTGTTTAGCCCCGAGAATCTGGCCAAGACCAGCATCAAGCTGAA

CGGCCAGGCCGAACTGTTTTACCGGCCCAAGAGCCGGATGAAGCGGATGGCCCATAGACTGGGCGAG

AAGATGCTGAACAAGAAACTGAAGGACCAGAAAACCCCTATCCCCGACACACTGTATCAGGAACTGT

ACGACTACGTGAACCACCGGCTGAGCCACGACCTGTCCGACGAAGCTAGAGCACTGCTGCCCAACGT

GATCACAAAAGAGGTGTCCCACGAGATCATCAAGGACCGGCGGTTTACCTCCGATAAGTTCTTCTTC

CACGTGCCCATCACCCTGAACTACCAGGCCGCCAACAGCCCCAGCAAGTTCAACCAGAGAGTGAACG

CCTACCTGAAAGAGCACCCCGAGACACCCATCATTGGCATCGACAGAGGCGAGCGGAACCTGATCTA

CATCACCGTGATCGACAGCACAGGCAAAATCCTGGAACAGAGAAGCCTGAACACCATCCAGCAGTTC

GACTACCAGAAGAAACTGGACAACCGGGAAAAAGAACGGGTGGCCGCCAGACAGGCTTGGAGCGTCG

TGGGCACCATTAAGGACCTGAAGCAGGGCTACCTGAGCCAAGTGATTCACGAGATCGTGGACCTGAT

GATCCACTATCAGGCTGTGGTGGTGCTGGAAAACCTGAACTTCGGCTTCAAGAGCAAGCGGACCGGA

ATCGCCGAGAAAGCCGTGTACCAGCAGTTTGAGAAAATGCTGATCGACAAGCTGAATTGCCTGGTGC

TGAAAGACTACCCCGCTGAGAAAGTGGGGAGGCGTGCTGAATCCCTACCAGCTGACCGACCAGTTCAC

CTCCTTTGCCAAGATGGGAACCCAGAGCGGCTTCCTGTTCTACGTGCCAGCCCCCTACACCAGCAAG

ATCGACCCTCTGACCGGCTTCGTGGACCCCTTCGTGTGGAAAACCATCAAGAACCACGAGTCCCGGA

AGCACTTCCTGGAAGGCTTTGACTTCCTGCACTACGACGTGAAAACAGGCGATTTCATCCTGCACTT

CAAGATGAATCGGAATCTGTCCTTCCAGAGGGGCCTGCCCGGCTTCATGCCTGCCTGGGATATCGTG

TTCGAGAAGAATGAGACACAGTTCGACGCCAAGGGAACCCCCTTTATCGCCGGCAAGAGGATCGTGC

CTGTGATCGAGAACCACAGATTCACCGGCAGATACCGGGACCTGTACCCCGCCAACGAGCTGATTGC

CCTGCTGGAAGAGAAGGGCATCGTGTTCCGGGACGGCAGCAACATCCTGCCCAAGCTGCTGGAAAAT

GACGACAGCCACGCCATCGATACCATGGTGGCACTGATCCGCAGCGTGCTGCAGATGCGGAACAGCA

ATGCCGCCACCGGCGAGGACTACATCAATAGCCCAGTGCGGGACCTGAACGGCGTGTGCTTCGACAG

CAGATTCCAGAACCCCGAGTGGCCCATGGATGCCGACGCCAATGGCGCCTACCACATTGCCCTGAAG

GGACAGCTGCTGCTGAACCATCTGAAAGAGAGCAAAGACCTGAAACTGCAGAACGGCATCTCCAACC

AGGACTGGCTGGCCTATATCCAGGAACTGCGGAACTGA

*E. coli* optimized As Cpf1 with flanking NLS's, V5 tag
and 6x His - DNA

SEQ ID NO: 11

ATGGGTCGGGATCCAGGTAAACCGATTCCGAATCCGCTGCTGGGTCTGGATAGCACCGCACCGAAAA

AAAACGTAAAGTTGGTATTCATGGTGTTCCGGCAGCAACCCAGTTTGAAGGTTTCACCAATCTGTA

TCAGGTTAGCAAAACCCTGCGTTTTGAACTGATTCCGCAGGGTAAAAACCCTGAAACATATTCAAGAA

CAGGGCTTCATCGAAGAGGATAAAGCACGTAACGATCACTACAAAGAACTGAAACCGATTATCGACC

GCATCTATAAAACCTATGCAGATCAGTGTCTGCAGCTGGTTCAGCTGGATTGGGAAAATCTGAGCGC

AGCAATTGATAGTTATCGCAAAGAAAAAACCGAAGAAACCCGTAATGCACTGATTGAAGAACAGGCA

ACCTATCGTAATGCCATCCATGATTATTTCATTGGTCGTACCGATAATCTGACCGATGCAATTAACA

AACGTCACGCCGAAATCTATAAAGGCCTGTTTAAAGCCGAACTGTTTAATGGCAAAGTTCTGAAACA

GCTGGGCACCGTTACCACCACCGAACATGAAAATGCACTGCTGCGTAGCTTTGATAAATTCACCACC

TATTTCAGCGGCTTTTATGAGAATCGCAAAAACGTGTTTAGCGCAGAAGATATTAGCACCGCAATTC

CGCATCGTATTGTGCAGGATAATTTCCCGAAATTCAAAGAGAACTGCCACATTTTTACCCGTCTGAT

TACCGCAGTTCCGAGCCTGCGTGAACATTTTGAAAACGTTAAAAAAGCCATCGGCATCTTTGTTAGC

ACCAGCATTGAAGAAGTTTTTAGCTTCCCGTTTTACAATCAGCTGCTGACCCAGACCCAGATTGATC

TGTATAACCAACTGCTGGGTGGTATTAGCCGTGAAGCAGGCACCGAAAAAATCAAAGGTCTGAATGA

AGTGCTGAATCTGGCCATTCAGAAAAATGATGAAACCGCACATATTATTGCAAGCCTGCCGCATCGT

TTTATTCCGCTGTTCAAACAAATTCTGAGCGATCGTAATACCCTGAGCTTTATTCTGGAAGAATTCA

AATCCGATGAAGAGGTGATTCAGAGCTTTTGCAAATACAAAACGCTGCTGCGCAATGAAAATGTTCT

GGAAACTGCCGAAGCACTGTTTAACGAACTGAATAGCATTGATCTGACCCACATCTTTATCAGCCAC

AAAAAACTGGAAACCATTTCAAGCGCACTGTGTGATCATTGGGATACCCTGCGTAATGCCCTGTATG

-continued

```
AACGTCGTATTAGCGAACTGACCGGTAAAATTACCAAAAGCGCGAAAGAAAAAGTTCAGCGCAGTCT

GAAACATGAGGATATTAATCTGCAAGAGATTATTAGCGCAGCCGGTAAAGAACTGTCAGAAGCATTT

AAACAGAAAACCAGCGAAATTCTGTCACATGCACATGCAGCACTGGATCAGCCGCTGCCGACCACCC

TGAAAAAACAAGAAGAAAAAGAAATCCTGAAAAGCCAGCTGGATAGCCTGCTGGGTCTGTATCATCT

GCTGGACTGGTTTGCAGTTGATGAAAGCAATGAAGTTGATCCGGAATTTAGCGCACGTCTGACCGGC

ATTAAACTGGAAATGGAACCGAGCCTGAGCTTTTATAACAAAGCCCGTAATTATGCCACCAAAAAAC

CGTATAGCGTCGAAAAATTCAAACTGAACTTTCAGATGCCGACCCTGGCAAGCGGTTGGGATGTTAA

TAAAGAAAAAAACAACGGTGCCATCCTGTTCGTGAAAAATGGCCTGTATTATCTGGGTATTATGCCG

AAACAGAAAGGTCGTTATAAAGCGCTGAGCTTTGAACCGACGGAAAAAACCAGTGAAGGTTTTGATA

AAATGTACTACGACTATTTTCCGGATGCAGCCAAAATGATTCCGAAATGTAGCACCCAGCTGAAAGC

AGTTACCGCACATTTTCAGACCCATACCACCCCGATTCTGCTGAGCAATAACTTTATTGAACCGCTG

GAAATCACCAAAGAGATCTACGATCTGAATAACCCGGAAAAAGAGCCGAAAAAATTCCAGACCGCAT

ATGCAAAAAAAACCGGTGATCAGAAAGGTTATCGTGAAGCGCTGTGTAAATGGATTGATTTCACCCG

TGATTTTCTGAGCAAATACACCAAAACCACCAGTATCGATCTGAGCAGCCTGCGTCCGAGCAGCCAG

TATAAAGATCTGGGCGAATATTATGCAGAACTGAATCCGCTGCTGTATCATATTAGCTTTCAGCGTA

TTGCCGAGAAAGAAATCATGGACGCAGTTGAAACCGGTAAACTGTACCTGTTCCAGATCTACAATAA

AGATTTTGCCAAAGGCCATCATGGCAAACCGAATCTGCATACCCTGTATTGGACCGGTCTGTTTAGC

CCTGAAAATCTGGCAAAAACCTCGATTAAACTGAATGGTCAGGCGGAACTGTTTTATCGTCCGAAAA

GCCGTATGAAACGTATGGCACATCGTCTGGGTGAAAAAATGCTGAACAAAAAACTGAAAGACCAGAA

AACCCCGATCCCGGATACACTGTATCAAGAACTGTATGATTATGTGAACCATCGTCTGAGCCATGAT

CTGAGTGATGAAGCACGTGCCCTGCTGCCGAATGTTATTACCAAAGAAGTTAGCCACGAGATCATTA

AAGATCGTCGTTTTACCAGCGACAAATTCTTTTTTCATGTGCCGATTACCCTGAATTATCAGGCAGC

AAATAGCCCGAGCAAATTTAACCAGCGTGTTAATGCATATCTGAAAGAACATCCAGAAACGCCGATT

ATTGGTATTGATCGTGGTGAACGTAACCTGATTTATATCACCGTTATTGATAGCACCGGCAAAATCC

TGGAACAGCGTAGCCTGAATACCATTCAGCAGTTTGATTACCAGAAAAAACTGGATAATCGCGAGAA

AGAACGTGTTGCAGCACGTCAGGCATGGTCAGTTGTTGGTACAATTAAAGACCTGAAACAGGGTTAT

CTGAGCCAGGTTATTCATGAAATTGTGGATCTGATGATTCACTATCAGGCCGTTGTTGTGCTGGAAA

ACCTGAATTTTGGCTTTAAAAGCAAACGTACCGGCATTGCAGAAAAAGCAGTTTATCAGCAGTTCGA

GAAAATGCTGATTGACAAACTGAATTGCCTGGTGCTGAAAGATTATCCGGCTGAAAAAGTTGGTGGT

GTTCTGAATCCGTATCAGCTGACCGATCAGTTTACCAGCTTTGCAAAAATGGGCACCCAGAGCGGAT

TTCTGTTTTATGTTCCGGCACCGTATACGAGCAAAATTGATCCGCTGACCGGTTTTGTTGATCCGTT

TGTTTGGAAAACCATCAAAAACCATGAAAGCCGCAAACATTTTCTGGAAGGTTTCGATTTTCTGCAT

TACGACGTTAAAACGGGTGATTTCATCCTGCACTTTAAAATGAATCGCAATCTGAGTTTTCAGCGTG

GCCTGCCTGGTTTTATGCCTGCATGGGATATTGTGTTTGAGAAAAACGAAACACAGTTCGATGCAAA

AGGCACCCCGTTTATTGCAGGTAAACGTATTGTTCCGGTGATTGAAAATCATCGTTTCACCGGTCGT

TATCGCGATCTGTATCCGGCAAATGAACTGATCGCACTGCTGGAAGAGAAAGGTATTGTTTTTCGTG

ATGGCTCAAACATTCTGCCGAAACTGCTGGAAAATGATGATAGCCATGCAATTGATACCATGGTTGC

ACTGATTCGTAGCGTTCTGCAGATGCGTAATAGCAATGCAGCAACCGGTGAAGATTACATTAATAGT
```

-continued

CCGGTTCGTGATCTGAATGGTGTTTGTTTTGATAGCCGTTTTCAGAATCCGGAATGGCCGATGGATG

CAGATGCAAATGGTGCATATCATATTGCACTGAAAGGACAGCTGCTGCTGAACCACCTGAAAGAAAG

CAAAGATCTGAAACTGCAAAACGGCATTAGCAATCAGGATTGGCTGGCATATATCCAAGAACTGCGT

AACCCTAAAAAAAAACGCAAAGTGAAGCTTGCGGCCGCACTCGAGCACCACCACCACCACCACTGA

*E. coli* optimized As Cpf1 with 5'- and 3'-flanking
NLS's, 5'-V5 tag and 3'-6x His

SEQ ID NO: 12

MGRDPGKPIPNPLLGLDSTAPKKKRKVGIHGVPAATQFEGFTNLYQVSKTLRFELIPQGKTLKHIQE

QGFIEEDKARNDHYKELKPIIDRIYKTYADQCLQLVQLDWENLSAAIDSYRKEKTEETRNALIEEQA

TYRNAIHDYFIGRTDNLTDAINKRHAEIYKGLFKAELFNGKVLKQLGTVTTTEHENALLRSFDKFTT

YFSGFYENRKNVFSAEDISTAIPHRIVQDNFPKFKENCHIFTRLITAVPSLREHFENVKKAIGIFVS

TSIEEVFSFPFYNQLLTQTQIDLYNQLLGGISREAGTEKIKGLNEVLNLAIQKNDETAHIIASLPHR

FIPLFKQILSDRNTLSFILEEFKSDEEVIQSFCKYKTLLRNENVLETAEALFNELNSIDLTHIFISH

KKLETISSALCDHWDTLRNALYERRISELTGKITKSAKEKVQRSLKHEDINLQEIISAAGKELSEAF

KQKTSEILSHAHAALDQPLPTTLKKQEEKEILKSQLDSLLGLYHLLDWFAVDESNEVDPEFSARLTG

IKLEMEPSLSFYNKARNYATKKPYSVEKFKLNFQMPTLASGWDVNKEKNNGAILFVKNGLYYLGIMP

KQKGRYKALSFEPTEKTSEGFDKMYYDYFPDAAKMIPKCSTQLKAVTAHFQTHTTPILLSNNFIEPL

EITKEIYDLNNPEKEPKKFQTAYAKKTGDQKGYREALCKWIDFTRDFLSKYTKTTSIDLSSLRPSSQ

YKDLGEYYAELNPLLYHISFQRIAEKEIMDAVETGKLYLFQTYNKDFAKGHHGKPNLHTLYWTGLFS

PENLAKTSIKLNGQAELFYRPKSRMKRMAHRLGEKMLNKKLKDQKTPIPDTLYQELYDYVNHRLSHD

LSDEARALLPNVITKEVSHEIIKDRRFTSDKFFFHVPITLNYQAANSPSKFNQRVNAYLKEHPETPI

IGIDRGERNLIYITVIDSTGKILEQRSLNTIQQFDYQKKLDNREKERVAARQAWSVVGTIKDLKQGY

LSQVIHEIVDLMIHYQAVVVLENLNFGFKSKRTGIAEKAVYQQFEKMLIDKLNCLVLKDYPAEKVGG

VLNPYQLTDQFTSFAKMGTQSGFLFYVPAPYTSKIDPLTGFVDPFVWKTIKNHESRKHFLEGFDFLH

YDVKTGDFILHFKMNRNLSFQRGLPGFMPAWDIVFEKNETQFDAKGTPFIAGKRIVPVIENHRFTGR

YRDLYPANELIALLEEKGIVERDGSNILPKLLENDDSHAIDTMVALIRSVLQMRNSNAATGEDYINS

PVRDLNGVCFDSRFQNPEWPMDADANGAYHIALKGQLLLNHLKESKDLKLQNGISNQDWLAYIQELR

NPKKKRKVKLAAALEHHHHHH

Hs optimized As Cpf1 with flanking NLS's, V5 tag and
6x His - DNA

SEQ ID NO: 15

ATGGGCAAGCCCATTCCTAATCCTCTGCTGGGCCTCGACAGCACAGCCCCTAAGAAAAAGCGGAAAG

TGGGCATCCATGGCGTGCCAGCCGCCACACAGTTTGAGGGCTTCACCAACCTGTACCAGGTGTCCAA

GACACTGCGCTTCGAGCTGATCCCTCAGGGCAAGACCCTGAAGCACATCCAAGAGCAGGGCTTCATC

GAAGAGGACAAGGCCCGGAACGACCACTACAAAGAGCTGAAGCCCATCATCGACCGGATCTACAAGA

CCTACGCCGACCAGTGTCTGCAGCTGGTGCAGCTCGATTGGGAGAATCTGAGCGCCGCCATCGACAG

CTACCGGAAAGAGAAACCGAGGAAACCCGGAACGCCCTGATCGAGGAACAGGCCACCTACAGAAAC

GCCATCCACGACTACTTCATCGGCCGGACCGACAACCTGACCGACGCCATCAACAAGAGACACGCCG

AGATCTATAAGGGCCTGTTCAAGGCCGAGCTGTTCAACGGCAAGGTGCTGAAGCAGCTGGGCACCGT

GACAACCACCGAGCACGAAAATGCCCTGCTGCGGAGCTTCGACAAGTTCACCACCTACTTCAGCGGC

TTCTACGAGAACCGGAAGAACGTGTTCAGCGCCGAGGACATCAGCACCGCCATTCCTCACAGAATCG

TGCAGGACAACTTCCCCAAGTTCAAAGAGAACTGCCACATCTTCACCCGGCTGATCACAGCCGTGCC

TAGCCTGAGAGAACACTTCGAGAACGTGAAGAAGGCCATCGGCATCTTCGTGTCCACCAGCATCGAG

GAAGTGTTCAGCTTCCCATTCTACAACCAGCTGCTGACCCAGACACAGATCGACCTGTATAATCAGC

-continued

```
TGCTCGGCGGCATCAGCAGAGAGGCCGGAACAGAGAAGATCAAGGGCCTGAACGAAGTGCTGAACCT

GGCCATCCAGAAGAACGACGAGACAGCCCACATCATTGCCAGCCTGCCTCACCGGTTCATCCCTCTG

TTCAAGCAGATCCTGAGCGACAGAAACACCCTGAGCTTCATCCTGGAAGAGTTCAAGTCCGATGAGG

AAGTGATCCAGAGCTTCTGCAAGTATAAGACCCTGCTGAGGAACGAGAATGTGCTGGAAACCGCCGA

GGCTCTGTTTAACGAGCTGAACAGCATCGATCTGACCCACATCTTTATCAGCCACAAGAAGCTCGAG

ACAATCAGCAGCGCCCTGTGCGACCACTGGGATACCCTGAGAAACGCCCTGTACGAGCGGAGAATCA

GCGAGCTGACCGGCAAGATCACCAAGAGCGCCAAAGAAAAGGTGCAGCGGAGCCTGAAACACGAGGA

TATCAACCTGCAAGAGATCATCAGCGCCGCTGGCAAAGAACTGAGCGAGGCCTTTAAGCAGAAAACC

AGCGAGATCCTGTCTCACGCCCACGCTGCTCTTGATCAGCCTCTGCCTACCACACTGAAGAAGCAAG

AGGAAAAAGAGATCCTGAAGTCCCAGCTGGACAGCCTGCTGGGACTGTACCATCTGCTGGATTGGTT

CGCCGTGGACGAGAGCAATGAGGTGGACCCTGAGTTCTCCGCCAGACTGACAGGCATCAAGCTGGAA

ATGGAACCCAGCCTGTCCTTCTACAACAAGGCCAGAAACTACGCCACCAAGAAGCCCTACAGCGTCG

AGAAGTTCAAGCTCAACTTCCAGATGCCTACACTGGCCAGCGGCTGGGACGTGAACAAAGAGAAGAA

CAACGGCGCCATCCTGTTCGTGAAGAACGGACTGTACTACCTGGGCATCATGCCAAAGCAGAAGGGC

AGATACAAGGCCCTGTCCTTTGAGCCCACCGAAAAGACCAGCGAGGGCTTCGATAAGATGTACTACG

ATTACTTCCCCGACGCCGCCAAGATGATCCCCAAGTGTAGCACACAGCTGAAGGCCGTGACCGCTCA

CTTTCAGACCCACACCACACCTATCCTGCTGAGCAACAACTTCATCGAGCCCCTGGAAATCACCAAA

GAGATCTACGACCTGAACAACCCCGAGAAAGAGCCCAAGAAGTTCCAGACCGCCTACGCCAAGAAAA

CCGGCGACCAGAAGGGCTACAGAGAAGCCCTGTGCAAGTGGATCGACTTTACCCGGGACTTCCTGAG

CAAGTACACCAAGACCACCTCCATCGACCTGAGCAGCCTGAGGCCTAGCAGCCAGTATAAGGACCTG

GGCGAGTACTACGCCGAGCTGAATCCACTGCTGTACCACATCAGCTTCCAGCGGATCGCCGAAAAAG

AAATCATGGACGCCGTGGAAACCGGCAAGCTGTACCTGTTCCAGATATACAACAAAGACTTCGCCAA

GGGCCACCACGGCAAGCCTAATCTGCACACCCTGTACTGGACCGGCCTGTTTAGCCCTGAGAATCTG

GCCAAGACCTCTATCAAGCTGAACGGCCAGGCCGAACTGTTTTACAGACCCAAGAGCCGGATGAAGC

GGATGGCCCACAGACTGGGAGAGAAGATGCTGAACAAGAAACTGAAGGACCAGAAAACGCCCATTCC

GGACACACTGTACCAAGAGCTGTACGACTACGTGAACCACCGGCTGAGCCACGATCTGAGCGACGAA

GCTAGAGCACTGCTGCCCAACGTGATCACAAAAGAGGTGTCCCACGAGATCATTAAGGACCGGCGGT

TTACCTCCGATAAGTTCTTCTTCCACGTGCCGATCACACTGAACTACCAGGCCGCCAACTCTCCCAG

CAAGTTCAACCAGAGAGTGAACGCCTACCTGAAAGAGCACCCCGAGACACCCATCATTGGCATCGAC

AGAGGCGAGCGGAACCTGATCTACATCACCGTGATCGACTCCACAGGCAAGATCCTGGAACAGCGGT

CCCTGAACACCATCCAGCAGTTCGACTACCAGAAGAAGCTGGACAACCGAGAGAAAGAAAGAGTGGC

CGCCAGACAGGCTTGGAGCGTTGTGGGCACAATCAAGGATCTGAAGCAGGGCTACCTGAGCCAAGTG

ATTCACGAGATCGTGGACCTGATGATCCACTATCAGGCTGTGGTGGTGCTCGAGAACCTGAACTTCG

GCTTCAAGAGCAAGCGGACCGGAATCGCCGAGAAAGCCGTGTACCAGCAGTTTGAGAAAATGCTGAT

CGACAAGCTGAATTGCCTGGTCCTGAAGGACTACCCCGCTGAGAAAGTTGGCGGAGTGCTGAATCCC

TACCAGCTGACCGATCAGTTCACCAGCTTTGCCAAGATGGGAACCCAGAGCGGCTTCCTGTTCTACG

TGCCAGCTCCTTACACCTCCAAGATCGACCCTCTGACCGGCTTCGTGGACCCCTTCGTGTGGAAAAC

CATCAAGAACCACGAGTCCCGGAAGCACTTCCTGGAAGGCTTTGACTTCCTGCACTACGACGTGAAA

ACAGGCGATTTCATCCTGCACTTCAAGATGAATCGGAATCTGTCCTTCCAGAGGGGCCTGCCTGGCT

TCATGCCTGCTTGGGATATCGTGTTCGAGAAGAATGAGACTCAGTTCGACGCCAAGGGGACCCCTTT
```

-continued

TATCGCCGGCAAGAGAATTGTGCCTGTGATCGAGAACCACAGGTTCACCGGCAGATACCGGGATCTG

TACCCCGCCAATGAGCTGATCGCCCTGCTGGAAGAGAAGGGCATCGTGTTTAGAGATGGCAGCAACA

TCCTGCCTAAGCTGCTGGAAAACGACGACAGCCACGCCATCGATACCATGGTGGCACTGATCAGATC

CGTGCTGCAGATGCGGAACAGCAATGCCGCTACCGGCGAGGACTACATCAATAGCCCCGTGCGGGAT

CTGAACGGCGTGTGCTTCGACAGCAGATTTCAGAACCCCGAGTGGCCTATGGATGCCGACGCCAATG

GCGCCTATCACATTGCCCTGAAAGGACAGCTGCTGCTGAACCATCTGAAAGAGAGCAAGGACCTGAA

ACTGCAGAACGGCATCTCCAACCAGGACTGGCTGGCCTACATTCAAGAGCTGCGGAATCCCAAAAAG

AAACGGAAAGTGAAGCTGGCCGCTGCTCTGGAACACCACCACCATCACCAT

Hs optimized As Cpf1 with 5'- and 3'-flanking NLS's,
5'-V5 tag and 3'-6x His - AA

SEQ ID NO: 16

MGKPIPNPLLGLDSTAPKKKRKVGIHGVPAATQFEGFTNLYQVSKTLRFELIPQGKTLKHIQEQGFI

EEDKARNDHYKELKPIIDRIYKTYADQCLQLVQLDWENLSAAIDSYRKEKTEETRNALIEEQATYRN

AIHDYFIGRTDNLTDAINKRHAEIYKGLFKAELFNGKVLKQLGTVTTTEHENALLRSFDKFTTYFSG

FYENRKNVFSAEDISTAIPHRIVQDNFPKFKENCHIFTRLITAVPSLREHFENVKKAIGIFVSTSIE

EVFSFPFYNQLLTQTQIDLYNQLLGGISREAGTEKIKGLNEVLNLAIQKNDETAHIIASLPHRFIPL

FKQILSDRNTLSFILEEFKSDEEVIQSFCKYKTLLRNENVLETAEALFNELNSIDLTHIFISHKKLE

TISSALCDHWDTLRNALYERRISELTGKITKSAKEKVQRSLKHEDINLQEIISAAGKELSEAFKQKT

SEILSHAHAALDQPLPTTLKKQEEKEILKSQLDSLLGLYHLLDWFAVDESNEVDPEFSARLTGIKLE

MEPSLSFYNKARNYATKKPYSVEKFKLNFQMPTLASGWDVNKEKNNGAILFVKNGLYYLGIMPKQKG

RYKALSFEPTEKTSEGFDKMYYDYFPDAAKMIPKCSTQLKAVTAHFQTHTTPILLSNNFIEPLEITK

EIYDLNNPEKEPKKFQTAYAKKTGDQKGYREALCKWIDFTRDFLSKYTKTTSIDLSSLRPSSQYKDL

GEYYAELNPLLYHISFQRIAEKEIMDAVETGKLYLFQTYNKDFAKGHHGKPNLHTLYWTGLFSPENL

AKTSIKLNGQAELFYRPKSRMKRMAHRLGEKMLNKKLKDQKTPIPDTLYQELYDYVNHRLSHDLSDE

ARALLPNVITKEVSHEIIKDRRFTSDKFFFHVPITLNYQAANSPSKFNQRVNAYLKEHPETPIIGID

RGERNLIYITVIDSTGKILEQRSLNTIQQFDYQKKLDNREKERVAARQAWSVVGTIKDLKQGYLSQV

IHEIVDLMIHYQAVVVLENLNFGFKSKRTGIAEKAVYQQFEKMLIDKLNCLVLKDYPAEKVGGVLNP

YQLTDQFTSFAKMGTQSGFLFYVPAPYTSKIDPLTGFVDPFVWKTIKNHESRKHFLEGFDFLHYDVK

TGDFILHFKMNRNLSFQRGLPGFMPAWDIVFEKNETQFDAKGTPFIAGKRIVPVIENHRFTGRYRDL

YPANELIALLEEKGIVERDGSNILPKLLENDDSHAIDTMVALIRSVLQMRNSNAATGEDYINSPVRD

LNGVCFDSRFQNPEWPMDADANGAYHIALKGQLLLNHLKESKDLKLQNGISNQDWLAYIQELRN**PKK

KRKVKLAAALEHHHHHH**

*E. coli* optimized As Cpf1 with OpT NLS and 6x His - DNA

SEQ ID NO: 18

ATGACCCAGTTTGAAGGTTTCACCAATCTGTATCAGGTTAGCAAAACCCTGCGTTTTGAACTGATTC

CGCAGGGTAAAACCCTGAAACATATTCAAGAACAGGGCTTCATCGAAGAGGATAAAGCACGTAACGA

TCACTACAAAGAACTGAAACCGATTATCGACCGCATCTATAAAACCTATGCAGATCAGTGTCTGCAG

CTGGTTCAGCTGGATTGGGAAAATCTGAGCGCAGCAATTGATAGTTATCGCAAAGAAAAAACCGAAG

AAACCCGTAATGCACTGATTGAAGAACAGGCAACCTATCGTAATGCCATCCATGATTATTTCATTGG

TCGTACCGATAATCTGACCGATGCAATTAACAAACGTCACGCCGAAATCTATAAAGGCCTGTTTAAA

GCCGAACTGTTTAATGGCAAAGTTCTGAAACAGCTGGGCACCGTTACCACCACCGAACATGAAAATG

CACTGCTGCGTAGCTTTGATAAATTCACCACCTATTTCAGCGGCTTTTATGAGAATCGCAAAAACGT

GTTTAGCGCAGAAGATATTAGCACCGCAATTCCGCATCGTATTGTGCAGGATAATTTCCCGAAATTC

-continued

```
AAAGAGAACTGCCACATTTTTACCCGTCTGATTACCGCAGTTCCGAGCCTGCGTGAACATTTTGAAA

ACGTTAAAAAAGCCATCGGCATCTTTGTTAGCACCAGCATTGAAGAAGTTTTTAGCTTCCCGTTTTA

CAATCAGCTGCTGACCCAGACCCAGATTGATCTGTATAACCAACTGCTGGGTGGTATTAGCCGTGAA

GCAGGCACCGAAAAAATCAAAGGTCTGAATGAAGTGCTGAATCTGGCCATTCAGAAAAATGATGAAA

CCGCACATATTATTGCAAGCCTGCCGCATCGTTTTATTCCGCTGTTCAAACAAATTCTGAGCGATCG

TAATACCCTGAGCTTTATTCTGGAAGAATTCAAATCCGATGAAGAGGTGATTCAGAGCTTTTGCAAA

TACAAAACGCTGCTGCGCAATGAAAATGTTCTGGAAACTGCCGAAGCACTGTTTAACGAACTGAATA

GCATTGATCTGACCCACATCTTTATCAGCCACAAAAAACTGGAAACCATTTCAAGCGCACTGTGTGA

TCATTGGGATACCCTGCGTAATGCCCTGTATGAACGTCGTATTAGCGAACTGACCGGTAAAATTACC

AAAAGCGCGAAAGAAAAAGTTCAGCGCAGTCTGAAACATGAGGATATTAATCTGCAAGAGATTATTA

GCGCAGCCGGTAAAGAACTGTCAGAAGCATTTAAACAGAAAACCAGCGAAATTCTGTCACATGCACA

TGCAGCACTGGATCAGCCGCTGCCGACCACCCTGAAAAAACAAGAAGAAAAAGAAATCCTGAAAAGC

CAGCTGGATAGCCTGCTGGGTCTGTATCATCTGCTGGACTGGTTTGCAGTTGATGAAAGCAATGAAG

TTGATCCGGAATTTAGCGCACGTCTGACCGGCATTAAACTGGAAATGGAACCGAGCCTGAGCTTTTA

TAACAAAGCCCGTAATTATGCCACCAAAAAACCGTATAGCGTCGAAAAATTCAAACTGAACTTTCAG

ATGCCGACCCTGGCAAGCGGTTGGGATGTTAATAAAGAAAAAAACAACGGTGCCATCCTGTTCGTGA

AAAATGGCCTGTATTATCTGGGTATTATGCCGAAACAGAAAGGTCGTTATAAAGCGCTGAGCTTTGA

ACCGACGGAAAAAACCAGTGAAGGTTTTGATAAAATGTACTACGACTATTTTCCGGATGCAGCCAAA

ATGATTCCGAAATGTAGCACCCAGCTGAAAGCAGTTACCGCACATTTTCAGACCCATACCACCCCGA

TTCTGCTGAGCAATAACTTTATTGAACCGCTGGAAATCACCAAAGAGATCTACGATCTGAATAACCC

GGAAAAAGAGCCGAAAAAATTCCAGACCGCATATGCAAAAAAAACCGGTGATCAGAAAGGTTATCGT

GAAGCGCTGTGTAAATGGATTGATTTCACCCGTGATTTTCTGAGCAAATACACCAAAACCACCAGTA

TCGATCTGAGCAGCCTGCGTCCGAGCAGCCAGTATAAAGATCTGGGCGAATATTATGCAGAACTGAA

TCCGCTGCTGTATCATATTAGCTTTCAGCGTATTGCCGAGAAAGAAATCATGGACGCAGTTGAAACC

GGTAAACTGTACCTGTTCCAGATCTACAATAAAGATTTTGCCAAAGGCCATCATGGCAAACCGAATC

TGCATACCCTGTATTGGACCGGTCTGTTTAGCCCTGAAAATCTGGCAAAAACCTCGATTAAACTGAA

TGGTCAGGCGGAACTGTTTTATCGTCCGAAAAGCCGTATGAAACGTATGGCACATCGTCTGGGGTGAA

AAAATGCTGAACAAAAACTGAAAGACCAGAAAACCCCGATCCCGGATACACTGTATCAAGAACTGT

ATGATTATGTGAACCATCGTCTGAGCCATGATCTGAGTGATGAAGCACGTGCCCTGCTGCCGAATGT

TATTACCAAAGAAGTTAGCCACGAGATCATTAAAGATCGTCGTTTTACCAGCGACAAATTCTTTTTT

CATGTGCCGATTACCCTGAATTATCAGGCAGCAAATAGCCCGAGCAAATTTAACCAGCGTGTTAATG

CATATCTGAAAGAACATCCAGAAACGCCGATTATTGGTATTGATCGTGGTGAACGTAACCTGATTTA

TATCACCGTTATTGATAGCACCGGCAAAATCCTGGAACAGCGTAGCCTGAATACCATTCAGCAGTTT

GATTACCAGAAAAAACTGGATAATCGCGAGAAGAACGTGTTGCAGCACGTCAGGCATGGTCAGTTG

TTGGTACAATTAAAGACCTGAAACAGGGTTATCTGAGCCAGGTTATTCATGAAATTGTGGATCTGAT

GATTCACTATCAGGCCGTTGTTGTGCTGGAAAACCTGAATTTTGGCTTTAAAAGCAAACGTACCGGC

ATTGCAGAAAAAGCAGTTTATCAGCAGTTCGAGAAAATGCTGATTGACAAACTGAATTGCCTGGTGC

TGAAAGATTATCCGGCTGAAAAAGTTGGTGGTGTTCTGAATCCGTATCAGCTGACCGATCAGTTTAC

CAGCTTTGCAAAAATGGGCACCCAGAGCGGATTTCTGTTTTATGTTCCGGCACCGTATACGAGCAAA

ATTGATCCGCTGACCGGTTTTGTTGATCCGTTTGTTTGGAAAACCATCAAAAACCATGAAAGCCGCA

AACATTTTCTGGAAGGTTTCGATTTTCTGCATTACGACGTTAAAACGGGTGATTTCATCCTGCACTT
```

-continued

TAAAATGAATCGCAATCTGAGTTTTCAGCGTGGCCTGCCTGGTTTTATGCCTGCATGGGATATTGTG

TTTGAGAAAAACGAAACACAGTTCGATGCAAAAGGCACCCCGTTTATTGCAGGTAAACGTATTGTTC

CGGTGATTGAAAATCATCGTTTCACCGGTCGTTATCGCGATCTGTATCCGGCAAATGAACTGATCGC

ACTGCTGGAAGAGAAAGGTATTGTTTTTCGTGATGGCTCAAACATTCTGCCGAAACTGCTGGAAAAT

GATGATAGCCATGCAATTGATACCATGGTTGCACTGATTCGTAGCGTTCTGCAGATGCGTAATAGCA

ATGCAGCAACCGGTGAAGATTACATTAATAGTCCGGTTCGTGATCTGAATGGTGTTTGTTTTGATAG

CCGTTTTCAGAATCCGGAATGGCCGATGGATGCAGATGCAAATGGTGCATATCATATTGCACTGAAA

GGACAGCTGCTGCTGAACCACCTGAAAGAAAGCAAAGATCTGAAACTGCAAAACGGCATTAGCAATC

AGGATTGGCTGGCATATATCCAAGAACTGCGTAACGGTCGTAGCAGTGATGATGAAGCAACCGCAGA

TAGCCAGCATGCAGCACCGCCTAAAAAGAAACGTAAAGTTGGTGGTAGCGGTGGTTCAGGTGGTAGT

GGCGGTAGTGGTGGCTCAGGGGGGTTCTGGTGGCTCTGGTGGTAGCCTCGAGCACCACCACCACCACC

ACTGA

Amino acid sequence for AsCpf1 fusion with OpT NLS
and 6x His used for gene editing in both *E. coli* and human cells
                                                    SEQ ID NO: 19
MTQFEGFTNLYQVSKTLRFELIPQGKTLKHIQEQGFIEEDKARNDHYKELKPIIDRIYKTYADQCLQ

LVQLDWENLSAAIDSYRKEKTEETRNALIEEQATYRNAIHDYFIGRTDNLTDAINKRHAEIYKGLFK

AELFNGKVLKQLGTVTTTEHENALLRSFDKFTTYFSGFYENRKNVFSAEDISTAIPHRIVQDNFPKF

KENCHIFTRLITAVPSLREHFENVKKAIGIFVSTSIEEVFSFPFYNQLLTQTQIDLYNQLLGGISRE

AGTEKIKGLNEVLNLAIQKNDETAHIIASLPHRFIPLFKQILSDRNTLSFILEEFKSDEEVIQSFCK

YKTLLRNENVLETAEALFNELNSIDLTHIFISHKKLETISSALCDHWDTLRNALYERRISELTGKIT

KSAKEKVQRSLKHEDINLQEIISAAGKELSEAFKQKTSEILSHAHAALDQPLPTTLKKQEEKEILKS

QLDSLLGLYHLLDWFAVDESNEVDPEFSARLTGIKLEMEPSLSFYNKARNYATKKPYSVEKFKLNFQ

MPTLASGWDVNKEKNNGAILFVKNGLYYLGIMPKQKGRYKALSFEPTEKTSEGFDKMYYDYFPDAAK

MIPKCSTQLKAVTAHFQTHTTPILLSNNFIEPLEITKEIYDLNNPEKEPKKFQTAYAKKTGDQKGYR

EALCKWIDFTRDFLSKYTKTTSIDLSSLRPSSQYKDLGEYYAELNPLLYHISFQRIAEKEIMDAVET

GKLYLFQTYNKDFAKGHHGKPNLHTLYWTGLFSPENLAKTSIKLNGQAELFYRPKSRMKRMAHRLGE

KMLNKKLKDQKTPIPDTLYQELYDYVNHRLSHDLSDEARALLPNVITKEVSHEIIKDRRFTSDKFFF

HVPITLNYQAANSPSKFNQRVNAYLKEHPETPIIGIDRGERNLIYITVIDSTGKILEQRSLNTIQQF

DYQKKLDNREKERVAARQAWSVVGTIKDLKQGYLSQVIHEIVDLMIHYQAVVVLENLNFGFKSKRTG

IAEKAVYQQFEKMLIDKLNCLVLKDYPAEKVGGVLNPYQLTDQFTSFAKMGTQSGFLFYVPAPYTSK

IDPLTGFVDPFVWKTIKNHESRKHFLEGFDFLHYDVKTGDFILHFKMNRNLSFQRGLPGFMPAWDIV

FEKNETQFDAKGTPFIAGKRIVPVIENHRFTGRYRDLYPANELIALLEEKGIVERDGSNILPKLLEN

DDSHAIDTMVALIRSVLQMRNSNAATGEDYINSPVRDLNGVCFDSRFQNPEWPMDADANGAYHIALK

GQLLLNHLKESKDLKLQNGISNQDWLAYIQELRNGRSSDDEATADSQHAAPPKKKRKVGGSGGSGGS

GGSGGSGGSGGSGGSLEHHHHHH

Hs optimized As Cpf1 with OpT NLS and 6x His - DNA
                                                    SEQ ID NO: 21
ATGGGCGACCCTCTGAAGAACGTGGGCATCGACAGACTGGACGTGGAAAAGGGCAGAAAGAACATGA

GCAAGCTCGAGAAGTTCACCAACTGCTACAGCCTGAGCAAGACCCTGCGGTTCAAGGCCATTCCTGT

GGGCAAGACCCAAGAGAACATCGACAACAAGCGGCTGCTGGTGGAAGATGAGAAGAGAGCCGAGGAC

TACAAGGGCGTGAAGAAGCTGCTGGACCGGTACTACCTGAGCTTCATCAACGACGTGCTGCACAGCA

TCAAGCTGAAGAACCTGAACAACTACATCAGCCTGTTCCGGAAGAAAACCCGGACCGAGAAGAGAA

CAAAGAGCTGGAAAACCTCGAGATCAACCTGCGGAAAGAGATCGCCAAGGCCTTCAAGGGCAACGAG

GGCTACAAGAGCCTGTTCAAGAAGGACATCATCGAGACAATCCTGCCTGAGTTCCTGGACGACAAGG

ACGAGATCGCCCTGGTCAACAGCTTCAACGGCTTCACAACCGCCTTCACCGGCTTTTTCGACAACCG

CGAGAATATGTTCAGCGAGGAAGCCAAGAGCACCTCTATCGCCTTCCGGTGCATCAACGAGAATCTG

ACCCGGTACATCAGCAACATGGATATCTTCGAGAAGGTGGACGCCATCTTCGACAAGCACGAGGTGC

AAGAGATCAAAGAAAAGATCCTGAACAGCGACTACGACGTCGAGGACTTCTTCGAGGGCGAGTTCTT

CAACTTCGTGCTGACACAAGAGGGCATCGATGTGTACAACGCCATCATCGGCGGCTTCGTGACAGAG

AGCGGCGAGAAGATCAAGGGCCTGAACGAGTACATCAACCTCTACAACCAGAAAACGAAGCAGAAGC

TGCCCAAGTTCAAGCCCCTGTACAAACAGGTGCTGAGCGACAGAGAGAGCCTGTCCTTTTACGGCGA

GGGCTATACCAGCGACGAAGAGGTGCTGGAAGTGTTCAGAAACACCCTGAACAAGAACAGCGAGATC

TTCAGCTCCATCAAGAAGCTCGAAAAGCTGTTTAAGAACTTCGACGAGTACAGCAGCGCCGGCATCT

TCGTGAAGAATGGCCCTGCCATCAGCACCATCTCCAAGGACATCTTCGGCGAGTGGAACGTGATCCG

GGACAAGTGGAACGCCGAGTACGACGACATCCACCTGAAGAAAAAGGCCGTGGTCACCGAGAAGTAC

GAGGACGACAGAAGAAAGAGCTTCAAGAAGATCGGCAGCTTCAGCCTGGAACAGCTGCAAGAGTACG

CCGACGCCGATCTGAGCGTGGTGGAAAAGCTGAAAGAGATTATCATCCAGAAGGTCGACGAGATCTA

CAAGGTGTACGGCAGCAGCGAGAAGCTGTTCGACGCCGACTTTGTGCTGGAAAAGAGCCTCAAAAAG

AACGACGCCGTGGTGGCCATCATGAAGGACCTGCTGGATAGCGTGAAGTCCTTCGAGAACTATATTA

AGGCCTTCTTTGGCGAGGGCAAAGAGACAAACCGGGACGAGAGCTTCTACGGCGATTTCGTGCTGGC

CTACGACATCCTGCTGAAAGTGGACCACATCTACGACGCCATCCGGAACTACGTGACCCAGAAGCCT

TACAGCAAGGACAAGTTTAAGCTGTACTTCCAGAATCCGCAGTTCATGGGCGGCTGGGACAAAGACA

AAGAAACCGACTACCGGGCCACCATCCTGAGATACGGCTCCAAGTACTATCTGGCCATTATGGACAA

GAAATACGCCAAGTGCCTGCAGAAGATCGATAAGGACGACGTGAACGGCAACTACGAGAAGATTAAC

TACAAGCTGCTGCCCGGACCTAACAAGATGCTGCCTAAGGTGTTCTTTAGCAAGAAATGGATGGCCT

ACTACAACCCCAGCGAGGATATCCAGAAAATCTACAAGAACGGCACCTTCAAGAAAGGCGACATGTT

CAACCTGAACGACTGCCACAAGCTGATCGATTTCTTCAAGGACAGCATCAGCAGATACCCCAAGTGG

TCCAACGCCTACGACTTCAATTTCAGCGAGACAGAGAAGTATAAGGATATCGCCGGGTTCTACCGCG

AGGTGGAAGAACAGGGCTATAAGGTGTCCTTTGAGAGCGCCAGCAAGAAAGAGGTGGACAAGCTGGT

CGAAGAGGGCAAGCTGTACATGTTCCAGATCTATAACAAGGACTTCTCCGACAAGAGCCACGGCACC

CCTAACCTGCACACCATGTACTTTAAGCTGCTGTTCGATGAGAACAACCACGGCCAGATCAGACTGT

CTGGCGGAGCCGAGCTGTTTATGAGAAGGGCCAGCCTGAAAAAAGAGGAACTGGTCGTTCACCCCGC

CAACTCTCCAATCGCCAACAAGAACCCCGACAATCCCAAGAAAACCACCACACTGAGCTACGACGTG

TACAAGGATAAGCGGTTCTCCGAGGACCAGTACGAGCTGCACATCCCTATCGCCATCAACAAGTGCC

CCAAGAATATCTTCAAGATCAACACCGAAGTGCGGGTGCTGCTGAAGCACGACGACAACCCTTACGT

GATCGGCATCGATCGGGGCGAGAGAAACCTGCTGTATATCGTGGTGGTGGACGGCAAGGGCAATATC

GTGGAACAGTACTCCCTGAATGAGATCATCAACAACTTCAATGGCATCCGGATCAAGACGGACTACC

ACAGCCTGCTGGACAAAAAAGAGAAAGAACGCTTCGAGGCCCGGCAGAACTGGACCAGCATCGAGAA

CATCAAAGAACTGAAGGCCGGCTACATCTCCCAGGTGGTGCACAAGATCTGCGAGCTGGTTGAGAAG

TATGACGCCGTGATTGCCCTGGAAGATCTGAATAGCGGCTTTAAGAACAGCCGCGTGAAGGTCGAGA

AACAGGTGTACCAGAAATTCGAGAAGATGCTGATCGACAAGCTGAACTACATGGTCGACAAGAAGTC

TAACCCCTGCGCCACAGGCGGAGCCCTGAAGGGATATCAGATCACCAACAAGTTCGAGTCCTTCAAG

-continued

```
AGCATGAGCACCCAGAATGGCTTCATCTTCTACATCCCCGCCTGGCTGACCAGCAAGATCGATCCTA

GCACCGGATTCGTGAACCTGCTCAAGACCAAGTACACCAGCATTGCCGACAGCAAGAAGTTCATCTC

CAGCTTCGACCGGATTATGTACGTGCCCGAAGAGGACCTGTTCGAATTCGCCCTGGATTACAAGAAC

TTCAGCCGGACCGATGCCGACTATATCAAGAAGTGGAAGCTGTATAGCTACGGCAACCGCATCCGCA

TCTTCAGAAACCCGAAGAAAAACAACGTGTTCGACTGGGAAGAAGTGTGCCTGACCAGCGCCTACAA

AGAACTCTTCAACAAATACGGCATCAACTACCAGCAGGGCGACATCAGAGCCCTGCTGTGCGAGCAG

AGCGACAAGGCCTTTTACAGCTCCTTCATGGCCCTGATGAGCCTGATGCTGCAGATGCGGAATAGCA

TCACCGGCAGGACCGACGTGGACTTCCTGATCAGCCCTGTGAAGAATTCCGACGGGATCTTCTACGA

CAGCAGAAACTACGAGGCTCAAGAGAACGCCATCCTGCCTAAGAACGCCGATGCCAACGGCGCCTAT

AATATCGCCAGAAAGGTGCTGTGGGCCATCGGCCAGTTTAAGAAGGCCGAGGACGAGAAACTGGACA

AAGTGAAGATCGCCATCTCTAACAAAGAGTGGCTGGAATACGCCCAGACCAGCGTGAAGCACGGCAG

ATCTAGTGACGATGAGGCCACCGCCGATAGCCAGCATGCAGCCCCTCCAAAGAAAAAGCGGAAAGTG

CTGGAACACCACCACCATCACCAC
```

Hs optimized As Cpf1 with OpT NLS and 6x His - AA

SEQ ID NO: 22

```
MTQFEGFTNLYQVSKTLRFELIPQGKTLKHIQEQGFIEEDKARNDHYKELKPIIDRIYKTYADQCLQ

LVQLDWENLSAAIDSYRKEKTEETRNALIEEQATYRNAIHDYFIGRTDNLTDAINKRHAEIYKGLFK

AELFNGKVLKQLGTVTTTEHENALLRSFDKFTTYFSGFYENRKNVFSAEDISTAIPHRIVQDNFPKF

KENCHIFTRLITAVPSLREHFENVKKAIGIFVSTSIEEVFSFPFYNQLLTQTQIDLYNQLLGGISRE

AGTEKIKGLNEVLNLAIQKNDETAHIIASLPHRFIPLFKQILSDRNTLSFILEEFKSDEEVIQSFCK

YKTLLRNENVLETAEALFNELNSIDLTHIFISHKKLETISSALCDHWDTLRNALYERRISELTGKIT

KSAKEKVQRSLKHEDINLQEIISAAGKELSEAFKQKTSEILSHAHAALDQPLPTTLKKQEEKEILKS

QLDSLLGLYHLLDWFAVDESNEVDPEFSARLTGIKLEMEPSLSFYNKARNYATKKPYSVEKFKLNFQ

MPTLASGWDVNKEKNNGAILFVKNGLYYLGIMPKQKGRYKALSFEPTEKTSEGFDKMYYDYFPDAAK

MIPKCSTQLKAVTAHFQTHTTPILLSNNFIEPLEITKEIYDLNNPEKEPKKFQTAYAKKTGDQKGYR

EALCKWIDFTRDFLSKYTKTTSIDLSSLRPSSQYKDLGEYYAELNPLLYHISFQRIAEKEIMDAVET

GKLYLFQTYNKDFAKGHHGKPNLHTLYWTGLFSPENLAKTSIKLNGQAELFYRPKSRMKRMAHRLGE

KMLNKKLKDQKTPIPDTLYQELYDYVNHRLSHDLSDEARALLPNVITKEVSHEIIKDRRFTSDKFFF

HVPITLNYQAANSPSKFNQRVNAYLKEHPETPIIGIDRGERNLIYITVIDSTGKILEQRSLNTIQQF

DYQKKLDNREKERVAARQAWSVVGTIKDLKQGYLSQVIHEIVDLMIHYQAVVVLENLNFGFKSKRTG

IAEKAVYQQFEKMLIDKLNCLVLKDYPAEKVGGVLNPYQLTDQFTSFAKMGTQSGFLFYVPAPYTSK

IDPLTGFVDPFVWKTIKNHESRKHFLEGFDFLHYDVKTGDFILHFKMNRNLSFQRGLPGFMPAWDIV

FEKNETQFDAKGTPFIAGKRIVPVIENHRFTGRYRDLYPANELIALLEEKGIVERDGSNILPKLLEN

DDSHAIDTMVALIRSVLQMRNSNAATGEDYINSPVRDLNGVCFDSRFQNPEWPMDADANGAYHIALK

GQLLLNHLKESKDLKLQNGISNQDWLAYIQELRNGRSSDDEATADSQHAAPPKKKRKVGGSGGSGGS

GGSGGSGGSGGSGGSLEHHHHHH
```

Example 2

Figure 2:
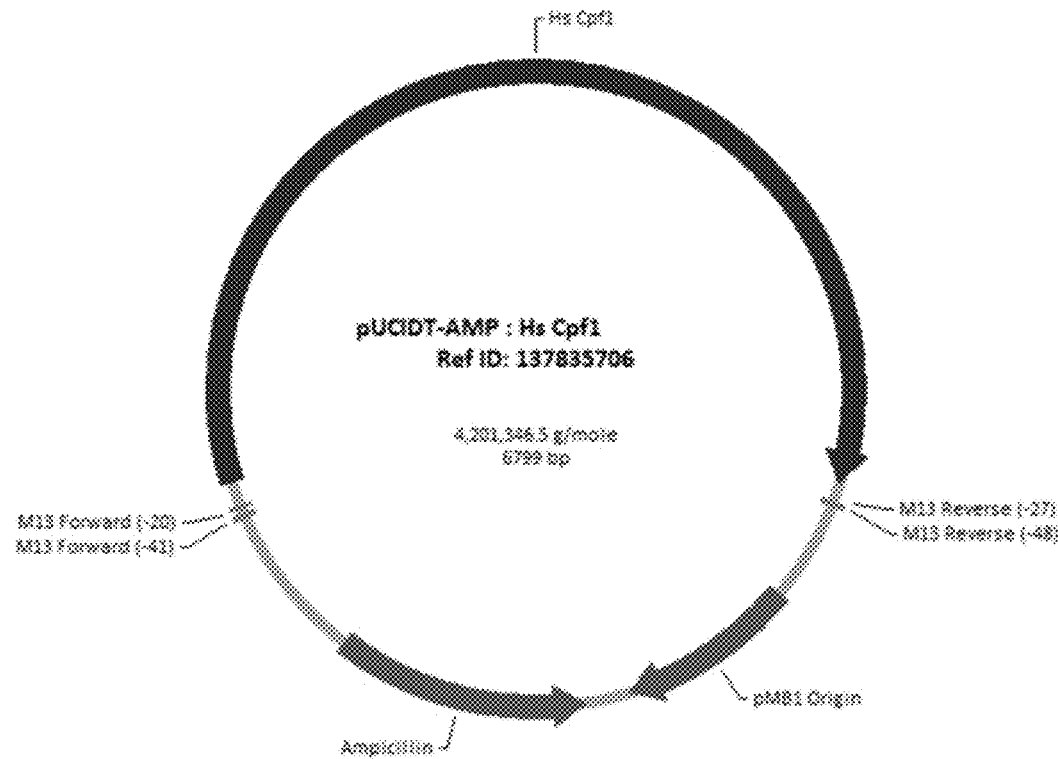
FIG. 2 depicts the map of a plasmid vector designed to express recombinant, synthetic, codon-optimized AsCpf1.

Preparation of Isolated Vectors Expressing Nucleic Acid Encoding Human Codon-Optimized AsCpf1 Polypeptide Fusion Protein and Human Cell Lines Stably Expressing the as Cpf1 Polypeptide Fusion Protein The reference amino acid for AsCpf1 has been published. See Zetsche, B., Gootenberg, J. S., Abudayyeh, O. O., Slaymaker, I. M., Makarova, K. S., Essletzbichler, P., Volz, S. E., Joung, J., van der Oost, J., Regev, A., Koonin, E. V., and Zhang, F. (2015) Cpf1 is a single RNA-guided endonuclease of a class 2 CRISPR-Cas system. *Cell* 163:1-13. A plasmid encoding human codon optimized AsCpf1, flanking nuclear localization signals (NLS) and 5'-V5 epitope tag, was generated by the Synthetic Biology department at Integrated DNA Technologies. Flanking the expression cassette was a 5' XhoI and 3' EcoRI restriction enzyme sites (FIG. 2). The Cpf1 plasmid was digested with XhoI and

43

44

Figure 3:
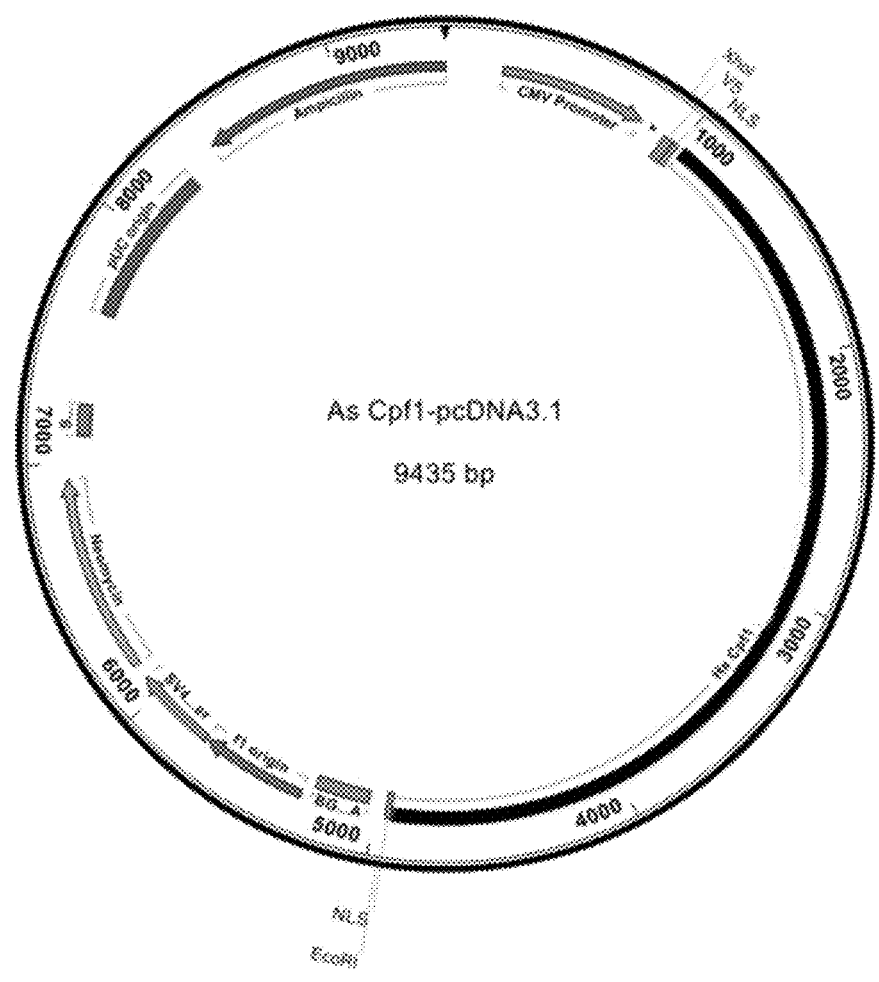
FIG. 3 depicts a schematic showing the final plasmid construct used to generate AsCpf1 stable cell lines.

EcoRI (NEB), gel purified using a column based purification system (Qiagen) and ligated using T4 DNA Ligase (NEB) into a predigested mammalian expression vector, pcDNA3.1-, from Life Technologies (FIG. 3). The resulting ligated construct was transformed into DH5α chemically competent *E. coli* cells. The resulting colonies were grown in LB media at 37° C. overnight and subjected to DNA isolation using a Promega miniprep plasmid DNA kit. Flanking primers (T7 forward and BGH reverse) as well as 10 internal Cpf1 specific primers were used for sequence verification of correct insertion using automated Sanger sequencing with BigDye Terminator reagents (ABI). The nucleic acid sequence of the Cpf1 clone employed herein is shown in SEQ ID NO:15. The amino acid sequence of the expressed recombinant protein is shown in SEQ ID NO:16.

Figure 4:
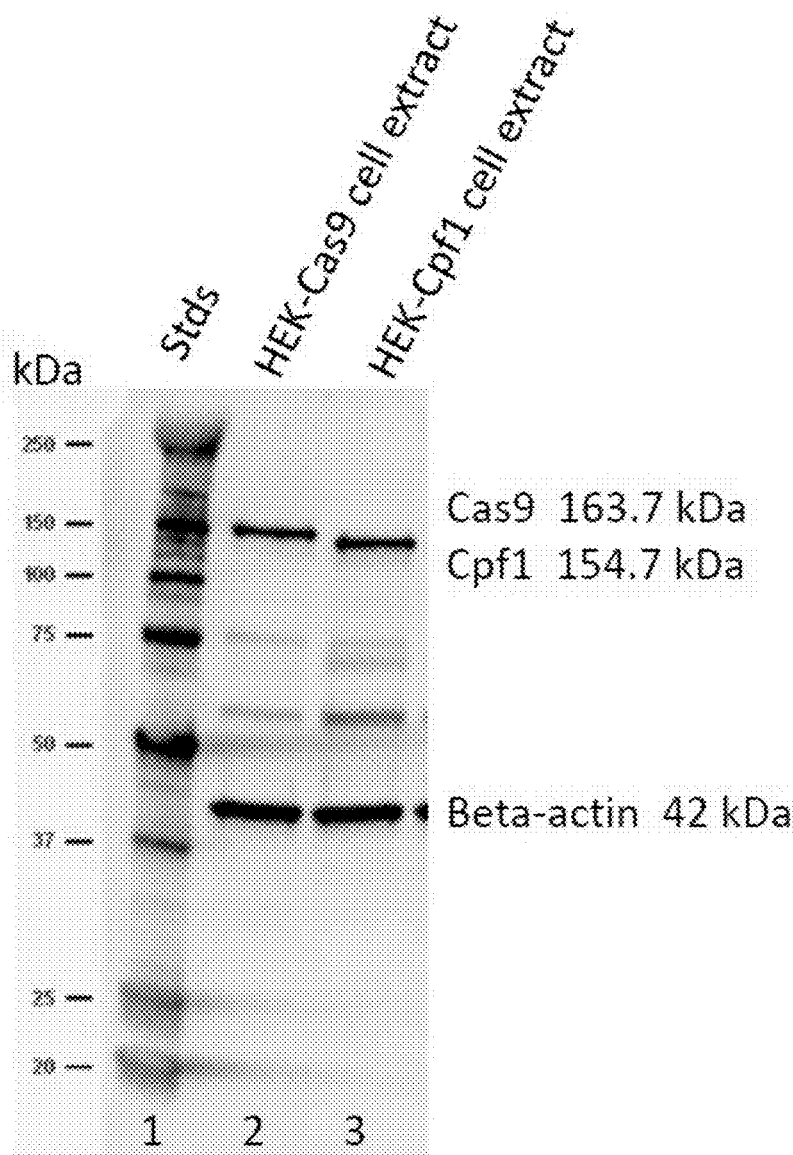
FIG. 4 depicts an exemplary Western blot showing expression of V5-tagged proteins. Cell extract from a monoclonal HEK cell line that stably expresses Cas9 with a V5 tag was run in Lane 2. Cell extract from the new polyclonal HEK cell culture that expresses a V5-tagged AsCpf1 was run in Lane 3. Beta-actin is indicated and represents a mass loading control. Lane 1 was run with mass standard markers.

The AsCpf1-pcDNA3.1 vector was linearized with PvuI (NEB), which is located within the ampicillin resistance gene, and transfected into HEK293 cells. Transfection employed 500,000 HEK293 cells plated in 100 mm dishes 24 hours prior to transfection. Using the transfection reagent TransIT-X2 (Minis), the linearized vector containing AsCpf1 and a neomycin-resistance gene was complexed and transfected into adherent cells. The transfection media was removed after 24 hrs and the cells were cultured in complete media for 48 hours. Using methods previously optimized for generation of stable transgenic HEK293 cells containing a stably integrated pcDNA3.1(–) vector neomycin resistance, we cultured transfected cells in the presence of the antibiotic total protein was loaded onto an SDS-PAGE Stainfree 4-20% gradient gel (Bio-Rad). As a positive control, protein from a previous cell line, SpyCas9-pcDNA3.1(–), was run in parallel for size and expression comparisons. The gel was run for 45 minutes at 180 volts and transferred to a PVDF membrane with the Bio-Rad TransBlot for 7 minutes. The blot was then blocked in SuperBlock T20 Blocking Buffer (Thermo), followed by a 1:1000 dilution of V5 primary antibody (Abcam) and 1:5000 β-actin primary antibody (Abcam) for 1 hour at room temperature. Next, the blot was washed 3 times for 15 minutes each in tris-buffered saline with Tween-20 (TBST). Goat anti-mouse HRP secondary antibody was used at a 1:3000 dilution along with the ladder specific StrepTactin secondary antibody and incubated at room temperature for 1 hour at room temperature. The blot was then washed 3 times for 15 minutes in TB ST. Luminescence detection was done using the Pierce West-Femto ECL (Thermo) substrate and results are shown in FIG. 4, which confirm expression of a recombinant protein of the expected size.

Cells were continuously grown under selection in G418-containing media, and individual cells (monoclonal colonies) were allowed to expand. Viable colonies were characterized for the presence of AsCpf1 by RT-qPCR, Western blotting and functional testing of crRNA guided dsDNA cleavage. Four RT-qPCR assays were designed to detect different locations within the large AsCpf1 mRNA. Sequences are shown in Table 1 below.

TABLE 1

| RT-qPCR assays in AsCpf1 | | | |
|---|---|---|---|
| Assay# | Location | Primers and Probe | SEQ ID NO |
| 1 | 34-153 | F34 GTGTCCAAGACCCTGAGATTC | 25 |
| | | R153 GGGCTTCAGCTCTTTGTAGT | 26 |
| | | P68 FAM-AGGGCAAG(ZEN)ACACTGAAGCACATCC-IBFQ | 27 |
| 2 | 1548-1656 | F1548 CAGAAACTACGCCACCAAGA | 28 |
| | | R1656 GCCGTTGTTCTTCTCTTTGTTC | 29 |
| | | P1590 HEX-TAAGCTGAA(ZEN)CTTCCAGATGCCCACC-IBFQ | 30 |
| 3 | 2935-3037 | F2935 GTGGACCTGATGATCCACTATC | 31 |
| | | R3037 GCTGGTACACGGCTTTCT | 32 |
| | | P2978 FAM-ACCTGAACT(ZEN)TCGGCTTCAAGAGCA-IBFQ | 33 |
| 4 | 3827-3918 | F3827 TGCTGAACCATCTGAAAGAGAG | 34 |
| | | R3918 GTTCCGCAGTTCCTGGATATAG | 35 |
| | | P3889 HEX-AGTCCTGGT(ZEN)TGGAGATGCCGTTC-IBFQ | 36 |

DNA bases are shown 5'-3' orientation. Location is specified within the AsCpf1 gene construct employed herein. FAM-6 carboxyfluorescein, HEX = hexachlorofluorescein, IBFQ = Iowa Black dark quencher, and ZEN = internal ZEN dark quencher.

50

Geneticin (G418; Gibco), which is a neomycin analog, in the complete media to select for cells that had been transfected with AsCpf1-pcDNA3.1(–) and would thus be resistant to this antibiotic. Initial G418 dosing was at 800 ug/ml with periodic media changes until the surviving cells began to recover and grow over a 10-day period. The parent HEK293 cell line was confirmed to be sensitive to the minimum dose of G418. The resulting polyclonal AsCpf1-pcDNA3.1(–) cell line, which showed G418 resistance, was split using limited dilutions. The cells were trypsinized, resuspended in complete media, counted to determine concentration and diluted in 96-well plates to a concentration of theoretically less than one cell per well.

Figure 5:
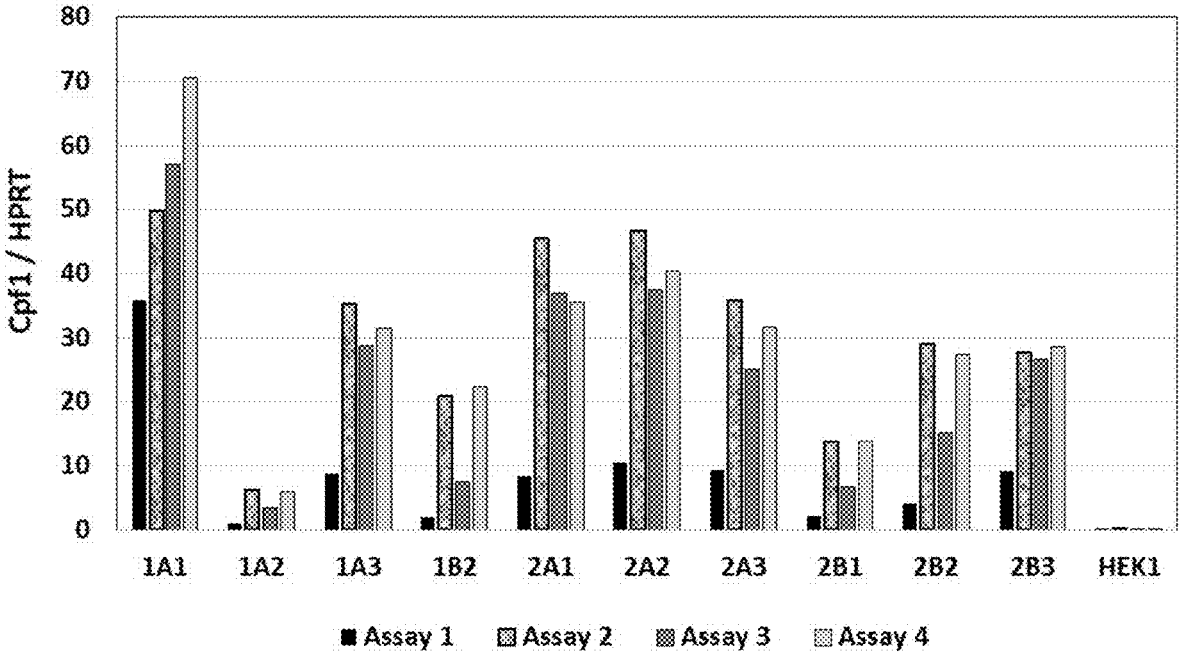
FIG. 5 depicts exemplary expression profiles of AsCpf1 mRNA normalized to internal control HPRT1 mRNA in 10 clonal transgenic cell lines. RT-qPCR assay locations vary in position along the AsCpf1 mRNA. Negative control non-transgenic HEK1 cells are shown on the far right.

At this time, aliquots of the cells were taken and lysed with a protein lysis buffer (RIPA) to determine, via western blot, if AsCpf1 was expressed. Cellular protein was quantitated using the Bio-Rad Protein Assay (Bio-Rad) and 15 ug Monoclonal cell lines resistant to G418 were plated in 6-well plates and cultured for 24 hrs. Cells were lysed with GITC-containing buffer and RNA was isolated using the Wizard 96-well RNA isolation binding plates (Promega) on a Corbett liquid handling robot. Liquid handling robotics (Perkin Elmer) were used to synthesize complementary DNA (cDNA) using SuperScriptII (Invitrogen) and set-up qPCR assays using Immolase (Bioline) along with 500 nmol primers and 250 nmol probes (IDT). qPCR plates were run on the AB7900-HT and analyzed using the associated software (Applied Biosystems). FIG. 5 shows the relative level of AsCpf1 mRNA expression normalized to HPRT1 expression for a series of clonal lines. Not surprisingly, different clones showed different levels of AsCpf1 mRNA expression.

Figure 6:
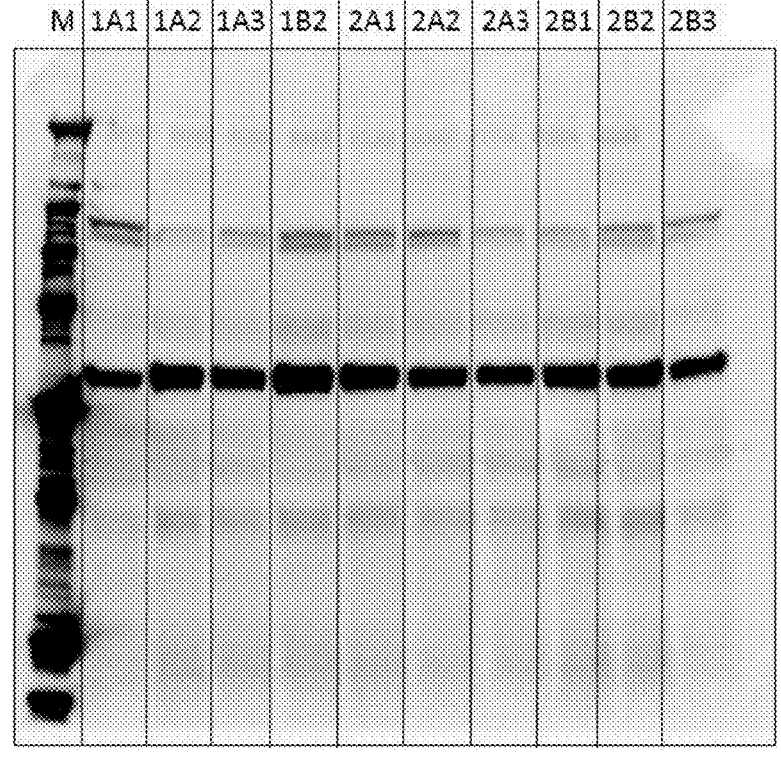
FIG. 6 depicts exemplary Western blot showing relative expression levels of AsCpf1 protein in 10 monoclonal transgenic cell lines based on detection of the V5 epitope. Beta-actin loading control is seen below the AsCpf1 bands.

Total protein was isolated from the same AsCpf1-expressing monoclonal cells lines in cultures grown in parallel. Cells were lysed in RIPA buffer in the presence of a proteinase inhibitor. Protein concentration in each lysate was determined by BCA assay (Pierce). Fifteen micrograms of total protein from each sample was loaded onto an SDS-PAGE stainfree 4-20% gradient gel (Bio-Rad) and run at 180V for 45 minutes in 1× Tris/Glycine running buffer alongside the broad-range molecular weight marker (Bio-Rad). Protein was transferred to a PDVF membrane using Bio-Rad TransBlot transfer unit for 7 minutes. The blot was blocked in SuperBlock T20 Blocking Buffer (Thermo), followed by incubation with a 1:1000 dilution of V5 primary antibody (Abcam) and 1:5000 (3-actin primary antibody (Abcam) for 1 hour at room temperature. The blot was washed 3 times for 15 minutes each in tris-buffered saline with Tween-20 (TBST). Goat anti-mouse HRP secondary antibody was used at a 1:3000 dilution along with the ladder specific StrepTactin secondary antibody and incubated at room temperature for 1 hour at room temperature. The blot was then washed 3 times for 15 minutes in TB ST. Luminescence detection was done using the Pierce West-Femto ECL (Thermo) substrate. FIG. 6 shows detection of V5-tagged AsCpf1 recombinant protein expression levels in 10 monoclonal cell lines. There is good concordance between observed protein levels seen in FIG. 6 and the corresponding mRNA levels from the same cell lines shown in FIG. 5.

Three monoclonal AsCpf1 stable cell lines (1A1, 2A2 and 2B1) were expanded and tested for the ability to support AsCpf1-directed genome editing. Based on AsCpf1 mRNA and protein levels previously determined, 1A1 is a "high" expressing line, 2A2 is a "medium" expressing line, and 2B1 is a "low" expressing line. The cell lines were transfected with 6 different crRNAs targeting different sites within an exon of the human HRPT1 gene, shown below in Table 2. The crRNAs comprise a universal 20 base Cpf1-binding domain at the 5'-end and a 24 base target-specific protospacer domain at the 3'-end.

TABLE 2

AsCpf1 crRNAs targeting human HPRT1

| Site | Sequence | SEQ ID NO: |
|------|----------|------------|
| 38171_AS | uaauuucuacucuuguagauuaaacacuguuucauuucauccgu | 37 |
| 38254_AS | uaauuucuacucuuguagauaccagcaagcuguuaauuacaaaa | 38 |
| 38325_S | uaauuucuacucuuguagauaccaucuuuaaccuaaaagaguuu | 39 |
| 38337_AS | uaauuucuacucuuguagaugguuaaagaugguuaaaugauuga | 40 |
| 38351_S | uaauuucuacucuuguagauugugaaauggcuuauaauugcuua | 41 |
| 38538_S | uaauuucuacucuuguagauaaauguaaguaauugcuucuuuuuc | 42 |

RNA bases are shown 5'-3' orientation, RNA bases are shown in lower case. Locations are specified within the human HPRT1 gene with orientation relative to the sense coding strand indicated (S = sense, AS = antisense).

55

In a reverse transfection format, anti-HPRT1 crRNAs were individually mixed with Lipofectamine RNAiMAX (Life Technologies) and transfected into each of the 3 HEK-Cpf1 cell lines. Transfections were done with 40,000 cells per well in 96 well plate format. RNAs were introduced at a final concentration of 30 nM in 0.75 μl of the lipid reagent. Cells were incubated at 37° C. for 48 hours. Genomic DNA was isolated using QuickExtract solution (Epicentre). Genomic DNA was amplified with KAPA HiFi DNA Polymerase (Roche) and primers targeting the HPRT region of interest (HPRT-low forward primer: AAGAATGTTGTGATAAAAGGTGATGCT (SEQ ID NO:394); HPRT-low reverse primer: ACACATC-CATGGGACTTCTGCCTC (SEQ ID NO:395). PCR products were melted and re-annealed in NEB buffer 2 (New England Biolabs) to allow for heteroduplex formation followed by digestion with 2 units of T7 endonuclease 1 (T7EI; New England Biolabs) for 1 hour at 37° C. The digested products were visualized on a Fragment Analyzer (Advanced Analytical Technologies). Percent cleavage of targeted DNA was calculated as the average molar concentration of the cut products/(average molar concentration of the cut products+molar concentration of the uncut band)×100. The cleavage efficiencies seen in the 3 cell lines are shown in Table 3 below.

TABLE 3

Gene targeting efficiency of 6 HPRT1 crRNAs in 3 HEK-Cpf1 cell lines

| Site | % Cleavage in T7EI assays | | |
|------|------|------|------|
| | 1A1 | 2A2 | 2B1 |
| 38171_AS | 19 | 19.1 | 8.3 |
| 38254_AS | 41 | 42.4 | 30.3 |
| 38325_S | 27.8 | 26.5 | 14.8 |
| 38337_AS | 65.3 | 73.7 | 71.6 |
| 38351_S | 73.3 | 78.6 | 73.4 |
| 38538_S | 44.6 | 47.9 | 32.8 |

Locations of the crRNAs are specified within the human HPRT1 gene with orientation relative to the sense coding strand indicated (S = sense, AS = antisense). % Cleavage demonstrates alteration in the sequence of the cell line after Cpf1-mediated genome editing at the HPRT1 locus relative to wild-type.

As expected, the different crRNAs targeting different sites in HPRT1 showed different levels of gene editing activity. In cell line 1A1 this ranged from 18% to 73%. The "high" and "medium" Cpf1-expressing clones 1A1 and 2A2 showed nearly identical gene editing activity, indicating that both clones expressed Cpf1 at sufficient levels to reach maximal gene editing activity at each site. Clone 2B1, the "low" expressing clone, showed reduced editing activity. Clones 1A1 and 2A2 are therefore both suitable for Cpf1 crRNA optimization and site screening.

Example 3 crRNA Length Optimization: Testing Truncation of the 5'-20-Base Universal Loop Domain.

A set of 6 sites in the human HPRT1 gene were chosen to study length optimization of AsCpf1 crRNAs. A series of crRNAs were synthesized all having a 3'-24 base target-specific protospacer domain and having 5'-loop domains of 20, 19, 18, and 17 bases, representing a set of serial 1-base deletions from the 5'-end. A second set of crRNAs were synthesized at the same sites all having a 3'-21 base target-specific protospacer domain, likewise with 5'-loop domains of 20, 19, 18, and 17 bases.

An HEK cell line that stably expresses the AsCpf1 endonuclease was employed in these studies (Example 2). In a reverse transfection format, anti-HPRT1 crRNAs were individually mixed with Lipofectamine RNAiMAX (Life Technologies) and transfected into the HEK-Cpf1 cell line. Transfections were done with 40,000 cells per well in 96 well plate format. RNAs were introduced at a final concentration of 30 nM in 0.75 µl of the lipid reagent. Cells were incubated at 37° C. for 48 hours. Genomic DNA was isolated using QuickExtract solution (Epicentre). Genomic DNA was amplified with KAPA HiFi DNA Polymerase (Roche) and primers targeting the HPRT region of interest (HPRT-low forward primer: AAGAATGTTGTGATAAAAGGT-GATGCT (SEQ ID NO:394); HPRT-low reverse primer: ACACATCCATGGGACTTCTGCCTC (SEQ ID NO:395). PCR products were melted and re-annealed in NEB buffer 2 (New England Biolabs) to allow for heteroduplex formation followed by digestion with 2 units of T7 endonuclease 1 (T7EI; New England Biolabs) for 1 hour at 37° C. The digested products were visualized on a Fragment Analyzer (Advanced Analytical Technologies). Percent cleavage of targeted DNA was calculated as the average molar concentration of the cut products/(average molar concentration of the cut products+molar concentration of the uncut band)× 100. Results are shown in Table 4 below and demonstrate that 5'-universal loop domains of 20 and 19 base lengths work well but a significant loss of activity is seen when 18 or 17 base loops domains are employed. The observations are nearly identical whether a 24 base or 21 base protospacer domain is employed.

TABLE 4

Effect of truncation in the 5'-loop domain with 24 or 21 base
3'-protospacer domains

| Seq Name | Sequence 5'-3' | % Cleavage T7E1 Assay | SEQ ID NO: |
|---|---|---|---|
| 38171_AS 20-24 | uaauuucuacucuuguagauuaaacacuguuucauuucauccgu | 12% | 37 |
| 38171-AS 19-24 | aauuucuacucuuguagauuaaacacuguuucauuucauccgu | 15% | 43 |
| 38171-AS 18-24 | auuucuacucuuguagauuaaacacuguuucauuucauccgu | 4% | 44 |
| 38171-AS 17-24 | uuucuacucuuguagauuaaacacuguuucauuucauccgu | 1% | 45 |
| 38254_AS 20-24 | uaauuucuacucuuguagauaccagcaagcuguuaauuacaaaa | 15% | 38 |
| 38254-AS 19-24 | aauuucuacucuuguagauaccagcaagcuguuaauuacaaaa | 36% | 46 |
| 38254-AS 18-24 | auuucuacucuuguagauaccagcaagcuguuaauuacaaaa | 23% | 47 |
| 38254-AS 17-24 | uuucuacucuuguagauaccagcaagcuguuaauuacaaaa | 0% | 48 |
| 38325_S 20-24 | uaauuucuacucuuguagauaccaucuuuaaccuaaaagaguuu | 9% | 39 |
| 38325-S 19-24 | aauuucuacucuuguagauaccaucuuuaaccuaaaagaguuu | 37% | 49 |
| 38325-S 18-24 | auuucuacucuuguagauaccaucuuuaaccuaaaagaguuu | 27% | 50 |
| 38325-S 17-24 | uuucuacucuuguagauaccaucuuuaaccuaaaagaguuu | 0% | 51 |
| 38337_AS 20-24 | uaauuucuacucuuguagaugguuaaagaugguuaaaugauuga | 63% | 40 |
| 38337-AS 19-24 | aauuucuacucuuguagaugguuaaagaugguuaaaugauuga | 65% | 52 |
| 38337-AS 18-24 | auuucuacucuuguagaugguuaaagaugguuaaaugauuga | 46% | 53 |
| 38337-AS 17-24 | uuucuacucuuguagaugguuaaagaugguuaaaugauuga | 4% | 54 |
| 38351_S 20-24 | uaauuucuacucuuguagauugugaaauggcuuauaauugcuua | 57% | 41 |
| 38351-S 19-24 | aauuucuacucuuguagauugugaaauggcuuauaauugcuua | 76% | 55 |
| 38351-S 18-24 | auuucuacucuuguagauugugaaauggcuuauaauugcuua | 6% | 56 |
| 38351-S 17-24 | uuucuacucuuguagauugugaaauggcuuauaauugcuua | 0% | 57 |
| 38538_S 20-24 | uaauuucuacucuuguagauaauguaaguaauugcuucuuuuuc | 16% | 42 |
| 38538-S 19-24 | aauuucuacucuuguagauaauguaaguaauugcuucuuuuuc | 34% | 58 |
| 38538-S 18-24 | auuucuacucuuguagauaauguaaguaauugcuucuuuuuc | 2% | 59 |
| 38538-S 17-24 | uuucuacucuuguagauaauguaaguaauugcuucuuuuuc | 1% | 60 |
| 38171-AS 20-21 | uaauuucuacucuuguagauuaaacacuguuucauuucauc | 32% | 61 |

TABLE 4-continued

Effect of truncation in the 5'-loop domain with 24 or 21 base
3'-protospacer domains

| Seq Name | Sequence 5'-3' | % Cleavage T7E1 Assay | SEQ ID NO: |
|---|---|---|---|
| 38171-AS 19-21 | aauuucuacucuuguagauuaaacacuguuucauuucauc | 44% | 62 |
| 38171-AS 18-21 | auuucuacucuuguagauuaaacacuguuucauuucauc | 16% | 63 |
| 38171-AS 17-21 | uuucuacucuuguagauuaaacacuguuucauuucauc | 1% | 64 |
| 38254-AS 20-21 | uaauuucuacucuuguagauaccagcaagcuguuaauuaca | 45% | 65 |
| 38254-AS 19-21 | aauuucuacucuuguagauaccagcaagcuguuaauuaca | 28% | 66 |
| 38254-AS 18-21 | auuucuacucuuguagauaccagcaagcuguuaauuaca | 50% | 67 |
| 38254-AS 17-21 | uuucuacucuuguagauaccagcaagcuguuaauuaca | 0% | 68 |
| 38325-S 20-21 | uaauuucuacucuuguagauaccaucuuuaaccuaaaagag | 50% | 69 |
| 38325-S 19-21 | aauuucuacucuuguagauaccaucuuuaaccuaaaagag | 49% | 70 |
| 38325-S 18-21 | auuucuacucuuguagauaccaucuuuaaccuaaaagag | 36% | 71 |
| 38325-S 17-21 | uuucuacucuuguagauaccaucuuuaaccuaaaagag | 0% | 72 |
| 38337-AS 20-21 | uaauuucuacucuuguagaugguuaaagaugguuaaaugau | 72% | 73 |
| 38337-AS 19-21 | aauuucuacucuuguagaugguuaaagaugguuaaaugau | 73% | 74 |
| 38337-AS 18-21 | auuucuacucuuguagaugguuaaagaugguuaaaugau | 62% | 75 |
| 38337-AS 17-21 | uuucuacucuuguagaugguuaaagaugguuaaaugau | 12% | 76 |
| 38351-S 20-21 | uaauuucuacucuuguagauugugaaauggcuuauaauugc | 81% | 77 |
| 38351-S 19-21 | aauuucuacucuuguagauugugaaauggcuuauaauugc | 81% | 78 |
| 38351-S 18-21 | auuucuacucuuguagauugugaaauggcuuauaauugc | 20% | 79 |
| 38351-S 17-21 | uuucuacucuuguagauugugaaauggcuuauaauugc | 0% | 80 |
| 38538-S 20-21 | uaauuucuacucuuguagauaauguaaguaauugcuucuuu | 65% | 81 |
| 38538-S 19-21 | aauuucuacucuuguagauaauguaaguaauugcuucuuu | 41% | 82 |
| 38538-S 18-21 | auuucuacucuuguagauaauguaaguaauugcuucuuu | 11% | 83 |
| 38538-S 17-21 | uuucuacucuuguagauaauguaaguaauugcuucuuu | 1% | 84 |

RNA bases are shown in lower case. Locations are specified within the human HPRT1 gene with orientation relative to the sense coding strand indicated (S = sense, AS = antisense). Sequence names include length of the 5'-universal loop domain (17-20 bases) and the 3'-target specific protospacer domain (24 or 21 bases).

Example 4 crRNA Length Optimization: Testing Truncation of the 3'-24-Base Target Specific Protospacer Domain.

The same set of 6 sites in the human HPRT1 gene was used to study the effects of truncation in the 3'-protospacer (target specific) domain. A series of AsCpf1 crRNAs were synthesized all having the same 5'-20 base universal loop domain. These were paired with 3'-target specific protospacer domains of 21, 19, 18, or 17 bases, having serial deletions from the 3'-end.

An HEK cell line that stably expresses the AsCpf1 endonuclease was employed in these studies (Example 2). In a reverse transfection format, anti-HPRT1 AsCpf1 crRNAs were individually mixed with Lipofectamine RNAiMAX (Life Technologies) and transfected into the HEK-Cpf1 cell line. Transfections were done with 40,000 cells per well in 96 well plate format. RNAs were introduced at a final concentration of 30 nM in 0.75 μl of the lipid reagent. Cells were incubated at 37° C. for 48 hours. Genomic DNA was isolated using QuickExtract solution (Epicentre). Genomic DNA was amplified with KAPA HiFi DNA Polymerase (Roche) and primers targeting the HPRT region of interest (HPRT-low forward primer: AAGAATGTTGTGA-TAAAAGGTGATGCT (SEQ ID NO:394); HPRT-low reverse primer: ACACATCCATGGGACTTCTGCCTC (SEQ ID NO:395). PCR products were melted and re-annealed in NEB buffer 2 (New England Biolabs) to allow for heteroduplex formation followed by digestion with 2 units of T7 endonuclease 1 (T7EI; New England Biolabs) for 1 hour at 37° C. The digested products were visualized on a Fragment Analyzer (Advanced Analytical Technologies). Percent cleavage of targeted DNA was calculated as the average molar concentration of the cut products/(average molar concentration of the cut products+molar concentration of the uncut band)×100. Results are shown in Table 5 below and demonstrate that a 3'-protospacer (target specific) domain of 21 base lengths work well but loss of activity is observed in a sequence/site dependent fashion as this domain is shortened. Some highly active sites (such as 38351) maintain appreciate activity even when truncated to 17 bases, however to maintain the highest likelihood of functionality at all sites a protospacer of 21 bases is recommended. Therefore, a prudent minimal length AsCpf1 crRNA is 41 bases, comprising a 20-base 5'-universal loop domain and a 21-base 3'-protospacer target-specific domain.

position within AsCpf1 crRNAs. Given the possibility of sequence-specific tolerance to modification, it was necessary to perform this screening at two sites. A series of crRNAs were synthesized having a single 2'OMe residue at every possible position in single-base steps. The crRNAs were either 44 base or 41 base lengths. All had a 5'-end 20 base universal loop domain followed by a 3'-end 21 or 24 base protospacer target-specific domain.

An HEK cell line that stably expresses the AsCpf1 endonuclease was employed in these studies (HEK-Cpf1)

TABLE 5

| Effect of truncation in the 3'-protospacer domain with a 20 base 5'-loop domain | | | |
|---|---|---|---|
| Seq Name | Sequence 5'-3' | % Cleavage T7E1 Assay | SEQ ID NO: |
| 38171-AS 20-21 | uaauuucuacucuuguagauuaaacacuguuucauuucauc | 59% | 61 |
| 38171-AS 20-19 | uaauuucuacucuuguagauuaaacacuguuucauuuca | 13% | 85 |
| 38171-AS 20-18 | uaauuucuacucuuguagauuaaacacuguuucauuuc | 2% | 86 |
| 38171-AS 20-17 | uaauuucuacucuuguagauuaaacacuguuucauuu | 3% | 87 |
| 38254-AS 20-21 | uaauuucuacucuuguagauaccagcaagcuguuaauuaca | 61% | 65 |
| 38254-AS 20-19 | uaauuucuacucuuguagauaccagcaagcuguuaauua | 5% | 88 |
| 38254-AS 20-18 | uaauuucuacucuuguagauaccagcaagcuguuaauu | 0% | 89 |
| 38254-AS 20-17 | uaauuucuacucuuguagauaccagcaagcuguuaau | 0% | 90 |
| 38325-S 20-21 | uaauuucuacucuuguagauaccaucuuuaaccuaaaagag | 70% | 69 |
| 38325-S 20-19 | uaauuucuacucuuguagauaccaucuuuaaccuaaaag | 34% | 91 |
| 38325-S 20-18 | uaauuucuacucuuguagauaccaucuuuaaccuaaaa | 0% | 92 |
| 38325-S 20-17 | uaauuucuacucuuguagauaccaucuuuaaccuaaa | 0% | 93 |
| 38337-AS 20-21 | uaauuucuacucuuguagaugguuaaagaugguuaaaugau | 80% | 73 |
| 38337-AS 20-19 | uaauuucuacucuuguagaugguuaaagaugguuaaaug | 78% | 94 |
| 38337-AS 20-18 | uaauuucuacucuuguagaugguuaaagaugguuaaau | 3% | 95 |
| 38337-AS 20-17 | uaauuucuacucuuguagaugguuaaagaugguuaaa | 0% | 96 |
| 38351-S 20-21 | uaauuucuacucuuguagauugugaaauggcuuauaauugc | 85% | 77 |
| 38351-S 20-19 | uaauuucuacucuuguagauugugaaauggcuuauaauu | 87% | 97 |
| 38351-S 20-18 | uaauuucuacucuuguagauugugaaauggcuuauaau | 85% | 98 |
| 38351-S 20-17 | uaauuucuacucuuguagauugugaaauggcuuauaa | 67% | 99 |
| 38538-S 20-21 | uaauuucuacucuuguagauaauguaaguaauugcuucuuu | 75% | 81 |
| 38538-S 20-19 | uaauuucuacucuuguagauaauguaaguaauugcuucu | 55% | 100 |
| 38538-S 20-18 | uaauuucuacucuuguagauaauguaaguaauugcuuc | 11% | 101 |
| 38538-S 20-17 | uaauuucuacucuuguagauaauguaaguaauugcuu | 0% | 102 |

RNA bases are shown in lower case. Locations are specified within the human HPRT1 gene with orientation relative to the sense-coding strand indicated (S = sense, AS = antisense). Sequence names include length of the 5'-universal loop domain (20 bases) and the 3'-protospacer target-specific domain (21, 19, 18, or 17 bases).

Example 5

A Single-Base 2'OMe Modification Walk Through Two AsCpf1 crRNAs.

Two sites in the human HPRT1 gene were chosen (38351 and 38595) to study the effects of replacement of a single RNA residue with a 2'OMe-RNA residue at every possible (Example 2). In a reverse transfection format, anti-HPRT1 crRNAs were individually mixed with Lipofectamine RNAiMAX (Life Technologies) and transfected into the HEK-Cpf1 cell line. Transfections were done with 40,000 cells per well in 96 well plate format. RNAs were introduced at a final concentration of 30 nM in 0.75 μl of the lipid reagent. Cells were incubated at 37° C. for 48 hours.

Genomic DNA was isolated using QuickExtract solution (Epicentre). Genomic DNA was amplified with KAPA HiFi DNA Polymerase (Roche) and primers targeting the HPRT region of interest (HPRT-low forward primer: AAGAATGTTGTGATAAAAGGTGATGCT (SEQ ID NO:394); HPRT-low reverse primer: ACACATC-CATGGGACTTCTGCCTC (SEQ ID NO:395). PCR products were melted and re-annealed in NEB buffer 2 (New England Biolabs) to allow for heteroduplex formation followed by digestion with 2 units of T7 endonuclease 1 (T7EI; New England Biolabs) for 1 hour at 37° C. The digested products were visualized on a Fragment Analyzer (Advanced Analytical Technologies). Percent cleavage of targeted DNA was calculated as the average molar concentration of the cut products/(average molar concentration of the cut products+molar concentration of the uncut band)×100. Results for HPRT1 site 38351 are shown in Table 6 below and for HRPT1 site 38595 in Table 7 below. The results demonstrate the locations of sites that reduce activity or totally kill activity of Cpf1 to cleave dsDNA when the 2'OMe modified replaced an RNA residue. The results are nearly identical whether a 24 base or 21 base protospacer domain is employed.

Sites where substitution of a 2'OMe RNA residue for an RNA residue showed loss of activity in the genome editing assay were mapped to location within the 5'-universal loop domain or the 3'-target specific protospacer domain. Results are summarized in FIG. 7. Modification of residues A2, A3, U4, U11, G15, and U20 within the universal loop domain leads to loss of activity; the same sites were identified for all 4 crRNA classes studied (Site 38351 44mer, Site 38351 41mer, Site 38595 44mer, and Site 38595 41mer). In contrast, the precise pattern of modification effects varied for sites within the protospacer domain, which is expected as it is common for modification tolerance to vary with sequence context and the protospacer domain has a different sequence for every target site. For the sequences studied, positions 5, 6, 13, 16, and 18 showed loss of activity with modification for all 4 crRNA classes and therefore are identified positions to avoid the 2'OMe RNA chemical modification.

TABLE 6

Single-base 2'OMe modification walk through HPRT1 Site 38351 AsCpf1 crRNAs

| Seq Name | Sequence 5'-3' | % Cleavage T7E1 Assay | SEQ ID NO: |
|---|---|---|---|
| 38351-44 unmod | uaauuucuacucuuguagauugugaaauggcuuauaauugcuua | 77% | 103 |
| 38351-44-L1 | uaauuucuacucuuguagauugugaaauggcuuauaauugcuua | 83% | 104 |
| 38351-44-L2 | uaauuucuacucuuguagauugugaaauggcuuauaauugcuua | 32% | 105 |
| 38351-44-L3 | uaauuucuacucuuguagauugugaaauggcuuauaauugcuua | 4% | 106 |
| 38351-44-L4 | uaauuucuacucuuguagauugugaaauggcuuauaauugcuua | 2% | 107 |
| 38351-44-L5 | uaauuucuacucuuguagauugugaaauggcuuauaauugcuua | 88% | 108 |
| 38351-44-L6 | uaauuucuacucuuguagauugugaaauggcuuauaauugcuua | 87% | 109 |
| 38351-44-L7 | uaauuucuacucuuguagauugugaaauggcuuauaauugcuua | 85% | 110 |
| 38351-44-L8 | uaauuucuacucuuguagauugugaaauggcuuauaauugcuua | 76% | 111 |
| 38351-44-L9 | uaauuucuacucuuguagauugugaaauggcuuauaauugcuua | 89% | 112 |
| 38351-44-L10 | uaauuucuacucuuguagauugugaaauggcuuauaauugcuua | 85% | 113 |
| 38351-44-L11 | uaauuucuacucuuguagauugugaaauggcuuauaauugcuua | 34% | 114 |
| 38351-44-L12 | uaauuucuacucuuguagauugugaaauggcuuauaauugcuua | 86% | 115 |
| 38351-44-L13 | uaauuucuacucuuguagauugugaaauggcuuauaauugcuua | 85% | 116 |

TABLE 6-continued

Single-base 2'OMe modification walk through HPRT1 Site 38351
AsCpf1 crRNAs

| Seq Name | Sequence 5'-3' | % Cleavage T7E1 Assay | SEQ ID NO: |
|---|---|---|---|
| 38351-44-L14 | uaauuucuacucuuguagauugugaaauggcuuauaauugcuua | 86% | 117 |
| 38351-44-L15 | uaauuucuacucuuguagauugugaaauggcuuauaauugcuua | 58% | 118 |
| 38351-44-L16 | uaauuucuacucuuguagauugugaaauggcuuauaauugcuua | 89% | 119 |
| 38351-44-L17 | uaauuucuacucuuguagauugugaaauggcuuauaauugcuua | 88% | 120 |
| 38351-44-L18 | uaauuucuacucuuguagauugugaaauggcuuauaauugcuua | 82% | 121 |
| 38351-44-L19 | uaauuucuacucuuguagauugugaaauggcuuauaauugcuua | 87% | 122 |
| 38351-44-L20 | uaauuucuacucuuguagauugugaaauggcuuauaauugcuua | 52% | 123 |
| 38351-44-T1 | uaauuucuacucuuguagauugugaaauggcuuauaauugcuua | 87% | 124 |
| 38351-44-T2 | uaauuucuacucuuguagauugugaaauggcuuauaauugcuua | 79% | 125 |
| 38351-44-T3 | uaauuucuacucuuguagauugugaaauggcuuauaauugcuua | 86% | 126 |
| 38351-44-T4 | uaauuucuacucuuguagauugugaaauggcuuauaauugcuua | 81% | 127 |
| 38351-44-T5 | uaauuucuacucuuguagauugugaaauggcuuauaauugcuua | 69% | 128 |
| 38351-44-T6 | uaauuucuacucuuguagauugugaaauggcuuauaauugcuua | 57% | 129 |
| 38351-44-T7 | uaauuucuacucuuguagauugugaaauggcuuauaauugcuua | 84% | 130 |
| 38351-44-T8 | uaauuucuacucuuguagauugugaaauggcuuauaauugcuua | 90% | 131 |
| 38351-44-T9 | uaauuucuacucuuguagauugugaaauggcuuauaauugcuua | 86% | 132 |
| 38351-44-T10 | uaauuucuacucuuguagauugugaaauggcuuauaauugcuua | 89% | 133 |
| 38351-44-T11 | uaauuucuacucuuguagauugugaaauggcuuauaauugcuua | 86% | 134 |
| 38351-44-T12 | uaauuucuacucuuguagauugugaaauggcuuauaauugcuua | 90% | 135 |
| 38351-44-T13 | uaauuucuacucuuguagauugugaaauggcuuauaauugcuua | 15% | 136 |
| 38351-44-T14 | uaauuucuacucuuguagauugugaaauggcuuauaauugcuua | 71% | 137 |
| 38351-44-T15 | uaauuucuacucuuguagauugugaaauggcuuauaauugcuua | 72% | 138 |
| 38351-44-T16 | uaauuucuacucuuguagauugugaaauggcuuauaauugcuua | 68% | 139 |
| 38351-44-T17 | uaauuucuacucuuguagauugugaaauggcuuauaauugcuua | 72% | 140 |

TABLE 6-continued

Single-base 2'OMe modification walk through HPRT1 Site 38351
AsCpf1 crRNAs

| Seq Name | Sequence 5'-3' | % Cleavage T7E1 Assay | SEQ ID NO: |
|----------|----------------|------------------------|------------|
| 38351-44-T18 | uaauuucuacucuuguagauugugaaauggcuuauaauugcuua | 64% | 141 |
| 38351-44-T19 | uaauuucuacucuuguagauugugaaauggcuuauaauugcuua | 75% | 142 |
| 38351-44-T20 | uaauuucuacucuuguagauugugaaauggcuuauaauugcuua | 71% | 143 |
| 38351-44-T21 | uaauuucuacucuuguagauugugaaauggcuuauaauugcuua | 72% | 144 |
| 38351-44-T22 | uaauuucuacucuuguagauugugaaauggcuuauaauugcuua | 69% | 145 |
| 38351-44-T23 | uaauuucuacucuuguagauugugaaauggcuuauaauugcuua | 72% | 146 |
| 38351-44-T24 | uaauuucuacucuuguagauugugaaauggcuuauaauugcuua | 70% | 147 |
| 38351-41 unmod | uaauuucuacucuuguagauugugaaauggcuuauaauugc | 77% | 148 |
| 38351-41-L1 | uaauuucuacucuuguagauugugaaauggcuuauaauugc | 87% | 149 |
| 38351-41-L2 | uaauuucuacucuuguagauugugaaauggcuuauaauugc | 63% | 150 |
| 38351-41-L3 | uaauuucuacucuuguagauugugaaauggcuuauaauugc | 15% | 151 |
| 38351-41-L4 | uaauuucuacucuuguagauugugaaauggcuuauaauugc | 6% | 152 |
| 38351-41-L5 | uaauuucuacucuuguagauugugaaauggcuuauaauugc | 88% | 153 |
| 38351-41-L6 | uaauuucuacucuuguagauugugaaauggcuuauaauugc | 88% | 154 |
| 38351-41-L7 | uaauuucuacucuuguagauugugaaauggcuuauaauugc | 81% | 155 |
| 38351-41-L8 | uaauuucuacucuuguagauugugaaauggcuuauaauugc | 78% | 156 |
| 38351-41-L9 | uaauuucuacucuuguagauugugaaauggcuuauaauugc | 90% | 157 |
| 38351-41-L10 | uaauuucuacucuuguagauugugaaauggcuuauaauugc | 88% | 158 |
| 38351-41-L11 | uaauuucuacucuuguagauugugaaauggcuuauaauugc | 59% | 159 |
| 38351-41-L12 | uaauuucuacucuuguagauugugaaauggcuuauaauugc | 88% | 160 |
| 38351-41-L13 | uaauuucuacucuuguagauugugaaauggcuuauaauugc | 89% | 161 |
| 38351-41-L14 | uaauuucuacucuuguagauugugaaauggcuuauaauugc | 88% | 162 |
| 38351-41-L15 | uaauuucuacucuuguagauugugaaauggcuuauaauugc | 41% | 163 |
| 38351-41-L16 | uaauuucuacucuuguagauugugaaauggcuuauaauugc | 90% | 164 |

TABLE 6-continued

Single-base 2'OMe modification walk through HPRT1 Site 38351
AsCpf1 crRNAs

| Seq Name | Sequence 5'-3' | % Cleavage T7E1 Assay | SEQ ID NO: |
|---|---|---|---|
| 38351-41-L17 | uaauuucuacucuuguagauugugaaauggcuuauaauugc | 89% | 165 |
| 38351-41-L18 | uaauuucuacucuuguagauugugaaauggcuuauaauugc | 89% | 166 |
| 38351-41-L19 | uaauuucuacucuuguagauugugaaauggcuuauaauugc | 88% | 167 |
| 38351-41-L20 | uaauuucuacucuuguagauugugaaauggcuuauaauugc | 77% | 168 |
| 38351-41-T1 | uaauuucuacucuuguagauugugaaauggcuuauaauugc | 89% | 169 |
| 38351-41-T2 | uaauuucuacucuuguagauugugaaauggcuuauaauugc | 84% | 170 |
| 38351-41-T3 | uaauuucuacucuuguagauugugaaauggcuuauaauugc | 87% | 171 |
| 38351-41-T4 | uaauuucuacucuuguagauugugaaauggcuuauaauugc | 86% | 172 |
| 38351-41-T5 | uaauuucuacucuuguagauugugaaauggcuuauaauugc | 80% | 173 |
| 38351-41-T6 | uaauuucuacucuuguagauugugaaauggcuuauaauugc | 79% | 174 |
| 38351-41-T7 | uaauuucuacucuuguagauugugaaauggcuuauaauugc | 86% | 175 |
| 38351-41-T8 | uaauuucuacucuuguagauugugaaauggcuuauaauugc | 89% | 176 |
| 38351-41-T9 | uaauuucuacucuuguagauugugaaauggcuuauaauugc | 89% | 177 |
| 38351-41-T10 | uaauuucuacucuuguagauugugaaauggcuuauaauugc | 89% | 178 |
| 38351-41-T11 | uaauuucuacucuuguagauugugaaauggcuuauaauugc | 89% | 179 |
| 38351-41-T12 | uaauuucuacucuuguagauugugaaauggcuuauaauugc | 88% | 180 |
| 38351-41-T13 | uaauuucuacucuuguagauugugaaauggcuuauaauugc | 23% | 181 |
| 38351-41-T14 | uaauuucuacucuuguagauugugaaauggcuuauaauugc | 75% | 182 |
| 38351-41-T15 | uaauuucuacucuuguagauugugaaauggcuuauaauugc | 77% | 183 |
| 38351-41-T16 | uaauuucuacucuuguagauugugaaauggcuuauaauugc | 72% | 184 |
| 38351-41-T17 | uaauuucuacucuuguagauugugaaauggcuuauaauugc | 76% | 185 |
| 38351-41-T18 | uaauuucuacucuuguagauugugaaauggcuuauaauugc | 71% | 186 |
| 38351-41-T19 | uaauuucuacucuuguagauugugaaauggcuuauaauugc | 77% | 187 |
| 38351-41-T20 | uaauuucuacucuuguagauugugaaauggcuuauaauugc | 75% | 188 |

TABLE 6-continued

Single-base 2'OMe modification walk through HPRT1 Site 38351
AsCpf1 crRNAs

| Seq Name | Sequence 5'-3' | % Cleavage T7E1 Assay | SEQ ID NO: |
|---|---|---|---|
| 38351-41-T21 | uaauuucuacucuuguagauugugaaauggcuuauaauug*c* | 77% | 189 |

Oligonucleotide sequences are shown 5'-3'. Lowercase = RNA; Underlined lowercase
= 2'-O-methyl RNA. The relative functional activity of each species is indicated
by the % cleavage in a T7EI heteroduplex assay. The sequence name indicates if the
crRNA is a 44mer with a 24 base target domain or a 41mer with a 21 base target domain.
The position of the 2'OMe residue with either the loop domain (L) or target domain
(T) is indicated.

TABLE 7

Single-base 2'OMe modification walk through HPRT1 Site 38595
AsCpf1 crRNAs

| Seq Name | Sequence 5'-3' | % Cleavage T7E1 Assay | SEQ ID NO: |
|---|---|---|---|
| 38595-44 unmod | uaauuucuacucuuguagauggaaagagaauuguuuucuccuuc | 49% | 190 |
| 38595-44-L1 | *u*aauuucuacucuuguagauggaaagagaauuguuuucuccuuc | 48% | 191 |
| 38595-44-L2 | u*a*auuucuacucuuguagauggaaagagaauuguuuucuccuuc | 34% | 192 |
| 38595-44-L3 | ua*a*uuucuacucuuguagauggaaagagaauuguuuucuccuuc | 6% | 193 |
| 38595-44-L4 | uaa*u*uucuacucuuguagauggaaagagaauuguuuucuccuuc | 3% | 194 |
| 38595-44-L5 | uaau*u*ucuacucuuguagauggaaagagaauuguuuucuccuuc | 59% | 195 |
| 38595-44-L6 | uaauu*u*cuacucuuguagauggaaagagaauuguuuucuccuuc | 54% | 196 |
| 38595-44-L7 | uaauuu*c*uacucuuguagauggaaagagaauuguuuucuccuuc | 56% | 197 |
| 38595-44-L8 | uaauuuc*u*acucuuguagauggaaagagaauuguuuucuccuuc | 52% | 198 |
| 38595-44-L9 | uaauuucu*a*cucuuguagauggaaagagaauuguuuucuccuuc | 60% | 199 |
| 38595-44-L10 | uaauuucua*c*ucuuguagauggaaagagaauuguuuucuccuuc | 56% | 200 |
| 38595-44-L11 | uaauuucuac*u*cuuguagauggaaagagaauuguuuucuccuuc | 23% | 201 |
| 38595-44-L12 | uaauuucuacu*c*uuguagauggaaagagaauuguuuucuccuuc | 51% | 202 |
| 38595-44-L13 | uaauuucuacuc*u*uguagauggaaagagaauuguuuucuccuuc | 58% | 203 |
| 38595-44-L14 | uaauuucuacucu*u*guagauggaaagagaauuguuuucuccuuc | 52% | 204 |
| 38595-44-L15 | uaauuucuacucuu*g*uagauggaaagagaauuguuuucuccuuc | 33% | 205 |
| 38595-44-L16 | uaauuucuacucuug*u*agauggaaagagaauuguuuucuccuuc | 55% | 206 |
| 38595-44-L17 | uaauuucuacucuugu*a*gauggaaagagaauuguuuucuccuuc | 58% | 207 |

TABLE 7-continued

Single-base 2'OMe modification walk through HPRT1 Site 38595
AsCpf1 crRNAs

| Seq Name | Sequence 5'-3' | % Cleavage T7E1 Assay | SEQ ID NO: |
|---|---|---|---|
| 38595-44-L18 | uaauuucuacucuuguagauggaaagagaauuguuuucuccuuc | 61% | 208 |
| 38595-44-L19 | uaauuucuacucuuguagauggaaagagaauuguuuucuccuuc | 54% | 209 |
| 38595-44-L20 | uaauuucuacucuuguagauggaaagagaauuguuuucuccuuc | 29% | 210 |
| 38595-44-T1 | uaauuucuacucuuguagauggaaagagaauuguuuucuccuuc | 55% | 211 |
| 38595-44-T2 | uaauuucuacucuuguagauggaaagagaauuguuuucuccuuc | 53% | 212 |
| 38595-44-T3 | uaauuucuacucuuguagauggaaagagaauuguuuucuccuuc | 49% | 213 |
| 38595-44-T4 | uaauuucuacucuuguagauggaaagagaauuguuuucuccuuc | 20% | 214 |
| 38595-44-T5 | uaauuucuacucuuguagauggaaagagaauuguuuucuccuuc | 17% | 215 |
| 38595-44-T6 | uaauuucuacucuuguagauggaaagagaauuguuuucuccuuc | 23% | 216 |
| 38595-44-T7 | uaauuucuacucuuguagauggaaagagaauuguuuucuccuuc | 47% | 217 |
| 38595-44-T8 | uaauuucuacucuuguagauggaaagagaauuguuuucuccuuc | 52% | 218 |
| 38595-44-T9 | uaauuucuacucuuguagauggaaagagaauuguuuucuccuuc | 51% | 219 |
| 38595-44-T10 | uaauuucuacucuuguagauggaaagagaauuguuuucuccuuc | 55% | 220 |
| 38595-44-T11 | uaauuucuacucuuguagauggaaagagaauuguuuucuccuuc | 53% | 221 |
| 38595-44-T12 | uaauuucuacucuuguagauggaaagagaauuguuuucuccuuc | 58% | 222 |
| 38595-44-T13 | uaauuucuacucuuguagauggaaagagaauuguuuucuccuuc | 20% | 223 |
| 38595-44-T14 | uaauuucuacucuuguagauggaaagagaauuguuuucuccuuc | 62% | 224 |
| 38595-44-T15 | uaauuucuacucuuguagauggaaagagaauuguuuucuccuuc | 60% | 225 |
| 38595-44-T16 | uaauuucuacucuuguagauggaaagagaauuguuuucuccuuc | 15% | 226 |
| 38595-44-T17 | uaauuucuacucuuguagauggaaagagaauuguuuucuccuuc | 49% | 227 |
| 38595-44-T18 | uaauuucuacucuuguagauggaaagagaauuguuuucuccuuc | 46% | 228 |
| 38595-44-T19 | uaauuucuacucuuguagauggaaagagaauuguuuucuccuuc | 64% | 229 |
| 38595-44-T20 | uaauuucuacucuuguagauggaaagagaauuguuuucuccuuc | 57% | 230 |
| 38595-44-T21 | uaauuucuacucuuguagauggaaagagaauuguuuucuccuuc | 55% | 231 |

TABLE 7-continued

Single-base 2'OMe modification walk through HPRT1 Site 38595
AsCpf1 crRNAs

| Seq Name | Sequence 5'-3' | % Cleavage T7E1 Assay | SEQ ID NO: |
|---|---|---|---|
| 38595-44-T22 | uaauuucuacucuuguagauggaaagagaauuguuuucuccuuc | 54% | 232 |
| 38595-44-T23 | uaauuucuacucuuguagauggaaagagaauuguuuucuccuuc | 56% | 233 |
| 38595-44-T24 | uaauuucuacucuuguagauggaaagagaauuguuuucuccuuc | 54% | 234 |
| 38595-41 unmod | uaauuucuacucuuguagauggaaagagaauuguuuucucc | 59% | 235 |
| 38595-41-L1 | uaauuucuacucuuguagauggaaagagaauuguuuucucc | 60% | 236 |
| 38595-41-L2 | uaauuucuacucuuguagauggaaagagaauuguuuucucc | 49% | 237 |
| 38595-41-L3 | uaauuucuacucuuguagauggaaagagaauuguuuucucc | 10% | 238 |
| 38595-41-L4 | uaauuucuacucuuguagauggaaagagaauuguuuucucc | 5% | 239 |
| 38595-41-L5 | uaauuucuacucuuguagauggaaagagaauuguuuucucc | 63% | 240 |
| 38595-41-L6 | uaauuucuacucuuguagauggaaagagaauuguuuucucc | 55% | 241 |
| 38595-41-L7 | uaauuucuacucuuguagauggaaagagaauuguuuucucc | 56% | 242 |
| 38595-41-L8 | uaauuucuacucuuguagauggaaagagaauuguuuucucc | 55% | 243 |
| 38595-41-L9 | uaauuucuacucuuguagauggaaagagaauuguuuucucc | 63% | 244 |
| 38595-41-L10 | uaauuucuacucuuguagauggaaagagaauuguuuucucc | 64% | 245 |
| 38595-41-L11 | uaauuucuacucuuguagauggaaagagaauuguuuucucc | 35% | 246 |
| 38595-41-L12 | uaauuucuacucuuguagauggaaagagaauuguuuucucc | 55% | 247 |
| 38595-41-L13 | uaauuucuacucuuguagauggaaagagaauuguuuucucc | 56% | 248 |
| 38595-41-L14 | uaauuucuacucuuguagauggaaagagaauuguuuucucc | 58% | 249 |
| 38595-41-L15 | uaauuucuacucuuguagauggaaagagaauuguuuucucc | 47% | 250 |
| 38595-41-L16 | uaauuucuacucuuguagauggaaagagaauuguuuucucc | 55% | 251 |
| 38595-41-L17 | uaauuucuacucuuguagauggaaagagaauuguuuucucc | 64% | 252 |
| 38595-41-L18 | uaauuucuacucuuguagauggaaagagaauuguuuucucc | 69% | 253 |
| 38595-41-L19 | uaauuucuacucuuguagauggaaagagaauuguuuucucc | 63% | 254 |

TABLE 7-continued

Single-base 2'OMe modification walk through HPRT1 Site 38595
AsCpf1 crRNAs

| Seq Name | Sequence 5'-3' | % Cleavage T7E1 Assay | SEQ ID NO: |
|---|---|---|---|
| 38595-41-L20 | uaauuucuacucuuguagauggaaagagaauuguuuucucc | 45% | 255 |
| 38595-41-T1 | uaauuucuacucuuguagauggaaagagaauuguuuucucc | 60% | 256 |
| 38595-41-T2 | uaauuucuacucuuguagauggaaagagaauuguuuucucc | 59% | 257 |
| 38595-41-T3 | uaauuucuacucuuguagauggaaagagaauuguuuucucc | 53% | 258 |
| 38595-41-T4 | uaauuucuacucuuguagauggaaagagaauuguuuucucc | 21% | 259 |
| 38595-41-T5 | uaauuucuacucuuguagauggaaagagaauuguuuucucc | 20% | 260 |
| 38595-41-T6 | uaauuucuacucuuguagauggaaagagaauuguuuucucc | 25% | 261 |
| 38595-41-T7 | uaauuucuacucuuguagauggaaagagaauuguuuucucc | 50% | 262 |
| 38595-41-T8 | uaauuucuacucuuguagauggaaagagaauuguuuucucc | 64% | 263 |
| 38595-41-T9 | uaauuucuacucuuguagauggaaagagaauuguuuucucc | 54% | 264 |
| 38595-41-T10 | uaauuucuacucuuguagauggaaagagaauuguuuucucc | 57% | 265 |
| 38595-41-T11 | uaauuucuacucuuguagauggaaagagaauuguuuucucc | 45% | 266 |
| 38595-41-T12 | uaauuucuacucuuguagauggaaagagaauuguuuucucc | 52% | 267 |
| 38595-41-T13 | uaauuucuacucuuguagauggaaagagaauuguuuucucc | 14% | 268 |
| 38595-41-T14 | uaauuucuacucuuguagauggaaagagaauuguuuucucc | 66% | 269 |
| 38595-41-T15 | uaauuucuacucuuguagauggaaagagaauuguuuucucc | 63% | 270 |
| 38595-41-T16 | uaauuucuacucuuguagauggaaagagaauuguuuucucc | 16% | 271 |
| 38595-41-T17 | uaauuucuacucuuguagauggaaagagaauuguuuucucc | 47% | 272 |
| 38595-41-T18 | uaauuucuacucuuguagauggaaagagaauuguuuucucc | 52% | 273 |
| 38595-41-T19 | uaauuucuacucuuguagauggaaagagaauuguuuucucc | 64% | 274 |
| 38595-41-T20 | uaauuucuacucuuguagauggaaagagaauuguuuucucc | 64% | 275 |
| 38595-41-T21 | uaauuucuacucuuguagauggaaagagaauuguuuucucc | 66% | 276 |

Oligonucleotide sequences are shown 5'-3'. Lowercase = RNA; Underlined lowercase = 2'-O-methyl RNA. The relative functional activity of each species is indicated by the % cleavage in a T7EI heteroduplex assay. The sequence name indicates if the crRNA is a 44mer with a 24 base target domain or a 41mer with a 21 base target domain. The position of the 2'OMe residue with either the loop domain (L) or target domain (T) is indicated.

Example 6

Modification of Blocks of Sequence in AsCpf1 crRNAs.

Three sites in the human HPRT1 gene were chosen (38351, 38595, and 38104) to study the effects of replacement of a blocks of RNA residues with 2'OMe-RNA, 2'F RNA, or LNA residues within the AsCpf1 crRNA. Modification of internucleotide linkages with phosphorothioate bonds (PS) as well as non-nucleotide end-modifiers were also tested. The crRNAs were either 44 base or 41 base lengths. All had a 5'-end 20 base universal loop domain followed by a 3'-end 21 or 24 base protospacer target-specific domain.

An HEK cell line that stably expresses the AsCpf1 endonuclease was employed in these studies (HEK-Cpf1) (Example 2). In a reverse transfection format, anti-HPRT1 crRNAs were individually mixed with Lipofectamine RNAiMAX (Life Technologies) and transfected into the HEK-Cpf1 cell line. Transfections were done with 40,000 cells per well in 96 well plate format. RNAs were introduced at a final concentration of 30 nM in 0.75 µl of the lipid reagent. Cells were incubated at 37° C. for 48 hours. Genomic DNA was isolated using QuickExtract solution (Epicentre). Genomic DNA was amplified with KAPA HiFi DNA Polymerase (Roche) and primers targeting the HPRT region of interest (HPRT-low forward primer: AAGAATGTTGTGATAAAAGGTGATGCT (SEQ ID NO:394); HPRT-low reverse primer: ACACATC-CATGGGACTTCTGCCTC (SEQ ID NO:395). PCR products were melted and re-annealed in NEB buffer 2 (New England Biolabs) to allow for heteroduplex formation followed by digestion with 2 units of T7 endonuclease 1 (T7EI; New England Biolabs) for 1 hour at 37° C. The digested products were visualized on a Fragment Analyzer (Advanced Analytical Technologies). Percent cleavage of targeted DNA was calculated as the average molar concentration of the cut products/(average molar concentration of the cut products+molar concentration of the uncut band)×100. Results are shown in Table 8 below.

Large blocks of the universal 5-loop domain can be modified and retain activity (14/20 bases). However, the target-specific 3'-protospacer domain shows significant loss of activity when 2-3 consecutive 2'OMe residues replace RNA residues, even when those positions did not show any loss of activity in the single base walk (Example 5). Modification patterns in the protospacer domain are often expected to be impacted by sequence context, such that one modification pattern works well for one sequence but not for another sequence. The modification map shown in FIG. 7 displays modification patterns that range from minimal to high levels of modification that showed high performance at several sites and likely can be used regardless of sequence context.

2'F residues could be placed at any position that was tolerant of 2'OMe modification. LNA residues can also be placed within the AsCpf1 crRNA, and use of end-modifiers are shown below in Table 8. The phosphorothioate (PS) internucleotide linkage confers nuclease resistance and can be placed at the ends of the crRNA to block exonuclease attack or in the central regions to block endonuclease attack. Modification of large blocks of the crRNA (such as entire modification of the loop domain or the protospacer domain) with PS linkages are not compatible with crRNA function and significant loss of activity is seen when this modification pattern is employed. Limited use, such as 2-3 internucleotide linkages at each end, can be effectively employed, and such patterns are useful to block exonuclease attack. Non-base modifiers (such as a C3 spacer propanediol group or a ZEN modifier napthyl-azo group) can be placed at one or both ends of the crRNA without loss of activity and also block exonuclease attack.

TABLE 8

| Functional impact of extensive modification of AsCpf1 crRNAs | | | |
|---|---|---|---|
| Seq Name | Sequence 5'-3' | % Cleavage T7E1 Assay | SEQ ID NO: |
| 38351-44-L | uaauuucuacucuuguagauugugaaauggcuuauaauugcuua | 51% | 277 |
| 38351-44-T | uaauuucuacucuuguagauugugaaauggcuuauaauugcuua | 1% | 278 |
| 38351-44-LT | uaauuucuacucuuguagauugugaaauggcuuauaauugcuua | 1% | 279 |
| 38351-41-L | uaauuucuacucuuguagauugugaaauggcuuauaauugc | 53% | 280 |
| 38351-41-T | uaauuucuacucuuguagauugugaaauggcuuauaauugc | 1% | 281 |
| 38351-41-LT | uaauuucuacucuuguagauugugaaauggcuuauaauugc | 1% | 282 |
| 38595-44-L | uaauuucuacucuuguagauggaaagagaauuguuuucuccuuc | 51% | 283 |
| 38595-44-T | uaauuucuacucuuguagauggaaagagaauuguuuucuccuuc | 1% | 284 |
| 38595-44-LT | uaauuucuacucuuguagauggaaagagaauuguuuucuccuuc | 1% | 285 |
| 38595-41-L | uaauuucuacucuuguagauggaaagagaauuguuuucucc | 51% | 286 |
| 38595-41-T | uaauuucuacucuuguagauggaaagagaauuguuuucucc | 1% | 287 |
| 38595-41-LT | uaauuucuacucuuguagauggaaagagaauuguuuucucc | 1% | 288 |

TABLE 8-continued

Functional impact of extensive modification of AsCpf1 crRNAs

| Seq Name | Sequence 5'-3' | % Cleavage T7E1 Assay | SEQ ID NO: |
|---|---|---|---|
| 38595-41 unmod | uaauuucuacucuuguagaugggaaagagaauuguuuucucc | 35% | 235 |
| 38595-41-T1-3 | uaauuucuacucuuguagauggaaagagaauuguuuucucc | 24% | 289 |
| 38595-41-T7-12 | uaauuucuacucuuguagauggaaagagaauuguuuucucc | 2% | 290 |
| 38595-41-T1445 | uaauuucuacucuuguagauggaaagagaauuguuuucucc | 37% | 291 |
| 38595-41-T17-21 | uaauuucuacucuuguagauggaaagagaauuguuuucucc | 22% | 292 |
| 38595-41-T6-9, 18-21 | uaauuucuacucuuguagauggaaagagaauuguuuucucc | 1% | 293 |
| 38595-41-5'C3 | C3-uaauuucuacucuuguagauggaaagagaauuguuuucucc | 35% | 294 |
| 38595-41-3'C3 | uaauuucuacucuuguagauggaaagagaauuguuuucucc-C3 | 41% | 295 |
| 38595-41-2xC3 | C3-uaauuucuacucuuguagauggaaagagaauuguuuucucc-C3 | 41% | 296 |
| 38595-41-L1-20 | uaauuucuacucuuguagauggaaagagaauuguuuucucc | 1% | 297 |
| 38595-41-L + 2 | uaauuucuacucuuguagauggaaagagaauuguuuucucc | 2% | 298 |
| 38595-41-L + 3 | uaauuucuacucuuguagauggaaagagaauuguuuucucc | 1% | 299 |
| 38595-41-L + 4 | uaauuucuacucuuguagauggaaagagaauuguuuucucc | 1% | 300 |
| 38595-41-L + 11 | uaauuucuacucuuguagauggaaagagaauuguuuucucc | 5% | 301 |
| 38595-41-L + 15 | uaauuucuacucuuguagauggaaagagaauuguuuucucc | 38% | 302 |
| 38595-41-L + 20 | uaauuucuacucuuguagauggaaagagaauuguuuucucc | 2% | 303 |
| 38595-41-61 | C3-uaauuucuacucuuguagauggaaagagaauuguuuucucc-C3 | 67% | 304 |
| 38595-41-62 | u*a*a*uuucuacucuuguagauggaaagagaauuguuuuc*u*c*c | 58% | 305 |
| 38595-41-63 | u*a*a*uuucuacucuuguagauggaaagagaauuguuuuc*u*c*c | 63% | 306 |
| 38595-41-64 | u*a*a*u*u*u*c*u*a*c*u*c*u*u*g*u*a*g*a*uggaaagagaa uuguuuucucc | 10% | 307 |
| 38595-41-65 | uaauuucuacucuuguagau*g*g*a*a*a*g*a*g*a*a*u*u*g*u* u*u*u*c*u*c*c | 2% | 308 |
| 38595-41-66 | uaauuucuacucuuguagauggaaagagaauuguuuucucc | 57% | 309 |
| 38595-41-67 | uaauuucuacucuuguagauggaaagagaauuguuuucucc | 51% | 310 |
| 38595-41-68 | uaauuucuacucuuguagauggaaagagaauuguuuucucc | 20% | 311 |
| 38595-41-69 | uaauuucuacucuuguagauggaaagagaauuguuuucucc | 19% | 312 |
| 38595-41-70 | uaauuucuacucuuguagauggaaagagaauuguuuucucc | 27% | 313 |
| 38595-41-71 | uaauuucuacucuuguagauggaaagagaauuguuuucucc | 37% | 314 |
| 38595-41-72 | uaauuucuacucuuguagauggaaagagaauuguuuucucc | 65% | 315 |

TABLE 8-continued

Functional impact of extensive modification of AsCpf1 crRNAs

| Seq Name | Sequence 5'-3' | % Cleavage T7E1 Assay | SEQ ID NO: |
|---|---|---|---|
| 38595-41-73 | uaauuucuacucuuguagauggaaagagaauuguuuucucc | 67% | 316 |
| 38595-41-74 | uaauuucuacucuuguagauggaaagagaauuguuuucucc | 65% | 317 |
| 38595-41-75 | uaauuucuacucuuguagauggaaagagaauuguuuucucc | 57% | 318 |
| 38595-41-76 | uaauuucuacucuuguagauggaaagagaauuguuuucucc | 65% | 319 |
| 38595-41-77 | uaauuucuacucuuguagauggaaagagaauuguuuucucc | 16% | 320 |
| 38595-41-78 | uaauuucuacucuuguagauggaaagagaauuguuuucucc | 49% | 321 |
| 38595-41-79 | uaauuucuacucuuguagauggaaagagaauuguuuucucc | 70% | 322 |
| 38595-41-80 | uaauuucuacucuuguagauggaaagagaauuguuuucucc | 1% | 323 |
| 38595-41-81 | uaauuucuacucuuguagauggaaagagaauuguuuucucc | 13% | 324 |
| 38595-41-82 | uaauuucuacucuuguagauggaaagagaauuguuuucucc | 51% | 325 |
| 38595-41-83 | uaauuucuacucuuguagauggaaagagaauuguuuucucc | 64% | 326 |
| 38595-41-84 | uaauuucuacucuuguagauggaaagagaauuguuuucucc | 69% | 327 |
| 38595-41-85 | uaauuucuacucuuguagauggaaagagaauuguuuucucc | 69% | 328 |
| 38595-41-86 | u*a*a*uuucuacucuuguagauggaaagagaauuguuuuc*u*c*c | 61% | 329 |
| 38595-41-87 | + taauuucuacucuuguagauggaaagagaauuguuuucu + c + c | 60% | 330 |
| 38595-41-88 | uaauuucuacucuuguagauggaaagagaauuguuuucucc | 63% | 331 |
| 38595-41-89 | uaauuucuacucuuguagaugaaagagaauuguuuucucc | 34% | 332 |
| 38595-41-90 | uaauuucuacucuuguagauggaaagagaauuguuuucucc | 65% | 333 |
| 38595-41-91 | uaauuucuacucuuguagauggaaagagaauuguuuucucc | 66% | 334 |
| 38595-41-92 | uaauuucuacucuuguagauggaaagagaauuguuuucucc | 60% | 335 |
| 38595-41-93 | ZEN-uaauuucuacucuuguagauggaaagagaauuguuuucucc-ZEN | 61% | 336 |
| 38595-41-94 | ZEN-uaauuucuacucuuguagauggaaagagaauuguuuucucc-C3 | 59% | 337 |
| 38595-41-95 | C3-uaauuucuacucuuguagauggaaagagaauuguuuucucc-ZEN | 58% | 338 |
| 38104-41-96 | uaauuucuacucuuguagaucuugggguguguuaaaagugac | 63% | 339 |
| 38104-41-97 | C3-uaauuucuacucuuguagaucuuggggguguguuaaaagugac-C3 | 63% | 340 |
| 38104-41-98 | uaauuucuacucuuguagaucuuggggguguguuaaaagugac | 63% | 341 |
| 38104-41-99 | u*a*auuucuacucuuguagaucuuggggguguguuaaaagu*g*a*c | 67% | 342 |

Oligonucleotide sequences are shown 5'-3'. Lowercase = RNA; Underlined lowercase =
2'-O-methyl RNA; Italics lowercase = 2'-fluoro RNA; +a, +c, +t, +g = LNA; C3 = C3 spacer
(propanediol modifier); * = phosphorothioate internucleotide linkage; ZEN-napthyl-azo
modifier. The relative functional activity of each species is indicated by the % cleavage
in a T7EI heteroduplex assay. The sequence name indicates if the crRNA ia a 44mer with a
24 base target domain or a 41mer with a 21 base target domain and the HPRT target site is
indicated (38104, 38351, or 38595).

Example 7

Use of Modified crRNAs with AsCpf1 Protein Delivered as an RNP Complex.

A site in the human HPRT1 gene (38104) was chosen to study the ability to use chemically modified crRNAs with AsCpf1 protein to perform genome editing in HEK-293 cells using electroporation to deliver the ribonucleoprotein (RNP) complex into the cells.

Purified recombinant AsCpf1 protein was employed in this example, isolated from *E. coli* using standard techniques. The amino-acid sequence of the recombinant protein is shown in SEQ ID NO:12.

followed by digestion with 2 units of T7 endonuclease 1 (T7EI; New England Biolabs) for 1 hour at 37° C. The digested products were visualized on a Fragment Analyzer (Advanced Analytical Technologies). Percent cleavage of targeted DNA was calculated as the average molar concentration of the cut products/(average molar concentration of the cut products+molar concentration of the uncut band)× 100. Results are shown in Table 9 below. AsCpf1 crRNAs bearing low or high levels of modification, as shown below, are compatible with delivery via electroporation as an RNP complex to mediate genome editing in mammalian cells.

TABLE 9

| Editing in mammalian cells using chemically-modified crRNAs with recombinant AsCpf1 as RNP complexes | | | |
|---|---|---|---|
| Seq Name | Sequence 5'-3' | % Cleavage T7E1 Assay | SEQ ID NO: |
| 38104-41-96 | uaauuucuacucuuguagaucuugggguguguuaaaagugac | 57% | 339 |
| 38104-41-97 | C3-uaauuucuacucuuguagaucuugggguguguuaaaagugac-C3 | 53% | 340 |
| 38104-41-98 | uaauuucuacucuuguagaucuugggguguguuaaaagugac | 42% | 341 |
| 38104-41-99 | u*a*auuucuacucuuguagaucuugggguguguuaaaagu*g*a*c | 43% | 342 |
| 38104-41-101 | u*a*auuucuacucuuguagaucuugggguguguuaaaagug*a*c | 43% | 343 |

Oligonucleotide sequences are shown 5'-3'. Lowercase = RNA; Underlined = 2'-O-methyl RNA; C3 = C3 spacer (propanediol modifier); * = phosphorothioate internucleotide linkage. The relative functional activity of each species is indicated by the % cleavage in a T7EI heteroduplex assay. The sequence name indicates that the crRNAs are all 41mers with a 21 base target domain.

The AsCpf1 crRNAs were heated to 95° C. for 5 minutes then allowed to cool to room temperature. The crRNAs were mixed with AsCpf1 protein at a molar ratio of 1.2:1 RNA:protein in phosphate buffered saline (PBS) (202 pmoles RNA with 168 pmoles protein in 6 μL volume, for a single transfection). The RNP complex was allowed to form at room temperature for 15 minutes. HEK293 cells were resuspended following trypsinization and washed in medium and washed a second time in PBS before use. Cells were resuspended in at a final concentration of $3.5×10^5$ cells in 20 μL of Nucleofection solution. 20 μL of cell suspension was placed in the V-bottom 96-well plate and 5 μL of the Cpf1 RNP complex was added to each well (5 μM final concentration) and 3 μL of Cpf1 Electroporation Enhancer Solution was added to each well (Integrated DNA Technologies). 25 μL of the final mixture was transferred to each well of a 96 well Nucleocuvette electroporation module. Cells were electroporated using Amaxa 96 well shuttle protocol, program 96-DS-150. Following electroporation, 75 μL of medium was added to each well and 25 μL of the final cell mixture was transferred to 175 μL of pre-warmed medium in 96 well incubation plates (final volume 200 Cells were incubated at 37° C. for 48 hours. Genomic DNA was isolated using QuickExtract solution (Epicentre). Genomic DNA was amplified with KAPA HiFi DNA Polymerase (Roche) and primers targeting the HPRT region of interest (HPRT-low forward primer: AAGAATGTTGTGATAAAAGGT-GATGCT (SEQ ID NO:394); HPRT-low reverse primer: ACACATCCATGGGACTTCTGCCTC (SEQ ID NO:395). PCR products were melted and re-annealed in NEB buffer 2 (New England Biolabs) to allow for heteroduplex formation

Example 8

Use of Modified crRNAs with an AsCpf1 Expression Plasmid in *E. coli*.

A site in the human HPRT1 gene (38346) was cloned onto an *E. coli* plasmid and was used to study the ability to use chemically modified crRNAs to perform site-specific cleavage in *E. coli* cells. AsCpf1 was expressed from a plasmid. Electroporation was used to deliver both the AsCpf1 expression plasmid and chemically-synthesized crRNAs.

The AsCpf1 protein was expressed from a plasmid in this example, using a phage T7 promoter and standard *E. coli* translation elements. The amino-acid sequence of the expression construct is shown in SEQ ID NO:16).

The AsCpf1 crRNAs were heated to 95° C. for 5 minutes then allowed to cool to room temperature. The crRNAs and AsCpf1 plasmid were mixed in TE (60 femtomoles AsCpf1 plasmid with 400 pmoles RNA in 5 μL volume, for a single transformation), and added directly to 20 μL of competent *E. coli* cells). A bacterial strain where survival is linked to successful cleavage by Cpf1 was made competent by growing cells to mid-log phase, washing 3 times in ice cold 10% glycerol, and final suspension in $1:100^{th}$ volume 10% glycerol. Electroporations were performed by adding the 25 μL transformation mixture to a pre-chilled 0.1 cm electroporation cuvette and pulsing 1.8 kV exponential decay. Following electroporation, 980 μL of SOB medium was added to the electroporation cuvette with mixing and the resulting cell suspension was transferred to a sterile 15 ml culture tube. Cells were incubated with shaking (250 rpm) at 37° C. for 1.5 hours, at which time IPTG was added (1 mM) followed by further shaking incubation at 37° C. for 1 hour. Following incubation cells were plated on selective media to assess survival.

This example demonstrates that chemically-modified synthetic crRNAs can be used with Cpf1 for gene editing in bacteria. However, high efficiency is only seen using RNAs that have been more extensively modified with exonuclease-blocking PS internucleotide linkages. The modification patterns that work best in bacterial cells perform poorly in mammalian cells (Table 10).

TABLE 10

| Chemically-modified crRNAs compatible with Cpf1 function in bacteria | | | | |
|---|---|---|---|---|
| Seq Name | Sequence 5'-3' | % Cleavage Human | % Cleavage Bacteria | SEQ ID NO: |
| 38346-41-1 | uaauuucuacucuuguagauacauaaaaacucuuuuagguua | 21% | 0% | 344 |
| 38346-41-2 | u*a*a*uuucuacucuuguagauacauaaaaacucuuuuagguua | 17% | 0% | 345 |
| 38346-41-3 | u*a*a*u*u*u*cuacucuuguagauacauaaaaacucuuuuagguua | 10% | 2% | 346 |
| 38346-41-4 | uaauuucuacucuuguagauacauaaaaacucuuuu*a*g*g*u*u*a | 14% | 18% | 347 |
| 38346-41-5 | u*a*a*uuucuacucuuguagauacauaaaaacucuuuuagg*u*u*a | 8% | 5% | 348 |
| 38346-41-6 | u*a*a*uuucuacucuuguagauacauaaaaacucuuuu*a*g*g*u*u*a | 5% | 40% | 349 |
| 38346-41-7 | u*a*a*u*u*u*cuacucuuguagauacauaaaaacucuuuu*a*g*g*u*u*a | 2% | 88% | 350 |
| 38346-41-8 | u̲a̲a̲u̲u̲u̲cuacu̲cuu̲gu̲agauacauaaaaacucuuuuagg*u*u*a | 14% | 7% | 351 |
| 38346-41-9 | u̲a̲a̲u̲u̲u̲cuacu̲cuu̲gu̲agauacauaaaaacucuuuu*a*g*g*u*u*a | 8% | 35% | 352 |
| 38346-41-10 | u̲*a̲*a̲*u̲u̲u̲cuacu̲cuu̲gu̲agauacauaaaaacucuuuuagg*u*u*a | 12% | 27% | 353 |
| 38346-41-11 | u̲*a̲*a̲*u̲u̲u̲cuacu̲cuu̲gu̲agauacauaaaaacucuuuuag*g*u*u*a | 8% | 85% | 354 |
| 38346-41-12 | u̲*a̲*a̲*u̲u̲u̲cuacu̲cuu̲gu̲agauacauaaaaacucuuuua*g*g*u*u*a | 5% | 92% | 355 |
| 38346-41-13 | u̲*a̲*a̲*u̲u̲u̲cuacu̲cuu̲gu̲agauacauaaaaacucuuuu*a*g*g*u*u*a | 4% | 100% | 356 |
| 38346-41-14 | u̲*a̲*a̲*u̲*u̲*u̲*cuacu̲cuu̲gu̲agauacauaaaaacucuuuu*a*g*g*u*u*a | 1% | 90% | 357 |

Oligonucleotide sequences are shown 5'-3'. Lowercase = RNA; Underlined lowercase = 2'-O-methyl RNA; C3 = C3 spacer (propanediol modifier); * = phosphorothioate internucleotide linkage. The relative functional activity in human cells is indicated by the % cleavage in a T7EI heteroduplex assay, and in bacteria is indicated by % survival in a Cpf1 reporter strain. The sequence name indicates that the crRNAs are all 41mers with a 21 base target domain.

Example 9

DNA and Amino Acid Sequences of Wild Type Lb Cpf1 Polypeptide, as Encoded in Isolated Nucleic Acid Vectors The list below shows wild type (WT) Lb Cpf1 nucleases expressed as polypeptide fusion proteins as described in the present invention. It will be appreciated by one with skill in the art that many different DNA sequences can encode/express the same amino acid (AA) sequence since in many cases more than one codon can encode for the same amino acid. The DNA sequences shown below only serve as examples, and other DNA sequences that encode the same protein (e.g., same amino acid sequence) are contemplated. It is further appreciated that additional features, elements or tags may be added to said sequences, such as NLS domains and the like.

Examples are shown for WT LbCpf1 showing amino acid and DNA sequences for those proteins as LbCpf1 alone and LbCpf1 fused to an N-terminal V5-tag, an N-terminal SV40 NLS domain, a C-terminal SV40 NLS domain, and a C-terminal 6×His-tag.

LbCpf1 Native DNA Sequence

SEQ ID NO: 3

ATGAGCAAACTGGAAAAATTTACGAATTGTTATAGCCTGTCCAAGACCCTGCGTTTCAAAGCCATCC

CCGTTGGCAAAACCCAGGAGAATATTGATAATAAACGTCTGCTGGTTGAGGATGAAAAAAGAGCAGA

-continued

```
AGACTATAAGGGAGTCAAAAAACTGCTGGATCGGTACTACCTGAGCTTTATAAATGACGTGCTGCAT

AGCATTAAACTGAAAAATCTGAATAACTATATTAGTCTGTTCCGCAAGAAAACCCGAACAGAGAAAG

AAAATAAAGAGCTGGAAAACCTGGAGATCAATCTGCGTAAAGAGATCGCAAAAGCTTTTAAAGGAAA

TGAAGGTTATAAAAGCCTGTTCAAAAAAGACATTATTGAAACCATCCTGCCGGAATTTCTGGATGAT

AAAGACGAGATAGCGCTCGTGAACAGCTTCAACGGGTTCACGACCGCCTTCACGGGCTTTTTCGATA

ACAGGGAAAATATGTTTTCAGAGGAAGCCAAAAGCACCTCGATAGCGTTCCGTTGCATTAATGAAAA

TTTGACAAGATATATCAGCAACATGGATATTTTCGAGAAAGTTGATGCGATCTTTGACAAACATGAA

GTGCAGGAGATTAAGGAAAAAATTCTGAACAGCGATTATGATGTTGAGGATTTTTTCGAGGGGGAAT

TTTTTAACTTTGTACTGACACAGGAAGGTATAGATGTGTATAATGCTATTATCGGCGGGTTCGTTAC

CGAATCCGGCGAGAAAATTAAGGGTCTGAATGAGTACATCAATCTGTATAACCAAAAGACCAAACAG

AAACTGCCAAAATTCAAACCGCTGTACAAGCAAGTCCTGAGCGATCGGGAAAGCTTGAGCTTTTACG

GTGAAGGTTATACCAGCGACGAGGAGGTACTGGAGGTCTTTCGCAATACCCTGAACAAGAACAGCGA

AATTTTCAGCTCCATTAAAAAGCTGGAGAAACTGTTTAAGAATTTTGACGAGTACAGCAGCGCAGGT

ATTTTTGTGAAGAACGGACCTGCCATAAGCACCATTAGCAAGGATATTTTTGGAGAGTGGAATGTTA

TCCGTGATAAATGGAACGCGGAATATGATGACATACACCTGAAAAAGAAGGCTGTGGTAACTGAGAA

ATATGAAGACGATCGCCGCAAAAGCTTTAAAAAAATCGGCAGCTTTAGCCTGGAGCAGCTGCAGGAA

TATGCGGACGCCGACCTGAGCGTGGTCGAGAAACTGAAGGAAATTATTATCCAAAAAGTGGATGAGA

TTTACAAGGTATATGGTAGCAGCGAAAAACTGTTTGATGCGGACTTCGTTCTGGAAAAAAGCCTGAA

AAAAAATGATGCTGTTGTTGCGATCATGAAAGACCTGCTCGATAGCGTTAAGAGCTTTGAAAATTAC

ATTAAAGCATTCTTTGGCGAGGGCAAAGAAACAAACAGAGACGAAAGCTTTTATGGCGACTTCGTCC

TGGCTTATGACATCCTGTTGAAGGTAGATCATATATATGATGCAATTCGTAATTACGTAACCCAAAA

GCCGTACAGCAAAGATAAGTTCAAACTGTATTTCCAGAACCCGCAGTTTATGGGTGGCTGGGACAAA

GACAAGGAGACAGACTATCGCGCCACTATTCTGCGTTACGGCAGCAAGTACTATCTCGCCATCATGG

ACAAAAAATATGCAAAGTGTCTGCAGAAAATCGATAAAGACGACGTGAACGGAAATTACGAAAAGAT

TAATTATAAGCTGCTGCCAGGGCCCAACAAGATGTTACCGAAAGTATTTTTTTCCAAAAAATGGATG

GCATACTATAACCCGAGCGAGGATATACAGAAGATTTACAAAAATGGGACCTTCAAAAAGGGGGATA

TGTTCAATCTGAATGACTGCCACAAACTGATCGATTTTTTTAAAGATAGCATCAGCCGTTATCCTAA

ATGGTCAAACGCGTATGATTTTAATTTCTCCGAAACGGAGAAATATAAAGACATTGCTGGTTTCTAT

CGCGAAGTCGAAGAACAGGGTTATAAAGTTAGCTTTGAATCGGCCAGCAAGAAAGAGGTTGATAAAC

TGGTGGAGGAGGGTAAGCTGTATATGTTTCAGATTTATAACAAAGACTTTAGCGACAAAAGCCACGG

TACTCCTAATCTGCATACGATGTACTTTAAACTGCTGTTTGATGAGAATAACCACGGCCAAATCCGT

CTCTCCGGTGGAGCAGAACTTTTTATGCGGCGTGCGAGCCTAAAAAAGGAAGAACTGGTGGTGCATC

CCGCCAACAGCCCGATTGCTAACAAAAATCCAGATAATCCTAAGAAGACCACCACACTGTCGTACGA

TGTCTATAAGGATAAACGTTTCTCGGAAGACCAGTATGAATTGCATATACCGATAGCAATTAATAAA

TGCCCAAAAAACATTTTCAAAATCAACACTGAAGTTCGTGTGCTGCTGAAACATGATGATAATCCGT

ATGTGATCGGAATTGACCGTGGGGAGAGAAATCTGCTGTATATTGTAGTCGTTGATGGCAAGGGCAA

CATCGTTGAGCAGTATAGCCTGAATGAAATAATTAATAATTTTAACGGTATACGTATTAAAACCGAC

TATCATAGCCTGCTGGATAAAAAGGAGAAAGAGCGTTTTGAGGCACGCCAAAATTGGACGAGCATCG

AAAACATCAAGGAACTGAAGGCAGGATATATCAGCCAAGTAGTCCATAAAATCTGTGAACTGGTGGA

GAAGTACGACGCTGTCATTGCCCTGGAAGACCTCAATAGCGGCTTTAAAAACAGCCGGGTGAAGGTG
```

GAGAAACAGGTATACCAAAAGTTTGAAAAGATGCTCATTGATAAGCTGAACTATATGGTTGATAAAA

AGAGCAACCCGTGCGCCACTGGCGGTGCACTGAAAGGGTACCAAATTACCAATAAATTTGAAAGCTT

TAAAAGCATGAGCACGCAGAATGGGTTTATTTTTTATATACCAGCATGGCTGACGAGCAAGATTGAC

CCCAGCACTGGTTTTGTCAATCTGCTGAAAACCAAATACACAAGCATTGCGGATAGCAAAAAATTTA

TTTCGAGCTTCGACCGTATTATGTATGTTCCGGAGGAAGATCTGTTTGAATTTGCCCTGGATTATAA

AAACTTCAGCCGCACCGATGCAGATTATATCAAAAAATGGAAGCTGTACAGTTATGGTAATCGTATA

CGTATCTTCCGTAATCCGAAGAAAAACAATGTGTTCGATTGGGAAGAGGTCTGTCTGACCAGCGCGT

ATAAAGAACTGTTCAACAAGTACGGAATAAATTATCAGCAAGGTGACATTCGCGCACTGCTGTGTGA

ACAGTCAGATAAAGCATTTTATAGCAGCTTTATGGCGCTGATGAGCCTGATGCTCCAGATGCGCAAC

AGCATAACCGGTCGCACAGATGTTGACTTTCTGATCAGCCCTGTGAAGAATAGCGACGGCATCTTCT

ACGATTCCAGGAACTATGAAGCACAGGAAAACGCTATTCTGCCTAAAAATGCCGATGCCAACGGCGC

CTATAATATTGCACGGAAGGTTCTGTGGGCGATTGGACAGTTCAAGAAAGCGGAAGATGAGAAGCTG

GATAAGGTAAAAATTGCTATTAGCAATAAGGAATGGCTGGAGTACGCACAGACATCGGTTAAACACG

CGGCCGCTTCCCTGCAGGTAATTAAATAA

LbCpf1 Native Protein Sequence

SEQ ID NO: 4

MLKNVGIDRLDVEKGRKNMSKLEKFINCYSLSKTLRFKAIPVGKTQENIDNKRLLVEDEKRAEDYKG

VKKLLDRYYLSFINDVLHSIKLKNLNNYISLFRKKIRTEKENKELENLEINLRKEIAKAFKGNEGYK

SLFKKDIIETILPEFLDDKDEIALVNSFNGFITAFTGFFDNRENMFSEEAKSTSIAFRCINENLTRY

ISNMDIFEKVDAIFDKHEVQEIKEKILNSDYDVEDFFEGEFFNFVLIQEGIDVYNAIIGGFVTESGE

KIKGLNEYINLYNQKTKQKLPKFKPLYKQVLSDRESLSFYGEGYISDEEVLEVERNTLNKNSEIFSS

IKKLEKLFKNFDEYSSAGIFVKNGPAISTISKDIFGEWNVIRDKWNAEYDDIHLKKKAVVIEKYEDD

RRKSFKKIGSFSLEQLQEYADADLSVVEKLKEIIIQKVDEIYKVYGSSEKLFDADFVLEKSLKKNDA

VVAIMKDLLDSVKSFENYIKAFFGEGKETNRDESFYGDFVLAYDILLKVDHIYDAIRNYVTQKPYSK

DKFKLYFQNPQFMGGWDKDKETDYRATILRYGSKYYLAIMDKKYAKCLQKIDKDDVNGNYEKINYKL

LPGPNKMLPKVFFSKKWMAYYNPSEDIQKIYKNGTFKKGDMFNLNDCHKLIDFFKDSISRYPKWSNA

YDFNFSETEKYKDIAGFYREVEEQGYKVSFESASKKEVDKLVEEGKLYMFQIYNKDFSDKSHGTPNL

HIMYFKLLFDENNHGQIRLSGGAELFMRRASLKKEELVVHPANSPIANKNPDNPKKITTLSYDVYKD

KRFSEDQYELHIPIAINKCPKNIFKINTEVRVLLKHDDNPYVIGIDRGERNLLYIVVVDGKGNIVEQ

YSLNEIINNFNGIRIKTDYHSLLDKKEKERFEARQNWTSIENIKELKAGYISQVVHKICELVEKYDA

VIALEDLNSGFKNSRVKVEKQVYQKFEKMLIDKLNYMVDKKSNPCATGGALKGYQIINKFESFKSMS

TQNGFIFYIPAWLISKIDPSTGFVNLLKIKYTSIADSKKFISSFDRIMYVPEEDLFEFALDYKNFSR

IDADYIKKWKLYSYGNRIRIFRNPKKNNVFDWEEVCLISAYKELFNKYGINYQQGDIRALLCEQSDK

AFYSSFMALMSLMQMRNSITGRIDVDFLISPVKNSDGIFYDSRNYEAQENAILPKNADANGAYNIA

RKVLWAIGQFKKAEDEKLDKVKIAISNKEWLEYAQTSVKH

*E. coli* optimized Lb Cpf1 DNA

SEQ ID NO: 6

ATGCTGAAAAACGTGGGTATTGATCGTCTGGATGTTGAAAAAGGTCGCAAAAATATGAGCAAACTGG

AAAAGTTCACCAACTGTTATAGCCTGAGCAAAACCCTGCGTTTTAAAGCAATTCCGGTTGGTAAAAC

CCAAGAGAACATTGATAATAAACGCCTGCTGGTCGAAGATGAAAAACGCGCTGAAGATTATAAAGGC

GTGAAAAAACTGCTGGATCGCTATTATCTGAGCTTCATTAACGATGTGCTGCACAGCATTAAACTGA

AGAACCTGAACAACTATATCAGCCTGTTTCGTAAAAAAACCCGCACCGAAAAGAAAACAAAGAGCT

GGAAAACCTGGAAATCAATCTGCGTAAAGAAATCGCCAAAGCGTTTAAAGGTAACGAGGGTTATAAA

-continued

```
AGCCTGTTCAAGAAAGACATCATCGAAACCATTCTGCCGGAATTTCTGGATGATAAAGATGAAATTG

CCCTGGTGAATAGCTTTAATGGCTTTACCACCGCATTTACCGGCTTTTTTGATAATCGCGAAAACAT

GTTCAGCGAAGAAGCAAAAAGCACCAGCATTGCATTTCGCTGCATTAATGAAAATCTGACCCGCTAC

ATTAGCAACATGGATATCTTTGAAAAAGTGGACGCGATCTTCGATAAACACGAAGTGCAAGAGATCA

AAGAGAAAATCCTGAACAGCGATTATGACGTCGAAGATTTTTTTGAAGGCGAGTTCTTTAACTTCGT

TCTGACCCAAGAAGGTATCGACGTTTATAACGCAATTATTGGTGGTTTTGTTACCGAAAGCGGTGAG

AAAATCAAAGGCCTGAATGAATATATCAACCTGTATAACCAGAAAACCAAACAGAAACTGCCGAAAT

TCAAACCGCTGTATAAACAGGTTCTGAGCGATCGTGAAAGCCTGAGCTTTTATGGTGAAGGTTATAC

CAGTGATGAAGAGGTTCTGGAAGTTTTTCGTAACACCCTGAATAAAAACAGCGAGATCTTTAGCAGC

ATCAAAAAGCTTGAGAAACTGTTCAAAAACTTTGATGAGTATAGCAGCGCAGGCATCTTTGTTAAAA

ATGGTCCGGCAATTAGCACCATCAGCAAAGATATTTTTGGCGAATGGAATGTGATCCGCGATAAATG

GAATGCCGAATATGATGATATCCACCTGAAAAAAAAGGCCGTGGTGACCGAGAAATATGAAGATGAT

CGTCGTAAAAGCTTCAAGAAAATTGGTAGCTTTAGCCTGGAACAGCTGCAAGAATATGCAGATGCAG

ATCTGAGCGTTGTGGAAAAACTGAAAGAAATCATCATTCAGAAGGTGGACGAGATCTATAAAGTTTA

TGGTAGCAGCGAAAAACTGTTCGATGCAGATTTTGTTCTGGAAAAAAGCCTGAAAAAGAATGATGCC

GTTGTGGCCATTATGAAAGATCTGCTGGATAGCGTTAAGAGCTTCGAGAATTACATCAAAGCCTTTT

TTGGTGAGGGCAAAGAAACCAATCGTGATGAAAGTTTCTATGGCGATTTTGTGCTGGCCTATGATAT

TCTGCTGAAAGTGGACCATATTTATGATGCCATTCGCAATTATGTTACCCAGAAACCGTATAGCAAA

GACAAGTTCAAACTGTACTTTCAGAACCCGCAGTTTATGGGTGGTTGGGATAAAGATAAAGAAACCG

ATTATCGTGCCACCATCCTGCGTTATGGTAGTAAATACTATCTGGCCATCATGGACAAAAAATACGC

AAAATGCCTGCAGAAAATCGACAAAGATGATGTGAATGGCAACTATGAAAAAATCAACTACAAACTG

CTGCCTGGTCCGAATAAAATGCTGCCGAAAGTGTTCTTTAGCAAGAAATGGATGGCCTATTATAACC

CGAGCGAGGATATTCAAAAGATCTACAAAAATGGCACCTTTAAAAAGGGCGACATGTTCAATCTGAA

CGATTGCCACAAACTGATCGATTTCTTCAAAGATTCAATTTCGCGTTATCCGAAATGGTCCAATGCC

TATGATTTTAACTTTAGCGAAACCGAAAAATACAAAGACATTGCCGGTTTTTATCGCGAAGTGGAAG

AACAGGGCTATAAAGTGAGCTTTGAAAGCGCAAGCAAAAAAGAGGTTGATAAGCTGGTTGAAGAGGG

CAAACTGTATATGTTCCAGATTTACAACAAAGATTTTAGCGACAAAAGCCATGGCACCCCGAATCTG

CATACCATGTACTTTAAACTGCTGTTCGACGAAAATAACCATGGTCAGATTCGTCTGAGCGGTGGTG

CCGAACTGTTTATGCGTCGTGCAAGTCTGAAAAAAGAAGAACTGGTTGTTCATCCGGCAAATAGCCC

GATTGCAAACAAAAATCCGGACAATCCGAAAAAAACCACGACACTGAGCTATGATGTGTATAAAGAC

AAACGTTTTAGCGAGGATCAGTATGAACTGCATATCCCGATTGCCATCAATAAATGCCCGAAAAACA

TCTTTAAGATCAACACCGAAGTTCGCGTGCTGCTGAAACATGATGATAATCCGTATGTGATTGGCAT

TGATCGTGGTGAACGTAACCTGCTGTATATTGTTGTTGTTGATGGTAAAGGCAACATCGTGGAACAG

TATAGTCTGAACGAAATTATCAACAACTTTAACGGCATCCGCATCAAAACCGACTATCATAGCCTGC

TGGACAAGAAAGAAAAAGAACGTTTTGAAGCACGTCAGAACTGGACCAGTATTGAAAACATCAAAGA

ACTGAAAGCCGGTTATATTAGCCAGGTGGTTCATAAAATCTGTGAGCTGGTAGAAAAATACGATGCA

GTTATTGCACTGGAAGATCTGAATAGCGGTTTCAAAAATAGCCGTGTGAAAGTCGAAAAACAGGTGT

ATCAGAAATTCGAGAAAATGCTGATCGACAAACTGAACTACATGGTCGACAAAAAAAGCAATCCGTG

TGCAACCGGTGGTGCACTGAAAGGTTATCAGATTACCAACAAATTTGAAAGCTTTAAAAGCATGAGC

ACCCAGAACGGCTTTATCTTCTATATTCCGGCATGGCTGACCAGCAAAATTGATCCGAGCACCGGTT
```

-continued

```
TTGTGAACCTGCTGAAAACAAAATATACCTCCATTGCCGACAGCAAGAAGTTTATTAGCAGCTTTGA

TCGCATTATGTATGTTCCGGAAGAGGACCTGTTTGAATTCGCACTGGATTACAAAAATTTCAGCCGT

ACCGATGCCGACTACATCAAAAAATGGAAACTGTACAGCTATGGTAACCGCATTCGCATTTTTCGCA

ACCCGAAGAAAAACAATGTGTTCGATTGGGAAGAAGTTTGTCTGACCAGCGCATATAAAGAACTTTT

CAACAAATACGGCATCAACTATCAGCAGGGTGATATTCGTGCACTGCTGTGTGAACAGAGCGATAAA

GCGTTTTATAGCAGTTTTATGGCACTGATGAGCCTGATGCTGCAGATGCGTAATAGCATTACCGGTC

GCACCGATGTGGATTTTCTGATTAGTCCGGTGAAAAATTCCGATGGCATCTTTTATGATAGCCGCAA

TTACGAAGCACAAGAAAATGCAATTCTGCCGAAAAACGCAGATGCAAATGGTGCATATAACATTGCA

CGTAAAGTTCTGTGGGCAATTGGCCAGTTTAAGAAAGCAGAAGATGAGAAGCTGGACAAAGTGAAAA

TTGCGATCAGCAATAAAGAGTGGCTGGAATACGCACAGACCAGCGTTAAACATTGA
```

E. *coli* optimized Lb Cpf1 AA

SEQ ID NO: 7

```
MLKNVGIDRLDVEKGRKNMSKLEKFTNCYSLSKTLRFKAIPVGKTQENIDNKRLLVEDEKRAEDYKG

VKKLLDRYYLSFINDVLHSIKLKNLNNYISLFRKKTRTEKENKELENLEINLRKEIAKAFKGNEGYK

SLFKKDIIETILPEFLDDKDEIALVNSFNGFTTAFTGFFDNRENMFSEEAKSTSIAFRCINENLTRY

ISNMDIFEKVDAIFDKHEVQEIKEKILNSDYDVEDFFEGEFFNFVLTQEGIDVYNAIIGGFVTESGE

KIKGLNEYINLYNQKTKQKLPKFKPLYKQVLSDRESLSFYGEGYTSDEEVLEVERNTLNKNSEIFSS

IKKLEKLFKNFDEYSSAGIFVKNGPAISTISKDIFGEWNVIRDKWNAEYDDIHLKKKAVVTEKYEDD

RRKSFKKIGSFSLEQLQEYADADLSVVEKLKEIIIQKVDEIYKVYGSSEKLFDADFVLEKSLKKNDA

VVAIMKDLLDSVKSFENYIKAFFGEGKETNRDESFYGDFVLAYDILLKVDHIYDAIRNYVTQKPYSK

DKFKLYFQNPQFMGGWDKDKETDYRATILRYGSKYYLAIMDKKYAKCLQKIDKDDVNGNYEKINYKL

LPGPNKMLPKVFFSKKWMAYYNPSEDIQKIYKNGTFKKGDMFNLNDCHKLIDFFKDSISRYPKWSNA

YDFNFSETEKYKDIAGFYREVEEQGYKVSFESASKKEVDKLVEEGKLYMFQTYNKDFSDKSHGTPNL

HTMYFKLLFDENNHGQIRLSGGAELFMRRASLKKEELVVHPANSPIANKNPDNPKKTTTLSYDVYKD

KRFSEDQYELHIPIAINKCPKNIFKINTEVRVLLKHDDNPYVIGIDRGERNLLYIVVVDGKGNIVEQ

YSLNEIINNFNGIRIKTDYHSLLDKKEKERFEARQNWTSIENIKELKAGYISQVVHKICELVEKYDA

VIALEDLNSGFKNSRVKVEKQVYQKFEKMLIDKLNYMVDKKSNPCATGGALKGYQITNKFESFKSMS

TQNGFIFYIPAWLTSKIDPSTGFVNLLKTKYTSIADSKKFISSFDRIMYVPEEDLFEFALDYKNFSR

TDADYIKKWKLYSYGNRIRIFRNPKKNNVFDWEEVCLTSAYKELFNKYGINYQQGDIRALLCEQSDK

AFYSSFMALMSLMLQMRNSITGRTDVDFLISPVKNSDGIFYDSRNYEAQENAILPKNADANGAYNIA

RKVLWAIGQFKKAEDEKLDKVKIAISNKEWLEYAQTSVKH
```

Hs optimized Lb Cpf1 DNA

SEQ ID NO: 9

```
ATGCTGAAGAACGTGGGCATCGACCGGCTGGACGTGGAAAAGGGCAGAAAGAACATGAGCAAGCTCG

AGAAGTTCACCAACTGCTACAGCCTGAGCAAGACCCTGCGGTTCAAGGCCATTCCTGTGGGCAAGAC

CCAAGAGAACATCGACAACAAGCGGCTGCTGGTGGAAGATGAGAAGAGAGCCGAGGACTACAAGGGC

GTGAAGAAGCTGCTGGACCGGTACTACCTGAGCTTCATCAACGACGTGCTGCACAGCATCAAGCTCA

AGAACCTGAACAACTACATCAGCCTGTTCCGGAAGAAACCCGGACCGAGAAAGAGAACAAAGAGCT

GGAAAACCTCGAGATCAACCTGCGGAAAGAGATCGCCAAGGCCTTCAAGGGCAACGAGGGCTACAAG

AGCCTGTTCAAGAAGGACATCATCGAGACAATCCTGCCTGAGTTCCTGGACGACAAGGACGAGATCG

CCCTGGTCAACAGCTTCAACGGCTTCACAACCGCCTTCACCGGCTTTTTCGACAACCGCGAGAATAT

GTTCAGCGAGGAAGCCAAGAGCACCTCTATCGCCTTCCGGTGCATCAACGAGAATCTGACCCGGTAC

ATCAGCAACATGGATATCTTCGAGAAGGTGGACGCCATCTTCGACAAGCACGAGGTGCAAGAGATCA
```

-continued

```
AAGAAAAGATCCTGAACAGCGACTACGACGTCGAGGACTTCTTCGAGGGCGAGTTCTTCAACTTCGT

GCTGACACAAGAGGGCATCGATGTGTACAACGCCATCATCGGCGGCTTCGTGACAGAGAGCGGCGAG

AAGATCAAGGGCCTGAACGAGTACATCAACCTCTACAACCAGAAAACGAAGCAGAAGCTGCCCAAGT

TCAAGCCCCTGTACAAACAGGTGCTGAGCGACAGAGAGAGCCTGTCCTTTTACGGCGAGGGCTATAC

CAGCGACGAAGAGGTGCTGGAAGTGTTCAGAAACACCCTGAACAAGAACAGCGAGATCTTCAGCTCC

ATCAAGAAGCTCGAAAAGCTGTTTAAGAACTTCGACGAGTACAGCAGCGCCGGCATCTTCGTGAAGA

ATGGCCCTGCCATCAGCACCATCTCCAAGGACATCTTCGGCGAGTGGAACGTGATCCGGGACAAGTG

GAACGCCGAGTACGACGACATCCACCTGAAGAAAAAGGCCGTGGTCACCGAGAAGTACGAGGACGAC

AGAAGAAAGAGCTTCAAGAAGATCGGCAGCTTCAGCCTGGAACAGCTGCAAGAGTACGCCGACGCCG

ATCTGAGCGTGGTGGAAAAGCTGAAAGAGATTATCATCCAGAAGGTCGACGAGATCTACAAGGTGTA

CGGCAGCAGCGAGAAGCTGTTCGACGCCGACTTTGTGCTGGAAAAGAGCCTCAAAAAGAACGACGCC

GTGGTGGCCATCATGAAGGACCTGCTGGATAGCGTGAAGTCCTTCGAGAACTATATTAAGGCCTTCT

TTGGCGAGGGCAAAGAGACAAACCGGGACGAGAGCTTCTACGGCGATTTCGTGCTGGCCTACGACAT

CCTGCTGAAAGTGGACCACATCTACGACGCCATCCGGAACTACGTGACCCAGAAGCCTTACAGCAAG

GACAAGTTTAAGCTGTACTTCCAGAATCCGCAGTTCATGGGCGGCTGGGACAAAGACAAAGAAACCG

ACTACCGGGCCACCATCCTGAGATACGGCTCCAAGTACTATCTGGCCATTATGGACAAGAAATACGC

CAAGTGCCTGCAGAAGATCGATAAGGACGACGTGAACGGCAACTACGAGAAGATTAACTACAAGCTG

CTGCCCGGACCTAACAAGATGCTGCCTAAGGTGTTCTTTAGCAAGAAATGGATGGCCTACTACAACC

CCAGCGAGGATATCCAGAAAATCTACAAGAACGGCACCTTCAAGAAAGGCGACATGTTCAACCTGAA

CGACTGCCACAAGCTGATCGATTTCTTCAAGGACAGCATCAGCGAGATACCCCAAGTGGTCCAACGCC

TACGACTTCAATTTCAGCGAGACAGAGAAGTATAAGGATATCGCCGGGTTCTACCGCGAGGTGGAAG

AACAGGGCTATAAGGTGTCCTTTGAGAGCGCCAGCAAGAAAGAGGTGGACAAGCTGGTCGAAGAGGG

CAAGCTGTACATGTTCCAGATCTATAACAAGGACTTCTCCGACAAGAGCCACGGCACCCCTAACCTG

CACACCATGTACTTTAAGCTGCTGTTCGATGAGAACAACCACGGCCAGATCAGACTGTCTGGCGGAG

CCGAGCTGTTTATGAGAAGGGCCAGCCTGAAAAAAGAGGAACTGGTCGTTCACCCCGCCAACTCTCC

AATCGCCAACAAGAACCCCGACAATCCCAAGAAAACCACCACACTGAGCTACGACGTGTACAAGGAT

AAGCGGTTCTCCGAGGACCAGTACGAGCTGCACATCCCTATCGCCATCAACAAGTGCCCCAAGAATA

TCTTCAAGATCAACACCGAAGTGCGGGTGCTGCTGAAGCACGACGACAACCCTTACGTGATCGGCAT

CGACAGAGGCGAGCGGAACCTGCTGTATATCGTGGTGGTGGACGGCAAGGGCAATATCGTGGAACAG

TACTCCCTGAATGAGATCATCAACAACTTCAATGGCATCCGGATCAAGACGGACTACCACAGCCTGC

TGGACAAAAAAGAGAAAGAACGCTTCGAGGCCCGGCAGAACTGGACCAGCATCGAGAACATCAAAGA

ACTGAAGGCCGGCTACATCTCCCAGGTGGTGCACAAGATCTGCGAGCTGGTTGAGAAGTATGACGCC

GTGATTGCCCTGGAAGATCTGAATAGCGGCTTTAAGAACAGCCGCGTGAAGGTCGAGAAACAGGTGT

ACCAGAAATTCGAGAAGATGCTGATCGACAAGCTGAACTACATGGTCGACAAGAAGTCTAACCCCTG

CGCCACAGGCGGAGCCCTGAAGGGATATCAGATCACCAACAAGTTCGAGTCCTTCAAGAGCATGAGC

ACCCAGAATGGCTTCATCTTCTACATCCCCGCCTGGCTGACCAGCAAGATCGATCCTAGCACCGGAT

TCGTGAACCTGCTCAAGACCAAGTACACCAGCATTGCCGACAGCAAGAAGTTCATCTCCAGCTTCGA

CCGGATTATGTACGTGCCCGAAGAGGACCTGTTCGAATTCGCCCTGGATTACAAGAACTTCAGCCGG

ACCGATGCCGACTATATCAAGAAGTGGAAGCTGTATAGCTACGGCAACCGCATCCGCATCTTCAGAA

ACCCGAAGAAAAACAACGTGTTCGACTGGGAAGAAGTGTGCCTGACCAGCGCCTACAAAGAACTCTT
```

-continued

CAACAAATACGGCATCAACTACCAGCAGGGCGACATCAGAGCCCTGCTGTGCGAGCAGAGCGACAAG

GCCTTTTACAGCTCCTTCATGGCCCTGATGTCCCTGATGCTGCAGATGCGGAATAGCATCACCGGCA

GGACCGACGTGGACTTCCTGATCAGCCCTGTGAAGAATTCCGACGGGATCTTCTACGACAGCAGAAA

CTACGAGGCTCAAGAGAACGCCATCCTGCCTAAGAACGCCGATGCCAACGGCGCCTATAATATCGCC

AGAAAGGTGCTGTGGGCCATCGGCCAGTTTAAGAAGGCCGAGGACGAGAAACTGGACAAAGTGAAGA

TCGCCATCTCTAACAAAGAGTGGCTGGAATACGCCCAGACCAGCGTGAAACAC

Hs optimized Lb Cpf1 AA

SEQ ID NO: 10

MLKNVGIDRLDVEKGRKNMSKLEKFTNCYSLSKTLRFKAIPVGKTQENIDNKRLLVEDEKRAEDYKG

VKKLLDRYYLSFINDVLHSIKLKNLNNYISLFRKKTRTEKENKELENLEINLRKEIAKAFKGNEGYK

SLFKKDIIETILPEFLDDKDEIALVNSFNGFTTAFTGFFDNRENMFSEEAKSTSIAFRCINENLTRY

ISNMDIFEKVDAIFDKHEVQEIKEKILNSDYDVEDFFEGEFFNFVLTQEGIDVYNAIIGGFVTESGE

KIKGLNEYINLYNQKTKQKLPKFKPLYKQVLSDRESLSFYGEGYTSDEEVLEVERNTLNKNSEIFSS

IKKLEKLFKNFDEYSSAGIFVKNGPAISTISKDIFGEWNVIRDKWNAEYDDIHLKKKAVVTEKYEDD

RRKSFKKIGSFSLEQLQEYADADLSVVEKLKEIIIQKVDEIYKVYGSSEKLFDADFVLEKSLKKNDA

VVAIMKDLLDSVKSFENYIKAFFGEGKETNRDESFYGDFVLAYDILLKVDHIYDAIRNYVTQKPYSK

DKFKLYFQNPQFMGGWDKDKETDYRATILRYGSKYYLAIMDKKYAKCLQKIDKDDVNGNYEKINYKL

LPGPNKMLPKVFFSKKWMAYYNPSEDIQKIYKNGTFKKGDMFNLNDCHKLIDFFKDSISRYPKWSNA

YDFNFSETEKYKDIAGFYREVEEQGYKVSFESASKKEVDKLVEEGKLYMFQTYNKDFSDKSHGTPNL

HTMYFKLLFDENNHGQIRLSGGAELFMRRASLKKEELVVHPANSPIANKNPDNPKKTTTLSYDVYKD

KRFSEDQYELHIPIAINKCPKNIFKINTEVRVLLKHDDNPYVIGIDRGERNLLYIVVVDGKGNIVEQ

YSLNEIINNFNGIRIKTDYHSLLDKKEKERFEARQNWTSIENIKELKAGYISQVVHKICELVEKYDA

VIALEDLNSGFKNSRVKVEKQVYQKFEKMLIDKLNYMVDKKSNPCATGGALKGYQITNKFESFKSMS

TQNGFIFYIPAWLTSKIDPSTGFVNLLKTKYTSIADSKKFISSFDRIMYVPEEDLFEFALDYKNFSR

TDADYIKKWKLYSYGNRIRIFRNPKKNNVFDWEEVCLTSAYKELFNKYGINYQQGDIRALLCEQSDK

AFYSSFMALMSLMLQMRNSITGRTDVDFLISPVKNSDGIFYDSRNYEAQENAILPKNADANGAYNIA

RKVLWAIGQFKKAEDEKLDKVKIAISNKEWLEYAQTSVKH

*E. coli* optimized Lb Cpf1 with flanking NLS's, V5 tag and 6x
His-DNA

SEQ ID NO: 13

ATGGGTAAACCGATTCCGAATCCGCTGCTGGGTCTGGATAGCACCGCACCGAAAAAAAAACGTAAAG

TTGGTATTCATGGTGTTCCGGCAGCACTGAAAAACGTGGGTATTGATCGTCTGGATGTTGAAAAAGG

TCGCAAAAATATGAGCAAACTGGAAAAGTTCACCAACTGTTATAGCCTGAGCAAAACCCTGCGTTTT

AAAGCAATTCCGGTTGGTAAAACCCAAGAGAACATTGATAATAAACGCCTGCTGGTCGAAGATGAAA

AACGCGCTGAAGATTATAAAGGCGTGAAAAAACTGCTGGATCGCTATTATCTGAGCTTCATTAACGA

TGTGCTGCACAGCATTAAACTGAAGAACCTGAACAACTATATCAGCCTGTTTCGTAAAAAAACCCGC

ACCGAAAAAGAAACAAAGAGCTGGAAAACCTGGAAATCAATCTGCGTAAAGAAATCGCCAAAGCGT

TTAAAGGTAACGAGGGTTATAAAAAGCCTGTTCAAGAAAGACATCATCGAAACCATTCTGCCGGAATT

TCTGGATGATAAAGATGAAATTGCCCTGGTGAATAGCTTTAATGGCTTTACCACCGCATTTACCGGC

TTTTTTGATAATCGCGAAAACATGTTCAGCGAAGAAGCAAAAAGCACCAGCATTGCATTTCGCTGCA

TTAATGAAAATCTGACCCGCTACATTAGCAACATGGATATCTTTGAAAAAGTGGACGCGATCTTCGA

TAAACACGAAGTGCAAGAGATCAAAGAGAAAATCCTGAACAGCGATTATGACGTCGAAGATTTTTTT

GAAGGCGAGTTCTTTAACTTCGTTCTGACCCAAGAAGGTATCGACGTTTATAACGCAATTATTGGTG

-continued

GTTTTGTTACCGAAAGCGGTGAGAAAATCAAAGGCCTGAATGAATATATCAACCTGTATAACCAGAA

AACCAAACAGAAACTGCCGAAATTCAAACCGCTGTATAAACAGGTTCTGAGCGATCGTGAAAGCCTG

AGCTTTTATGGTGAAGGTTATACCAGTGATGAAGAGGTTCTGGAAGTTTTTCGTAACACCCTGAATA

AAAACAGCGAGATCTTTAGCAGCATCAAAAAGCTTGAGAAACTGTTCAAAAACTTTGATGAGTATAG

CAGCGCAGGCATCTTTGTTAAAAATGGTCCGGCAATTAGCACCATCAGCAAAGATATTTTTGGCGAA

TGGAATGTGATCCGCGATAAATGGAATGCCGAATATGATGATATCCACCTGAAAAAAAAGGCCGTGG

TGACCGAGAAATATGAAGATGATCGTCGTAAAAGCTTCAAGAAAATTGGTAGCTTTAGCCTGGAACA

GCTGCAAGAATATGCAGATGCAGATCTGAGCGTTGTGGAAAAACTGAAAGAAATCATCATTCAGAAG

GTGGACGAGATCTATAAAGTTTATGGTAGCAGCGAAAAACTGTTCGATGCAGATTTTGTTCTGGAAA

AAAGCCTGAAAAAGAATGATGCCGTTGTGGCCATTATGAAAGATCTGCTGGATAGCGTTAAGAGCTT

CGAGAATTACATCAAAGCCTTTTTTGGTGAGGGCAAAGAAACCAATCGTGATGAAAGTTTCTATGGC

GATTTTGTGCTGGCCTATGATATTCTGCTGAAAGTGGACCATATTTATGATGCCATTCGCAATTATG

TTACCCAGAAACCGTATAGCAAAGACAAGTTCAAACTGTACTTTCAGAACCCGCAGTTTATGGGTGG

TTGGGATAAAGATAAAGAAACCGATTATCGTGCCACCATCCTGCGTTATGGTAGTAAATACTATCTG

GCCATCATGGACAAAAAATACGCAAAATGCCTGCAGAAAATCGACAAAGATGATGTGAATGGCAACT

ATGAAAAAATCAACTACAAACTGCTGCCTGGTCCGAATAAAATGCTGCCGAAAGTGTTCTTTAGCAA

GAAATGGATGGCCTATTATAACCCGAGCGAGGATATTCAAAAGATCTACAAAAATGGCACCTTTAAA

AAGGGCGACATGTTCAATCTGAACGATTGCCACAAACTGATCGATTTCTTCAAAGATTCAATTTCGC

GTTATCCGAAATGGTCCAATGCCTATGATTTTAACTTTAGCGAAACCGAAAAATACAAAGACATTGC

CGGTTTTTATCGCGAAGTGGAAGAACAGGGCTATAAAGTGAGCTTTGAAAGCGCAAGCAAAAAGAG

GTTGATAAGCTGGTTGAAGAGGGCAAACTGTATATGTTCCAGATTTACAACAAAGATTTTAGCGACA

AAAGCCATGGCACCCCGAATCTGCATACCATGTACTTTAAACTGCTGTTCGACGAAAATAACCATGG

TCAGATTCGTCTGAGCGGTGGTGCCGAACTGTTTATGCGTCGTGCAAGTCTGAAAAAAGAAGAACTG

GTTGTTCATCCGGCAAATAGCCCGATTGCAAACAAAAATCCGGACAATCCGAAAAAAACCACGACAC

TGAGCTATGATGTGTATAAAGACAAACGTTTTAGCGAGGATCAGTATGAACTGCATATCCCGATTGC

CATCAATAAATGCCCGAAAAACATCTTTAAGATCAACACCGAAGTTCGCGTGCTGCTGAAACATGAT

GATAATCCGTATGTGATTGGCATTGATCGTGGTGAACGTAACCTGCTGTATATTGTTGTTGTTGATG

GTAAAGGCAACATCGTGGAACAGTATAGTCTGAACGAAATTATCAACAACTTTAACGGCATCCGCAT

CAAAACCGACTATCATAGCCTGCTGGACAAGAAAGAAAAAGAACGTTTTGAAGCACGTCAGAACTGG

ACCAGTATTGAAAACATCAAAGAACTGAAAGCCGGTTATATTAGCCAGGTGGTTCATAAAATCTGTG

AGCTGGTAGAAAAATACGATGCAGTTATTGCACTGGAAGATCTGAATAGCGGTTTCAAAAATAGCCG

TGTGAAAGTCGAAAAACAGGTGTATCAGAAATTCGAGAAAATGCTGATCGACAAACTGAACTACATG

GTCGACAAAAAAAGCAATCCGTGTGCAACCGGTGGTGCACTGAAAGGTTATCAGATTACCAACAAAT

TTGAAAGCTTTAAAAGCATGAGCACCCAGAACGGCTTTATCTTCTATATTCCGGCATGGCTGACCAG

CAAAATTGATCCGAGCACCGGTTTTGTGAACCTGCTGAAAACAAAATATACCTCCATTGCCGACAGC

AAGAAGTTTATTAGCAGCTTTGATCGCATTATGTATGTTCCGGAAGAGGACCTGTTTGAATTCGCAC

TGGATTACAAAAATTTCAGCCGTACCGATGCCGACTACATCAAAAAATGGAAACTGTACAGCTATGG

TAACCGCATTCGCATTTTTCGCAACCCGAAGAAAAACAATGTGTTCGATTGGGAAGAAGTTTGTCTG

ACCAGCGCATATAAAGAACTTTTCAACAAATACGGCATCAACTATCAGCAGGGTGATATTCGTGCAC

TGCTGTGTGAACAGAGCGATAAAGCGTTTTATAGCAGTTTTATGGCACTGATGAGCCTGATGCTGCA

GATGCGTAATAGCATTACCGGTCGCACCGATGTGGATTTTCTGATTAGTCCGGTGAAAAATTCCGAT

-continued

GGCATCTTTTATGATAGCCGCAATTACGAAGCACAAGAAAATGCAATTCTGCCGAAAAACGCAGATG

CAAATGGTGCATATAACATTGCACGTAAAGTTCTGTGGGCAATTGGCCAGTTTAAGAAAGCAGAAGA

TGAGAAGCTGGACAAAGTGAAAATTGCGATCAGCAATAAAGAGTGGCTGGAATACGCACAGACCAGC

GTTAAACATCCGAAAAAAAAACGCAAAGTGCTCGAGCACCACCACCACCACCACTGA

Amino acid sequence for LbCpf1 fusion, with 5'-and 3'-flanking
NLS's, 5'-V5 tag and 3'-6x His, used for gene editing in both
E. coli and human cells

SEQ ID NO: 14

MGKPIPNPLLGLDSTAPKKKRKVGIHGVPAALKNVGIDRLDVEKGRKNMSKLEKFTNCYSLSKTLRF

KAIPVGKTQENIDNKRLLVEDEKRAEDYKGVKKLLDRYYLSFINDVLHSIKLKNLNNYISLFRKKTR

TEKENKELENLEINLRKEIAKAFKGNEGYKSLFKKDIIETILPEFLDDKDEIALVNSFNGFTTAFTG

FFDNRENMFSEEAKSTSIAFRCINENLTRYISNMDIFEKVDAIFDKHEVQEIKEKILNSDYDVEDFF

EGEFFNFVLTQEGIDVYNAIIGGFVTESGEKIKGLNEYINLYNQKTKQKLPKFKPLYKQVLSDRESL

SFYGEGYTSDEEVLEVERNTLNKNSEIFSSIKKLEKLFKNFDEYSSAGIFVKNGPAISTISKDIFGE

WNVIRDKWNAEYDDIHLKKKAVVTEKYEDDRRKSFKKIGSFSLEQLQEYADADLSVVEKLKEIIIQK

VDEIYKVYGSSEKLFDADFVLEKSLKKNDAVVAIMKDLLDSVKSFENYIKAFFGEGKETNRDESFYG

DFVLAYDILLKVDHIYDAIRNYVTQKPYSKDKFKLYFQNPQFMGGWDKDKETDYRATILRYGSKYYL

AIMDKKYAKCLQKIDKDDVNGNYEKINYKLLPGPNKMLPKVFFSKKWMAYYNPSEDIQKIYKNGTFK

KGDMFNLNDCHKLIDFFKDSISRYPKWSNAYDFNFSETEKYKDIAGFYREVEEQGYKVSFESASKKE

VDKLVEEGKLYMFQTYNKDFSDKSHGTPNLHTMYFKLLFDENNHGQIRLSGGAELFMRRASLKKEEL

VVHPANSPIANKNPDNPKKTTTLSYDVYKDKRFSEDQYELHIPIAINKCPKNIFKINTEVRVLLKHD

DNPYVIGIDRGERNLLYIVVVDGKGNIVEQYSLNEIINNFNGIRIKTDYHSLLDKKEKERFEARQNW

TSIENIKELKAGYISQVVHKICELVEKYDAVIALEDLNSGFKNSRVKVEKQVYQKFEKMLIDKLNYM

VDKKSNPCATGGALKGYQITNKFESFKSMSTQNGFIFYIPAWLTSKIDPSTGFVNLLKTKYTSIADS

KKFISSFDRIMYVPEEDLFEFALDYKNFSRTDADYIKKWKLYSYGNRIRIFRNPKKNNVFDWEEVCL

TSAYKELFNKYGINYQQGDIRALLCEQSDKAFYSSFMALMSLMLQMRNSITGRTDVDFLISPVKNSD

GIFYDSRNYEAQENAILPKNADANGAYNIARKVLWAIGQFKKAEDEKLDKVKIAISNKEWLEYAQTS

VKHPKKKRKVLEHHHHHH

Hs optimized Lb Cpf1 with flanking NLS's, V5 tag and 6x His-DNA

SEQ ID NO: 17

ATGGGCAAGCCCATTCCTAATCCTCTGCTGGGCCTCGACAGCACAGCCCCTAAGAAAAAGCGGAAAG

TGGGCATCCATGGCGTGCCAGCCGCTCTGAAGAATGTGGGCATCGACAGACTGGACGTGGAAAAGGG

CAGAAAGAACATGAGCAAGCTCGAGAAGTTCACCAACTGCTACAGCCTGAGCAAGACCCTGCGGTTC

AAGGCCATTCCTGTGGGCAAGACCCAAGAGAACATCGACAACAAGCGGCTGCTGGTGGAAGATGAGA

AGAGAGCCGAGGACTACAAGGGCGTGAAGAAGCTGCTGGACCGGTACTACCTGAGCTTCATCAACGA

CGTGCTGCACAGCATCAAGCTGAAGAACCTGAACAACTACATCAGCCTGTTCCGGAAGAAAACCCGG

ACCGAGAAGAGAACAAAGAGCTGGAAAACCTCGAGATCAACCTGCGGAAAGAGATCGCCAAGGCCT

TCAAGGGCAACGAGGGCTACAAGAGCCTGTTCAAGAAGGACATCATCGAGACAATCCTGCCTGAGTT

CCTGGACGACAAGGACGAGATCGCCCTGGTCAACAGCTTCAACGGCTTCACAACCGCCTTCACCGGC

TTTTTCGACAACCGCGAGAATATGTTCAGCGAGGAAGCCAAGAGCACCTCTATCGCCTTCCGGTGCA

TCAACGAGAATCTGACCCGGTACATCAGCAACATGGATATCTTCGAGAAGGTGGACGCCATCTTCGA

CAAGCACGAGGTGCAAGAGATCAAAGAAAAGATCCTGAACAGCGACTACGACGTCGAGGACTTCTTC

GAGGGCGAGTTCTTCAACTTCGTGCTGACACAAGAGGGCATCGATGTGTACAACGCCATCATCGGCG

-continued

```
GCTTCGTGACAGAGAGCGGCGAGAAGATCAAGGGCCTGAACGAGTACATCAACCTCTACAACCAGAA

AACGAAGCAGAAGCTGCCCAAGTTCAAGCCCCTGTACAAACAGGTGCTGAGCGACAGAGAGAGCCTG

TCCTTTTACGGCGAGGGCTATACCAGCGACGAAGAGGTGCTGGAAGTGTTCAGAAACACCCTGAACA

AGAACAGCGAGATCTTCAGCTCCATCAAGAAGCTCGAAAAGCTGTTTAAGAACTTCGACGAGTACAG

CAGCGCCGGCATCTTCGTGAAGAATGGCCCTGCCATCAGCACCATCTCCAAGGACATCTTCGGCGAG

TGGAACGTGATCCGGGACAAGTGGAACGCCGAGTACGACGACATCCACCTGAAGAAAAAGGCCGTGG

TCACCGAGAAGTACGAGGACGACAGAAGAAAGAGCTTCAAGAAGATCGGCAGCTTCAGCCTGGAACA

GCTGCAAGAGTACGCCGACGCCGATCTGAGCGTGGTGGAAAAGCTGAAAGAGATTATCATCCAGAAG

GTCGACGAGATCTACAAGGTGTACGGCAGCAGCGAGAAGCTGTTCGACGCCGACTTTGTGCTGGAAA

AGAGCCTCAAAAAGAACGACGCCGTGGTGGCCATCATGAAGGACCTGCTGGATAGCGTGAAGTCCTT

CGAGAACTATATTAAGGCCTTCTTTGGCGAGGGCAAAGAGACAAACCGGGACGAGAGCTTCTACGGC

GATTTCGTGCTGGCCTACGACATCCTGCTGAAAGTGGACCACATCTACGACGCCATCCGGAACTACG

TGACCCAGAAGCCTTACAGCAAGGACAAGTTTAAGCTGTACTTCCAGAATCCGCAGTTCATGGGCGG

CTGGGACAAAGACAAAGAAACCGACTACCGGGCCACCATCCTGAGATACGGCTCCAAGTACTATCTG

GCCATTATGGACAAGAAATACGCCAAGTGCCTGCAGAAGATCGATAAGGACGACGTGAACGGCAACT

ACGAGAAGATTAACTACAAGCTGCTGCCCGGACCTAACAAGATGCTGCCTAAGGTGTTCTTTAGCAA

GAAATGGATGGCCTACTACAACCCCAGCGAGGATATCCAGAAAATCTACAAGAACGGCACCTTCAAG

AAAGGCGACATGTTCAACCTGAACGACTGCCACAAGCTGATCGATTTCTTCAAGGACAGCATCAGCA

GATACCCCAAGTGGTCCAACGCCTACGACTTCAATTTCAGCGAGACAGAGAAGTATAAGGATATCGC

CGGGTTCTACCGCGAGGTGGAAGAACAGGGCTATAAGGTGTCCTTTGAGAGCGCCAGCAAGAAAGAG

GTGGACAAGCTGGTCGAAGAGGGCAAGCTGTACATGTTCCAGATCTATAACAAGGACTTCTCCGACA

AGAGCCACGGCACCCCTAACCTGCACACCATGTACTTTAAGCTGCTGTTCGATGAGAACAACCACGG

CCAGATCAGACTGTCTGGCGGAGCCGAGCTGTTTATGAGAAGGGCCAGCCTGAAAAAAGAGGAACTG

GTCGTTCACCCCGCCAACTCTCCAATCGCCAACAAGAACCCCGACAATCCCAAGAAAACCACCACAC

TGAGCTACGACGTGTACAAGGATAAGCGGTTCTCCGAGGACCAGTACGAGCTGCACATCCCTATCGC

CATCAACAAGTGCCCCAAGAATATCTTCAAGATCAACACCGAAGTGCGGGTGCTGCTGAAGCACGAC

GACAACCCTTACGTGATCGGCATCGATCGGGGCGAGAGAAACCTGCTGTATATCGTGGTGGTGGACG

GCAAGGGCAATATCGTGGAACAGTACTCCCTGAATGAGATCATCAACAACTTCAATGGCATCCGGAT

CAAGACGGACTACCACAGCCTGCTGGACAAAAAAGAGAAAGAACGCTTCGAGGCCAGGCAGAACTGG

ACCAGCATCGAGAACATCAAAGAACTGAAGGCCGGCTACATCTCCCAGGTGGTGCACAAGATCTGCG

AGCTGGTTGAGAAGTATGACGCCGTGATTGCCCTGGAAGATCTGAATAGCGGCTTTAAGAACAGCCG

CGTGAAGGTCGAGAAACAGGTGTACCAGAAATTCGAGAAGATGCTGATCGACAAGCTGAACTACATG

GTCGACAAGAAGTCTAACCCCTGCGCCACAGGCGGAGCCCTGAAGGGATATCAGATCACCAACAAGT

TCGAGTCCTTCAAGAGCATGAGCACCCAGAATGGCTTCATCTTCTACATCCCCGCCTGGCTGACCAG

CAAGATCGATCCTAGCACCGGATTCGTGAACCTGCTCAAGACCAAGTACACCAGCATTGCCGACAGC

AAGAAGTTCATCTCCAGCTTCGACCGGATTATGTACGTGCCCGAAGAGGACCTGTTCGAATTCGCCC

TGGATTACAAGAACTTCAGCCGGACCGATGCCGACTATATCAAGAAGTGGAAGCTGTATAGCTACGG

CAACCGCATCCGCATCTTCAGAAACCCGAAGAAAAACAACGTGTTCGACTGGGAAGAAGTGTGCCTG

ACCAGCGCCTACAAAGAACTCTTCAACAAATACGGCATCAACTACCAGCAGGGCGACATCAGAGCCC

TGCTGTGCGAGCAGAGCGACAAGGCCTTTTACAGCTCCTTCATGGCCCTGATGAGCCTGATGCTGCA

GATGCGGAATAGCATCACCGGCAGAACCGACGTGGACTTCCTGATCAGCCCCGTGAAAAACTCCGAC
```

-continued

GGCATCTTTTACGACAGCCGGAATTACGAGGCTCAAGAGAACGCCATCCTGCCTAAGAACGCCGATG

CCAACGGCGCCTATAATATCGCCAGAAAGGTGCTGTGGGCCATCGGCCAGTTTAAGAAGGCCGAGGA

CGAGAAACTGGACAAAGTGAAGATCGCCATCTCTAACAAAGAGTGGCTGGAATACGCCCAGACCAGC

GTGAAGCACCCCAAAAAGAAACGGAAAGTGCTGGAACACCACCACCATCACCAC

*E. coli* optimized Lb Cpf1 with OpTNLS and 6x His-AA

SEQ ID NO: 20

MGDPLKNVGIDRLDVEKGRKNMSKLEKFTNCYSLSKTLRFKAIPVGKTQENIDNKRLLVEDEKRAED

YKGVKKLLDRYYLSFINDVLHSIKLKNLNNYISLFRKKTRTEKENKELENLEINLRKEIAKAFKGNE

GYKSLFKKDIIETILPEFLDDKDEIALVNSFNGFTTAFTGFFDNRENMFSEEAKSTSIAFRCINENL

TRYISNMDIFEKVDAIFDKHEVQEIKEKILNSDYDVEDFFEGEFFNFVLTQEGIDVYNAIIGGFVTE

SGEKIKGLNEYINLYNQKTKQKLPKFKPLYKQVLSDRESLSFYGEGYTSDEEVLEVERNTLNKNSEI

FSSIKKLEKLFKNFDEYSSAGIFVKNGPAISTISKDIFGEWNVIRDKWNAEYDDIHLKKKAVVTEKY

EDDRRKSFKKIGSFSLEQLQEYADADLSVVEKLKEIIIQKVDEIYKVYGSSEKLFDADFVLEKSLKK

NDAVVAIMKDLLDSVKSFENYIKAFFGEGKETNRDESFYGDFVLAYDILLKVDHIYDAIRNYVTQKP

YSKDKFKLYFQNPQFMGGWDKDKETDYRATILRYGSKYYLAIMDKKYAKCLQKIDKDDVNGNYEKIN

YKLLPGPNKMLPKVFFSKKWMAYYNPSEDIQKIYKNGTFKKGDMFNLNDCHKLIDFFKDSISRYPKW

SNAYDFNFSETEKYKDIAGFYREVEEQGYKVSFESASKKEVDKLVEEGKLYMFQTYNKDFSDKSHGT

PNLHTMYFKLLFDENNHGQIRLSGGAELFMRRASLKKEELVVHPANSPIANKNPDNPKKTTTLSYDV

YKDKRFSEDQYELHIPIAINKCPKNIFKINTEVRVLLKHDDNPYVIGIDRGERNLLYIVVVDGKGNI

VEQYSLNEIINNFNGIRIKTDYHSLLDKKEKERFEARQNWTSIENIKELKAGYISQVVHKICELVEK

YDAVIALEDLNSGFKNSRVKVEKQVYQKFEKMLIDKLNYMVDKKSNPCATGGALKGYQITNKFESFK

SMSTQNGFIFYIPAWLTSKIDPSTGFVNLLKTKYTSIADSKKFISSFDRIMYVPEEDLFEFALDYKN

FSRTDADYIKKWKLYSYGNRIRIFRNPKKNNVFDWEEVCLTSAYKELFNKYGINYQQGDIRALLCEQ

SDKAFYSSFMALMSLMLQMRNSITGRTDVDFLISPVKNSDGIFYDSRNYEAQENAILPKNADANGAY

NIARKVLWAIGQFKKAEDEKLDKVKIAISNKEWLEYAQTSVKHGRSSDDEATADSQHAAPPKKKRKV

LEHHHHHH

*E. coli* optimized Lb Cpf1 with OpTNLS and 6x His-DNA

SEQ ID NO: 23

ATGGGGGATCCACTGAAAAACGTGGGTATTGATCGTCTGGATGTTGAAAAAGGTCGCAAAAATATGA

GCAAACTGGAAAAGTTCACCAACTGTTATAGCCTGAGCAAAACCCTGCGTTTTAAAGCAATTCCGGT

TGGTAAAACCCAAGAGAACATTGATAATAAACGCCTGCTGGTCGAAGATGAAAAACGCGCTGAAGAT

TATAAAGGCGTGAAAAAACTGCTGGATCGCTATTATCTGAGCTTCATTAACGATGTGCTGCACAGCA

TTAAACTGAAGAACCTGAACAACTATATCAGCCTGTTTCGTAAAAAAACCCGCACCGAAAAAGAAA

CAAAGAGCTGGAAAACCTGGAAATCAATCTGCGTAAAGAAATCGCCAAAGCGTTTAAAGGTAACGAG

GGTTATAAAAGCCTGTTCAAGAAAGACATCATCGAAACCATTCTGCCGGAATTTCTGGATGATAAAG

ATGAAATTGCCCTGGTGAATAGCTTTAATGGCTTTACCACCGCATTTACCGGCTTTTTTGATAATCG

CGAAAACATGTTCAGCGAAGAAGCAAAAAGCACCAGCATTGCATTTCGCTGCATTAATGAAAATCTG

ACCCGCTACATTAGCAACATGGATATCTTTGAAAAAGTGGACGCGATCTTCGATAAACACGAAGTGC

AAGAGATCAAAGAGAAAATCCTGAACAGCGATTATGACGTCGAAGATTTTTTTGAAGGCGAGTTCTT

TAACTTCGTTCTGACCCAAGAAGGTATCGACGTTTATAACGCAATTATTGGTGGTTTTGTTACCGAA

AGCGGTGAGAAAATCAAAGGCCTGAATGAATATATCAACCTGTATAACCAGAAAACCAAACAGAAAC

TGCCGAAATTCAAACCGCTGTATAAACAGGTTCTGAGCGATCGTGAAAGCCTGAGCTTTTATGGTGA

-continued

```
AGGTTATACCAGTGATGAAGAGGTTCTGGAAGTTTTTCGTAACACCCTGAATAAAAACAGCGAGATC

TTTAGCAGCATCAAAAAGCTTGAGAAACTGTTCAAAAACTTTGATGAGTATAGCAGCGCAGGCATCT

TTGTTAAAAATGGTCCGGCAATTAGCACCATCAGCAAAGATATTTTTGGCGAATGGAATGTGATCCG

CGATAAATGGAATGCCGAATATGATGATATCCACCTGAAAAAAAAGGCCGTGGTGACCGAGAAATAT

GAAGATGATCGTCGTAAAAGCTTCAAGAAAATTGGTAGCTTTAGCCTGGAACAGCTGCAAGAATATG

CAGATGCAGATCTGAGCGTTGTGGAAAAACTGAAAGAAATCATCATTCAGAAGGTGGACGAGATCTA

TAAAGTTTATGGTAGCAGCGAAAAACTGTTCGATGCAGATTTTGTTCTGGAAAAAAGCCTGAAAAAG

AATGATGCCGTTGTGGCCATTATGAAAGATCTGCTGGATAGCGTTAAGAGCTTCGAGAATTACATCA

AAGCCTTTTTTGGTGAGGGCAAAGAAACCAATCGTGATGAAAGTTTCTATGGCGATTTTGTGCTGGC

CTATGATATTCTGCTGAAAGTGGACCATATTTATGATGCCATTCGCAATTATGTTACCCAGAAACCG

TATAGCAAAGACAAGTTCAAACTGTACTTTCAGAACCCGCAGTTTATGGGTGGTTGGGATAAAGATA

AAGAAACCGATTATCGTGCCACCATCCTGCGTTATGGTAGTAAATACTATCTGGCCATCATGGACAA

AAAATACGCAAAATGCCTGCAGAAAATCGACAAAGATGATGTGAATGGCAACTATGAAAAAATCAAC

TACAAACTGCTGCCTGGTCCGAATAAAATGCTGCCGAAAGTGTTCTTTAGCAAGAAATGGATGGCCT

ATTATAACCCGAGCGAGGATATTCAAAAGATCTACAAAAATGGCACCTTTAAAAAGGGCGACATGTT

CAATCTGAACGATTGCCACAAACTGATCGATTTCTTCAAAGATTCAATTTCGCGTTATCCGAAATGG

TCCAATGCCTATGATTTTAACTTTAGCGAAACCGAAAAATACAAAGACATTGCCGGTTTTTATCGCG

AAGTGGAAGAACAGGGCTATAAAGTGAGCTTTGAAAGCGCAAGCAAAAAAGAGGTTGATAAGCTGGT

TGAAGAGGGCAAACTGTATATGTTCCAGATTTACAACAAAGATTTTAGCGACAAAAGCCATGGCACC

CCGAATCTGCATACCATGTACTTTAAACTGCTGTTCGACGAAAATAACCATGGTCAGATTCGTCTGA

GCGGTGGTGCCGAACTGTTTATGCGTCGTGCCAAGTCTGAAAAAAAGAAGAACTGGTTGTTCATCCGGC

AAATAGCCCGATTGCAAACAAAAATCCGGACAATCCGAAAAAAACCACGACACTGAGCTATGATGTG

TATAAAGACAAACGTTTTAGCGAGGATCAGTATGAACTGCATATCCCGATTGCCATCAATAAATGCC

CGAAAAACATCTTTAAGATCAACACCGAAGTTCGCGTGCTGCTGAAACATGATGATAATCCGTATGT

GATTGGCATTGATCGTGGTGAACGTAACCTGCTGTATATTGTTGTTGTTGATGGTAAAGGCAACATC

GTGGAACAGTATAGTCTGAACGAAATTATCAACAACTTTAACGGCATCCGCATCAAAACCGACTATC

ATAGCCTGCTGGACAAGAAAGAAAAAGAACGTTTTGAAGCACGTCAGAACTGGACCAGTATTGAAAA

CATCAAAGAACTGAAAGCCGGTTATATTAGCCAGGTGGTTCATAAAATCTGTGAGCTGGTAGAAAAA

TACGATGCAGTTATTGCACTGGAAGATCTGAATAGCGGTTTCAAAAATAGCCGTGTGAAAGTCGAAA

AACAGGTGTATCAGAAATTCGAGAAAATGCTGATCGACAAACTGAACTACATGGTCGACAAAAAAAG

CAATCCGTGTGCAACCGGTGGTGCACTGAAAGGTTATCAGATTACCAACAAATTTGAAAGCTTTAAA

AGCATGAGCACCCAGAACGGCTTTATCTTCTATATTCCGGCATGGCTGACCAGCAAAATTGATCCGA

GCACCGGTTTTGTGAACCTGCTGAAAACAAAATATACCTCCATTGCCGACAGCAAGAAGTTTATTAG

CAGCTTTGATCGCATTATGTATGTTCCGGAAGAGGACCTGTTTGAATTCGCACTGGATTACAAAAAT

TTCAGCCGTACCGATGCCGACTACATCAAAAAATGGAAACTGTACAGCTATGGTAACCGCATTCGCA

TTTTTCGCAACCCGAAGAAAAACAATGTGTTCGATTGGGAAGAAGTTTGTCTGACCAGCGCATATAA

AGAACTTTTCAACAAATACGGCATCAACTATCAGCAGGGTGATATTCGTGCACTGCTGTGTGAACAG

AGCGATAAAGCGTTTTATAGCAGTTTTATGGCACTGATGAGCCTGATGCTGCAGATGCGTAATAGCA

TTACCGGTCGCACCGATGTGGATTTTCTGATTAGTCCGGTGAAAAATTCCGATGGCATCTTTTATGA

TAGCCGCAATTACGAAGCACAAGAAAATGCAATTCTGCCGAAAAACGCGAGATGCAAATGGTGCATAT

AACATTGCACGTAAAGTTCTGTGGGCAATTGGCCAGTTTAAGAAAGCAGAAGATGAGAAGCTGGACA
```

-continued

AAGTGAAAATTGCGATCAGCAATAAAGAGTGGCTGGAATACGCACAGACCAGCGTTAAACATGGTCG

TAGCAGTGATGATGAAGCAACCGCAGATAGCCAGCATGCAGCACCGCCGAAAAAAAAAACGCAAAGTG

CTCGAGCACCACCACCACCACCACTGA

Hs optimized Lb Cpf1 with OpT NLS and 6x His-DNA

SEQ ID NO: 396

ATGCTGAAGAACGTGGGCATCGACCGGCTGGACGTGGAAAAGGGCAGAAAGAACATGAGCAAGCTCG

AGAAGTTCACCAACTGCTACAGCCTGAGCAAGACCCTGCGGTTCAAGGCCATTCCTGTGGGCAAGAC

CCAAGAGAACATCGACAACAAGCGGCTGCTGGTGGAAGATGAGAAGAGAGCCGAGGACTACAAGGGC

GTGAAGAAGCTGCTGGACCGGTACTACCTGAGCTTCATCAACGACGTGCTGCACAGCATCAAGCTCA

AGAACCTGAACAACTACATCAGCCTGTTCCGGAAGAAAACCCGGACCGAGAAAGAGAACAAAGAGCT

GGAAAACCTCGAGATCAACCTGCGGAAAGAGATCGCCAAGGCCTTCAAGGGCAACGAGGGCTACAAG

AGCCTGTTCAAGAAGGACATCATCGAGACAATCCTGCCTGAGTTCCTGGACGACAAGGACGAGATCG

CCCTGGTCAACAGCTTCAACGGCTTCACAACCGCCTTCACCGGCTTTTTCGACAACCGCGAGAATAT

GTTCAGCGAGGAAGCCAAGAGCACCTCTATCGCCTTCCGGTGCATCAACGAGAATCTGACCCGGTAC

ATCAGCAACATGGATATCTTCGAGAAGGTGGACGCCATCTTCGACAAGCACGAGGTGCAAGAGATCA

AAGAAAAGATCCTGAACAGCGACTACGACGTCGAGGACTTCTTCGAGGGCGAGTTCTTCAACTTCGT

GCTGACACAAGAGGGCATCGATGTGTACAACGCCATCATCGGCGGCTTCGTGACAGAGAGCGGCGAG

AAGATCAAGGGCCTGAACGAGTACATCAACCTCTACAACCAGAAAACGAAGCAGAAGCTGCCCAAGT

TCAAGCCCCTGTACAAACAGGTGCTGAGCGACAGAGAGAGCCTGTCCTTTTACGGCGAGGGCTATAC

CAGCGACGAAGAGGTGCTGGAAGTGTTCAGAAACACCCTGAACAAGAACAGCGAGATCTTCAGCTCC

ATCAAGAAGCTCGAAAAGCTGTTTAAGAACTTCGACGAGTACAGCAGCGCCGGCATCTTCGTGAAGA

ATGGCCCTGCCATCAGCACCATCTCCAAGGACATCTTCGGCGAGTGGAACGTGATCCGGGACAAGTG

GAACGCCGAGTACGACGACATCCACCTGAAGAAAAAGGCCGTGGTCACCGAGAAGTACGAGGACGAC

AGAAGAAAGAGCTTCAAGAAGATCGGCAGCTTCAGCCTGGAACAGCTGCAAGAGTACGCCGACGCCG

ATCTGAGCGTGGTGGAAAAGCTGAAAGAGATTATCATCCAGAAGGTCGACGAGATCTACAAGGTGTA

CGGCAGCAGCGAGAAGCTGTTCGACGCCGACTTTGTGCTGGAAAAGAGCCTCAAAAAGAACGACGCC

GTGGTGGCCATCATGAAGGACCTGCTGGATAGCGTGAAGTCCTTCGAGAACTATATTAAGGCCTTCT

TTGGCGAGGGCAAAGAGACAAACCGGGACGAGAGCTTCTACGGCGATTTCGTGCTGGCCTACGACAT

CCTGCTGAAAGTGGACCACATCTACGACGCCATCCGGAACTACGTGACCCAGAAGCCTTACAGCAAG

GACAAGTTTAAGCTGTACTTCCAGAATCCGCAGTTCATGGGCGGCTGGGACAAAGACAAAGAAACCG

ACTACCGGGCCACCATCCTGAGATACGGCTCCAAGTACTATCTGGCCATTATGGACAAGAAATACGC

CAAGTGCCTGCAGAAGATCGATAAGGACGACGTGAACGGCAACTACGAGAAGATTAACTACAAGCTG

CTGCCCGGACCTAACAAGATGCTGCCTAAGGTGTTCTTTAGCAAGAAATGGATGGCCTACTACAACC

CCAGCGAGGATATCCAGAAAATCTACAAGAACGGCACCTTCAAGAAAGGCGACATGTTCAACCTGAA

CGACTGCCACAAGCTGATCGATTTCTTCAAGGACAGCATCAGCAGATACCCCAAGTGGTCCAACGCC

TACGACTTCAATTTCAGCGAGACAGAGAAGTATAAGGATATCGCCGGGTTCTACCGCGAGGTGGAAG

AACAGGGCTATAAGGTGTCCTTTGAGAGCGCCAGCAAGAAAGAGGTGGACAAGCTGGTCGAAGAGGG

CAAGCTGTACATGTTCCAGATCTATAACAAGGACTTCTCCGACAAGAGCCACGGCACCCCTAACCTG

CACACCATGTACTTTAAGCTGCTGTTCGATGAGAACAACCACGGCCAGATCAGACTGTCTGGCGGAG

CCGAGCTGTTTATGAGAAGGGCCAGCCTGAAAAAAGAGGAACTGGTCGTTCACCCCGCCAACTCTCC

AATCGCCAACAAGAACCCCGACAATCCCAAGAAAACCACCACACTGAGCTACGACGTGTACAAGGAT

```
AAGCGGTTCTCCGAGGACCAGTACGAGCTGCACATCCCTATCGCCATCAACAAGTGCCCCAAGAATA

TCTTCAAGATCAACACCGAAGTGCGGGTGCTGCTGAAGCACGACGACAACCCTTACGTGATCGGCAT

CGACAGAGGCGAGCGGAACCTGCTGTATATCGTGGTGGTGGACGGCAAGGGCAATATCGTGGAACAG

TACTCCCTGAATGAGATCATCAACAACTTCAATGGCATCCGGATCAAGACGGACTACCACAGCCTGC

TGGACAAAAAGAGAAAGAACGCTTCGAGGCCCGGCAGAACTGGACCAGCATCGAGAACATCAAAGA

ACTGAAGGCCGGCTACATCTCCCAGGTGGTGCACAAGATCTGCGAGCTGGTTGAGAAGTATGACGCC

GTGATTGCCCTGGAAGATCTGAATAGCGGCTTTAAGAACAGCCGCGTGAAGGTCGAGAAACAGGTGT

ACCAGAAATTCGAGAAGATGCTGATCGACAAGCTGAACTACATGGTCGACAAGAAGTCTAACCCCTG

CGCCACAGGCGGAGCCCTGAAGGGATATCAGATCACCAACAAGTTCGAGTCCTTCAAGAGCATGAGC

ACCCAGAATGGCTTCATCTTCTACATCCCCGCCTGGCTGACCAGCAAGATCGATCCTAGCACCGGAT

TCGTGAACCTGCTCAAGACCAAGTACACCAGCATTGCCGACAGCAAGAAGTTCATCTCCAGCTTCGA

CCGGATTATGTACGTGCCCGAAGAGGACCTGTTCGAATTCGCCCTGGATTACAAGAACTTCAGCCGG

ACCGATGCCGACTATATCAAGAAGTGGAAGCTGTATAGCTACGGCAACCGCATCCGCATCTTCAGAA

ACCCGAAGAAAAACAACGTGTTCGACTGGGAAGAAGTGTGCCTGACCAGCGCCTACAAGAACTCTT

CAACAAATACGGCATCAACTACCAGCAGGGCGACATCAGAGCCCTGCTGTGCGAGCAGAGCGACAAG

GCCTTTTACAGCTCCTTCATGGCCCTGATGTCCCTGATGCTGCAGATGCGGAATAGCATCACCGGCA

GGACCGACGTGGACTTCCTGATCAGCCCTGTGAAGAATTCCGACGGGATCTTCTACGACAGCAGAAA

CTACGAGGCTCAAGAGAACGCCATCCTGCCTAAGAACGCCGATGCCAACGGCGCCTATAATATCGCC

AGAAAGGTGCTGTGGGCCATCGGCCAGTTTAAGAAGGCCGAGGACGAGAAACTGGACAAAGTGAAGA

TCGCCATCTCTAACAAAGAGTGGCTGGAATACGCCCAGACCAGCGTGAAGCACGGCAGATCTAGTGA

CGATGAGGCCACCGCCGATAGCCAGCATGCAGCCCCTCCAAAGAAAAAGCGGAAAGTGCTGGAACAC

CACCACCATCACCAC
```

Hs optimized Lb Cpf1 with OpTNLS and 6x His-AA

SEQ ID NO: 24

```
MLKNVGIDRLDVEKGRKNMSKLEKFTNCYSLSKTLRFKAIPVGKTQENIDNKRLLVEDEKRAEDYKG

VKKLLDRYYLSFINDVLHSIKLKNLNNYISLFRKKTRTEKENKELENLEINLRKEIAKAFKGNEGYK

SLFKKDIIETILPEFLDDKDEIALVNSFNGFTTAFTGFFDNRENMFSEEAKSTSIAFRCINENLTRY

ISNMDIFEKVDAIFDKHEVQEIKEKILNSDYDVEDFFEGEFFNFVLTQEGIDVYNAIIGGFVTESGE

KIKGLNEYINLYNQKTKQKLPKFKPLYKQVLSDRESLSFYGEGYTSDEEVLEVERNTLNKNSEIFSS

IKKLEKLFKNFDEYSSAGIFVKNGPAISTISKDIFGEWNVIRDKWNAEYDDIHLKKKAVVTEKYEDD

RRKSFKKIGSFSLEQLQEYADADLSVVEKLKEIIIQKVDEIYKVYGSSEKLFDADFVLEKSLKKNDA

VVAIMKDLLDSVKSFENYIKAFFGEGKETNRDESFYGDFVLAYDILLKVDHIYDAIRNYVTQKPYSK

DKFKLYFQNPQFMGGWDKDKETDYRATILRYGSKYYLAIMDKKYAKCLQKIDKDDVNGNYEKINYKL

LPGPNKMLPKVFFSKKWMAYYNPSEDIQKIYKNGTFKKGDMFNLNDCHKLIDFFKDSISRYPKWSNA

YDFNFSETEKYKDIAGFYREVEEQGYKVSFESASKKEVDKLVEEGKLYMFQTYNKDFSDKSHGTPNL

HTMYFKLLFDENNHGQIRLSGGAELFMRRASLKKEELVVHPANSPIANKNPDNPKKTTTLSYDVYKD

KRFSEDQYELHIPIAINKCPKNIFKINTEVRVLLKHDDNPYVIGIDRGERNLLYIVVVDGKGNIVEQ

YSLNEIINNFNGIRIKTDYHSLLDKKEKERFEARQNWTSIENIKELKAGYISQVVHKICELVEKYDA

VIALEDLNSGFKNSRVKVEKQVYQKFEKMLIDKLNYMVDKKSNPCATGGALKGYQITNKFESFKSMS

TQNGFIFYIPAWLTSKIDPSTGFVNLLKTKYTSIADSKKFISSFDRIMYVPEEDLFEFALDYKNFSR
```

-continued
TDADYIKKWKLYSYGNRIRIFRNPKKNNVFDWEEVCLTSAYKELFNKYGINYQQGDIRALLCEQSDK

AFYSSFMALMSLMLQMRNSITGRTDVDFLISPVKNSDGIFYDSRNYEAQENAILPKNADANGAYNIA

RKVLWAIGQFKKAEDEKLDKVKIAISNKEWLEYAQTSVKHGRSSDDEATADSQHAAPPKKKRKVLEH

HHHHH

Example 10

Use of Modified crRNAs with LbCpf1 Protein Delivered as an RNP Complex.

Twelve sites in the human HPRT1 gene, 38094-S(SEQ ID No. 358), 38104-S (SEQ ID No. 361), 38115-AS (SEQ ID No. 364), 38146-AS (SEQ ID No. 367), 38164-AS (SEQ ID No. 370), 38164-5 (SEQ ID No. 372), 38186-5 (SEQ ID No. 376), 38228-5 (SEQ ID No. 379), 38330-AS (SEQ ID No. 382), 38343-5 (SEQ ID No. 385), 38455-5 (SEQ ID No. 388) and 38486-S(SEQ ID No. 391) (where A and AS represent the sense and antisense strand, respectively), were chosen to study the target editing activity of LbCpf1, as compared to that of AsCpf1 and SpyCas9. Studies were done comparing the ability to use chemically modified crRNAs with LbCpf1 protein to perform genome editing in HEK-293 cells using electroporation to deliver the ribonucleoprotein protein (RNP) complexes into cells.

Purified recombinant LbCpf1 protein was employed in this example, isolated from *E. coli* using standard techniques. The amino-acid sequence of the recombinant protein is shown in SEQ ID NO:14.

Figure 9:
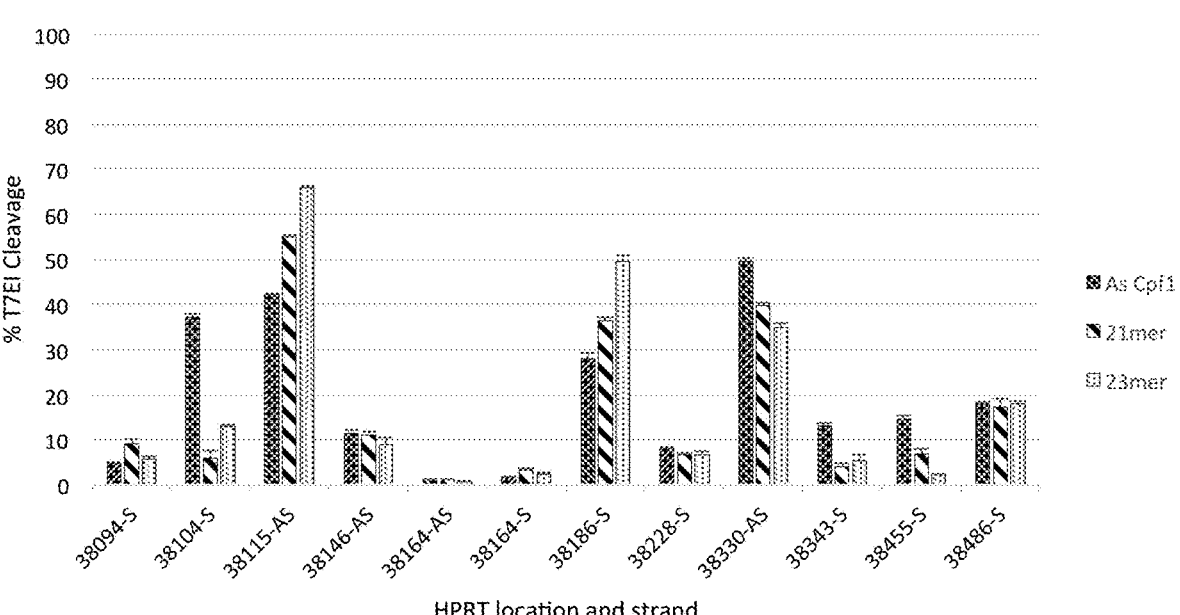
FIG. 9 depicts exemplary results that compare the target editing activity of LbCpf1 with that of AsCpf1 and SpyCas9 for 12 regions of the HPRT gene with low GC content via T7EI mismatch endonuclease assay. In this study, all enzymes and crRNA were delivered as RNP complexes (5 μM), into HEK293 cells by nucleofection using the Amaxa system from Lonza, and DNA was extracted after 48 hr. Percent editing was determined by T7E1 mismatch endo-nuclease assay. Error bars represent standard errors of the means. Of note, the crRNA's for LbCpf1 were tested at the native 23mer nucleotide length as well as the previously optimized AsCpf1 length of 21 bases.

The LbCpf1 crRNAs, and AsCpf1 control crRNAs, were heated to 95° C. for 5 minutes then allowed to cool to room temperature. The crRNAs were mixed with LbCpf1, or AsCpf1, at a molar ratio of 1:1 RNA:protein in PBS (5 RNP complex in 10 volume, for a single transfection). The RNP complex was allowed to form at room temperature for 15 minutes. HEK293 cells were resuspended following trypsinization and washed in medium and washed a second time in PBS before use. Cells were resuspended in at a final concentration of $3.5 \times 10^5$ cells in 20 μL of Nucleofection solution. 20 μL of cell suspension was placed in the V-bottom 96-well plate and 5 μL of the Cpf1 RNP complex was added to each well (5 μM final concentration) and 3 μM of Cpf1 Electroporation Enhancer Solution was added to each well (Integrated DNA Technologies). 25 μL of the final mixture was transferred to each well of a 96 well Nucleocuvette electroporation module. Cells were electroporated using Amaxa 96 well shuttle protocol, program 96-DS-150. Following electroporation, 75 μL of medium was added to each well and 25 μL of the final cell mixture was transferred to 175 μL of pre-warmed medium in 96 well incubation plates (final volume 200 Cells were incubated at 37° C. for 48 hours. Genomic DNA was isolated using QuickExtract solution (Epicentre). Genomic DNA was amplified with KAPA HiFi DNA Polymerase (Roche) and primers targeting the HPRT region of interest (HPRT-low forward primer: AAGAATGTTGTGATAAAAGGTGATGCT (SEQ ID No. 394); HPRT-low reverse primer: ACACATC-CATGGGACTTCTGCCTC (SEQ ID No. 395)). PCR products were melted and re-annealed in NEB buffer 2 (New England Biolabs) to allow for heteroduplex formation followed by digestion with 2 units of T7 endonuclease 1 (T7EI; New England Biolabs) for 1 hour at 37° C. The digested products were visualized on a Fragment Analyzer (Advanced Analytical Technologies). Percent cleavage of targeted DNA was calculated as the average molar concentration of the cut products/(average molar concentration of the cut products+molar concentration of the uncut band)×100. The sequences are shown in Table 10, and the results are graphically represented in FIG. 9.

TABLE 10

Sequences of modified AsCpf1 and LbCpf1 crRNAs tested

| Seq Name | Sequence 5'-3' | SEQ ID NO: |
|---|---|---|
| 38094-S-Control | C3-uaauuucuacucuuguagauauagucuuuccuuggguguguu-C3 | 358 |
| 38094-S-21 | C3-uaauuucuacuaaguguagauauagucuuuccuuggguguguu-C3 | 359 |
| 38094-S-23 | C3-uaauuucuacuaaguguagauauagucuuuccuuggguguguua-C3 | 360 |
| 38104-S-Cpf1 | C3-uaauuucuacucuuguagaucuugggguguguuaaaagugac-C3 | 361 |
| 38104-S-41-97 | C3-uaauuucuacuaaguguagaucuugggguguguuaaaagugac-C3 | 362 |
| 38104-S-23 | C3-uaauuucuacuaaguguagaucuugggguguguuaaaagugacca-C3 | 363 |
| 38115-AS-Cpf1 | C3-uaauuucuacucuuguagauacacacccaaggaaagacuau-C3 | 364 |
| 38115-AS-21 | C3-uaauuucuacuaaguguagauacacacccaaggaaagacuau-C3 | 365 |
| 38115-AS-23 | C3-uaauuucuacuaaguguagauacacacccaaggaaagacuauga-C3 | 366 |
| 38146-AS-Cpf1 | C3-uaauuucuacucuuguagauauccgugcugaguguaccaug-C3 | 367 |
| 38146-AS-21 | C3-uaauuucuacuaaguguagauauccgugcugaguguaccaug-C3 | 368 |
| 38146-AS-23 | C3-uaauuucuacuaaguguagauauccgugcugaguguaccaugca-C3 | 369 |
| 38164-AS-Cpf1 | C3-uaauuucuacucuuguagauuaaacacuguuucauuucauc-C3 | 370 |

TABLE 10-continued

| Sequences of modified AsCpf1 and LbCpf1 crRNAs tested | | |
|---|---|---|
| Seq Name | Sequence 5'-3' | SEQ ID NO: |
| 38164-AS-21 | C3-uaauuucuacuaaguguagauuaaacacuguuucauuucauc-C3 | 371 |
| 38164-AS-23 | C3-uaauuucuacuaaguguagauuaaacacuguuucauuucauccg-C3 | 372 |
| 38164-S-Cpf1 | C3-uaauuucuacucuuguagaugaaacgucagucuucucuuuu-C3 | 373 |
| 38164-S-21 | C3-uaauuucuacuaaguguagaugaaacgucagucuucucuuuu-C3 | 374 |
| 38164-S-23 | C3-uaauuucuacuaaguguagaugaaacgucagucuucucuuuugu-C3 | 375 |
| 38186-S-Cpf1 | C3-uaauuucuacucuuguagauuaaugcccuguagucucucug-C3 | 376 |
| 38186-S-21 | C3-uaauuucuacuaaguguagauuaaugcccuguagucucucug-C3 | 377 |
| 38186-S-23 | C3-uaauuucuacuaaguguagauuaaugcccuguagucucucugua-C3 | 378 |
| 38228-S-Cpf1 | C3-uaauuucuacucuuguagauuaauuaacagcuugcugguga-C3 | 379 |
| 38228-S-21 | C3-uaauuucuacuaaguguagauuaauuaacagcuugcugguga-C3 | 380 |
| 38228-S-23 | C3-uaauuucuacuaaguguagauuaauuaacagcuugcuggugaaa-C3 | 381 |
| 38330-AS-Cpf1 | C3-uaauuucuacucuuguagaugguuaaagaugguuaaaugau-C3 | 382 |
| 38330-AS-21 | C3-uaauuucuacuaaguguagaugguuaaagaugguuaaaugau-C3 | 383 |
| 38330-AS-23 | C3-uaauuucuacuaaguguagaugguuaaagaugguuaaaugauug-C3 | 384 |
| 38343-S-Cpf1 | C3-uaauuucuacucuuguagauugugaaauggcuuauaauugc-C3 | 385 |
| 38343-S-21 | C3-uaauuucuacuaaguguagauugugaaauggcuuauaauugc-C3 | 386 |
| 38343-S-23 | C3-uaauuucuacuaaguguagauugugaaauggcuuauaauugcuu-C3 | 387 |
| 38455-S-Cpf1 | C3-uaauuucuacucuuguagauguuguuggauuugaaauucca-C3 | 388 |
| 38455-S-21 | C3-uaauuucuacuaaguguagauguuguuggauuugaaauucca-C3 | 389 |
| 38455-S-23 | C3-uaauuucuacuaaguguagauguuguuggauuugaaauuccaga-C3 | 390 |
| 38486-S-Cpf1 | C3-uaauuucuacucuuguagauuuguaggauaugcccuugacu-C3 | 391 |
| 38486-S-21 | C3-uaauuucuacuaaguguagauuuguaggauaugcccuugacu-C3 | 392 |
| 38486-S-23 | C3-uaauuucuacuaaguguagauuuguaggauaugcccuugacuau-C3 | 393 |

RNA bases are shown 5'-3' orientation, RNA bases are shown in lower case. Locations
are specified within the human HPRT1 gene with orientation relative to the sense coding
strand indicated (S = sense, AS = antisense). C3 = C3 spacer (propanediol modifier). Cpf1 =
Cpf1 crRNA control. 21 and 23 represent the length of the 3' protospacer for each crRNA.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated AsCpf1 crRNA, wherein the isolated AsCpf1 crRNA is active in a Clustered Regularly Inter-spaced Short Palindromic Repeats (CRISPR)/CRISPR-associated protein endonuclease system, wherein the isolated AsCpf1 crRNA is a length-truncated AsCpf1 crRNA comprising a 5'-universal loop domain of 19 to 20 nucleotides in length and a 3'-target specific protospacer domain of 19 to 21 nucleotides in length and having at least one chemical modification at a position, counting from the 5'-end, selected from the group consisting of: RNA residues at position 1, 5, 6, 7, 8, 9, 10, 12, 13, 14, 16, 17, 18, 19, 21, 22, 23, 28, 29, 30, 32, 34, 35, 39, 40, 41, and combinations thereof.

2. The isolated AsCpf1 crRNA of claim 1, wherein the at least one chemical modification is selected from the group consisting of an end-group modification, 2'OMe modification, a 2'-fluoro modification and an LNA modification.

3. A method of performing gene editing, comprising: contacting a candidate editing target site locus with an active CRISPR/Cpf1 endonuclease system having a wild-type AsCpf1 polypeptide and the isolated AsCpf1 crRNA of claim 1.

4. The isolated AsCpf1 crRNA of claim 1, wherein the at least one chemical modification is 2'OMe modification.

5. The isolated AsCpf1 crRNA of claim 1, wherein the crRNA comprises 2'OMe modifications at position 1, 5, 6, 7, 8, 9, 10, 12, 13, 14, 16, 17, 18, and 19.

6. The isolated AsCpf1 crRNA of claim 1, wherein the crRNA comprises 2'OMe modifications at positions 21, 22, 23, 28, 29, 30, 32, 34, 35, 39, 40, and 41.

7. The isolated AsCpf1 crRNA of claim 1, wherein the 5'-universal loop domain is 20 nucleotides in length.

8. The isolated AsCpf1 crRNA of claim 1, wherein the 3'-target specific protospacer domain is 21 nucleotides in length.

*   *   *   *   *

SEQUENCE LISTING

<160> NUMBER OF SEQ ID NOS: 395

<210> SEQ ID NO 1
<211> LENGTH: 3924
<212> TYPE: DNA
<213> ORGANISM: Acidaminococcus sp. BV3L6

<400> SEQUENCE: 1
atgacccaat ttgaaggttt taccaattta taccaagttt cgaagaccct tcgttttgaa      60
ctgattcccc aaggaaaaac actcaaacat atccaggagc aagggttcat tgaggaggat     120
aaagctcgca atgaccatta caaagagtta aaaccaatca ttgaccgcat ctataagact     180
tatgctgatc aatgtctcca actggtacag cttgactggg agaatctatc tgcagccata     240
gactcctatc gtaaggaaaa aaccgaagaa acacgaaatg cgctgattga ggagcaagca     300
acatatagaa atgcgattca tgactacttt ataggtcgga cggataatct gacagatgcc     360
ataaataagc gccatgctga aatctataaa ggacttttta agctgaact tttcaatgga     420 aaagttttaa agcaattagg gaccgtaacc cgacagaac atgaaaatgc tctactccgt     480
tcgtttgaca aatttacgac ctatttttcc ggcttttatg aaaaccgaaa aaatgtcttt     540
agcgctgaag atatcagcac ggcaattccc catcgaatcg tccaggacaa tttccctaaa     600
tttaaggaaa actgccatat ttttacaaga ttgataaccg cagttccttc tttgcgggag     660 catttttgaaa atgtcaaaaa ggccattgga atctttgtta gtacgtctat tgaagaagtc     720 tttttcctttc cctttttataa tcaacttcta acccaaacgc aaattgatct ttataatcaa     780
cttctcggcg gcatatctag ggaagcaggc acagaaaaaa tcaagggact taatgaagtt     840
ctcaatctgg ctatccaaaa aaatgatgaa acagcccata taatcgcgtc cctgccgcat     900 cgtttttattc ctctttttaa acaaattctt tccgatcgaa atacgttatc ctttattttg     960
gaagaattca aaagcgatga ggaagtcatc caatccttct gcaaatataa aacccctcttg    1020 agaaacgaaa atgtactgga gactgcagaa gcccttttca atgaattaaa ttccattgat    1080
ttgactcata tctttatttc ccataaaaag ttagaaacca tctcttcagc gctttgtgac    1140
cattgggata ccttgcgcaa tgcactttac gaaagacgga tttctgaact cactggcaaa    1200
ataacaaaaa gtgccaaaga aaaagttcaa aggtcattaa acatgaggga tataaatctc    1260
caagaaatta tttctgctgc aggaaaagaa ctatcagaag cattcaaaca aaaaacaagt    1320
gaaattcttt cccatgccca tgctgcactt gaccagcctc ttcccacaac attaaaaaaa    1380
caggaagaaa aagaaatcct caaatcacag ctcgattcgc ttttaggcct ttatcatctt    1440
cttgattggt ttgctgtcga tgaaagcaat gaagtcgacc cagaattctc agcacggctg    1500
acaggcatta aactagaaat ggaaccaagc ctttcgtttt ataataaagc aagaaattat    1560
gcgacaaaaa agcccctattc ggtggaaaaa tttaaattga attttcaaat gccaacccctt    1620 gcctctggtt gggatgtcaa taaagaaaaa aataatggag ctattttatt cgtaaaaaat    1680
ggtctctatt accttggtat catgcctaaa cagaaggggc gctataaagc cctgtctttt    1740
gagccgacag aaaaaacatc agaaggattc gataagatgt actatgacta cttcccagat    1800
gccgcaaaaa tgattcctaa gtgttccact cagctaaagg ctgtaaccgc tcattttcaa    1860
actcatacca ccccccattct tctctcaaat aatttcattg aacctcttga aatcacaaaa    1920
gaaatttatg acctgaacaa tcctgaaaag gagcctaaaa agtttcaaac ggcttatgca    1980
aagaagacag cgatcaaaaa aggctataga gaagcgcttt gcaaatggat tgactttacg    2040 cgggatttttc tctctaaata tacgaaaaca acttcaatcg atttatcttc actccgccct    2100

```
tcttcgcaat ataaagattt aggggaatat tacgccgaac tgaatccgct tctctatcat    2160
atctccttcc aacgaattgc tgaaaaggaa atcatggatg ctgtagaaac gggaaaattg    2220
tatctgttcc aaatctacaa taaggatttt gcgaagggcc atcacgggaa accaaatctc    2280
cacaccctgt attggacagg tctcttcagt cctgaaaacc ttgcgaaaac cagcatcaaa    2340
cttaatggtc aagcagaatt gttctatcga cctaaaagcc gcatgaagcg gatggcccat    2400
cgtcttgggg aaaaaatgct gaacaaaaaa ctaaaggacc agaagacacc gattccagat    2460
accctctacc aagaactgta cgattatgtc aaccaccggc taagccatga tctttccgat    2520
gaagcaaggg ccctgcttcc aaatgttatc accaagaag tctcccatga aattataaag     2580
gatcggcggt ttacttccga taaattttc ttccatgttc ccattacact gaattatcaa      2640
gcagccaata gtcccagtaa attcaaccag cgtgtcaatg cctaccttaa ggagcatccg    2700
gaaacgccca tcattggtat cgatcgtgga aacgcaatc taatctatat taccgtcatt      2760
gacagtactg ggaaaatttt ggagcagcgt tccctgaata ccatccagca atttgactac    2820
caaaaaaaat tggacaacag ggaaaaagag cgtgttgccg cccgtcaagc ctggtccgtc    2880
gtcggaacga tcaaagacct taaacaaggc tacttgtcac aggtcatcca tgaaattgta    2940
gacctgatga ttcattacca agctgttgtc gtccttgaaa acctcaactt cggatttaaa    3000
tcaaaacgga caggcattgc cgaaaaagca gtctaccaac aatttgaaaa gatgctaata    3060
gataaactca actgtttggt tctcaaagat tatcctgctg agaaagtggg aggcgtctta    3120
aacccgtatc aacttacaga tcagttcacg agctttgcaa aaatgggcac gcaaagcggc    3180
ttccttttct atgtaccggc cccttatacc tcaaagattg atcccctgac tggttttgtc    3240
gatccctttg tatggaagac cattaaaaat catgaaagtc ggaagcattt cctagaagga    3300
tttgatttcc tgcattatga tgtcaaaaca ggtgatttta cctccatttt taaaatgaat    3360
cggaatctct ctttccagag agggcttcct ggcttcatgc cagcttggga tattgttttc    3420
gaaaagaatg aaacccaatt tgatgcaaaa gggacgccct tcattgcagg aaaacgaatt    3480
gttcctgtaa tcgaaaatca tcgtttacg ggtcgttaca gagacctcta tcccgctaat     3540
gaactcattg cccttctgga agaaaaaggc attgtcttta gagacggaag taatatatta    3600
cccaaacttt tagaaaatga tgattctcat gcaattgata cgatggtcgc cttgattcgc    3660
agtgtactcc aaatgagaaa cagcaatgcc gcaacggggg aagactacat caactctccc    3720
gttagggatc tgaacggggt gtgtttcgac agtcgattcc aaaatccaga atggccaatg    3780
gatgcggatg ccaacggagc ttatcatatt gccttaaaag ggcagcttct tctgaaccac    3840
ctcaaagaaa gcaaagatct gaaattacaa aacggcatca gcaaccaaga ttggctggcc    3900
tacattcagg aactgagaaa ctga                                            3924
```

```
<210> SEQ ID NO 2
<211> LENGTH: 1307
<212> TYPE: PRT
<213> ORGANISM: Acidaminococcus sp. BV3L6

<400> SEQUENCE: 2

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45
```

-continued

```
Glu Leu Lys Pro Ile Ile Asp Arg Ile Tyr Lys Thr Tyr Ala Asp Gln
    50              55              60

Cys Leu Gln Leu Val Gln Leu Asp Trp Glu Asn Leu Ser Ala Ala Ile
65              70              75              80

Asp Ser Tyr Arg Lys Glu Lys Thr Glu Glu Thr Arg Asn Ala Leu Ile
                85              90              95

Glu Glu Gln Ala Thr Tyr Arg Asn Ala Ile His Asp Tyr Phe Ile Gly
            100             105             110

Arg Thr Asp Asn Leu Thr Asp Ala Ile Asn Lys Arg His Ala Glu Ile
            115             120             125

Tyr Lys Gly Leu Phe Lys Ala Glu Leu Phe Asn Gly Lys Val Leu Lys
    130             135             140

Gln Leu Gly Thr Val Thr Thr Thr Glu His Glu Asn Ala Leu Leu Arg
145             150             155             160

Ser Phe Asp Lys Phe Thr Thr Tyr Phe Ser Gly Phe Tyr Glu Asn Arg
                165             170             175

Lys Asn Val Phe Ser Ala Glu Asp Ile Ser Thr Ala Ile Pro His Arg
                180             185             190

Ile Val Gln Asp Asn Phe Pro Lys Phe Lys Glu Asn Cys His Ile Phe
            195             200             205

Thr Arg Leu Ile Thr Ala Val Pro Ser Leu Arg Glu His Phe Glu Asn
    210             215             220

Val Lys Lys Ala Ile Gly Ile Phe Val Ser Thr Ser Ile Glu Glu Val
225             230             235             240

Phe Ser Phe Pro Phe Tyr Asn Gln Leu Leu Thr Gln Thr Gln Ile Asp
                245             250             255

Leu Tyr Asn Gln Leu Leu Gly Gly Ile Ser Arg Glu Ala Gly Thr Glu
            260             265             270

Lys Ile Lys Gly Leu Asn Glu Val Leu Asn Leu Ala Ile Gln Lys Asn
            275             280             285

Asp Glu Thr Ala His Ile Ile Ala Ser Leu Pro His Arg Phe Ile Pro
    290             295             300

Leu Phe Lys Gln Ile Leu Ser Asp Arg Asn Thr Leu Ser Phe Ile Leu
305             310             315             320

Glu Glu Phe Lys Ser Asp Glu Glu Val Ile Gln Ser Phe Cys Lys Tyr
                325             330             335

Lys Thr Leu Leu Arg Asn Glu Asn Val Leu Glu Thr Ala Glu Ala Leu
            340             345             350

Phe Asn Glu Leu Asn Ser Ile Asp Leu Thr His Ile Phe Ile Ser His
            355             360             365

Lys Lys Leu Glu Thr Ile Ser Ser Ala Leu Cys Asp His Trp Asp Thr
    370             375             380

Leu Arg Asn Ala Leu Tyr Glu Arg Arg Ile Ser Glu Leu Thr Gly Lys
385             390             395             400

Ile Thr Lys Ser Ala Lys Glu Lys Val Gln Arg Ser Leu Lys His Glu
                405             410             415

Asp Ile Asn Leu Gln Glu Ile Ile Ser Ala Ala Gly Lys Glu Leu Ser
            420             425             430

Glu Ala Phe Lys Gln Lys Thr Ser Glu Ile Leu Ser His Ala His Ala
            435             440             445

Ala Leu Asp Gln Pro Leu Pro Thr Thr Leu Lys Lys Gln Glu Glu Lys
    450             455             460
```

```
Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
            485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
            675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
            835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
```

-continued

```
                    885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
        930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
            995                 1000                1005

Lys Ala  Val Tyr Gln Gln Phe  Glu Lys Met Leu Ile  Asp Lys Leu
    1010                1015                1020

Asn Cys  Leu Val Leu Lys Asp  Tyr Pro Ala Glu Lys  Val Gly Gly
    1025                1030                1035

Val Leu  Asn Pro Tyr Gln Leu  Thr Asp Gln Phe Thr  Ser Phe Ala
    1040                1045                1050

Lys Met  Gly Thr Gln Ser Gly  Phe Leu Phe Tyr Val  Pro Ala Pro
    1055                1060                1065

Tyr Thr  Ser Lys Ile Asp Pro  Leu Thr Gly Phe Val  Asp Pro Phe
    1070                1075                1080

Val Trp  Lys Thr Ile Lys Asn  His Glu Ser Arg Lys  His Phe Leu
    1085                1090                1095

Glu Gly  Phe Asp Phe Leu His  Tyr Asp Val Lys Thr  Gly Asp Phe
    1100                1105                1110

Ile Leu  His Phe Lys Met Asn  Arg Asn Leu Ser Phe  Gln Arg Gly
    1115                1120                1125

Leu Pro  Gly Phe Met Pro Ala  Trp Asp Ile Val Phe  Glu Lys Asn
    1130                1135                1140

Glu Thr  Gln Phe Asp Ala Lys  Gly Thr Pro Phe Ile  Ala Gly Lys
    1145                1150                1155

Arg Ile  Val Pro Val Ile Glu  Asn His Arg Phe Thr  Gly Arg Tyr
    1160                1165                1170

Arg Asp  Leu Tyr Pro Ala Asn  Glu Leu Ile Ala Leu  Leu Glu Glu
    1175                1180                1185

Lys Gly  Ile Val Phe Arg Asp  Gly Ser Asn Ile Leu  Pro Lys Leu
    1190                1195                1200

Leu Glu  Asn Asp Asp Ser His  Ala Ile Asp Thr Met  Val Ala Leu
    1205                1210                1215

Ile Arg  Ser Val Leu Gln Met  Arg Asn Ser Asn Ala  Ala Thr Gly
    1220                1225                1230

Glu Asp  Tyr Ile Asn Ser Pro  Val Arg Asp Leu Asn  Gly Val Cys
    1235                1240                1245

Phe Asp  Ser Arg Phe Gln Asn  Pro Glu Trp Pro Met  Asp Ala Asp
    1250                1255                1260

Ala Asn  Gly Ala Tyr His Ile  Ala Leu Lys Gly Gln  Leu Leu Leu
    1265                1270                1275

Asn His  Leu Lys Glu Ser Lys  Asp Leu Lys Leu Gln  Asn Gly Ile
    1280                1285                1290
```

Ser Asn  Gln Asp Trp Leu Ala  Tyr Ile Gln Glu Leu  Arg Asn
    1295              1300              1305

<210> SEQ ID NO 3
<211> LENGTH: 3714
<212> TYPE: DNA
<213> ORGANISM: Lachnospiraceae bacterium ND2006

<400> SEQUENCE: 3
atgagcaaac tggaaaaatt tacgaattgt tatagcctgt ccaagaccct gcgtttcaaa      60
gccatccccg ttggcaaaac ccaggagaat attgataata aacgtctgct ggttgaggat     120
gaaaaaagag cagaagacta taagggagtc aaaaaactgc tggatcggta ctacctgagc     180
tttataaatg acgtgctgca tagcattaaa ctgaaaaatc tgaataacta tattagtctg     240
ttccgcaaga aaacccgaac agagaaagaa aataaagagc tggaaaacct ggagatcaat     300
ctgcgtaaag agatcgcaaa agcttttaaa ggaaatgaag gttataaaag cctgttcaaa     360
aaagacatta ttgaaaccat cctgccggaa tttctggatg ataaagacga gatagcgctc     420
gtgaacagct tcaacgggtt cacgaccgcc ttcacgggct ttttcgataa cagggaaaat     480 atgtttttcag aggaagccaa aagcacctcg atagcgttcc gttgcattaa tgaaaatttg     540
acaagatata tcagcaacat ggatattttc gagaaagttg atgcgatctt tgacaaacat     600
gaagtgcagg agattaagga aaaaattctg aacagcgatt atgatgttga ggattttttc     660
gagggggaat ttttttaactt tgtactgaca caggaaggta tagatgtgta taatgctatt     720
atcggcgggt cgttaccga atccggcgag aaaattaagg gtctgaatga gtacatcaat     780
ctgtataacc aaaagaccaa acagaaactg ccaaaattca aaccgctgta caagcaagtc     840
ctgagcgatc gggaaagctt gagcttttac ggtgaaggtt ataccagcga cgaggaggta     900
ctggaggtct ttcgcaatac cctgaacaag aacagcgaaa ttttcagctc cattaaaaag     960
ctggagaaac tgtttaagaa ttttgacgag tacagcagcg caggtatttt tgtgaagaac    1020
ggacctgcca taagcaccat tagcaaggat attttttggag agtggaatgt tatccgtgat    1080
aaatggaacg cggaatatga tgacatacac ctgaaaaaga aggctgtggt aactgagaaa    1140
tatgaagacg atcgccgcaa aagctttaaa aaaatcggca gctttagcct ggagcagctg    1200
caggaatatg cggacgccga cctgagcgtg tcgagaaac tgaaggaaat tattatccaa    1260
aaagtggatg agatttacaa ggtatatggt agcagcgaaa aactgtttga tgcggacttc    1320
gttctggaaa aaagcctgaa aaaaaatgat gctgttgttg cgatcatgaa agacctgctc    1380
gatagcgtta agagctttga aaattacatt aaagcattct ttggcgaggg caaagaaaca    1440
aacagagacg aaagctttta tggcgacttc gtcctggctt atgacatcct gttgaaggta    1500
gatcatatat atgatgcaat tcgtaattac gtaacccaaa agccgtacag caaagataag    1560
ttcaaactgt atttccagaa cccgcagttt atgggtggct gggacaaaga caggagaca    1620 gactatcgcg ccactattct gcgttacggc agcaagtact atctcgccat catggacaaa    1680
aaatatgcaa agtgtctgca gaaatcgat aaagacgacg tgaacggaaa ttacgaaaag    1740
attaattata agctgctgcc agggcccaac aagatgttac cgaaagtatt tttttccaaa    1800
aaatggatgg catactataa cccgagcgag gatatacaga agatttacaa aaatgggacc    1860
ttcaaaaagg gggatatgtt caatctgaat gactgccaca aactgatcga tttttttaaa    1920
gatagcatca gccgttatcc taaatggtca aacgcgtatg attttaattt ctccgaaacg    1980
gagaaatata aagacattgc tggtttctat cgcgaagtcg aagaacaggg ttataaagtt    2040

-continued

```
agctttgaat cggccagcaa gaaagaggtt gataaactgg tggaggaggg taagctgtat      2100
atgtttcaga tttataacaa agactttagc gacaaaagcc acggtactcc taatctgcat      2160
acgatgtact ttaaactgct gtttgatgag aataaccacg gccaaatccg tctctccggt      2220
ggagcagaac ttttttatgcg gcgtgcgagc ctaaaaaagg aagaactggt ggtgcatccc      2280
gccaacagcc cgattgctaa caaaaatcca gataatccta agaagaccac cacactgtcg      2340
tacgatgtct ataaggataa acgtttctcg gaagaccagt atgaattgca tataccgata      2400
gcaattaata aatgcccaaa aaacattttc aaaatcaaca ctgaagttcg tgtgctgctg      2460
aaacatgatg ataatccgta tgtgatcgga attgaccgtg gggagagaaa tctgctgtat      2520
attgtagtcg ttgatggcaa gggcaacatc gttgagcagt atagcctgaa tgaaataatt      2580
aataatttta cggtatacg tattaaaacc gactatcata gcctgctgga taaaaaggag      2640
aaagagcgtt ttgaggcacg ccaaaattgg acgagcatcg aaaacatcaa ggaactgaag      2700
gcaggatata tcagccaagt agtccataaa atctgtgaac tggtggagaa gtacgacgct      2760
gtcattgccc tggaagacct caatagcggc tttaaaaaca gccgggtgaa ggtggagaaa      2820
caggtatacc aaaagtttga aaagatgctc attgataagc tgaactatat ggttgataaa      2880
aagagcaacc cgtgcgccac tggcggtgca ctgaaagggt accaaattac caataaattt      2940
gaaagcttta aaagcatgag cacgcagaat gggtttattt tttatatacc agcatggctg      3000
acgagcaaga ttgaccccag cactggtttt gtcaatctgc tgaaaaccaa atacacaagc      3060
attgcggata gcaaaaaatt tatttcgagc ttcgaccgta ttatgtatgt tccggaggaa      3120
gatctgtttg aatttgccct ggattataaa aacttcagcc gcaccgatgc agattatatc      3180
aaaaaatgga agctgtacag ttatggtaat cgtatacgta tcttccgtaa tccgaagaaa      3240
aacaatgtgt tcgattggga agaggtctgt ctgaccagcg cgtataaaga actgttcaac      3300
aagtacggaa taaattatca gcaaggtgac attcgcgcac tgctgtgtga acagtcagat      3360
aaagcatttt atagcagctt tatggcgctg atgagcctga tgctccagat gcgcaacagc      3420
ataaccggtc gcacagatgt tgactttctg atcagccctg tgaagaatag cgacggcatc      3480
ttctacgatt ccaggaacta tgaagcacag gaaaacgcta ttctgcctaa aaatgccgat      3540
gccaacggcg cctataatat tgcacggaag gttctgtggg cgattggaca gttcaagaaa      3600
gcggaagatg agaagctgga taaggtaaaa attgctatta gcaataagga atggctggag      3660
tacgcacaga catcggttaa acacgcggcc gcttccctgc aggtaattaa ataa           3714
```

<210> SEQ ID NO 4
<211> LENGTH: 1246
<212> TYPE: PRT
<213> ORGANISM: Lachnospiraceae bacterium ND2006

<400> SEQUENCE: 4

```
Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
            20                  25                  30

Lys Thr Leu Arg Phe Lys Ala Ile Pro Val Gly Lys Thr Gln Glu Asn
        35                  40                  45

Ile Asp Asn Lys Arg Leu Leu Val Glu Asp Glu Lys Arg Ala Glu Asp
    50                  55                  60

Tyr Lys Gly Val Lys Lys Leu Leu Asp Arg Tyr Tyr Leu Ser Phe Ile
65                  70                  75                  80
```

-continued

```
Asn Asp Val Leu His Ser Ile Lys Leu Lys Asn Leu Asn Asn Tyr Ile
                85              90              95

Ser Leu Phe Arg Lys Lys Thr Arg Thr Glu Lys Glu Asn Lys Glu Leu
            100             105             110

Glu Asn Leu Glu Ile Asn Leu Arg Lys Glu Ile Ala Lys Ala Phe Lys
            115             120             125

Gly Asn Glu Gly Tyr Lys Ser Leu Phe Lys Lys Asp Ile Ile Glu Thr
        130             135             140

Ile Leu Pro Glu Phe Leu Asp Asp Lys Asp Glu Ile Ala Leu Val Asn
145             150             155             160

Ser Phe Asn Gly Phe Thr Thr Ala Phe Thr Gly Phe Phe Asp Asn Arg
                165             170             175

Glu Asn Met Phe Ser Glu Glu Ala Lys Ser Thr Ser Ile Ala Phe Arg
            180             185             190

Cys Ile Asn Glu Asn Leu Thr Arg Tyr Ile Ser Asn Met Asp Ile Phe
            195             200             205

Glu Lys Val Asp Ala Ile Phe Asp Lys His Glu Val Gln Glu Ile Lys
        210             215             220

Glu Lys Ile Leu Asn Ser Asp Tyr Asp Val Glu Asp Phe Phe Glu Gly
225             230             235             240

Glu Phe Phe Asn Phe Val Leu Thr Gln Glu Gly Ile Asp Val Tyr Asn
                245             250             255

Ala Ile Ile Gly Gly Phe Val Thr Glu Ser Gly Glu Lys Ile Lys Gly
            260             265             270

Leu Asn Glu Tyr Ile Asn Leu Tyr Asn Gln Lys Thr Lys Gln Lys Leu
        275             280             285

Pro Lys Phe Lys Pro Leu Tyr Lys Gln Val Leu Ser Asp Arg Glu Ser
    290             295             300

Leu Ser Phe Tyr Gly Glu Gly Tyr Thr Ser Asp Glu Glu Val Leu Glu
305             310             315             320

Val Phe Arg Asn Thr Leu Asn Lys Asn Ser Glu Ile Phe Ser Ser Ile
                325             330             335

Lys Lys Leu Glu Lys Leu Phe Lys Asn Phe Asp Glu Tyr Ser Ser Ala
            340             345             350

Gly Ile Phe Val Lys Asn Gly Pro Ala Ile Ser Thr Ile Ser Lys Asp
            355             360             365

Ile Phe Gly Glu Trp Asn Val Ile Arg Asp Lys Trp Asn Ala Glu Tyr
        370             375             380

Asp Asp Ile His Leu Lys Lys Lys Ala Val Val Thr Glu Lys Tyr Glu
385             390             395             400

Asp Asp Arg Arg Lys Ser Phe Lys Ile Gly Ser Phe Ser Leu Glu
            405             410             415

Gln Leu Gln Glu Tyr Ala Asp Ala Asp Leu Ser Val Val Glu Lys Leu
            420             425             430

Lys Glu Ile Ile Ile Gln Lys Val Asp Glu Ile Tyr Lys Val Tyr Gly
        435             440             445

Ser Ser Glu Lys Leu Phe Asp Ala Asp Phe Val Leu Glu Lys Ser Leu
    450             455             460

Lys Lys Asn Asp Ala Val Val Ala Ile Met Lys Asp Leu Leu Asp Ser
465             470             475             480

Val Lys Ser Phe Glu Asn Tyr Ile Lys Ala Phe Phe Gly Glu Gly Lys
                485             490             495
```

-continued

```
Glu Thr Asn Arg Asp Glu Ser Phe Tyr Gly Asp Phe Val Leu Ala Tyr
            500                 505                 510

Asp Ile Leu Leu Lys Val Asp His Ile Tyr Asp Ala Ile Arg Asn Tyr
            515                 520                 525

Val Thr Gln Lys Pro Tyr Ser Lys Asp Lys Phe Lys Leu Tyr Phe Gln
            530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Tyr Leu Ala Ile Met
                565                 570                 575

Asp Lys Lys Tyr Ala Lys Cys Leu Gln Lys Ile Asp Lys Asp Asp Val
                580                 585                 590

Asn Gly Asn Tyr Glu Lys Ile Asn Tyr Lys Leu Leu Pro Gly Pro Asn
                595                 600                 605

Lys Met Leu Pro Lys Val Phe Phe Ser Lys Lys Trp Met Ala Tyr Tyr
            610                 615                 620

Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
                645                 650                 655

Phe Lys Asp Ser Ile Ser Arg Tyr Pro Lys Trp Ser Asn Ala Tyr Asp
                660                 665                 670

Phe Asn Phe Ser Glu Thr Glu Lys Tyr Lys Asp Ile Ala Gly Phe Tyr
                675                 680                 685

Arg Glu Val Glu Glu Gln Gly Tyr Lys Val Ser Phe Glu Ser Ala Ser
            690                 695                 700

Lys Lys Glu Val Asp Lys Leu Val Glu Glu Gly Lys Leu Tyr Met Phe
705                 710                 715                 720

Gln Ile Tyr Asn Lys Asp Phe Ser Asp Lys Ser His Gly Thr Pro Asn
                725                 730                 735

Leu His Thr Met Tyr Phe Lys Leu Leu Phe Asp Glu Asn Asn His Gly
                740                 745                 750

Gln Ile Arg Leu Ser Gly Gly Ala Glu Leu Phe Met Arg Arg Ala Ser
            755                 760                 765

Leu Lys Lys Glu Glu Leu Val Val His Pro Ala Asn Ser Pro Ile Ala
            770                 775                 780

Asn Lys Asn Pro Asp Asn Pro Lys Lys Thr Thr Thr Leu Ser Tyr Asp
785                 790                 795                 800

Val Tyr Lys Asp Lys Arg Phe Ser Glu Asp Gln Tyr Glu Leu His Ile
                805                 810                 815

Pro Ile Ala Ile Asn Lys Cys Pro Lys Asn Ile Phe Lys Ile Asn Thr
                820                 825                 830

Glu Val Arg Val Leu Leu Lys His Asp Asp Asn Pro Tyr Val Ile Gly
            835                 840                 845

Ile Asp Arg Gly Glu Arg Asn Leu Leu Tyr Ile Val Val Val Asp Gly
        850                 855                 860

Lys Gly Asn Ile Val Glu Gln Tyr Ser Leu Asn Glu Ile Ile Asn Asn
865                 870                 875                 880

Phe Asn Gly Ile Arg Ile Lys Thr Asp Tyr His Ser Leu Leu Asp Lys
                885                 890                 895

Lys Glu Lys Glu Arg Phe Glu Ala Arg Gln Asn Trp Thr Ser Ile Glu
            900                 905                 910

Asn Ile Lys Glu Leu Lys Ala Gly Tyr Ile Ser Gln Val Val His Lys
```

```
                915                 920                 925

Ile Cys Glu Leu Val Glu Lys Tyr Asp Ala Val Ile Ala Leu Glu Asp
    930                 935                 940

Leu Asn Ser Gly Phe Lys Asn Ser Arg Val Lys Val Glu Lys Gln Val
945                 950                 955                 960

Tyr Gln Lys Phe Glu Lys Met Leu Ile Asp Lys Leu Asn Tyr Met Val
                965                 970                 975

Asp Lys Lys Ser Asn Pro Cys Ala Thr Gly Gly Ala Leu Lys Gly Tyr
                980                 985                 990

Gln Ile Thr Asn Lys Phe Glu Ser  Phe Lys Ser Met Ser  Thr Gln Asn
            995                 1000                1005

Gly Phe  Ile Phe Tyr Ile Pro  Ala Trp Leu Thr Ser  Lys Ile Asp
    1010                1015                1020

Pro Ser  Thr Gly Phe Val Asn  Leu Leu Lys Thr Lys  Tyr Thr Ser
    1025                1030                1035

Ile Ala  Asp Ser Lys Lys Phe  Ile Ser Ser Phe Asp  Arg Ile Met
    1040                1045                1050

Tyr Val  Pro Glu Glu Asp Leu  Phe Glu Phe Ala Leu  Asp Tyr Lys
    1055                1060                1065

Asn Phe  Ser Arg Thr Asp Ala  Asp Tyr Ile Lys Lys  Trp Lys Leu
    1070                1075                1080

Tyr Ser  Tyr Gly Asn Arg Ile  Arg Ile Phe Arg Asn  Pro Lys Lys
    1085                1090                1095

Asn Asn  Val Phe Asp Trp Glu  Glu Val Cys Leu Thr  Ser Ala Tyr
    1100                1105                1110

Lys Glu  Leu Phe Asn Lys Tyr  Gly Ile Asn Tyr Gln  Gln Gly Asp
    1115                1120                1125

Ile Arg  Ala Leu Leu Cys Glu  Gln Ser Asp Lys Ala  Phe Tyr Ser
    1130                1135                1140

Ser Phe  Met Ala Leu Met Ser  Leu Met Leu Gln Met  Arg Asn Ser
    1145                1150                1155

Ile Thr  Gly Arg Thr Asp Val  Asp Phe Leu Ile Ser  Pro Val Lys
    1160                1165                1170

Asn Ser  Asp Gly Ile Phe Tyr  Asp Ser Arg Asn Tyr  Glu Ala Gln
    1175                1180                1185

Glu Asn  Ala Ile Leu Pro Lys  Asn Ala Asp Ala Asn  Gly Ala Tyr
    1190                1195                1200

Asn Ile  Ala Arg Lys Val Leu  Trp Ala Ile Gly Gln  Phe Lys Lys
    1205                1210                1215

Ala Glu  Asp Glu Lys Leu Asp  Lys Val Lys Ile Ala  Ile Ser Asn
    1220                1225                1230

Lys Glu  Trp Leu Glu Tyr Ala  Gln Thr Ser Val Lys  His
    1235                1240                1245

<210> SEQ ID NO 5
<211> LENGTH: 3924
<212> TYPE: DNA
<213> ORGANISM: Artificial Sequence
<220> FEATURE:
<223> OTHER INFORMATION: Synthetic DNA

<400> SEQUENCE: 5
atgacccagt ttgaaggttt caccaatctg tatcaggtta gcaaaccct gcgttttgaa      60 ctgattccgc agggtaaaac cctgaaacat attcagaac agggcttcat cgaagaggat      120
```

-continued

```
aaagcacgta acgatcacta caaagaactg aaaccgatta tcgaccgcat ctataaaacc      180
tatgcagatc agtgtctgca gctggttcag ctggattggg aaaatctgag cgcagcaatt      240
gatagttatc gcaaagaaaa aaccgaagaa acccgtaatg cactgattga agaacaggca      300
acctatcgta atgccatcca tgattatttc attggtcgta ccgataatct gaccgatgca      360
attaacaaac gtcacgccga aatctataaa ggcctgttta aagccgaact gtttaatggc      420
aaagttctga aacagctggg caccgttacc accaccgaac atgaaaatgc actgctgcgt      480
agctttgata aattcaccac ctatttcagc ggcttttatg agaatcgcaa aaacgtgttt      540
agcgcagaag atattagcac cgcaattccg catcgtattg tgcaggataa tttcccgaaa      600
ttcaaagaga actgccacat ttttacccgt ctgattaccg cagttccgag cctgcgtgaa      660 catttttgaaa acgttaaaaa agccatcggc atctttgtta gcaccagcat tgaagaagtt      720
tttagcttcc cgttttacaa tcagctgctg acccagaccc agattgatct gtataaccaa      780
ctgctgggtg gtattagccg tgaagcaggc accgaaaaaa tcaaaggtct gaatgaagtg      840
ctgaatctgg ccattcagaa aaatgatgaa accgcacata ttattgcaag cctgccgcat      900
cgttttattc cgctgttcaa acaaattctg agcgatcgta ataccctgag ctttattctg      960
gaagaattca aatccgatga agaggtgatt cagagctttt gcaaatacaa aacgctgctg      1020
cgcaatgaaa atgttctgga aactgccgaa gcactgttta acgaactgaa tagcattgat      1080
ctgacccaca tctttatcag ccacaaaaaa ctggaaacca tttcaagcgc actgtgtgat      1140
cattgggata ccctgcgtaa tgccctgtat gaacgtcgta ttagcgaact gaccggtaaa      1200
attaccaaaa gcgcgaaaga aaaagttcag cgcagtctga acatgagga tattaatctg      1260 caagagatta ttagcgcagc cggtaaagaa ctgtcagaag catttaaaca gaaaaccagc      1320
gaaattctgt cacatgcaca tgcagcactg gatcagccgc tgccgaccac cctgaaaaaa      1380
caagaagaaa aagaaatcct gaaaagccag ctggatagcc tgctgggtct gtatcatctg      1440
ctggactggt ttgcagttga tgaaagcaat gaagttgatc cggaatttag cgcacgtctg      1500
accggcatta aactggaaat ggaaccgagc ctgagctttt ataacaaagc ccgtaattat      1560
gccaccaaaa aaccgtatag cgtcgaaaaa ttcaaactga actttcagat gccgaccctg      1620
gcaagcggtt gggatgttaa taaagaaaaa aacaacggtg ccatcctgtt cgtgaaaaat      1680
ggcctgtatt atctgggtat tatgccgaaa cagaaaggtc gttataaagc gctgagcttt      1740
gaaccgacgg aaaaaaccag tgaaggtttt gataaaatgt actacgacta ttttccggat      1800
gcagccaaaa tgattccgaa atgtagcacc cagctgaaag cagttaccgc acattttcag      1860
acccatacca ccccgattct gctgagcaat aactttattg aaccgctgga aatcaccaaa      1920
gagatctacg atctgaataa cccggaaaaa gagccgaaaa aattccagac cgcatatgca      1980
aaaaaaaccg gtgatcagaa aggttatcgt gaagcgctgt gtaaatggat tgatttcacc      2040
cgtgattttc tgagcaaata caccaaaacc accagtatcg atctgagcag cctgcgtccg      2100
agcagccagt ataaagatct gggcgaatat tatgcagaac tgaatccgct gctgtatcat      2160
attagctttc agcgtattgc cgagaaagaa atcatggacg cagttgaaac cggtaaactg      2220
tacctgttcc agatctacaa taaagatttt gccaaaggcc atcatggcaa accgaatctg      2280 catacccctgt attggaccgg tctgtttagc cctgaaaatc tggcaaaaac ctcgattaaa      2340
ctgaatggtc aggcggaact gttttatcgt ccgaaaagcc gtatgaaacg tatggcacat      2400
cgtctgggtg aaaaaatgct gaacaaaaaa ctgaaagacc agaaaacccc gatcccggat      2460
acactgtatc aagaactgta tgattatgtg aaccatcgtc tgagccatga tctgagtgat      2520
```

-continued

```
gaagcacgtg ccctgctgcc gaatgttatt accaaagaag ttagccacga gatcattaaa    2580
gatcgtcgtt ttaccagcga caaattcttt tttcatgtgc cgattaccct gaattatcag    2640
gcagcaaata gcccgagcaa atttaaccag cgtgttaatg catatctgaa agaacatcca    2700
gaaacgccga ttattggtat tgatcgtggt gaacgtaacc tgatttatat caccgttatt    2760
gatagcaccg gcaaaatcct ggaacagcgt agcctgaata ccattcagca gtttgattac    2820
cagaaaaaac tggataatcg cgagaaagaa cgtgttgcag cacgtcaggc atggtcagtt    2880
gttggtacaa ttaaagacct gaaacagggt tatctgagcc aggttattca tgaaattgtg    2940
gatctgatga ttcactatca ggccgttgtt gtgctggaaa acctgaattt ggctttaaa     3000 agcaaacgta ccggcattgc agaaaaagca gtttatcagc agttcgagaa aatgctgatt    3060
gacaaactga attgcctggt gctgaaagat tatccggctg aaaaagttgg tggtgttctg    3120
aatccgtatc agctgaccga tcagtttacc agctttgcaa aaatgggcac ccagagcgga    3180
tttctgtttt atgttccggc accgtatacg agcaaaattg atccgctgac cggttttgtt    3240
gatccgtttg tttggaaaac catcaaaaac catgaaagcc gcaaacattt tctggaaggt    3300
ttcgattttc tgcattacga cgttaaaacg ggtgatttca tcctgcactt taaaatgaat    3360
cgcaatctga gttttcagcg tggcctgcct ggttttatgc ctgcatggga tattgtgttt    3420
gagaaaaacg aaacacagtt cgatgcaaaa ggcacccgt ttattgcagg taaacgtatt      3480
gttccggtga ttgaaaatca tcgtttcacc ggtcgttatc gcgatctgta tccggcaaat    3540
gaactgatcg cactgctgga agagaaaggt attgttttc gtgatggctc aaacattctg      3600
ccgaaactgc tggaaaatga tgatagccat gcaattgata ccatggttgc actgattcgt    3660
agcgttctgc agatgcgtaa tagcaatgca gcaaccggtg aagattacat taatagtccg    3720
gttcgtgatc tgaatggtgt ttgtttttgat agccgttttc agaatccgga atggccgatg    3780
gatgcagatg caaatggtgc atatcatatt gcactgaaag acagctgct gctgaaccac      3840 ctgaaagaaa gcaaagatct gaaactgcaa aacggcatta gcaatcagga ttggctggca    3900
tatatccaag aactgcgtaa ctga                                          3924
```

```
<210> SEQ ID NO 6
<211> LENGTH: 3741
<212> TYPE: DNA
<213> ORGANISM: Artificial Sequence
<220> FEATURE:
<223> OTHER INFORMATION: Synthetic DNA

<400> SEQUENCE: 6
```

```
atgctgaaaa acgtgggtat tgatcgtctg gatgttgaaa aaggtcgcaa aaatatgagc     60
aaactggaaa agttcaccaa ctgttatagc ctgagcaaaa ccctgcgttt taaagcaatt     120
ccggttggta aaacccaaga gaacattgat aataaacgcc tgctggtcga agatgaaaaa     180
cgcgctgaag attataaagg cgtgaaaaaa ctgctggatc gctattatct gagcttcatt     240
aacgatgtgc tgcacagcat taaactgaag aacctgaaca actatatcag cctgtttcgt     300
aaaaaaaccc gcaccgaaaa agaaacaaa gagctggaaa acctggaaat caatctgcgt      360
aaagaaatcg ccaaagcgtt taaaggtaac gagggttata aaagcctgtt caagaaagac    420
atcatcgaaa ccattctgcc ggaatttctg gatgataaag atgaaattgc cctggtgaat    480
agctttaatg gctttaccac cgcatttacc ggcttttttg ataatcgcga aaacatgttc    540
agcgaagaag caaaaagcac cagcattgca tttcgctgca ttaatgaaaa tctgacccgc    600
```

-continued

```
tacattagca acatggatat cttttgaaaaa gtggacgcga tcttcgataa acacgaagtg      660
caagagatca aagagaaaat cctgaacagc gattatgacg tcgaagattt ttttgaaggc      720 gagttctttta acttcgttct gacccaagaa ggtatcgacg tttataacgc aattattggt      780
ggttttgtta ccgaaagcgg tgagaaaatc aaaggcctga atgaatatat caacctgtat      840
aaccagaaaa ccaaacagaa actgccgaaa ttcaaaccgc tgtataaaca ggttctgagc      900
gatcgtgaaa gcctgagctt ttatggtgaa ggttatacca gtgatgaaga ggttctggaa      960
gtttttcgta acaccctgaa taaaaacagc gagatcttta gcagcatcaa aaagcttgag     1020
aaactgttca aaaactttga tgagtatagc agcgcaggca tctttgttaa aaatggtccg     1080
gcaattagca ccatcagcaa agatatttttt ggcgaatgga atgtgatccg cgataaatgg     1140
aatgccgaat atgatgatat ccacctgaaa aaaaaggccg tggtgaccga gaaatatgaa     1200
gatgatcgtc gtaaaagctt caagaaaatt ggtagcttta gcctggaaca gctgcaagaa     1260
tatgcagatg cagatctgag cgttgtggaa aaactgaaag aaatcatcat tcagaaggtg     1320
gacgagatct ataaagttta tggtagcagc gaaaaactgt tcgatgcaga ttttgttctg     1380
gaaaaaagcc tgaaaaagaa tgatgccgtt gtggccatta tgaaagatct gctggatagc     1440
gttaagagct tcgagaatta catcaaagcc ttttttggtg agggcaaaga aaccaatcgt     1500
gatgaaagtt tctatggcga ttttgtgctg gcctatgata ttctgctgaa agtggaccat     1560
atttatgatg ccattcgcaa ttatgttacc cagaaaccgt atagcaaaga caagttcaaa     1620 ctgtacttttc agaacccgca gtttatgggt ggttgggata agataaaga aaccgattat     1680 cgtgccacca tcctgcgtta tggtagtaaa tactatctgg ccatcatgga caaaaaatac     1740
gcaaaatgcc tgcagaaaat cgacaaagat gatgtgaatg gcaactatga aaaaatcaac     1800
tacaaactgc tgcctggtcc gaataaaatg ctgccgaaag tgttctttag caagaaatgg     1860
atggcctatt ataacccgag cgaggatatt caaaagatct acaaaaatgg cacctttaaa     1920
aagggcgaca tgttcaatct gaacgattgc cacaaactga tcgatttctt caaagattca     1980
atttcgcgtt atccgaaatg gtccaatgcc tatgattttta actttagcga aaccgaaaaa     2040
tacaaagaca ttgccggttt ttatcgcgaa gtggaagaac agggctataa agtgagcttt     2100
gaaagcgcaa gcaaaaaga ggttgataag ctggttgaag agggcaaact gtatatgttc     2160
cagatttaca acaaagattt tagcgacaaa agccatggca ccccgaatct gcataccatg     2220
tactttaaac tgctgttcga cgaaaataac catggtcaga ttcgtctgag cggtggtgcc     2280 gaactgtttta tgcgtcgtgc aagtctgaaa aaagaagaac tggttgttca tccggcaaat     2340
agcccgattg caaacaaaaa tccggacaat ccgaaaaaaa ccacgacact gagctatgat     2400
gtgtataaag acaaacgttt tagcgaggat cagtatgaac tgcatatccc gattgccatc     2460
aataaatgcc cgaaaaacat ctttaagatc aacaccgaag ttcgcgtgct gctgaaacat     2520
gatgataatc cgtatgtgat tggcattgat cgtggtgaac gtaacctgct gtatattgtt     2580
gttgttgatg gtaaaggcaa catcgtggaa cagtatagtc tgaacgaaat tatcaacaac     2640
tttaacggca tccgcatcaa aaccgactat catagcctgc tggacaagaa agaaaaagaa     2700
cgttttgaag cacgtcagaa ctggaccagt attgaaaaca tcaaagaact gaaagccggt     2760
tatattagcc aggtggttca taaaatctgt gagctggtag aaaaaatacga tgcagttatt     2820 gcactggaag atctgaatag cggttttcaaa aatagccgtg tgaaagtcga aaaacaggtg     2880
tatcagaaat tcgagaaaat gctgatcgac aaactgaact acatggtcga caaaaaaagc     2940
aatccgtgtg caaccggtgg tgcactgaaa ggttatcaga ttaccaacaa atttgaaagc     3000
```

```
tttaaaagca tgagcaccca gaacggcttt atcttctata ttccggcatg gctgaccagc   3060
aaaattgatc cgagcaccgg ttttgtgaac ctgctgaaaa caaaatatac ctccattgcc   3120
gacagcaaga agtttattag cagctttgat cgcattatgt atgttccgga agaggacctg   3180
tttgaattcg cactggatta caaaaatttc agccgtaccg atgccgacta catcaaaaaa   3240
tggaaactgt acagctatgg taaccgcatt cgcatttttc gcaacccgaa gaaaaacaat   3300
gtgttcgatt gggaagaagt ttgtctgacc agcgcatata aagaactttt caacaaatac   3360
ggcatcaact atcagcaggg tgatattcgt gcactgctgt gtgaacagag cgataaagcg   3420 tttttatagca gttttatggc actgatgagc ctgatgctgc agatgcgtaa tagcattacc   3480
ggtcgcaccg atgtggattt tctgattagt ccggtgaaaa attccgatgg catcttttat   3540
gatagccgca attacgaagc acaagaaaat gcaattctgc cgaaaaacgc agatgcaaat   3600
ggtgcatata acattgcacg taaagttctg tgggcaattg gccagtttaa gaaagcagaa   3660
gatgagaagc tggacaaagt gaaaattgcg atcagcaata agagtggct ggaatacgca   3720 cagaccagcg ttaaacattg a                                             3741
```

<210> SEQ ID NO 7
<211> LENGTH: 1246
<212> TYPE: PRT
<213> ORGANISM: Artificial Sequence
<220> FEATURE:
<223> OTHER INFORMATION: Synthetic Amino Acid sequence

<400> SEQUENCE: 7

```
Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
            20                  25                  30

Lys Thr Leu Arg Phe Lys Ala Ile Pro Val Gly Lys Thr Gln Glu Asn
        35                  40                  45

Ile Asp Asn Lys Arg Leu Leu Val Glu Asp Glu Lys Arg Ala Glu Asp
    50                  55                  60

Tyr Lys Gly Val Lys Lys Leu Leu Asp Arg Tyr Tyr Leu Ser Phe Ile
65                  70                  75                  80

Asn Asp Val Leu His Ser Ile Lys Leu Lys Asn Leu Asn Asn Tyr Ile
                85                  90                  95

Ser Leu Phe Arg Lys Lys Thr Arg Thr Glu Lys Glu Asn Lys Glu Leu
            100                 105                 110

Glu Asn Leu Glu Ile Asn Leu Arg Lys Glu Ile Ala Lys Ala Phe Lys
        115                 120                 125

Gly Asn Glu Gly Tyr Lys Ser Leu Phe Lys Lys Asp Ile Ile Glu Thr
    130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
                165                 170                 175

Glu Asn Met Phe Ser Glu Glu Ala Lys Ser Thr Ser Ile Ala Phe Arg
            180                 185                 190

Cys Ile Asn Glu Asn Leu Thr Arg Tyr Ile Ser Asn Met Asp Ile Phe
        195                 200                 205

Glu Lys Val Asp Ala Ile Phe Asp Lys His Glu Val Gln Glu Ile Lys
    210                 215                 220
```

-continued

```
Glu Lys Ile Leu Asn Ser Asp Tyr Asp Val Glu Asp Phe Phe Glu Gly
225             230             235             240

Glu Phe Phe Asn Phe Val Leu Thr Gln Glu Gly Ile Asp Val Tyr Asn
            245             250             255

Ala Ile Ile Gly Gly Phe Val Thr Glu Ser Gly Glu Lys Ile Lys Gly
            260             265             270

Leu Asn Glu Tyr Ile Asn Leu Tyr Asn Gln Lys Thr Lys Gln Lys Leu
        275             280             285

Pro Lys Phe Lys Pro Leu Tyr Lys Gln Val Leu Ser Asp Arg Glu Ser
    290             295             300

Leu Ser Phe Tyr Gly Glu Gly Tyr Thr Ser Asp Glu Glu Val Leu Glu
305             310             315             320

Val Phe Arg Asn Thr Leu Asn Lys Asn Ser Glu Ile Phe Ser Ser Ile
            325             330             335

Lys Lys Leu Glu Lys Leu Phe Lys Asn Phe Asp Glu Tyr Ser Ser Ala
            340             345             350

Gly Ile Phe Val Lys Asn Gly Pro Ala Ile Ser Thr Ile Ser Lys Asp
            355             360             365

Ile Phe Gly Glu Trp Asn Val Ile Arg Asp Lys Trp Asn Ala Glu Tyr
        370             375             380

Asp Asp Ile His Leu Lys Lys Lys Ala Val Val Thr Glu Lys Tyr Glu
385             390             395             400

Asp Asp Arg Arg Lys Ser Phe Lys Lys Ile Gly Ser Phe Ser Leu Glu
            405             410             415

Gln Leu Gln Glu Tyr Ala Asp Ala Asp Leu Ser Val Val Glu Lys Leu
            420             425             430

Lys Glu Ile Ile Ile Gln Lys Val Asp Glu Ile Tyr Lys Val Tyr Gly
            435             440             445

Ser Ser Glu Lys Leu Phe Asp Ala Asp Phe Val Leu Glu Lys Ser Leu
    450             455             460

Lys Lys Asn Asp Ala Val Val Ala Ile Met Lys Asp Leu Leu Asp Ser
465             470             475             480

Val Lys Ser Phe Glu Asn Tyr Ile Lys Ala Phe Phe Gly Glu Gly Lys
            485             490             495

Glu Thr Asn Arg Asp Glu Ser Phe Tyr Gly Asp Phe Val Leu Ala Tyr
            500             505             510

Asp Ile Leu Leu Lys Val Asp His Ile Tyr Asp Ala Ile Arg Asn Tyr
        515             520             525

Val Thr Gln Lys Pro Tyr Ser Lys Asp Lys Phe Lys Leu Tyr Phe Gln
    530             535             540

Asn Pro Gln Phe Met Gly Gly Trp Asp Lys Asp Lys Glu Thr Asp Tyr
545             550             555             560

Arg Ala Thr Ile Leu Arg Tyr Gly Ser Lys Tyr Tyr Leu Ala Ile Met
            565             570             575

Asp Lys Lys Tyr Ala Lys Cys Leu Gln Lys Ile Asp Lys Asp Asp Val
            580             585             590

Asn Gly Asn Tyr Glu Lys Ile Asn Tyr Lys Leu Leu Pro Gly Pro Asn
            595             600             605

Lys Met Leu Pro Lys Val Phe Phe Ser Lys Lys Trp Met Ala Tyr Tyr
    610             615             620

Asn Pro Ser Glu Asp Ile Gln Lys Ile Tyr Lys Asn Gly Thr Phe Lys
625             630             635             640

Lys Gly Asp Met Phe Asn Leu Asn Asp Cys His Lys Leu Ile Asp Phe
```

-continued

```
                    645              650              655

Phe Lys Asp Ser Ile Ser Arg Tyr Pro Lys Trp Ser Asn Ala Tyr Asp
        660              665              670

Phe Asn Phe Ser Glu Thr Glu Lys Tyr Lys Asp Ile Ala Gly Phe Tyr
        675              680              685

Arg Glu Val Glu Glu Gln Gly Tyr Lys Val Ser Phe Glu Ser Ala Ser
    690              695              700

Lys Lys Glu Val Asp Lys Leu Val Glu Glu Gly Lys Leu Tyr Met Phe
705              710              715              720

Gln Ile Tyr Asn Lys Asp Phe Ser Asp Lys Ser His Gly Thr Pro Asn
            725              730              735

Leu His Thr Met Tyr Phe Lys Leu Leu Phe Asp Glu Asn Asn His Gly
            740              745              750

Gln Ile Arg Leu Ser Gly Gly Ala Glu Leu Phe Met Arg Arg Ala Ser
        755              760              765

Leu Lys Lys Glu Glu Leu Val Val His Pro Ala Asn Ser Pro Ile Ala
    770              775              780

Asn Lys Asn Pro Asp Asn Pro Lys Lys Thr Thr Thr Leu Ser Tyr Asp
785              790              795              800

Val Tyr Lys Asp Lys Arg Phe Ser Glu Asp Gln Tyr Glu Leu His Ile
            805              810              815

Pro Ile Ala Ile Asn Lys Cys Pro Lys Asn Ile Phe Lys Ile Asn Thr
            820              825              830

Glu Val Arg Val Leu Leu Lys His Asp Asp Asn Pro Tyr Val Ile Gly
        835              840              845

Ile Asp Arg Gly Glu Arg Asn Leu Leu Tyr Ile Val Val Val Asp Gly
    850              855              860

Lys Gly Asn Ile Val Glu Gln Tyr Ser Leu Asn Glu Ile Ile Asn Asn
865              870              875              880

Phe Asn Gly Ile Arg Ile Lys Thr Asp Tyr His Ser Leu Leu Asp Lys
            885              890              895

Lys Glu Lys Glu Arg Phe Glu Ala Arg Gln Asn Trp Thr Ser Ile Glu
            900              905              910

Asn Ile Lys Glu Leu Lys Ala Gly Tyr Ile Ser Gln Val Val His Lys
        915              920              925

Ile Cys Glu Leu Val Glu Lys Tyr Asp Ala Val Ile Ala Leu Glu Asp
    930              935              940

Leu Asn Ser Gly Phe Lys Asn Ser Arg Val Lys Val Glu Lys Gln Val
945              950              955              960

Tyr Gln Lys Phe Glu Lys Met Leu Ile Asp Lys Leu Asn Tyr Met Val
            965              970              975

Asp Lys Lys Ser Asn Pro Cys Ala Thr Gly Gly Ala Leu Lys Gly Tyr
        980              985              990

Gln Ile Thr Asn Lys Phe Glu Ser  Phe Lys Ser Met Ser  Thr Gln Asn
        995              1000              1005

Gly Phe  Ile Phe Tyr Ile Pro  Ala Trp Leu Thr Ser  Lys Ile Asp
    1010              1015              1020

Pro Ser  Thr Gly Phe Val Asn  Leu Leu Lys Thr Lys  Tyr Thr Ser
    1025              1030              1035

Ile Ala  Asp Ser Lys Lys Phe  Ile Ser Ser Phe Asp  Arg Ile Met
    1040              1045              1050

Tyr Val  Pro Glu Glu Asp Leu  Phe Glu Phe Ala Leu  Asp Tyr Lys
    1055              1060              1065
```

-continued

```
Asn Phe Ser Arg Thr Asp Ala  Asp Tyr Ile Lys Lys  Trp Lys Leu
    1070            1075             1080

Tyr Ser Tyr Gly Asn Arg Ile  Arg Ile Phe Arg Asn  Pro Lys Lys
    1085            1090             1095

Asn Asn Val Phe Asp Trp Glu  Glu Val Cys Leu Thr  Ser Ala Tyr
    1100            1105             1110

Lys Glu Leu Phe Asn Lys Tyr  Gly Ile Asn Tyr Gln  Gln Gly Asp
    1115            1120             1125

Ile Arg Ala Leu Leu Cys Glu  Gln Ser Asp Lys Ala  Phe Tyr Ser
    1130            1135             1140

Ser Phe Met Ala Leu Met Ser  Leu Met Leu Gln Met  Arg Asn Ser
    1145            1150             1155

Ile Thr Gly Arg Thr Asp Val  Asp Phe Leu Ile Ser  Pro Val Lys
    1160            1165             1170

Asn Ser Asp Gly Ile Phe Tyr  Asp Ser Arg Asn Tyr  Glu Ala Gln
    1175            1180             1185

Glu Asn Ala Ile Leu Pro Lys  Asn Ala Asp Ala Asn  Gly Ala Tyr
    1190            1195             1200

Asn Ile Ala Arg Lys Val Leu  Trp Ala Ile Gly Gln  Phe Lys Lys
    1205            1210             1215

Ala Glu Asp Glu Lys Leu Asp  Lys Val Lys Ile Ala  Ile Ser Asn
    1220            1225             1230

Lys Glu Trp Leu Glu Tyr Ala  Gln Thr Ser Val Lys  His
    1235            1240             1245

<210> SEQ ID NO 8
<211> LENGTH: 3924
<212> TYPE: DNA
<213> ORGANISM: Artificial Sequence
<220> FEATURE:
<223> OTHER INFORMATION: Synthetic DNA

<400> SEQUENCE: 8
atgacccagt tcgagggctt caccaacctg taccaggtgt ccaagaccct gagattcgag      60
ctgatccccc agggcaagac actgaagcac atccaggaac agggcttcat cgaagaggac     120
aaggcccgga cgaccactca aaagagctg aagcccatca tcgaccggat ctacaagacc     180
tacgccacca gtgcctgca gctggtgcag ctggactggg agaatctgag cgccgccatc     240
gacagctacc ggaaagagaa aaccgaggaa acccggaacg ccctgatcga ggaacaggcc     300
acctacagaa acgccatcca cgactacttc atcggccgga ccgacaacct gaccgacgcc     360
atcaacaagc ggcacgccga gatctataag ggcctgttca aggccgagct gttcaacggc     420
aaggtgctga agcagctggg caccgtgacc accaccgagc acgaaaacgc cctgctgcgg     480
agcttcgaca gttcaccac ctacttcagc ggcttctacg agaaccggaa gaacgtgttc     540
agcgccgagg acatcagcac cgccatcccc cacagaatcg tgcaggacaa cttccccaag     600
ttcaaagaga actgccacat cttcacccgg ctgatcaccg ccgtgcccag cctgagagaa     660
cacttcgaga acgtgaagaa ggccatcggc atcttcgtgt ccaccagcat cgaggaagtg     720
ttcagcttcc cattctacaa ccagctgctg acccagaccc agatcgacct gtataatcag     780
ctgctgggcg gcatcagcag agaggccggc accgagaaga tcaagggcct gaacgaagtg     840
ctgaacctgg ccatccagaa gaacgacgag acagcccaca tcattgccag cctgcccac     900 cggttcatcc ctctgttcaa gcagatcctg agcgacagaa acaccctgag cttcatcctg     960
```

-continued

```
gaagagttca agtccgatga ggaagtgatc cagagcttct gcaagtataa gaccctgctg      1020
aggaacgaga atgtgctgga aaccgccgag gccctgttca atgagctgaa cagcatcgac      1080
ctgacccaca tctttatcag ccacaagaag ctggaaacaa tcagcagcgc cctgtgcgac      1140
cactgggaca cactgcggaa tgccctgtac gagcggcgga tctctgagct gaccggcaag      1200
atcaccaaga gcgccaaaga aaaggtgcag cggagcctga agcacgagga tatcaacctg      1260
caggaaatca tcagcgccgc tggcaaagaa ctgagcgagg cctttaagca gaaaaccagc      1320
gagatcctgt cccacgccca cgccgcactg gatcagcctc tgcctaccac cctgaagaag      1380
caggaagaga aagagatcct gaagtcccag ctggacagcc tgctgggcct gtaccatctg      1440
ctggattggt tcgccgtgga cgagagcaac gaggtggacc ccgagttctc cgccagactg      1500
acaggcatca aactggaaat ggaacccagc ctgtccttct acaacaaggc cagaaactac      1560
gccaccaaga aaccctacag cgtggaaaag tttaagctga acttccagat gcccaccctg      1620
gccagcggct gggacgtgaa caaagagaag aacaacggcg ccatcctgtt cgtgaagaac      1680
ggactgtact acctgggcat catgcctaag cagaagggca gatacaaggc cctgtccttt      1740
gagcccaccg aaaagaccag cgagggcttt gacaagatgt actacgatta cttccccgac      1800
gccgccaaga tgatccccaa gtgcagcacc cagctgaagg ccgtgaccgc ccactttcag      1860
acccacacca cccccatcct gctgagcaac aacttcatcg agccctggaa aatcaccaaa      1920
gagatctacg acctgaacaa ccccgagaaa gagcccaaga agttccagac cgcctacgcc      1980
aagaaaaccg gcgaccagaa gggctaccgc gaggctctgt gcaagtggat cgactttacc      2040
cgggacttcc tgagcaagta caccaagacc acctccatcg atctgagcag cctgcggccc      2100
agctcccagt acaaggatct gggcgagtac tacgccgagc tgaaccctct gctgtaccac      2160
atcagcttcc agcggatcgc cgaaaaagaa atcatggacg ccgtggaaac cggcaagctg      2220
tacctgttcc agatctataa caaggacttc gccaagggcc accacggcaa gcccaatctg      2280
cacaccctgt actggaccgg cctgtttagc cccgagaatc tggccaagac cagcatcaag      2340
ctgaacggcc aggccgaact gtttttaccgg cccaagagcc ggatgaagcg gatggcccat      2400
agactgggcg agaagatgct gaacaagaaa ctgaaggacc agaaaacccc tatccccgac      2460
acactgtatc aggaactgta cgactacgtg aaccaccggc tgagccacga cctgtccgac      2520
gaagctagag cactgctgcc caacgtgatc acaaagagg tgtcccacga gatcatcaag      2580
gaccggcggt ttacctccga taagttcttc ttccacgtgc ccatcaccct gaactaccag      2640
gccgccaaca gccccagcaa gttcaaccag agagtgaacg cctacctgaa agagcacccc      2700
gagacaccca tcattggcat cgacagaggc gagcggaacc tgatctacat caccgtgatc      2760
gacagcacag gcaaaatcct ggaacagaga agcctgaaca ccatccagca gttcgactac      2820
cagaagaaac tggacaaccg ggaaaaagaa cgggtggccg ccagacaggc ttggagcgtc      2880
gtgggcacca ttaaggacct gaagcagggc tacctgagcc aagtgattca cgagatcgtg      2940
gacctgatga tccactatca ggctgtggtg gtgctggaaa acctgaactt cggcttcaag      3000
agcaagcgga ccggaatcgc cgagaaagcc gtgtaccagc agtttgagaa aatgctgatc      3060
gacaagctga attgcctggt gctgaaagac taccccgctg agaaagtggg aggcgtgctg      3120
aatccctacc agctgaccga ccagttcacc tcctttgcca gatgggaac ccagagcggc      3180 ttcctgttct acgtgccagc cccctacacc agcaagatcg accctctgac cggcttcgtg      3240 gacccctcg tgtggaaaac catcaagaac cacgagtccc ggaagcactt cctggaaggc      3300
tttgacttcc tgcactacga cgtgaaaaca ggcgatttca tcctgcactt caagatgaat      3360
```

-continued

```
cggaatctgt ccttccagag gggcctgccc ggcttcatgc ctgcctggga tatcgtgttc      3420
gagaagaatg agacacagtt cgacgccaag ggaaccccct ttatcgccgg caagaggatc      3480
gtgcctgtga tcgagaacca cagattcacc ggcagatacc gggacctgta ccccgccaac      3540
gagctgattg ccctgctgga agagaagggc atcgtgttcc gggacggcag caacatcctg      3600
cccaagctgc tggaaaatga cgacagccac gccatcgata ccatggtggc actgatccgc      3660
agcgtgctgc agatgcggaa cagcaatgcc gccaccggcg aggactacat caatagccca      3720
gtgcgggacc tgaacggcgt gtgcttcgac agcagattcc agaaccccga gtggcccatg      3780
gatgccgacg ccaatggcgc ctaccacatt gccctgaagg acagctgct gctgaaccat       3840 ctgaaagaga gcaaagacct gaaactgcag aacggcatct ccaaccagga ctggctggcc      3900
tatatccagg aactgcggaa ctga                                              3924
```

<210> SEQ ID NO 9
<211> LENGTH: 683
<212> TYPE: DNA
<213> ORGANISM: Artificial Sequence
<220> FEATURE:
<223> OTHER INFORMATION: Synthetic DNA

<400> SEQUENCE: 9

```
ccagcaagat cgatcctagc accggattcg tgaacctgct caagaccaag tacaccagca        60
ttgccgacag caagaagttc atctccagct tcgaccggat tatgtacgtg cccgaagagg       120
acctgttcga attcgccctg gattacaaga acttcagccg gaccgatgcc gactatatca       180
agaagtggaa gctgtatagc tacggcaacc gcatccgcat cttcagaaac ccgaagaaaa       240
acaacgtgtt cgactgggaa gaagtgtgcc tgaccagcgc ctacaaagaa ctcttcaaca       300
aatacggcat caactaccag cagggcgaca tcagagccct gctgtgcgag cagagcgaca       360
aggcctttta cagctccttc atggcccctga tgtccctgat gctgcagatg cggaatagca       420
tcaccggcag gaccgacgtg gacttcctga tcagccctgt gaagaattcc gacgggatct      480
tctacgacag cagaaactac gaggctcaag agaacgccat cctgcctaag aacgccgatg      540
ccaacggcgc ctataatatc gccagaaagg tgctgtgggc catcggccag tttaagaagg      600
ccgaggacga gaaactggac aaagtgaaga tcgccatctc taacaaagag tggctggaat      660
acgcccagac cagcgtgaaa cac                                              683
```

<210> SEQ ID NO 10
<211> LENGTH: 1246
<212> TYPE: PRT
<213> ORGANISM: Artificial Sequence
<220> FEATURE:
<223> OTHER INFORMATION: Synthetic Amino Acid Sequence

<400> SEQUENCE: 10

```
Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
                20                  25                  30

Lys Thr Leu Arg Phe Lys Ala Ile Pro Val Gly Lys Thr Gln Glu Asn
            35                  40                  45

Ile Asp Asn Lys Arg Leu Leu Val Glu Asp Glu Lys Arg Ala Glu Asp
        50                  55                  60

Tyr Lys Gly Val Lys Lys Leu Leu Asp Arg Tyr Tyr Leu Ser Phe Ile
65                  70                  75                  80
```

-continued

```
Asn Asp Val Leu His Ser Ile Lys Leu Lys Asn Leu Asn Asn Tyr Ile
                85                  90                  95

Ser Leu Phe Arg Lys Lys Thr Arg Thr Glu Lys Glu Asn Lys Glu Leu
               100                 105                 110

Glu Asn Leu Glu Ile Asn Leu Arg Lys Glu Ile Ala Lys Ala Phe Lys
               115                 120                 125

Gly Asn Glu Gly Tyr Lys Ser Leu Phe Lys Lys Asp Ile Ile Glu Thr
           130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
               165                 170                 175

Glu Asn Met Phe Ser Glu Glu Ala Lys Ser Thr Ser Ile Ala Phe Arg
               180                 185                 190

Cys Ile Asn Glu Asn Leu Thr Arg Tyr Ile Ser Asn Met Asp Ile Phe
               195                 200                 205

Glu Lys Val Asp Ala Ile Phe Asp Lys His Glu Val Gln Glu Ile Lys
           210                 215                 220

Glu Lys Ile Leu Asn Ser Asp Tyr Asp Val Glu Asp Phe Phe Glu Gly
225                 230                 235                 240

Glu Phe Phe Asn Phe Val Leu Thr Gln Glu Gly Ile Asp Val Tyr Asn
               245                 250                 255

Ala Ile Ile Gly Gly Phe Val Thr Glu Ser Gly Glu Lys Ile Lys Gly
               260                 265                 270

Leu Asn Glu Tyr Ile Asn Leu Tyr Asn Gln Lys Thr Lys Gln Lys Leu
           275                 280                 285

Pro Lys Phe Lys Pro Leu Tyr Lys Gln Val Leu Ser Asp Arg Glu Ser
       290                 295                 300

Leu Ser Phe Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
               325                 330                 335

Lys Lys Leu Glu Lys Leu Phe Lys Asn Phe Asp Glu Tyr Ser Ser Ala
           340                 345                 350

Gly Ile Phe Val Lys Asn Gly Pro Ala Ile Ser Thr Ile Ser Lys Asp
           355                 360                 365

Ile Phe Gly Glu Trp Asn Val Ile Arg Asp Lys Trp Asn Ala Glu Tyr
       370                 375                 380

Asp Asp Ile His Leu Lys Lys Lys Ala Val Val Thr Glu Lys Tyr Glu
385                 390                 395                 400

Asp Asp Arg Arg Lys Ser Phe Lys Lys Ile Gly Ser Phe Ser Leu Glu
               405                 410                 415

Gln Leu Gln Glu Tyr Ala Asp Ala Asp Leu Ser Val Val Glu Lys Leu
           420                 425                 430

Lys Glu Ile Ile Ile Gln Lys Val Asp Glu Ile Tyr Lys Val Tyr Gly
           435                 440                 445

Ser Ser Glu Lys Leu Phe Asp Ala Asp Phe Val Leu Glu Lys Ser Leu
       450                 455                 460

Lys Lys Asn Asp Ala Val Val Ala Ile Met Lys Asp Leu Leu Asp Ser
465                 470                 475                 480

Val Lys Ser Phe Glu Asn Tyr Ile Lys Ala Phe Phe Gly Glu Gly Lys
               485                 490                 495
```

-continued

```
Glu Thr Asn Arg Asp Glu Ser Phe Tyr Gly Asp Phe Val Leu Ala Tyr
        500                 505                 510

Asp Ile Leu Leu Lys Val Asp His Ile Tyr Asp Ala Ile Arg Asn Tyr
        515                 520                 525

Val Thr Gln Lys Pro Tyr Ser Lys Asp Lys Phe Lys Leu Tyr Phe Gln
        530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Tyr Leu Ala Ile Met
                565                 570                 575

Asp Lys Lys Tyr Ala Lys Cys Leu Gln Lys Ile Asp Lys Asp Asp Val
                580                 585                 590

Asn Gly Asn Tyr Glu Lys Ile Asn Tyr Lys Leu Leu Pro Gly Pro Asn
                595                 600                 605

Lys Met Leu Pro Lys Val Phe Phe Ser Lys Lys Trp Met Ala Tyr Tyr
        610                 615                 620

Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
                645                 650                 655

Phe Lys Asp Ser Ile Ser Arg Tyr Pro Lys Trp Ser Asn Ala Tyr Asp
                660                 665                 670

Phe Asn Phe Ser Glu Thr Glu Lys Tyr Lys Asp Ile Ala Gly Phe Tyr
                675                 680                 685

Arg Glu Val Glu Glu Gln Gly Tyr Lys Val Ser Phe Glu Ser Ala Ser
        690                 695                 700

Lys Lys Glu Val Asp Lys Leu Val Glu Glu Gly Lys Leu Tyr Met Phe
705                 710                 715                 720

Gln Ile Tyr Asn Lys Asp Phe Ser Asp Lys Ser His Gly Thr Pro Asn
                725                 730                 735

Leu His Thr Met Tyr Phe Lys Leu Leu Phe Asp Glu Asn Asn His Gly
                740                 745                 750

Gln Ile Arg Leu Ser Gly Gly Ala Glu Leu Phe Met Arg Arg Ala Ser
        755                 760                 765

Leu Lys Lys Glu Glu Leu Val Val His Pro Ala Asn Ser Pro Ile Ala
        770                 775                 780

Asn Lys Asn Pro Asp Asn Pro Lys Lys Thr Thr Thr Leu Ser Tyr Asp
785                 790                 795                 800

Val Tyr Lys Asp Lys Arg Phe Ser Glu Asp Gln Tyr Glu Leu His Ile
                805                 810                 815

Pro Ile Ala Ile Asn Lys Cys Pro Lys Asn Ile Phe Lys Ile Asn Thr
                820                 825                 830

Glu Val Arg Val Leu Leu Lys His Asp Asp Asn Pro Tyr Val Ile Gly
        835                 840                 845

Ile Asp Arg Gly Glu Arg Asn Leu Leu Tyr Ile Val Val Val Asp Gly
        850                 855                 860

Lys Gly Asn Ile Val Glu Gln Tyr Ser Leu Asn Glu Ile Ile Asn Asn
865                 870                 875                 880

Phe Asn Gly Ile Arg Ile Lys Thr Asp Tyr His Ser Leu Leu Asp Lys
                885                 890                 895

Lys Glu Lys Glu Arg Phe Glu Ala Arg Gln Asn Trp Thr Ser Ile Glu
                900                 905                 910

Asn Ile Lys Glu Leu Lys Ala Gly Tyr Ile Ser Gln Val Val His Lys
```

```
             915             920             925
Ile Cys Glu Leu Val Glu Lys Tyr Asp Ala Val Ile Ala Leu Glu Asp
   930             935             940

Leu Asn Ser Gly Phe Lys Asn Ser Arg Val Lys Val Glu Lys Gln Val
945             950             955             960

Tyr Gln Lys Phe Glu Lys Met Leu Ile Asp Lys Leu Asn Tyr Met Val
                965             970             975

Asp Lys Lys Ser Asn Pro Cys Ala Thr Gly Gly Ala Leu Lys Gly Tyr
                980             985             990

Gln Ile Thr Asn Lys Phe Glu Ser  Phe Lys Ser Met Ser  Thr Gln Asn
        995             1000            1005

Gly Phe  Ile Phe Tyr Ile Pro  Ala Trp Leu Thr Ser  Lys Ile Asp
    1010            1015            1020

Pro Ser  Thr Gly Phe Val Asn  Leu Leu Lys Thr Lys  Tyr Thr Ser
    1025            1030            1035

Ile Ala  Asp Ser Lys Lys Phe  Ile Ser Ser Phe Asp  Arg Ile Met
    1040            1045            1050

Tyr Val  Pro Glu Glu Asp Leu  Phe Glu Phe Ala Leu  Asp Tyr Lys
    1055            1060            1065

Asn Phe  Ser Arg Thr Asp Ala  Asp Tyr Ile Lys Lys  Trp Lys Leu
    1070            1075            1080

Tyr Ser  Tyr Gly Asn Arg Ile  Arg Ile Phe Arg Asn  Pro Lys Lys
    1085            1090            1095

Asn Asn  Val Phe Asp Trp Glu  Glu Val Cys Leu Thr  Ser Ala Tyr
    1100            1105            1110

Lys Glu  Leu Phe Asn Lys Tyr  Gly Ile Asn Tyr Gln  Gln Gly Asp
    1115            1120            1125

Ile Arg  Ala Leu Leu Cys Glu  Gln Ser Asp Lys Ala  Phe Tyr Ser
    1130            1135            1140

Ser Phe  Met Ala Leu Met Ser  Leu Met Leu Gln Met  Arg Asn Ser
    1145            1150            1155

Ile Thr  Gly Arg Thr Asp Val  Asp Phe Leu Ile Ser  Pro Val Lys
    1160            1165            1170

Asn Ser  Asp Gly Ile Phe Tyr  Asp Ser Arg Asn Tyr  Glu Ala Gln
    1175            1180            1185

Glu Asn  Ala Ile Leu Pro Lys  Asn Ala Asp Ala Asn  Gly Ala Tyr
    1190            1195            1200

Asn Ile  Ala Arg Lys Val Leu  Trp Ala Ile Gly Gln  Phe Lys Lys
    1205            1210            1215

Ala Glu  Asp Glu Lys Leu Asp  Lys Val Lys Ile Ala  Ile Ser Asn
    1220            1225            1230

Lys Glu  Trp Leu Glu Tyr Ala  Gln Thr Ser Val Lys  His
    1235            1240            1245

<210> SEQ ID NO 11
<211> LENGTH: 4086
<212> TYPE: DNA
<213> ORGANISM: Artificial Sequence
<220> FEATURE:
<223> OTHER INFORMATION: Synthetic DNA

<400> SEQUENCE: 11
atgggtcggg atccaggtaa accgattccg aatccgctgc tgggtctgga tagcaccgca      60
ccgaaaaaaa aacgtaaagt tggtattcat ggtgttccgg cagcaaccca gtttgaaggt     120
```

```
ttcaccaatc tgtatcaggt tagcaaaacc ctgcgttttg aactgattcc gcagggtaaa      180
accctgaaac atattcaaga acagggcttc atcgaagagg ataaagcacg taacgatcac      240
tacaaagaac tgaaaccgat tatcgaccgc atctataaaa cctatgcaga tcagtgtctg      300
cagctggttc agctggattg ggaaaatctg agcgcagcaa ttgatagtta tcgcaaagaa      360
aaaaccgaag aaaaccgtaa tgcactgatt gaagaacagg caacctatcg taatgccatc      420
catgattatt tcattggtcg taccgataat ctgaccgatg caattaacaa acgtcacgcc      480
gaaatctata aaggcctgtt taaagccgaa ctgtttaatg gcaaagttct gaaacagctg      540
ggcaccgtta ccaccaccga acatgaaaat gcactgctgc gtagctttga taaattcacc      600
acctatttca gcggctttta tgagaatcgc aaaaacgtgt ttagcgcaga agatattagc      660
accgcaattc cgcatcgtat tgtgcaggat aatttcccga aattcaaaga gaactgccac      720
atttttaccc gtctgattac cgcagttccg agcctgcgtg aacattttga aaacgttaaa      780
aaagccatcg gcatctttgt tagcaccagc attgaagaag tttttagctt cccgtttttac     840 aatcagctgc tgacccagac ccagattgat ctgtataacc aactgctggg tggtattagc      900
cgtgaagcag gcaccgaaaa aatcaaaggt ctgaatgaag tgctgaatct ggccattcag      960
aaaaatgatg aaaccgcaca tattattgca agcctgccgc atcgttttat tccgctgttc     1020
aaacaaattc tgagcgatcg taataccctg agctttattc tggaagaatt caaatccgat     1080
gaagaggtga ttcagagctt ttgcaaatac aaaacgctgc tgcgcaatga aaatgttctg     1140
gaaactgccg aagcactgtt taacgaactg aatagcattg atctgaccca catctttatc     1200
agccacaaaa aactggaaac catttcaagc gcactgtgtg atcattggga taccctgcgt     1260
aatgccctgt atgaacgtcg tattagcgaa ctgaccggta aaattaccaa aagcgcgaaa     1320
gaaaaagttc agcgcagtct gaaacatgag gatattaatc tgcaagagat tattagcgca     1380
gccggtaaag aactgtcaga agcatttaaa cagaaaacca gcgaaattct gtcacatgca     1440
catgcagcac tggatcagcc gctgccgacc accctgaaaa aacaagaaga aaaagaaatc     1500
ctgaaaagcc agctggatag cctgctgggt ctgtatcatc tgctggactg gtttgcagtt     1560
gatgaaagca atgaagttga tccggaattt agcgcacgtc tgaccggcat taaactggaa     1620
atggaaccga gcctgagctt ttataacaaa gcccgtaatt atgccaccaa aaaaccgtat     1680
agcgtcgaaa aattcaaact gaactttcag atgccgaccc tggcaagcgg ttgggatgtt     1740
aataaagaaa aaaacaacgg tgccatcctg ttcgtgaaaa atggcctgta ttatctgggt     1800
attatgccga aacagaaagg tcgttataaa gcgctgagct ttgaaccgac ggaaaaaacc     1860
agtgaaggtt ttgataaaat gtactacgac tattttccgg atgcagccaa aatgattccg     1920
aaatgtagca cccagctgaa agcagttacc gcacattttc agaccccatac cacccccgatt    1980 ctgctgagca ataactttat tgaaccgctg gaaatcacca aagagatcta cgatctgaat     2040
aacccggaaa aagagccgaa aaaattccag accgcatatg caaaaaaaac cggtgatcag     2100
aaaggttatc gtgaagcgct gtgtaaatgg attgatttca cccgtgattt tctgagcaaa     2160
tacaccaaaa ccaccagtat cgatctgagc agcctgcgtc cgagcagcca gtataaagat     2220
ctgggcgaat attatgcaga actgaatccg ctgctgtatc atattagctt tcagcgtatt     2280
gccgagaaag aaatcatgga cgcagttgaa accggtaaac tgtacctgtt ccagatctac     2340
aataaagatt ttgccaaagg ccatcatggc aaaccgaatc tgcataccct gtattggacc     2400 ggtctgtttta gccctgaaaa tctggcaaaa acctcgatta aactgaatgg tcaggcggaa     2460 ctgtttttatc gtccgaaaag ccgtatgaaa cgtatggcac atcgtctggg tgaaaaaatg     2520
```

```
ctgaacaaaa aactgaaaga ccagaaaacc ccgatcccgg atacactgta tcaagaactg    2580
tatgattatg tgaaccatcg tctgagccat gatctgagtg atgaagcacg tgccctgctg    2640
ccgaatgtta ttaccaaaga agttagccac gagatcatta agatcgtcg ttttaccagc     2700 gacaaattct tttttcatgt gccgattacc ctgaattatc aggcagcaaa tagcccgagc    2760
aaatttaacc agcgtgttaa tgcatatctg aaagaacatc cagaaacgcc gattattggt    2820
attgatcgtg gtgaacgtaa cctgatttat atcaccgtta ttgatagcac cggcaaaatc    2880
ctggaacagc gtagcctgaa taccattcag cagtttgatt accagaaaaa actggataat    2940
cgcgagaaag aacgtgttgc agcacgtcag gcatggtcag ttgttggtac aattaaagac    3000
ctgaaacagg gttatctgag ccaggttatt catgaaattg tggatctgat gattcactat    3060
caggccgttg ttgtgctgga aaacctgaat tttggcttta aaagcaaacg taccggcatt    3120
gcagaaaaag cagtttatca gcagttcgag aaaatgctga ttgacaaact gaattgcctg    3180
gtgctgaaaa attatccggc tgaaaaagtt ggtggtgttc tgaatccgta tcagctgacc    3240
gatcagttta ccagctttgc aaaaatgggc acccagagcg gatttctgtt ttatgttccg    3300
gcaccgtata cgagcaaaat tgatccgctg accggttttg ttgatccgtt tgtttggaaa    3360
accatcaaaa accatgaaag ccgcaaacat tttctggaag gtttcgattt tctgcattac    3420
gacgttaaaa cgggtgattt catcctgcac tttaaaatga atcgcaatct gagttttcag    3480
cgtggcctgc ctggttttat gcctgcatgg gatattgtgt ttgagaaaaa cgaaacacag    3540
ttcgatgcaa aaggcacccc gtttattgca ggtaaacgta ttgttccggt gattgaaaat    3600
catcgtttca ccggtcgtta tcgcgatctg tatccggcaa atgaactgat cgcactgctg    3660
gaagagaaag gtattgtttt tcgtgatggc tcaaacattc tgccgaaact gctggaaaat    3720
gatgatagcc atgcaattga taccatggtt gcactgattc gtagcgttct gcagatgcgt    3780
aatagcaatg cagcaaccgg tgaagattac attaatagtc cggttcgtga tctgaatggt    3840
gtttgttttg atagccgttt tcagaatccg gaatggccga tggatgcaga tgcaaatggt    3900
gcatatcata ttgcactgaa aggacagctg ctgctgaacc acctgaaaga aagcaaagat    3960
ctgaaactgc aaaacggcat tagcaatcag gattggctgg catatatcca agaactgcgt    4020
aaccctaaaa aaaacgcaa agtgaagctt gcggccgcac tcgagcacca ccaccaccac    4080
cactga                                                                  4086
```

```
<210> SEQ ID NO 12
<211> LENGTH: 1361
<212> TYPE: PRT
<213> ORGANISM: Artificial Sequence
<220> FEATURE:
<223> OTHER INFORMATION: Synthetic Amino Acid Sequence

<400> SEQUENCE: 12
```

```
Met Gly Arg Asp Pro Gly Lys Pro Ile Pro Asn Pro Leu Leu Gly Leu
1               5                   10                  15

Asp Ser Thr Ala Pro Lys Lys Lys Arg Lys Val Gly Ile His Gly Val
            20                  25                  30

Pro Ala Ala Thr Gln Phe Glu Gly Phe Thr Asn Leu Tyr Gln Val Ser
        35                  40                  45

Lys Thr Leu Arg Phe Glu Leu Ile Pro Gln Gly Lys Thr Leu Lys His
    50                  55                  60

Ile Gln Glu Gln Gly Phe Ile Glu Glu Asp Lys Ala Arg Asn Asp His
65                  70                  75                  80
```

```
Tyr Lys Glu Leu Lys Pro Ile Ile Asp Arg Ile Tyr Lys Thr Tyr Ala
                85              90              95

Asp Gln Cys Leu Gln Leu Val Gln Leu Asp Trp Glu Asn Leu Ser Ala
            100             105             110

Ala Ile Asp Ser Tyr Arg Lys Glu Lys Thr Glu Glu Thr Arg Asn Ala
            115             120             125

Leu Ile Glu Glu Gln Ala Thr Tyr Arg Asn Ala Ile His Asp Tyr Phe
        130             135             140

Ile Gly Arg Thr Asp Asn Leu Thr Asp Ala Ile Asn Lys Arg His Ala
145             150             155             160

Glu Ile Tyr Lys Gly Leu Phe Lys Ala Glu Leu Phe Asn Gly Lys Val
                165             170             175

Leu Lys Gln Leu Gly Thr Val Thr Thr Thr Glu His Glu Asn Ala Leu
            180             185             190

Leu Arg Ser Phe Asp Lys Phe Thr Thr Tyr Phe Ser Gly Phe Tyr Glu
            195             200             205

Asn Arg Lys Asn Val Phe Ser Ala Glu Asp Ile Ser Thr Ala Ile Pro
        210             215             220

His Arg Ile Val Gln Asp Asn Phe Pro Lys Phe Lys Glu Asn Cys His
225             230             235             240

Ile Phe Thr Arg Leu Ile Thr Ala Val Pro Ser Leu Arg Glu His Phe
                245             250             255

Glu Asn Val Lys Lys Ala Ile Gly Ile Phe Val Ser Thr Ser Ile Glu
            260             265             270

Glu Val Phe Ser Phe Pro Phe Tyr Asn Gln Leu Leu Thr Gln Thr Gln
            275             280             285

Ile Asp Leu Tyr Asn Gln Leu Leu Gly Gly Ile Ser Arg Glu Ala Gly
        290             295             300

Thr Glu Lys Ile Lys Gly Leu Asn Glu Val Leu Asn Leu Ala Ile Gln
305             310             315             320

Lys Asn Asp Glu Thr Ala His Ile Ile Ala Ser Leu Pro His Arg Phe
                325             330             335

Ile Pro Leu Phe Lys Gln Ile Leu Ser Asp Arg Asn Thr Leu Ser Phe
            340             345             350

Ile Leu Glu Glu Phe Lys Ser Asp Glu Glu Val Ile Gln Ser Phe Cys
            355             360             365

Lys Tyr Lys Thr Leu Leu Arg Asn Glu Asn Val Leu Glu Thr Ala Glu
        370             375             380

Ala Leu Phe Asn Glu Leu Asn Ser Ile Asp Leu Thr His Ile Phe Ile
385             390             395             400

Ser His Lys Lys Leu Glu Thr Ile Ser Ser Ala Leu Cys Asp His Trp
                405             410             415

Asp Thr Leu Arg Asn Ala Leu Tyr Glu Arg Arg Ile Ser Glu Leu Thr
            420             425             430

Gly Lys Ile Thr Lys Ser Ala Lys Glu Lys Val Gln Arg Ser Leu Lys
            435             440             445

His Glu Asp Ile Asn Leu Gln Glu Ile Ile Ser Ala Ala Gly Lys Glu
        450             455             460

Leu Ser Glu Ala Phe Lys Gln Lys Thr Ser Glu Ile Leu Ser His Ala
465             470             475             480

His Ala Ala Leu Asp Gln Pro Leu Pro Thr Thr Leu Lys Lys Gln Glu
                485             490             495
```

-continued

```
Glu Lys Glu Ile Leu Lys Ser Gln Leu Asp Ser Leu Leu Gly Leu Tyr
            500                 505                 510

His Leu Leu Asp Trp Phe Ala Val Asp Glu Ser Asn Glu Val Asp Pro
        515                 520                 525

Glu Phe Ser Ala Arg Leu Thr Gly Ile Lys Leu Glu Met Glu Pro Ser
        530                 535                 540

Leu Ser Phe Tyr Asn Lys Ala Arg Asn Tyr Ala Thr Lys Lys Pro Tyr
545                 550                 555                 560

Ser Val Glu Lys Phe Lys Leu Asn Phe Gln Met Pro Thr Leu Ala Ser
                565                 570                 575

Gly Trp Asp Val Asn Lys Glu Lys Asn Asn Gly Ala Ile Leu Phe Val
                580                 585                 590

Lys Asn Gly Leu Tyr Tyr Leu Gly Ile Met Pro Lys Gln Lys Gly Arg
            595                 600                 605

Tyr Lys Ala Leu Ser Phe Glu Pro Thr Glu Lys Thr Ser Glu Gly Phe
        610                 615                 620

Asp Lys Met Tyr Tyr Asp Tyr Phe Pro Asp Ala Ala Lys Met Ile Pro
625                 630                 635                 640

Lys Cys Ser Thr Gln Leu Lys Ala Val Thr Ala His Phe Gln Thr His
                645                 650                 655

Thr Thr Pro Ile Leu Leu Ser Asn Asn Phe Ile Glu Pro Leu Glu Ile
                660                 665                 670

Thr Lys Glu Ile Tyr Asp Leu Asn Asn Pro Glu Lys Glu Pro Lys Lys
            675                 680                 685

Phe Gln Thr Ala Tyr Ala Lys Lys Thr Gly Asp Gln Lys Gly Tyr Arg
        690                 695                 700

Glu Ala Leu Cys Lys Trp Ile Asp Phe Thr Arg Asp Phe Leu Ser Lys
705                 710                 715                 720

Tyr Thr Lys Thr Thr Ser Ile Asp Leu Ser Ser Leu Arg Pro Ser Ser
                725                 730                 735

Gln Tyr Lys Asp Leu Gly Glu Tyr Tyr Ala Glu Leu Asn Pro Leu Leu
            740                 745                 750

Tyr His Ile Ser Phe Gln Arg Ile Ala Glu Lys Glu Ile Met Asp Ala
            755                 760                 765

Val Glu Thr Gly Lys Leu Tyr Leu Phe Gln Ile Tyr Asn Lys Asp Phe
        770                 775                 780

Ala Lys Gly His His Gly Lys Pro Asn Leu His Thr Leu Tyr Trp Thr
785                 790                 795                 800

Gly Leu Phe Ser Pro Glu Asn Leu Ala Lys Thr Ser Ile Lys Leu Asn
                805                 810                 815

Gly Gln Ala Glu Leu Phe Tyr Arg Pro Lys Ser Arg Met Lys Arg Met
            820                 825                 830

Ala His Arg Leu Gly Glu Lys Met Leu Asn Lys Lys Leu Lys Asp Gln
        835                 840                 845

Lys Thr Pro Ile Pro Asp Thr Leu Tyr Gln Glu Leu Tyr Asp Tyr Val
        850                 855                 860

Asn His Arg Leu Ser His Asp Leu Ser Asp Glu Ala Arg Ala Leu Leu
865                 870                 875                 880

Pro Asn Val Ile Thr Lys Glu Val Ser His Glu Ile Ile Lys Asp Arg
                885                 890                 895

Arg Phe Thr Ser Asp Lys Phe Phe Phe His Val Pro Ile Thr Leu Asn
            900                 905                 910

Tyr Gln Ala Ala Asn Ser Pro Ser Lys Phe Asn Gln Arg Val Asn Ala
```

-continued

```
              915                920                925

Tyr Leu Lys Glu His Pro Glu Thr Pro Ile Ile Gly Ile Asp Arg Gly
    930                935                940

Glu Arg Asn Leu Ile Tyr Ile Thr Val Ile Asp Ser Thr Gly Lys Ile
945                950                955                960

Leu Glu Gln Arg Ser Leu Asn Thr Ile Gln Gln Phe Asp Tyr Gln Lys
                965                970                975

Lys Leu Asp Asn Arg Glu Lys Glu Arg Val Ala Ala Arg Gln Ala Trp
            980                985                990

Ser Val Val Gly Thr Ile Lys Asp  Leu Lys Gln Gly Tyr  Leu Ser Gln
        995                1000                1005

Val Ile  His Glu Ile Val Asp  Leu Met Ile His Tyr  Gln Ala Val
    1010                1015                1020

Val Val  Leu Glu Asn Leu Asn  Phe Gly Phe Lys Ser  Lys Arg Thr
    1025                1030                1035

Gly Ile  Ala Glu Lys Ala Val  Tyr Gln Gln Phe Glu  Lys Met Leu
    1040                1045                1050

Ile Asp  Lys Leu Asn Cys Leu  Val Leu Lys Asp Tyr  Pro Ala Glu
    1055                1060                1065

Lys Val  Gly Gly Val Leu Asn  Pro Tyr Gln Leu Thr  Asp Gln Phe
    1070                1075                1080

Thr Ser  Phe Ala Lys Met Gly  Thr Gln Ser Gly Phe  Leu Phe Tyr
    1085                1090                1095

Val Pro  Ala Pro Tyr Thr Ser  Lys Ile Asp Pro Leu  Thr Gly Phe
    1100                1105                1110

Val Asp  Pro Phe Val Trp Lys  Thr Ile Lys Asn His  Glu Ser Arg
    1115                1120                1125

Lys His  Phe Leu Glu Gly Phe  Asp Phe Leu His Tyr  Asp Val Lys
    1130                1135                1140

Thr Gly  Asp Phe Ile Leu His  Phe Lys Met Asn Arg  Asn Leu Ser
    1145                1150                1155

Phe Gln  Arg Gly Leu Pro Gly  Phe Met Pro Ala Trp  Asp Ile Val
    1160                1165                1170

Phe Glu  Lys Asn Glu Thr Gln  Phe Asp Ala Lys Gly  Thr Pro Phe
    1175                1180                1185

Ile Ala  Gly Lys Arg Ile Val  Pro Val Ile Glu Asn  His Arg Phe
    1190                1195                1200

Thr Gly  Arg Tyr Arg Asp Leu  Tyr Pro Ala Asn Glu  Leu Ile Ala
    1205                1210                1215

Leu Leu  Glu Glu Lys Gly Ile  Val Phe Arg Asp Gly  Ser Asn Ile
    1220                1225                1230

Leu Pro  Lys Leu Leu Glu Asn  Asp Asp Ser His Ala  Ile Asp Thr
    1235                1240                1245

Met Val  Ala Leu Ile Arg Ser  Val Leu Gln Met Arg  Asn Ser Asn
    1250                1255                1260

Ala Ala  Thr Gly Glu Asp Tyr  Ile Asn Ser Pro Val  Arg Asp Leu
    1265                1270                1275

Asn Gly  Val Cys Phe Asp Ser  Arg Phe Gln Asn Pro  Glu Trp Pro
    1280                1285                1290

Met Asp  Ala Asp Ala Asn Gly  Ala Tyr His Ile Ala  Leu Lys Gly
    1295                1300                1305

Gln Leu  Leu Leu Asn His Leu  Lys Glu Ser Lys Asp  Leu Lys Leu
    1310                1315                1320
```

-continued

```
Gln Asn  Gly Ile Ser Asn Gln  Asp Trp Leu Ala Tyr  Ile Gln Glu
    1325             1330              1335

Leu Arg  Asn Pro Lys Lys Lys  Arg Lys Val Lys Leu  Ala Ala Ala
    1340             1345              1350

Leu Glu  His His His His His  His
    1355             1360

<210> SEQ ID NO 13
<211> LENGTH: 3876
<212> TYPE: DNA
<213> ORGANISM: Artificial Sequence
<220> FEATURE:
<223> OTHER INFORMATION: Synthetic DNA

<400> SEQUENCE: 13
atgggtaaac cgattccgaa tccgctgctg ggtctggata gcaccgcacc gaaaaaaaaa      60
cgtaaagttg gtattcatgg tgttccggca gcactgaaaa cgtgggtat tgatcgtctg     120 gatgttgaaa aaggtcgcaa aaatatgagc aaactggaaa agttcaccaa ctgttatagc     180
ctgagcaaaa ccctgcgttt taaagcaatt ccggttggta aaacccaaga gaacattgat     240
aataaacgcc tgctggtcga agatgaaaaa cgcgctgaag attataaagg cgtgaaaaaa     300
ctgctggatc gctattatct gagcttcatt aacgatgtgc tgcacagcat taaactgaag     360
aacctgaaca actatatcag cctgtttcgt aaaaaaaccc gcaccgaaaa agaaaacaaa     420
gagctggaaa acctggaaat caatctgcgt aaagaaatcg ccaaagcgtt taaaggtaac     480
gagggttata aaagcctgtt caagaaagac atcatcgaaa ccattctgcc ggaatttctg     540
gatgataaag atgaaattgc cctggtgaat agctttaatg gctttaccac cgcatttacc     600
ggcttttttg ataatcgcga aaacatgttc agcgaagaag caaaaagcac cagcattgca     660
tttcgctgca ttaatgaaaa tctgacccgc tacattagca acatggatat ctttgaaaaa     720
gtggacgcga tcttcgataa acacgaagtg caagagatca agagaaaat cctgaacagc     780 gattatgacg tcgaagattt ttttgaaggc gagttcttta acttcgttct gacccaagaa     840
ggtatcgacg tttataacgc aattattggt ggttttgtta ccgaaagcgg tgagaaaatc     900
aaaggcctga tgaatatat caacctgtat aaccagaaaa ccaaacagaa actgccgaaa     960
ttcaaaccgc tgtataaaca ggttctgagc gatcgtgaaa gcctgagctt ttatggtgaa    1020
ggttatacca gtgatgaaga ggttctggaa gtttttcgta cacccctgaa taaaaacagc    1080
gagatcttta gcagcatcaa aaagcttgag aaactgttca aaaactttga tgagtatagc    1140
agcgcaggca tctttgttaa aaatggtccg gcaattagca ccatcagcaa agatattttt    1200
ggcgaatgga atgtgatccg cgataaatgg aatgccgaat atgatgatat ccacctgaaa    1260
aaaaaggccg tggtgaccga gaaatatgaa gatgatcgtc gtaaaagctt caagaaaatt    1320
ggtagcttta gcctggaaca gctgcaagaa tatgcagatg cagatctgag cgttgtggaa    1380
aaactgaaag aaatcatcat tcagaaggtg gacgagatct ataaagttta tggtagcagc    1440
gaaaaactgt tcgatgcaga ttttgttctg gaaaaaagcc tgaaaaagaa tgatgccgtt    1500
gtggccatta tgaaagatct gctggatagc gttaagagct tcgagaatta catcaaagcc    1560
ttttttggtg agggcaaaga aaccaatcgt gatgaaagtt tctatggcga ttttgtgctg    1620
gcctatgata ttctgctgaa agtggaccat atttatgatg ccattcgcaa ttatgttacc    1680
cagaaaccgt atagcaaaga caagttcaaa ctgtactttc agaacccgca gtttatgggt    1740
ggttgggata agataaaga aaccgattat cgtgccacca tcctgcgtta tggtagtaaa    1800
```

-continued

```
tactatctgg ccatcatgga caaaaaatac gcaaaatgcc tgcagaaaat cgacaaagat    1860
gatgtgaatg gcaactatga aaaaatcaac tacaaactgc tgcctggtcc gaataaaatg    1920
ctgccgaaag tgttctttag caagaaatgg atggcctatt ataacccgag cgaggatatt    1980
caaaagatct acaaaaatgg cacctttaaa aagggcgaca tgttcaatct gaacgattgc    2040
cacaaactga tcgatttctt caaagattca atttcgcgtt atccgaaatg gtccaatgcc    2100
tatgatttta actttagcga aaccgaaaaa tacaaagaca ttgccggttt ttatcgcgaa    2160
gtggaagaac agggctataa agtgagcttt gaaagcgcaa gcaaaaaaga ggttgataag    2220
ctggttgaag agggcaaact gtatatgttc cagatttaca acaaagattt tagcgacaaa    2280
agccatggca ccccgaatct gcataccatg tactttaaac tgctgttcga cgaaaataac    2340
catggtcaga ttcgtctgag cggtggtgcc gaactgtttta tgcgtcgtgc aagtctgaaa    2400
aaagaagaac tggttgttca tccggcaaat agcccgattg caaacaaaaa tccggacaat    2460
ccgaaaaaaa ccacgacact gagctatgat gtgtataaag acaaacgttt tagcgaggat    2520
cagtatgaac tgcatatccc gattgccatc aataaatgcc cgaaaaacat ctttaagatc    2580
aacaccgaag ttcgcgtgct gctgaaacat gatgataatc cgtatgtgat tggcattgat    2640
cgtggtgaac gtaacctgct gtatattgtt gttgttgatg gtaaaggcaa catcgtggaa    2700
cagtatagtc tgaacgaaat tatcaacaac tttaacggca tccgcatcaa aaccgactat    2760
catagcctgc tggacaagaa agaaaaagaa cgttttgaag cacgtcagaa ctggaccagt    2820
attgaaaaca tcaaagaact gaaagccggt tatattagcc aggtggttca taaaatctgt    2880
gagctggtag aaaaaatacga tgcagttatt gcactggaag atctgaatag cggtttcaaa    2940
aatagccgtg tgaaagtcga aaaacaggtg tatcagaaat cgagaaaaat gctgatcgac    3000
aaactgaact acatggtcga caaaaaaagc aatccgtgtg caaccggtgg tgcactgaaa    3060
ggttatcaga ttaccaacaa atttgaaagc tttaaaagca tgagcacca gaacggcttt    3120 atcttctata ttccggcatg gctgaccagc aaaattgatc cgagcaccgg ttttgtgaac    3180
ctgctgaaaa caaaatatac ctccattgcc gacagcaaga agtttattag cagctttgat    3240
cgcattatgt atgttccgga agaggacctg tttgaattcg cactggatta caaaaatttc    3300
agccgtaccg atgccgacta catcaaaaaa tggaaactgt acagctatgg taaccgcatt    3360 cgcattttc gcaacccgaa gaaaaacaat gtgttcgatt gggaagaagt ttgtctgacc    3420
agcgcatata aagaacttt caacaaatac ggcatcaact atcagcaggg tgatattcgt    3480
gcactgctgt gtaacagag cgataaagcg ttttatagca gttttatggc actgatgagc    3540
ctgatgctgc agatgcgtaa tagcattacc ggtcgcaccg atgtggattt tctgattagt    3600
ccggtgaaaa attccgatgg catcttttat gatagccgca attacgaagc acaagaaaat    3660
gcaattctgc cgaaaaacgc agatgcaaat ggtgcatata acattgcacg taaagttctg    3720
tgggcaattg gccagtttaa gaaagcagaa gatgagaagc tggacaaagt gaaaattgcg    3780
atcagcaata agagtggct ggaatacgca cagaccagcg ttaaacatcc gaaaaaaaaa    3840
cgcaaagtgc tcgagcacca ccaccaccac cactga                              3876
```

```
<210> SEQ ID NO 14
<211> LENGTH: 1291
<212> TYPE: PRT
<213> ORGANISM: Artificial Sequence
<220> FEATURE:
<223> OTHER INFORMATION: Synthetic Amino Acid Sequence
```

-continued

```
<400> SEQUENCE: 14

Met Gly Lys Pro Ile Pro Asn Pro Leu Leu Gly Leu Asp Ser Thr Ala
1               5                   10                  15

Pro Lys Lys Lys Arg Lys Val Gly Ile His Gly Val Pro Ala Ala Leu
                20                  25                  30

Lys Asn Val Gly Ile Asp Arg Leu Asp Val Glu Lys Gly Arg Lys Asn
            35                  40                  45

Met Ser Lys Leu Glu Lys Phe Thr Asn Cys Tyr Ser Leu Ser Lys Thr
    50                  55                  60

Leu Arg Phe Lys Ala Ile Pro Val Gly Lys Thr Gln Glu Asn Ile Asp
65                  70                  75                  80

Asn Lys Arg Leu Leu Val Glu Asp Glu Lys Arg Ala Glu Asp Tyr Lys
                85                  90                  95

Gly Val Lys Lys Leu Leu Asp Arg Tyr Tyr Leu Ser Phe Ile Asn Asp
            100                 105                 110

Val Leu His Ser Ile Lys Leu Lys Asn Leu Asn Asn Tyr Ile Ser Leu
            115                 120                 125

Phe Arg Lys Lys Thr Arg Thr Glu Lys Glu Asn Lys Glu Leu Glu Asn
    130                 135                 140

Leu Glu Ile Asn Leu Arg Lys Glu Ile Ala Lys Ala Phe Lys Gly Asn
145                 150                 155                 160

Glu Gly Tyr Lys Ser Leu Phe Lys Lys Asp Ile Ile Glu Thr Ile Leu
                165                 170                 175

Pro Glu Phe Leu Asp Asp Lys Asp Glu Ile Ala Leu Val Asn Ser Phe
            180                 185                 190

Asn Gly Phe Thr Thr Ala Phe Thr Gly Phe Phe Asp Asn Arg Glu Asn
            195                 200                 205

Met Phe Ser Glu Glu Ala Lys Ser Thr Ser Ile Ala Phe Arg Cys Ile
    210                 215                 220

Asn Glu Asn Leu Thr Arg Tyr Ile Ser Asn Met Asp Ile Phe Glu Lys
225                 230                 235                 240

Val Asp Ala Ile Phe Asp Lys His Glu Val Gln Glu Ile Lys Glu Lys
            245                 250                 255

Ile Leu Asn Ser Asp Tyr Asp Val Glu Asp Phe Phe Glu Gly Glu Phe
            260                 265                 270

Phe Asn Phe Val Leu Thr Gln Glu Gly Ile Asp Val Tyr Asn Ala Ile
    275                 280                 285

Ile Gly Gly Phe Val Thr Glu Ser Gly Glu Lys Ile Lys Gly Leu Asn
    290                 295                 300

Glu Tyr Ile Asn Leu Tyr Asn Gln Lys Thr Lys Gln Lys Leu Pro Lys
305                 310                 315                 320

Phe Lys Pro Leu Tyr Lys Gln Val Leu Ser Asp Arg Glu Ser Leu Ser
                325                 330                 335

Phe Tyr Gly Glu Gly Tyr Thr Ser Asp Glu Glu Val Leu Glu Val Phe
            340                 345                 350

Arg Asn Thr Leu Asn Lys Asn Ser Glu Ile Phe Ser Ser Ile Lys Lys
    355                 360                 365

Leu Glu Lys Leu Phe Lys Asn Phe Asp Glu Tyr Ser Ser Ala Gly Ile
    370                 375                 380

Phe Val Lys Asn Gly Pro Ala Ile Ser Thr Ile Ser Lys Asp Ile Phe
385                 390                 395                 400

Gly Glu Trp Asn Val Ile Arg Asp Lys Trp Asn Ala Glu Tyr Asp Asp
                405                 410                 415
```

-continued

```
Ile His Leu Lys Lys Lys Ala Val Val Thr Glu Lys Tyr Glu Asp Asp
            420                 425             430

Arg Arg Lys Ser Phe Lys Lys Ile Gly Ser Phe Ser Leu Glu Gln Leu
            435             440             445

Gln Glu Tyr Ala Asp Ala Asp Leu Ser Val Val Glu Lys Leu Lys Glu
            450             455             460

Ile Ile Ile Gln Lys Val Asp Glu Ile Tyr Lys Val Tyr Gly Ser Ser
465             470             475             480

Glu Lys Leu Phe Asp Ala Asp Phe Val Leu Glu Lys Ser Leu Lys Lys
                485             490             495

Asn Asp Ala Val Val Ala Ile Met Lys Asp Leu Leu Asp Ser Val Lys
            500             505             510

Ser Phe Glu Asn Tyr Ile Lys Ala Phe Phe Gly Glu Gly Lys Glu Thr
            515             520             525

Asn Arg Asp Glu Ser Phe Tyr Gly Asp Phe Val Leu Ala Tyr Asp Ile
            530             535             540

Leu Leu Lys Val Asp His Ile Tyr Asp Ala Ile Arg Asn Tyr Val Thr
545             550             555             560

Gln Lys Pro Tyr Ser Lys Asp Lys Phe Lys Leu Tyr Phe Gln Asn Pro
                565             570             575

Gln Phe Met Gly Gly Trp Asp Lys Asp Lys Glu Thr Asp Tyr Arg Ala
            580             585             590

Thr Ile Leu Arg Tyr Gly Ser Lys Tyr Tyr Leu Ala Ile Met Asp Lys
            595             600             605

Lys Tyr Ala Lys Cys Leu Gln Lys Ile Asp Lys Asp Asp Val Asn Gly
            610             615             620

Asn Tyr Glu Lys Ile Asn Tyr Lys Leu Leu Pro Gly Pro Asn Lys Met
625             630             635             640

Leu Pro Lys Val Phe Phe Ser Lys Lys Trp Met Ala Tyr Tyr Asn Pro
                645             650             655

Ser Glu Asp Ile Gln Lys Ile Tyr Lys Asn Gly Thr Phe Lys Lys Gly
            660             665             670

Asp Met Phe Asn Leu Asn Asp Cys His Lys Leu Ile Asp Phe Phe Lys
            675             680             685

Asp Ser Ile Ser Arg Tyr Pro Lys Trp Ser Asn Ala Tyr Asp Phe Asn
            690             695             700

Phe Ser Glu Thr Glu Lys Tyr Lys Asp Ile Ala Gly Phe Tyr Arg Glu
705             710             715             720

Val Glu Glu Gln Gly Tyr Lys Val Ser Phe Glu Ser Ala Ser Lys Lys
                725             730             735

Glu Val Asp Lys Leu Val Glu Glu Gly Lys Leu Tyr Met Phe Gln Ile
            740             745             750

Tyr Asn Lys Asp Phe Ser Asp Lys Ser His Gly Thr Pro Asn Leu His
            755             760             765

Thr Met Tyr Phe Lys Leu Leu Phe Asp Glu Asn Asn His Gly Gln Ile
            770             775             780

Arg Leu Ser Gly Gly Ala Glu Leu Phe Met Arg Arg Ala Ser Leu Lys
785             790             795             800

Lys Glu Glu Leu Val Val His Pro Ala Asn Ser Pro Ile Ala Asn Lys
                805             810             815

Asn Pro Asp Asn Pro Lys Lys Thr Thr Thr Leu Ser Tyr Asp Val Tyr
            820             825             830
```

```
Lys Asp Lys Arg Phe Ser Glu Asp Gln Tyr Glu Leu His Ile Pro Ile
    835              840              845

Ala Ile Asn Lys Cys Pro Lys Asn Ile Phe Lys Ile Asn Thr Glu Val
    850              855              860

Arg Val Leu Leu Lys His Asp Asp Asn Pro Tyr Val Ile Gly Ile Asp
865              870              875              880

Arg Gly Glu Arg Asn Leu Leu Tyr Ile Val Val Asp Gly Lys Gly
                885              890              895

Asn Ile Val Glu Gln Tyr Ser Leu Asn Glu Ile Ile Asn Asn Phe Asn
                900              905              910

Gly Ile Arg Ile Lys Thr Asp Tyr His Ser Leu Leu Asp Lys Lys Glu
                915              920              925

Lys Glu Arg Phe Glu Ala Arg Gln Asn Trp Thr Ser Ile Glu Asn Ile
    930              935              940

Lys Glu Leu Lys Ala Gly Tyr Ile Ser Gln Val Val His Lys Ile Cys
945              950              955              960

Glu Leu Val Glu Lys Tyr Asp Ala Val Ile Ala Leu Glu Asp Leu Asn
                965              970              975

Ser Gly Phe Lys Asn Ser Arg Val Lys Val Glu Lys Gln Val Tyr Gln
                980              985              990

Lys Phe Glu Lys Met Leu Ile Asp  Lys Leu Asn Tyr Met  Val Asp Lys
        995              1000              1005

Lys Ser  Asn Pro Cys Ala Thr  Gly Gly Ala Leu Lys  Gly Tyr Gln
    1010              1015              1020

Ile Thr  Asn Lys Phe Glu Ser  Phe Lys Ser Met Ser  Thr Gln Asn
    1025              1030              1035

Gly Phe  Ile Phe Tyr Ile Pro  Ala Trp Leu Thr Ser  Lys Ile Asp
    1040              1045              1050

Pro Ser  Thr Gly Phe Val Asn  Leu Leu Lys Thr Lys  Tyr Thr Ser
    1055              1060              1065

Ile Ala  Asp Ser Lys Lys Phe  Ile Ser Ser Phe Asp  Arg Ile Met
    1070              1075              1080

Tyr Val  Pro Glu Glu Asp Leu  Phe Glu Phe Ala Leu  Asp Tyr Lys
    1085              1090              1095

Asn Phe  Ser Arg Thr Asp Ala  Asp Tyr Ile Lys Lys  Trp Lys Leu
    1100              1105              1110

Tyr Ser  Tyr Gly Asn Arg Ile  Arg Ile Phe Arg Asn  Pro Lys Lys
    1115              1120              1125

Asn Asn  Val Phe Asp Trp Glu  Glu Val Cys Leu Thr  Ser Ala Tyr
    1130              1135              1140

Lys Glu  Leu Phe Asn Lys Tyr  Gly Ile Asn Tyr Gln  Gln Gly Asp
    1145              1150              1155

Ile Arg  Ala Leu Leu Cys Glu  Gln Ser Asp Lys Ala  Phe Tyr Ser
    1160              1165              1170

Ser Phe  Met Ala Leu Met Ser  Leu Met Leu Gln Met  Arg Asn Ser
    1175              1180              1185

Ile Thr  Gly Arg Thr Asp Val  Asp Phe Leu Ile Ser  Pro Val Lys
    1190              1195              1200

Asn Ser  Asp Gly Ile Phe Tyr  Asp Ser Arg Asn Tyr  Glu Ala Gln
    1205              1210              1215

Glu Asn  Ala Ile Leu Pro Lys  Asn Ala Asp Ala Asn  Gly Ala Tyr
    1220              1225              1230

Asn Ile  Ala Arg Lys Val Leu  Trp Ala Ile Gly Gln  Phe Lys Lys
```

```
        1235              1240              1245

Ala Glu  Asp Glu Lys Leu Asp  Lys Val Lys Ile Ala  Ile Ser Asn
        1250              1255              1260

Lys Glu  Trp Leu Glu Tyr Ala  Gln Thr Ser Val Lys  His Pro Lys
        1265              1270              1275

Lys Lys  Arg Lys Val Leu Glu  His His His His His  His
        1280              1285              1290
```

```
<210> SEQ ID NO 15
<211> LENGTH: 4071
<212> TYPE: DNA
<213> ORGANISM: Artificial Sequence
<220> FEATURE:
<223> OTHER INFORMATION: Synthetic DNA

<400> SEQUENCE: 15
atgggcaagc ccattcctaa tcctctgctg ggcctcgaca gcacagcccc taagaaaaag        60
cggaaagtgg gcatccatgg cgtgccagcc gccacacagt ttgagggctt caccaacctg       120
taccaggtgt ccaagacact gcgcttcgag ctgatccctc agggcaagac cctgaagcac       180
atccaagagc agggcttcat cgaagaggac aaggcccgga cgaccactca aaagagctg        240 aagcccatca tcgaccggat ctacaagacc tacgccgacc agtgtctgca gctggtgcag       300
ctcgattggg agaatctgag cgccgccatc gacagctacc ggaaagagaa aaccgaggaa       360
acccggaacg ccctgatcga ggaacaggcc acctacagaa acgccatcca cgactacttc       420
atcggccgga ccgacaacct gaccgacgcc atcaacaaga cacgccga gatctataag        480 ggcctgttca aggccgagct gttcaacggc aaggtgctga agcagctggg caccgtgaca       540
accaccgagc acgaaaatgc cctgctgcgg agcttcgaca gttcaccac ctacttcagc        600 ggcttctacg agaaccggaa gaacgtgttc agcgccgagg acatcagcac cgccattcct       660
cacagaatcg tgcaggacaa cttccccaag ttcaaagaga actgccacat cttcacccgg       720
ctgatcacag ccgtgcctag cctgagagaa cacttcgaga acgtgaagaa ggccatcggc       780
atcttcgtgt ccaccagcat cgaggaagtg ttcagcttcc cattctacaa ccagctgctg       840
acccagacac agatcgacct gtataatcag ctgctcggcg gcatcagcag agaggccgga       900
acagagaaga tcaagggcct gaacgaagtg ctgaacctgg ccatccagaa gaacgacgag       960
acagcccaca tcattgccag cctgcctcac cggttcatcc ctctgttcaa gcagatcctg      1020
agcgacagaa acaccctgag cttcatcctg gaagagttca gtccgatga ggaagtgatc       1080 cagagcttct gcaagtataa gaccctgctg aggaacgaga tgtgctgga aaccgccgag       1140 gctctgtttt acgagctgaa cagcatcgat ctgacccaca tctttatcag ccacaagaag      1200
ctcgagacaa tcagcagcgc cctgtgcgac cactgggata ccctgagaaa cgccctgtac      1260
gagcggagaa tcagcgagct gaccggcaag atcaccaaga gcgccaaaga aaaggtgcag      1320
cggagcctga acacgagga tatcaacctg aagagatca tcagcgccgc tggcaaagaa       1380
ctgagcgagg cctttaagca gaaaaccagc gagatcctgt ctcacgccca cgctgctctt      1440
gatcagcctc tgcctaccac actgaagaag aagaggaaa aagagatcct gaagtcccag       1500
ctggacagcc tgctgggact gtaccatctg ctggattggt cgccgtgga cgagagcaat       1560 gaggtggacc ctgagttctc cgccagactg acaggcatca gctggaaat ggaacccagc       1620 ctgtccttct acaacaaggc cagaaactac gccaccaaga gccctacag cgtcgagaag       1680 ttcaagctca cttccagat gcctacactg gccagcggct gggacgtgaa caaagagaag      1740
```

-continued

```
aacaacggcg ccatcctgtt cgtgaagaac ggactgtact acctgggcat catgccaaag    1800
cagaagggca gatacaaggc cctgtccttt gagcccaccg aaaagaccag cgagggcttc    1860
gataagatgt actacgatta cttccccgac gccgccaaga tgatccccaa gtgtagcaca    1920
cagctgaagg ccgtgaccgc tcactttcag acccacacca cacctatcct gctgagcaac    1980
aacttcatcg agcccctgga aatcaccaaa gagatctacg acctgaacaa ccccgagaaa    2040
gagcccaaga agttccagac cgcctacgcc aagaaaaccg gcgaccagaa gggctacaga    2100
gaagccctgt gcaagtggat cgactttacc cgggacttcc tgagcaagta caccaagacc    2160
acctccatcg acctgagcag cctgaggcct agcagccagt ataaggacct gggcgagtac    2220
tacgccgagc tgaatccact gctgtaccac atcagcttcc agcggatcgc cgaaaaagaa    2280
atcatggacg ccgtggaaac cggcaagctg tacctgttcc agatatacaa caaagacttc    2340
gccaagggcc accacggcaa gcctaatctg cacaccctgt actggaccgg cctgtttagc    2400
cctgagaatc tggccaagac ctctatcaag ctgaacggcc aggccgaact gttttacaga    2460
cccaagagcc ggatgaagcg gatggcccac agactgggag agaagatgct gaacaagaaa    2520
ctgaaggacc agaaaacgcc cattccggac acactgtacc aagagctgta cgactacgtg    2580
aaccaccggc tgagccacga tctgagcgac gaagctagag cactgctgcc caacgtgatc    2640
acaaaagagg tgtcccacga gatcattaag gaccggcggt ttacctccga taagttcttc    2700
ttccacgtgc cgatcacact gaactaccag gccgccaact ctcccagcaa gttcaaccag    2760
agagtgaacg cctacctgaa agagcacccc gagacaccca tcattggcat cgacagaggc    2820
gagcggaacc tgatctacat caccgtgatc gactccacag gcaagatcct ggaacagcgg    2880
tccctgaaca ccatccagca gttcgactac cagaagaagc tggacaaccg agagaaagaa    2940
agagtggccg ccagacaggc ttggagcgtt gtgggcacaa tcaaggatct gaagcagggc    3000
tacctgagcc aagtgattca cgagatcgtg acctgatga tccactatca ggctgtggtg    3060
gtgctcgaga acctgaactt cggcttcaag agcaagcgga ccggaatcgc cgagaaagcc    3120
gtgtaccagc agtttgagaa aatgctgatc gacaagctga attgcctggt cctgaaggac    3180 tacccgctg agaaagttgg cggagtgctg aatccctacc agctgaccga tcagttcacc    3240
agctttgcca agatgggaac ccagagcggc ttcctgttct acgtgccagc tccttacacc    3300
tccaagatcg accctctgac cggcttcgtg gacccctcg tgtggaaaac catcaagaac    3360
cacgagtccc ggaagcactt cctggaaggc tttgacttcc tgcactacga cgtgaaaaca    3420
ggcgatttca tcctgcactt caagatgaat cggaatctgt ccttccagag gggcctgcct    3480
ggcttcatgc ctgcttggga tatcgtgttc gagaagaatg agactcagtt cgacgccaag    3540
gggacccctt ttatcgccgg caagagaatt gtgcctgtga tcgagaacca caggttcacc    3600
ggcagatacc gggatctgta ccccgccaat gagctgatcg ccctgctgga agagaagggc    3660
atcgtgttta gagatggcag caacatcctg cctaagctgc tggaaaacga cgacagccac    3720
gccatcgata ccatggtggc actgatcaga tccgtgctgc agatgcggaa cagcaatgcc    3780
gctaccggcg aggactacat caatagcccc gtgcgggatc tgaacggcgt gtgcttcgac    3840
agcagatttc agaaccccga gtggcctatg atgccgacg ccaatggcgc ctatcacatt    3900
gccctgaaag acagctgct gctgaaccat ctgaaagaga gcaaggacct gaaactgcag    3960
aacggcatct ccaaccagga ctggctggcc tacattcaag agctgcggaa tcccaaaaag    4020
aaacggaaag tgaagctggc cgctgctctg gaacaccacc accatcacca t    4071
```

<210> SEQ ID NO 16
<211> LENGTH: 1357
<212> TYPE: PRT
<213> ORGANISM: Artificial Sequence
<220> FEATURE:
<223> OTHER INFORMATION: Synthetic Amino Acid Sequence

<400> SEQUENCE: 16

```
Met Gly Lys Pro Ile Pro Asn Pro Leu Leu Gly Leu Asp Ser Thr Ala
1               5                   10                  15

Pro Lys Lys Lys Arg Lys Val Gly Ile His Gly Val Pro Ala Ala Thr
                20                  25                  30

Gln Phe Glu Gly Phe Thr Asn Leu Tyr Gln Val Ser Lys Thr Leu Arg
            35                  40                  45

Phe Glu Leu Ile Pro Gln Gly Lys Thr Leu Lys His Ile Gln Glu Gln
        50                  55                  60

Gly Phe Ile Glu Glu Asp Lys Ala Arg Asn Asp His Tyr Lys Glu Leu
65                  70                  75                  80

Lys Pro Ile Ile Asp Arg Ile Tyr Lys Thr Tyr Ala Asp Gln Cys Leu
                85                  90                  95

Gln Leu Val Gln Leu Asp Trp Glu Asn Leu Ser Ala Ala Ile Asp Ser
            100                 105                 110

Tyr Arg Lys Glu Lys Thr Glu Glu Thr Arg Asn Ala Leu Ile Glu Glu
        115                 120                 125

Gln Ala Thr Tyr Arg Asn Ala Ile His Asp Tyr Phe Ile Gly Arg Thr
        130                 135                 140

Asp Asn Leu Thr Asp Ala Ile Asn Lys Arg His Ala Glu Ile Tyr Lys
145                 150                 155                 160

Gly Leu Phe Lys Ala Glu Leu Phe Asn Gly Lys Val Leu Lys Gln Leu
                165                 170                 175

Gly Thr Val Thr Thr Thr Glu His Glu Asn Ala Leu Leu Arg Ser Phe
            180                 185                 190

Asp Lys Phe Thr Thr Tyr Phe Ser Gly Phe Tyr Glu Asn Arg Lys Asn
        195                 200                 205

Val Phe Ser Ala Glu Asp Ile Ser Thr Ala Ile Pro His Arg Ile Val
        210                 215                 220

Gln Asp Asn Phe Pro Lys Phe Lys Glu Asn Cys His Ile Phe Thr Arg
225                 230                 235                 240

Leu Ile Thr Ala Val Pro Ser Leu Arg Glu His Phe Glu Asn Val Lys
                245                 250                 255

Lys Ala Ile Gly Ile Phe Val Ser Thr Ser Ile Glu Glu Val Phe Ser
            260                 265                 270

Phe Pro Phe Tyr Asn Gln Leu Leu Thr Gln Thr Gln Ile Asp Leu Tyr
        275                 280                 285

Asn Gln Leu Leu Gly Gly Ile Ser Arg Glu Ala Gly Thr Glu Lys Ile
        290                 295                 300

Lys Gly Leu Asn Glu Val Leu Asn Leu Ala Ile Gln Lys Asn Asp Glu
305                 310                 315                 320

Thr Ala His Ile Ile Ala Ser Leu Pro His Arg Phe Ile Pro Leu Phe
                325                 330                 335

Lys Gln Ile Leu Ser Asp Arg Asn Thr Leu Ser Phe Ile Leu Glu Glu
            340                 345                 350

Phe Lys Ser Asp Glu Glu Val Ile Gln Ser Phe Cys Lys Tyr Lys Thr
        355                 360                 365

Leu Leu Arg Asn Glu Asn Val Leu Glu Thr Ala Glu Ala Leu Phe Asn
```

-continued

```
        370             375             380

Glu Leu Asn Ser Ile Asp Leu Thr His Ile Phe Ile Ser His Lys Lys
385             390             395             400

Leu Glu Thr Ile Ser Ser Ala Leu Cys Asp His Trp Asp Thr Leu Arg
                405             410             415

Asn Ala Leu Tyr Glu Arg Arg Ile Ser Glu Leu Thr Gly Lys Ile Thr
                420             425             430

Lys Ser Ala Lys Glu Lys Val Gln Arg Ser Leu Lys His Glu Asp Ile
                435             440             445

Asn Leu Gln Glu Ile Ile Ser Ala Ala Gly Lys Glu Leu Ser Glu Ala
        450             455             460

Phe Lys Gln Lys Thr Ser Glu Ile Leu Ser His Ala His Ala Ala Leu
465             470             475             480

Asp Gln Pro Leu Pro Thr Thr Leu Lys Lys Gln Glu Glu Lys Glu Ile
                485             490             495

Leu Lys Ser Gln Leu Asp Ser Leu Leu Gly Leu Tyr His Leu Leu Asp
                500             505             510

Trp Phe Ala Val Asp Glu Ser Asn Glu Val Asp Pro Glu Phe Ser Ala
        515             520             525

Arg Leu Thr Gly Ile Lys Leu Glu Met Glu Pro Ser Leu Ser Phe Tyr
        530             535             540

Asn Lys Ala Arg Asn Tyr Ala Thr Lys Lys Pro Tyr Ser Val Glu Lys
545             550             555             560

Phe Lys Leu Asn Phe Gln Met Pro Thr Leu Ala Ser Gly Trp Asp Val
                565             570             575

Asn Lys Glu Lys Asn Asn Gly Ala Ile Leu Phe Val Lys Asn Gly Leu
                580             585             590

Tyr Tyr Leu Gly Ile Met Pro Lys Gln Lys Gly Arg Tyr Lys Ala Leu
                595             600             605

Ser Phe Glu Pro Thr Glu Lys Thr Ser Glu Gly Phe Asp Lys Met Tyr
        610             615             620

Tyr Asp Tyr Phe Pro Asp Ala Ala Lys Met Ile Pro Lys Cys Ser Thr
625             630             635             640

Gln Leu Lys Ala Val Thr Ala His Phe Gln Thr His Thr Thr Pro Ile
                645             650             655

Leu Leu Ser Asn Asn Phe Ile Glu Pro Leu Glu Ile Thr Lys Glu Ile
        660             665             670

Tyr Asp Leu Asn Asn Pro Glu Lys Glu Pro Lys Lys Phe Gln Thr Ala
        675             680             685

Tyr Ala Lys Lys Thr Gly Asp Gln Lys Gly Tyr Arg Glu Ala Leu Cys
        690             695             700

Lys Trp Ile Asp Phe Thr Arg Asp Phe Leu Ser Lys Tyr Thr Lys Thr
705             710             715             720

Thr Ser Ile Asp Leu Ser Ser Leu Arg Pro Ser Ser Gln Tyr Lys Asp
                725             730             735

Leu Gly Glu Tyr Tyr Ala Glu Leu Asn Pro Leu Leu Tyr His Ile Ser
                740             745             750

Phe Gln Arg Ile Ala Glu Lys Glu Ile Met Asp Ala Val Glu Thr Gly
        755             760             765

Lys Leu Tyr Leu Phe Gln Ile Tyr Asn Lys Asp Phe Ala Lys Gly His
        770             775             780

His Gly Lys Pro Asn Leu His Thr Leu Tyr Trp Thr Gly Leu Phe Ser
785             790             795             800
```

```
Pro Glu Asn Leu Ala Lys Thr Ser Ile Lys Leu Asn Gly Gln Ala Glu
            805                 810                 815

Leu Phe Tyr Arg Pro Lys Ser Arg Met Lys Arg Met Ala His Arg Leu
            820                 825                 830

Gly Glu Lys Met Leu Asn Lys Lys Leu Lys Asp Gln Lys Thr Pro Ile
            835                 840                 845

Pro Asp Thr Leu Tyr Gln Glu Leu Tyr Asp Tyr Val Asn His Arg Leu
    850                 855                 860

Ser His Asp Leu Ser Asp Glu Ala Arg Ala Leu Leu Pro Asn Val Ile
865                 870                 875                 880

Thr Lys Glu Val Ser His Glu Ile Ile Lys Asp Arg Arg Phe Thr Ser
                885                 890                 895

Asp Lys Phe Phe Phe His Val Pro Ile Thr Leu Asn Tyr Gln Ala Ala
            900                 905                 910

Asn Ser Pro Ser Lys Phe Asn Gln Arg Val Asn Ala Tyr Leu Lys Glu
            915                 920                 925

His Pro Glu Thr Pro Ile Ile Gly Ile Asp Arg Gly Glu Arg Asn Leu
    930                 935                 940

Ile Tyr Ile Thr Val Ile Asp Ser Thr Gly Lys Ile Leu Glu Gln Arg
945                 950                 955                 960

Ser Leu Asn Thr Ile Gln Gln Phe Asp Tyr Gln Lys Lys Leu Asp Asn
                965                 970                 975

Arg Glu Lys Glu Arg Val Ala Ala Arg Gln Ala Trp Ser Val Val Gly
            980                 985                 990

Thr Ile Lys Asp Leu Lys Gln Gly  Tyr Leu Ser Gln Val  Ile His Glu
            995                 1000                    1005

Ile Val  Asp Leu Met Ile His  Tyr Gln Ala Val  Val Leu Glu
    1010                1015                1020

Asn Leu  Asn Phe Gly Phe Lys  Ser Lys Arg Thr Gly  Ile Ala Glu
    1025                1030                1035

Lys Ala  Val Tyr Gln Gln Phe  Glu Lys Met Leu Ile  Asp Lys Leu
    1040                1045                1050

Asn Cys  Leu Val Leu Lys Asp  Tyr Pro Ala Glu Lys  Val Gly Gly
    1055                1060                1065

Val Leu  Asn Pro Tyr Gln Leu  Thr Asp Gln Phe Thr  Ser Phe Ala
    1070                1075                1080

Lys Met  Gly Thr Gln Ser Gly  Phe Leu Phe Tyr Val  Pro Ala Pro
    1085                1090                1095

Tyr Thr  Ser Lys Ile Asp Pro  Leu Thr Gly Phe Val  Asp Pro Phe
    1100                1105                1110

Val Trp  Lys Thr Ile Lys Asn  His Glu Ser Arg Lys  His Phe Leu
    1115                1120                1125

Glu Gly  Phe Asp Phe Leu His  Tyr Asp Val Lys Thr  Gly Asp Phe
    1130                1135                1140

Ile Leu  His Phe Lys Met Asn  Arg Asn Leu Ser Phe  Gln Arg Gly
    1145                1150                1155

Leu Pro  Gly Phe Met Pro Ala  Trp Asp Ile Val Phe  Glu Lys Asn
    1160                1165                1170

Glu Thr  Gln Phe Asp Ala Lys  Gly Thr Pro Phe Ile  Ala Gly Lys
    1175                1180                1185

Arg Ile  Val Pro Val Ile Glu  Asn His Arg Phe Thr  Gly Arg Tyr
    1190                1195                1200
```

-continued

```
Arg Asp  Leu Tyr Pro Ala Asn  Glu Leu Ile Ala Leu  Leu Glu Glu
    1205             1210             1215

Lys Gly  Ile Val Phe Arg Asp  Gly Ser Asn Ile Leu  Pro Lys Leu
    1220             1225             1230

Leu Glu  Asn Asp Asp Ser His  Ala Ile Asp Thr Met  Val Ala Leu
    1235             1240             1245

Ile Arg  Ser Val Leu Gln Met  Arg Asn Ser Asn Ala  Ala Thr Gly
    1250             1255             1260

Glu Asp  Tyr Ile Asn Ser Pro  Val Arg Asp Leu Asn  Gly Val Cys
    1265             1270             1275

Phe Asp  Ser Arg Phe Gln Asn  Pro Glu Trp Pro Met  Asp Ala Asp
    1280             1285             1290

Ala Asn  Gly Ala Tyr His Ile  Ala Leu Lys Gly Gln  Leu Leu Leu
    1295             1300             1305

Asn His  Leu Lys Glu Ser Lys  Asp Leu Lys Leu Gln  Asn Gly Ile
    1310             1315             1320

Ser Asn  Gln Asp Trp Leu Ala  Tyr Ile Gln Glu Leu  Arg Asn Pro
    1325             1330             1335

Lys Lys  Lys Arg Lys Val Lys  Leu Ala Ala Ala Leu  Glu His His
    1340             1345             1350

His His  His His
    1355
```

<210> SEQ ID NO 17
<211> LENGTH: 3873
<212> TYPE: DNA
<213> ORGANISM: Artificial Sequence
<220> FEATURE:
<223> OTHER INFORMATION: Synthetic DNA

<400> SEQUENCE: 17

```
atgggcaagc ccattcctaa tcctctgctg ggcctcgaca gcacagcccc taagaaaaag      60
cggaaagtgg gcatccatgg cgtgccagcc gctctgaaga atgtgggcat cgacagactg     120
gacgtggaaa agggcagaaa gaacatgagc aagctcgaga agttcaccaa ctgctacagc     180
ctgagcaaga ccctgcggtt caaggccatt cctgtgggca gacccaaga gaacatcgac      240 aacaagcggc tgctggtgga agatgagaag agagccgagg actacaaggg cgtgaagaag     300
ctgctggacc ggtactacct gagcttcatc aacgacgtgc tgcacagcat caagctgaag     360
aacctgaaca actacatcag cctgttccgg aagaaacccc ggaccgagaa agagaacaaa     420
gagctggaaa acctcgagat caacctgcgg aaagagatcg ccaaggcctt caagggcaac     480
gagggctaca gagcctgtt caagaaggac atcatcgaga caatcctgcc tgagttcctg      540
gacgacaagg acgagatcgc cctggtcaac agcttcaacg cttcacaac cgccttcacc      600 ggctttttcg acaaccgcga gaatatgttc agcgaggaag ccaagagcac ctctatcgcc     660
ttccggtgca tcaacgagaa tctgacccgg tacatcagca acatggatat cttcgagaag     720
gtggacgcca tcttcgacaa gcacgaggtg caagagatca agaaaaagat cctgaacagc     780
gactacgacg tcgaggactt cttcgagggc gagttcttca acttcgtgct gacacaagag     840
ggcatcgatg tgtacaacgc catcatcggc ggcttcgtga cagagagcgg cgagaagatc     900
aagggcctga cgagtacat caacctctac aaccagaaaa cgaagcagaa gctgcccaag     960
ttcaagcccc tgtacaaaca ggtgctgagc gacagagaga gcctgtcctt ttacggcgag    1020
ggctatacca gcgacgaaga ggtgctggaa gtgttcagaa acaccctgaa caagaacagc    1080
```

-continued

```
gagatcttca gctccatcaa gaagctcgaa aagctgttta agaacttcga cgagtacagc    1140
agcgccggca tcttcgtgaa gaatggccct gccatcagca ccatctccaa ggacatcttc    1200
ggcgagtgga acgtgatccg ggacaagtgg aacgccgagt acgacgacat ccacctgaag    1260
aaaaaggccg tggtcaccga gaagtacgag gacgacagaa gaaagagctt caagaagatc    1320
ggcagcttca gcctggaaca gctgcaagag tacgccgacg ccgatctgag cgtggtggaa    1380
aagctgaaag agattatcat ccagaaggtc gacgagatct acaaggtgta cggcagcagc    1440
gagaagctgt tcgacgccga ctttgtgctg gaaaagagcc tcaaaaagaa cgacgccgtg    1500
gtggccatca tgaaggacct gctggatagc gtgaagtcct tcgagaacta tattaaggcc    1560
ttctttggcg agggcaaaga gacaaaccgg gacgagagct tctacggcga tttcgtgctg    1620
gcctacgaca tcctgctgaa agtggaccac atctacgacg ccatccggaa ctacgtgacc    1680
cagaagcctt acagcaagga caagtttaag ctgtacttcc agaatccgca gttcatgggc    1740
ggctgggaca agacaaaga aaccgactac cgggccacca tcctgagata cggctccaag    1800
tactatctgg ccattatgga caagaaatac gccaagtgcc tgcagaagat cgataaggac    1860
gacgtgaacg gcaactacga gaagattaac tacaagctgc tgcccggacc taacaagatg    1920
ctgcctaagg tgttctttag caagaaatgg atggcctact acaaccccag cgaggatatc    1980
cagaaaatct acaagaacgg caccttcaag aaaggcgaca tgttcaacct gaacgactgc    2040
cacaagctga tcgatttctt caaggacagc atcagcagat accccaagtg gtccaacgcc    2100
tacgacttca atttcagcga gacagagaag tataaggata tcgccgggtt ctaccgcgag    2160
gtggaagaac agggctataa ggtgtccttt gagagcgcca gcaagaaaga ggtggacaag    2220
ctggtcgaag agggcaagct gtacatgttc cagatctata acaaggactt ctccgacaag    2280
agccacggca cccctaacct gcacaccatg tactttaagc tgctgttcga tgagaacaac    2340
cacggccaga tcagactgtc tggcggagcc gagctgtttta tgagaagggc cagcctgaaa    2400
aaagaggaac tggtcgttca ccccgccaac tctccaatcg ccaacaagaa ccccgacaat    2460
cccaagaaaa ccaccacact gagctacgac gtgtacaagg ataagcggtt ctccgaggac    2520
cagtacgagc tgcacatccc tatcgccatc aacaagtgcc ccaagaatat cttcaagatc    2580
aacaccgaag tgcgggtgct gctgaagcac gacgacaacc cttacgtgat cggcatcgat    2640
cggggcgaga gaaacctgct gtatatcgtg gtggtggacg gcaagggcaa tatcgtggaa    2700
cagtactccc tgaatgagat catcaacaac ttcaatggca tccggatcaa gacggactac    2760
cacagcctgc tggacaaaaa agagaaagaa cgcttcgagg ccaggcagaa ctggaccagc    2820
atcgagaaca tcaaagaact gaaggccggc tacatctccc aggtggtgca agatctgctg    2880
gagctggttg agaagtatga cgccgtgatt gccctggaag atctgaatag cggctttaag    2940
aacagccgcg tgaaggtcga gaaacaggtg taccagaaat tcgagaagat gctgatcgac    3000
aagctgaact acatggtcga caagaagtct aacccctgcg ccacaggcgg agccctgaag    3060
ggatatcaga tcaccaacaa gttcgagtcc ttcaagagca tgagcaccca gaatggcttc    3120
atcttctaca tccccgcctg gctgaccagc aagatcgatc ctagcaccgg attcgtgaac    3180
ctgctcaaga ccaagtacac cagcattgcc gacagcaaga agttcatctc cagcttcgac    3240
cggattatgt acgtgcccga agaggacctg ttcgaattcg ccctggatta caagaacttc    3300
agccggaccg atgccgacta tatcaagaag tggaagctgt atagctacgg caaccgcatc    3360
cgcatcttca gaaacccgaa gaaaaacaac gtgttcgact gggaagaagt gtgcctgacc    3420
agcgcctaca agaactctt caacaaatac ggcatcaact accagcaggg cgacatcaga    3480
```

-continued

```
gccctgctgt gcgagcagag cgacaaggcc ttttacagct ccttcatggc cctgatgagc      3540
ctgatgctgc agatgcggaa tagcatcacc ggcagaaccg acgtggactt cctgatcagc      3600
cccgtgaaaa actccgacgg catctttac gacagccgga attacgaggc tcaagagaac       3660
gccatcctgc ctaagaacgc cgatgccaac ggcgcctata atatcgccag aaaggtgctg      3720
tgggccatcg gccagtttaa gaaggccgag gacgagaaac tggacaaagt gaagatcgcc      3780
atctctaaca aagagtggct ggaatacgcc cagaccagcg tgaagcaccc caaaaagaaa      3840
cggaaagtgc tggaacacca ccaccatcac cac                                   3873
```

<210> SEQ ID NO 18
<211> LENGTH: 4092
<212> TYPE: DNA
<213> ORGANISM: Artificial Sequence
<220> FEATURE:
<223> OTHER INFORMATION: Synthetic DNA

<400> SEQUENCE: 18

```
atgacccagt ttgaaggttt caccaatctg tatcaggtta gcaaaccct gcgttttgaa        60 ctgattccgc agggtaaaac cctgaaacat attcaagaac agggcttcat cgaagaggat       120
aaagcacgta acgatcacta caaagaactg aaaccgatta tcgaccgcat ctataaaacc       180
tatgcagatc agtgtctgca gctggttcag ctggattggg aaaatctgag cgcagcaatt      240
gatagttatc gcaaagaaaa aaccgaagaa acccgtaatg cactgattga agaacaggca       300
acctatcgta atgccatcca tgattatttc attggtcgta ccgataatct gaccgatgca       360
attaacaaac gtcacgccga aatctataaa ggcctgttta agccgaact gtttaatggc        420 aaagttctga aacagctggg caccgttacc accaccgaac atgaaaatgc actgctgcgt       480
agctttgata aattcaccac ctatttcagc ggctttatg agaatcgcaa aaacgtgttt       540
agcgcagaag atattagcac cgcaattccg catcgtattg tgcaggataa tttcccgaaa       600
ttcaaagaga actgccacat ttttacccgt ctgattaccg cagttccgag cctgcgtgaa       660 catttttgaaa acgttaaaaa agccatcggc atctttgtta gcaccagcat tgaagaagtt       720
tttagcttcc cgtttttacaa tcagctgctg acccagaccc agattgatct gtataaccaa      780
ctgctgggtg gtattagccg tgaagcaggc accgaaaaaa tcaaaggtct gaatgaagtg      840
ctgaatctgg ccattcagaa aaatgatgaa accgcacata ttattgcaag cctgccgcat      900
cgttttattc cgctgttcaa acaaattctg agcgatcgta ataccctgag ctttattctg       960
gaagaattca aatccgatga gaggtgatt cagagctttt gcaaatacaa aacgctgctg       1020
cgcaatgaaa atgttctgga aactgccgaa gcactgttta acgaactgaa tagcattgat      1080
ctgacccaca tctttatcag ccacaaaaaa ctggaaacca tttcaagcgc actgtgtgat      1140
cattgggata ccctgcgtaa tgccctgtat gaacgtcgta ttagcgaact gaccggtaaa      1200
attaccaaaa gcgcgaaaga aaaagttcag cgcagtctga acatgagga tattaatctg      1260 caagagatta ttagcgcagc cggtaaagaa ctgtcagaag catttaaaca gaaaaccagc      1320
gaaattctgt cacatgcaca tgcagcactg gatcagccgc tgccgaccac cctgaaaaaa      1380
caagaagaaa agaaatcct gaaaagccag ctggatagcc tgctgggtct gtatcatctg      1440
ctggactggt ttgcagttga tgaaagcaat gaagttgatc cggaatttag cgcacgtctg      1500
accggcatta aactggaaat ggaaccgagc ctgagctttt ataacaaagc ccgtaattat      1560
gccaccaaaa aaccgtatag cgtcgaaaaa ttcaaactga actttcagat gccgacccctg      1620
```

-continued

```
gcaagcggtt gggatgttaa taaagaaaaa aacaacggtg ccatcctgtt cgtgaaaaat    1680
ggcctgtatt atctgggtat tatgccgaaa cagaaaggtc gttataaagc gctgagcttt    1740
gaaccgacgg aaaaaaccag tgaaggtttt gataaaatgt actacgacta ttttccggat    1800
gcagccaaaa tgattccgaa atgtagcacc cagctgaaag cagttaccgc acattttcag    1860
acccatacca ccccgattct gctgagcaat aactttattg aaccgctgga aatcaccaaa    1920
gagatctacg atctgaataa cccggaaaaa gagccgaaaa aattccagac cgcatatgca    1980
aaaaaaaccg gtgatcagaa aggttatcgt gaagcgctgt gtaaatggat tgatttcacc    2040
cgtgattttc tgagcaaata caccaaaacc accagtatcg atctgagcag cctgcgtccg    2100
agcagccagt ataaagatct gggcgaatat tatgcagaac tgaatccgct gctgtatcat    2160
attagctttc agcgtattgc cgagaaagaa atcatggacg cagttgaaac cggtaaactg    2220
tacctgttcc agatctacaa taaagatttt gccaaaggcc atcatggcaa accgaatctg    2280
cataccctgt attggaccgg tctgtttagc cctgaaaatc tggcaaaaac ctcgattaaa    2340
ctgaatggtc aggcggaact gttttatcgt ccgaaaagcc gtatgaaacg tatggcacat    2400
cgtctgggtg aaaaaatgct gaacaaaaaa ctgaaagacc agaaaacccc gatcccggat    2460
acactgtatc aagaactgta tgattatgtg aaccatcgtc tgagccatga tctgagtgat    2520
gaagcacgtg ccctgctgcc gaatgttatt accaagaag ttagccacga gatcattaaa    2580
gatcgtcgtt ttaccagcga caaattcttt tttcatgtgc cgattaccct gaattatcag    2640
gcagcaaata gcccgagcaa atttaaccag cgtgttaatg catatctgaa agaacatcca    2700
gaaacgccga ttattggtat tgatcgtggt gaacgtaacc tgatttatat caccgttatt    2760
gatagcaccg gcaaaatcct ggaacagcgt agcctgaata ccattcagca gtttgattac    2820
cagaaaaaac tggataatcg cgagaaagaa cgtgttgcag cacgtcaggc atggtcagtt    2880
gttggtacaa ttaaagacct gaaacagggt tatctgagcc aggttattca tgaaattgtg    2940
gatctgatga ttcactatca ggccgttgtt gtgctggaaa acctgaattt tggctttaaa    3000
agcaaacgta ccggcattgc agaaaaagca gtttatcagc agttcgagaa aatgctgatt    3060
gacaaactga attgcctggt gctgaaagat tatccggctg aaaaagttgg tggtgttctg    3120
aatccgtatc agctgaccga tcagtttacc agctttgcaa aaatgggcac ccagagcgga    3180
tttctgtttt atgttccggc accgtatacg agcaaaattg atccgctgac cggttttgtt    3240
gatccgtttg tttggaaaac catcaaaaac catgaaagcc gcaaacattt tctggaaggt    3300 ttcgatttc tgcattacga cgttaaaacg ggtgatttca tcctgcactt taaaatgaat    3360
cgcaatctga gttttcagcg tggcctgcct ggttttatgc ctgcatggga tattgtgttt    3420
gagaaaaacg aaacacagtt cgatgcaaaa ggcacccgt ttattgcagg taaacgtatt    3480
gttccggtga ttgaaaatca tcgtttcacc ggtcgttatc gcgatctgta tccggcaaat    3540
gaactgatcg cactgctgga agagaaaggt attgtttttc gtgatggctc aaacattctg    3600
ccgaaactgc tggaaaatga tgatagccat gcaattgata ccatggttgc actgattcgt    3660
agcgttctgc agatgcgtaa tagcaatgca gcaaccggtg aagattacat taatagtccg    3720
gttcgtgatc tgaatggtgt ttgttttgat agccgttttc agaatccgga atggccgatg    3780
gatgcagatg caaatggtgc atatcatatt gcactgaaag acagctgct gctgaaccac    3840 ctgaaagaaa gcaaagatct gaaactgcaa aacggcatta gcaatcagga ttggctggca    3900
tatatccaag aactgcgtaa cggtcgtagc agtgatgatg aagcaaccgc agatagccag    3960
catgcagcac cgcctaaaaa gaaacgtaaa gttggtggta gcggtggttc aggtggtagt    4020
```

-continued

```
ggcggtagtg gtggctcagg gggttctggt ggctctggtg gtagcctcga gcaccaccac      4080
caccaccact ga                                                          4092
```

<210> SEQ ID NO 19
<211> LENGTH: 1363
<212> TYPE: PRT
<213> ORGANISM: Artificial Sequence
<220> FEATURE:
<223> OTHER INFORMATION: Synthetic Amino Acid Sequence

<400> SEQUENCE: 19

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
                20                  25                  30

Glu Gln Gly Phe Ile Glu Glu Asp Lys Ala Arg Asn Asp His Tyr Lys
            35                  40                  45

Glu Leu Lys Pro Ile Ile Asp Arg Ile Tyr Lys Thr Tyr Ala Asp Gln
        50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
```

-continued

```
              340                345                350
Phe Asn Glu Leu Asn Ser Ile Asp Leu Thr His Ile Phe Ile Ser His
          355                360                365

Lys Lys Leu Glu Thr Ile Ser Ser Ala Leu Cys Asp His Trp Asp Thr
      370                375                380

Leu Arg Asn Ala Leu Tyr Glu Arg Arg Ile Ser Glu Leu Thr Gly Lys
385                390                395                400

Ile Thr Lys Ser Ala Lys Glu Lys Val Gln Arg Ser Leu Lys His Glu
              405                410                415

Asp Ile Asn Leu Gln Glu Ile Ile Ser Ala Ala Gly Lys Glu Leu Ser
          420                425                430

Glu Ala Phe Lys Gln Lys Thr Ser Glu Ile Leu Ser His Ala His Ala
          435                440                445

Ala Leu Asp Gln Pro Leu Pro Thr Thr Leu Lys Lys Gln Glu Glu Lys
      450                455                460

Glu Ile Leu Lys Ser Gln Leu Asp Ser Leu Leu Gly Leu Tyr His Leu
465                470                475                480

Leu Asp Trp Phe Ala Val Asp Glu Ser Asn Glu Val Asp Pro Glu Phe
              485                490                495

Ser Ala Arg Leu Thr Gly Ile Lys Leu Glu Met Glu Pro Ser Leu Ser
          500                505                510

Phe Tyr Asn Lys Ala Arg Asn Tyr Ala Thr Lys Lys Pro Tyr Ser Val
          515                520                525

Glu Lys Phe Lys Leu Asn Phe Gln Met Pro Thr Leu Ala Ser Gly Trp
      530                535                540

Asp Val Asn Lys Glu Lys Asn Asn Gly Ala Ile Leu Phe Val Lys Asn
545                550                555                560

Gly Leu Tyr Tyr Leu Gly Ile Met Pro Lys Gln Lys Gly Arg Tyr Lys
              565                570                575

Ala Leu Ser Phe Glu Pro Thr Glu Lys Thr Ser Glu Gly Phe Asp Lys
          580                585                590

Met Tyr Tyr Asp Tyr Phe Pro Asp Ala Ala Lys Met Ile Pro Lys Cys
          595                600                605

Ser Thr Gln Leu Lys Ala Val Thr Ala His Phe Gln Thr His Thr Thr
      610                615                620

Pro Ile Leu Leu Ser Asn Asn Phe Ile Glu Pro Leu Glu Ile Thr Lys
625                630                635                640

Glu Ile Tyr Asp Leu Asn Asn Pro Glu Lys Glu Pro Lys Lys Phe Gln
              645                650                655

Thr Ala Tyr Ala Lys Lys Thr Gly Asp Gln Lys Gly Tyr Arg Glu Ala
          660                665                670

Leu Cys Lys Trp Ile Asp Phe Thr Arg Asp Phe Leu Ser Lys Tyr Thr
          675                680                685

Lys Thr Thr Ser Ile Asp Leu Ser Ser Leu Arg Pro Ser Ser Gln Tyr
      690                695                700

Lys Asp Leu Gly Glu Tyr Tyr Ala Glu Leu Asn Pro Leu Leu Tyr His
705                710                715                720

Ile Ser Phe Gln Arg Ile Ala Glu Lys Glu Ile Met Asp Ala Val Glu
              725                730                735

Thr Gly Lys Leu Tyr Leu Phe Gln Ile Tyr Asn Lys Asp Phe Ala Lys
              740                745                750

Gly His His Gly Lys Pro Asn Leu His Thr Leu Tyr Trp Thr Gly Leu
          755                760                765
```

Phe Ser Pro Glu Asn Leu Ala Lys Thr Ser Ile Lys Leu Asn Gly Gln
    770             775              780

Ala Glu Leu Phe Tyr Arg Pro Lys Ser Arg Met Lys Arg Met Ala His
785             790              795              800

Arg Leu Gly Glu Lys Met Leu Asn Lys Lys Leu Lys Asp Gln Lys Thr
                805              810              815

Pro Ile Pro Asp Thr Leu Tyr Gln Glu Leu Tyr Asp Tyr Val Asn His
            820              825              830

Arg Leu Ser His Asp Leu Ser Asp Glu Ala Arg Ala Leu Leu Pro Asn
        835              840              845

Val Ile Thr Lys Glu Val Ser His Glu Ile Ile Lys Asp Arg Arg Phe
    850              855              860

Thr Ser Asp Lys Phe Phe Phe His Val Pro Ile Thr Leu Asn Tyr Gln
865              870              875              880

Ala Ala Asn Ser Pro Ser Lys Phe Asn Gln Arg Val Asn Ala Tyr Leu
            885              890              895

Lys Glu His Pro Glu Thr Pro Ile Ile Gly Ile Asp Arg Gly Glu Arg
        900              905              910

Asn Leu Ile Tyr Ile Thr Val Ile Asp Ser Thr Gly Lys Ile Leu Glu
        915              920              925

Gln Arg Ser Leu Asn Thr Ile Gln Gln Phe Asp Tyr Gln Lys Lys Leu
    930              935              940

Asp Asn Arg Glu Lys Glu Arg Val Ala Ala Arg Gln Ala Trp Ser Val
945             950              955              960

Val Gly Thr Ile Lys Asp Leu Lys Gln Gly Tyr Leu Ser Gln Val Ile
            965              970              975

His Glu Ile Val Asp Leu Met Ile His Tyr Gln Ala Val Val Val Leu
        980              985              990

Glu Asn Leu Asn Phe Gly Phe Lys  Ser Lys Arg Thr Gly  Ile Ala Glu
        995             1000                1005

Lys Ala  Val Tyr Gln Gln Phe  Glu Lys Met Leu Ile  Asp Lys Leu
    1010             1015              1020

Asn Cys  Leu Val Leu Lys Asp  Tyr Pro Ala Glu Lys  Val Gly Gly
    1025             1030              1035

Val Leu  Asn Pro Tyr Gln Leu  Thr Asp Gln Phe Thr  Ser Phe Ala
    1040             1045              1050

Lys Met  Gly Thr Gln Ser Gly  Phe Leu Phe Tyr Val  Pro Ala Pro
    1055             1060              1065

Tyr Thr  Ser Lys Ile Asp Pro  Leu Thr Gly Phe Val  Asp Pro Phe
    1070             1075              1080

Val Trp  Lys Thr Ile Lys Asn  His Glu Ser Arg Lys  His Phe Leu
    1085             1090              1095

Glu Gly  Phe Asp Phe Leu His  Tyr Asp Val Lys Thr  Gly Asp Phe
    1100             1105              1110

Ile Leu  His Phe Lys Met Asn  Arg Asn Leu Ser Phe  Gln Arg Gly
    1115             1120              1125

Leu Pro  Gly Phe Met Pro Ala  Trp Asp Ile Val Phe  Glu Lys Asn
    1130             1135              1140

Glu Thr  Gln Phe Asp Ala Lys  Gly Thr Pro Phe Ile  Ala Gly Lys
    1145             1150              1155

Arg Ile  Val Pro Val Ile Glu  Asn His Arg Phe Thr  Gly Arg Tyr
    1160             1165              1170

-continued

```
Arg Asp Leu Tyr Pro Ala Asn  Glu Leu Ile Ala Leu  Leu Glu Glu
    1175             1180             1185

Lys Gly Ile Val Phe Arg Asp  Gly Ser Asn Ile Leu  Pro Lys Leu
    1190             1195             1200

Leu Glu Asn Asp Asp Ser His  Ala Ile Asp Thr Met  Val Ala Leu
    1205             1210             1215

Ile Arg Ser Val Leu Gln Met  Arg Asn Ser Asn Ala  Ala Thr Gly
    1220             1225             1230

Glu Asp Tyr Ile Asn Ser Pro  Val Arg Asp Leu Asn  Gly Val Cys
    1235             1240             1245

Phe Asp Ser Arg Phe Gln Asn  Pro Glu Trp Pro Met  Asp Ala Asp
    1250             1255             1260

Ala Asn Gly Ala Tyr His Ile  Ala Leu Lys Gly Gln  Leu Leu Leu
    1265             1270             1275

Asn His Leu Lys Glu Ser Lys  Asp Leu Lys Leu Gln  Asn Gly Ile
    1280             1285             1290

Ser Asn Gln Asp Trp Leu Ala  Tyr Ile Gln Glu Leu  Arg Asn Gly
    1295             1300             1305

Arg Ser Ser Asp Asp Glu Ala  Thr Ala Asp Ser Gln  His Ala Ala
    1310             1315             1320

Pro Pro Lys Lys Lys Arg Lys  Val Gly Gly Ser Gly  Gly Ser Gly
    1325             1330             1335

Gly Ser Gly Gly Ser Gly Gly  Ser Gly Gly Ser Gly  Gly Ser Gly
    1340             1345             1350

Gly Ser Leu Glu His His His  His His His
    1355             1360
```

```
<210> SEQ ID NO 20
<211> LENGTH: 1281
<212> TYPE: PRT
<213> ORGANISM: Artificial Sequence
<220> FEATURE:
<223> OTHER INFORMATION: Synthetic Amino Acid Sequence

<400> SEQUENCE: 20

Met Gly Asp Pro Leu Lys Asn  Val Gly Ile Asp Arg  Leu Asp Val Glu
1             5                10                15

Lys Gly Arg Lys Asn Met Ser  Lys Leu Glu Lys Phe  Thr Asn Cys Tyr
            20               25               30

Ser Leu Ser Lys Thr Leu Arg  Phe Lys Ala Ile Pro  Val Gly Lys Thr
        35               40               45

Gln Glu Asn Ile Asp Asn Lys  Arg Leu Leu Val Glu  Asp Glu Lys Arg
    50               55               60

Ala Glu Asp Tyr Lys Gly Val  Lys Lys Leu Leu Asp  Arg Tyr Tyr Leu
65               70               75               80

Ser Phe Ile Asn Asp Val Leu  His Ser Ile Lys Leu  Lys Asn Leu Asn
                85               90               95

Asn Tyr Ile Ser Leu Phe Arg  Lys Lys Thr Arg Thr  Glu Lys Glu Asn
            100              105              110

Lys Glu Leu Glu Asn Leu Glu  Ile Asn Leu Arg Lys  Glu Ile Ala Lys
        115              120              125

Ala Phe Lys Gly Asn Glu Gly  Tyr Lys Ser Leu Phe  Lys Lys Asp Ile
    130              135              140

Ile Glu Thr Ile Leu Pro Glu  Phe Leu Asp Asp Lys  Asp Glu Ile Ala
145              150              155              160
```

-continued

```
Leu Val Asn Ser Phe Asn Gly Phe Thr Thr Ala Phe Thr Gly Phe Phe
                165                 170                 175

Asp Asn Arg Glu Asn Met Phe Ser Glu Glu Ala Lys Ser Thr Ser Ile
            180                 185                 190

Ala Phe Arg Cys Ile Asn Glu Asn Leu Thr Arg Tyr Ile Ser Asn Met
            195                 200                 205

Asp Ile Phe Glu Lys Val Asp Ala Ile Phe Asp Lys His Glu Val Gln
    210                 215                 220

Glu Ile Lys Glu Lys Ile Leu Asn Ser Asp Tyr Asp Val Glu Asp Phe
225                 230                 235                 240

Phe Glu Gly Glu Phe Phe Asn Phe Val Leu Thr Gln Glu Gly Ile Asp
                245                 250                 255

Val Tyr Asn Ala Ile Ile Gly Gly Phe Val Thr Glu Ser Gly Glu Lys
            260                 265                 270

Ile Lys Gly Leu Asn Glu Tyr Ile Asn Leu Tyr Asn Gln Lys Thr Lys
            275                 280                 285

Gln Lys Leu Pro Lys Phe Lys Pro Leu Tyr Lys Gln Val Leu Ser Asp
    290                 295                 300

Arg Glu Ser Leu Ser Phe Tyr Gly Glu Gly Tyr Thr Ser Asp Glu Glu
305                 310                 315                 320

Val Leu Glu Val Phe Arg Asn Thr Leu Asn Lys Asn Ser Glu Ile Phe
                325                 330                 335

Ser Ser Ile Lys Lys Leu Glu Lys Leu Phe Lys Asn Phe Asp Glu Tyr
            340                 345                 350

Ser Ser Ala Gly Ile Phe Val Lys Asn Gly Pro Ala Ile Ser Thr Ile
            355                 360                 365

Ser Lys Asp Ile Phe Gly Glu Trp Asn Val Ile Arg Asp Lys Trp Asn
    370                 375                 380

Ala Glu Tyr Asp Asp Ile His Leu Lys Lys Lys Ala Val Val Thr Glu
385                 390                 395                 400

Lys Tyr Glu Asp Asp Arg Arg Lys Ser Phe Lys Lys Ile Gly Ser Phe
                405                 410                 415

Ser Leu Glu Gln Leu Gln Glu Tyr Ala Asp Ala Asp Leu Ser Val Val
            420                 425                 430

Glu Lys Leu Lys Glu Ile Ile Ile Gln Lys Val Asp Glu Ile Tyr Lys
            435                 440                 445

Val Tyr Gly Ser Ser Glu Lys Leu Phe Asp Ala Asp Phe Val Leu Glu
    450                 455                 460

Lys Ser Leu Lys Lys Asn Asp Ala Val Val Ala Ile Met Lys Asp Leu
465                 470                 475                 480

Leu Asp Ser Val Lys Ser Phe Glu Asn Tyr Ile Lys Ala Phe Phe Gly
            485                 490                 495

Glu Gly Lys Glu Thr Asn Arg Asp Glu Ser Phe Tyr Gly Asp Phe Val
            500                 505                 510

Leu Ala Tyr Asp Ile Leu Leu Lys Val Asp His Ile Tyr Asp Ala Ile
            515                 520                 525

Arg Asn Tyr Val Thr Gln Lys Pro Tyr Ser Lys Asp Lys Phe Lys Leu
    530                 535                 540

Tyr Phe Gln Asn Pro Gln Phe Met Gly Gly Trp Asp Lys Asp Lys Glu
545                 550                 555                 560

Thr Asp Tyr Arg Ala Thr Ile Leu Arg Tyr Gly Ser Lys Tyr Tyr Leu
                565                 570                 575

Ala Ile Met Asp Lys Lys Tyr Ala Lys Cys Leu Gln Lys Ile Asp Lys
```

-continued

```
                580              585              590

Asp Asp Val Asn Gly Asn Tyr Glu Lys Ile Asn Tyr Lys Leu Leu Pro
        595              600              605

Gly Pro Asn Lys Met Leu Pro Lys Val Phe Phe Ser Lys Lys Trp Met
        610              615              620

Ala Tyr Tyr Asn Pro Ser Glu Asp Ile Gln Lys Ile Tyr Lys Asn Gly
625              630              635              640

Thr Phe Lys Lys Gly Asp Met Phe Asn Leu Asn Asp Cys His Lys Leu
                645              650              655

Ile Asp Phe Phe Lys Asp Ser Ile Ser Arg Tyr Pro Lys Trp Ser Asn
                660              665              670

Ala Tyr Asp Phe Asn Phe Ser Glu Thr Glu Lys Tyr Lys Asp Ile Ala
        675              680              685

Gly Phe Tyr Arg Glu Val Glu Glu Gln Gly Tyr Lys Val Ser Phe Glu
        690              695              700

Ser Ala Ser Lys Lys Glu Val Asp Lys Leu Val Glu Glu Gly Lys Leu
705              710              715              720

Tyr Met Phe Gln Ile Tyr Asn Lys Asp Phe Ser Asp Lys Ser His Gly
                725              730              735

Thr Pro Asn Leu His Thr Met Tyr Phe Lys Leu Leu Phe Asp Glu Asn
                740              745              750

Asn His Gly Gln Ile Arg Leu Ser Gly Gly Ala Glu Leu Phe Met Arg
                755              760              765

Arg Ala Ser Leu Lys Lys Glu Glu Leu Val Val His Pro Ala Asn Ser
        770              775              780

Pro Ile Ala Asn Lys Asn Pro Asp Asn Pro Lys Lys Thr Thr Thr Leu
785              790              795              800

Ser Tyr Asp Val Tyr Lys Asp Lys Arg Phe Ser Glu Asp Gln Tyr Glu
                805              810              815

Leu His Ile Pro Ile Ala Ile Asn Lys Cys Pro Lys Asn Ile Phe Lys
                820              825              830

Ile Asn Thr Glu Val Arg Val Leu Leu Lys His Asp Asp Asn Pro Tyr
                835              840              845

Val Ile Gly Ile Asp Arg Gly Glu Arg Asn Leu Leu Tyr Ile Val Val
        850              855              860

Val Asp Gly Lys Gly Asn Ile Val Glu Gln Tyr Ser Leu Asn Glu Ile
865              870              875              880

Ile Asn Asn Phe Asn Gly Ile Arg Ile Lys Thr Asp Tyr His Ser Leu
                885              890              895

Leu Asp Lys Lys Glu Lys Glu Arg Phe Glu Ala Arg Gln Asn Trp Thr
                900              905              910

Ser Ile Glu Asn Ile Lys Glu Leu Lys Ala Gly Tyr Ile Ser Gln Val
        915              920              925

Val His Lys Ile Cys Glu Leu Val Glu Lys Tyr Asp Ala Val Ile Ala
        930              935              940

Leu Glu Asp Leu Asn Ser Gly Phe Lys Asn Ser Arg Val Lys Val Glu
945              950              955              960

Lys Gln Val Tyr Gln Lys Phe Glu Lys Met Leu Ile Asp Lys Leu Asn
                965              970              975

Tyr Met Val Asp Lys Lys Ser Asn Pro Cys Ala Thr Gly Gly Ala Leu
                980              985              990

Lys Gly Tyr Gln Ile Thr Asn Lys  Phe Glu Ser Phe Lys  Ser Met Ser
        995              1000             1005
```

```
Thr Gln  Asn Gly Phe Ile Phe  Tyr Ile Pro Ala Trp  Leu Thr Ser
    1010                1015                1020

Lys Ile  Asp Pro Ser Thr Gly  Phe Val Asn Leu Leu  Lys Thr Lys
    1025                1030                1035

Tyr Thr  Ser Ile Ala Asp Ser  Lys Lys Phe Ile Ser  Ser Phe Asp
    1040                1045                1050

Arg Ile  Met Tyr Val Pro Glu  Glu Asp Leu Phe Glu  Phe Ala Leu
    1055                1060                1065

Asp Tyr  Lys Asn Phe Ser Arg  Thr Asp Ala Asp Tyr  Ile Lys Lys
    1070                1075                1080

Trp Lys  Leu Tyr Ser Tyr Gly  Asn Arg Ile Arg Ile  Phe Arg Asn
    1085                1090                1095

Pro Lys  Lys Asn Asn Val Phe  Asp Trp Glu Glu Val  Cys Leu Thr
    1100                1105                1110

Ser Ala  Tyr Lys Glu Leu Phe  Asn Lys Tyr Gly Ile  Asn Tyr Gln
    1115                1120                1125

Gln Gly  Asp Ile Arg Ala Leu  Leu Cys Glu Gln Ser  Asp Lys Ala
    1130                1135                1140

Phe Tyr  Ser Ser Phe Met Ala  Leu Met Ser Leu Met  Leu Gln Met
    1145                1150                1155

Arg Asn  Ser Ile Thr Gly Arg  Thr Asp Val Asp Phe  Leu Ile Ser
    1160                1165                1170

Pro Val  Lys Asn Ser Asp Gly  Ile Phe Tyr Asp Ser  Arg Asn Tyr
    1175                1180                1185

Glu Ala  Gln Glu Asn Ala Ile  Leu Pro Lys Asn Ala  Asp Ala Asn
    1190                1195                1200

Gly Ala  Tyr Asn Ile Ala Arg  Lys Val Leu Trp Ala  Ile Gly Gln
    1205                1210                1215

Phe Lys  Lys Ala Glu Asp Glu  Lys Leu Asp Lys Val  Lys Ile Ala
    1220                1225                1230

Ile Ser  Asn Lys Glu Trp Leu  Glu Tyr Ala Gln Thr  Ser Val Lys
    1235                1240                1245

His Gly  Arg Ser Ser Asp Asp  Glu Ala Thr Ala Asp  Ser Gln His
    1250                1255                1260

Ala Ala  Pro Pro Lys Lys Lys  Arg Lys Val Leu Glu  His His His
    1265                1270                1275

His His  His
    1280
```

```
<210> SEQ ID NO 21
<211> LENGTH: 3843
<212> TYPE: DNA
<213> ORGANISM: Artificial Sequence
<220> FEATURE:
<223> OTHER INFORMATION: Synthetic DNA

<400> SEQUENCE: 21
atgggcgacc ctctgaagaa cgtgggcatc gacagactgg acgtggaaaa gggcagaaag      60
aacatgagca agctcgagaa gttcaccaac tgctacagcc tgagcaagac cctgcggttc     120
aaggccattc ctgtgggcaa gacccaagag aacatcgaca acaagcggct gctggtggaa     180
gatgagaaga gagccgagga ctacaagggc gtgaagaagc tgctggaccg gtactacctg     240
agcttcatca cgacgtgct gcacagcatc aagctgaaga acctgaacaa ctacatcagc     300
ctgttccgga agaaaacccg gaccgagaaa gagaacaaag agctggaaaa cctcgagatc     360
```

-continued

```
aacctgcgga aagagatcgc caaggccttc aagggcaacg agggctacaa gagcctgttc      420
aagaaggaca tcatcgagac aatcctgcct gagttcctgg acgacaagga cgagatcgcc      480
ctggtcaaca gcttcaacgg cttcacaacc gccttcaccg gctttttcga caaccgcgag      540
aatatgttca gcgaggaagc caagagcacc tctatcgcct tccggtgcat caacgagaat      600
ctgacccggt acatcagcaa catggatatc ttcgagaagg tggacgccat cttcgacaag      660
cacgaggtgc aagagatcaa agaaaagatc ctgaacagcg actacgacgt cgaggacttc      720
ttcgagggcg agttcttcaa cttcgtgctg acacaagagg gcatcgatgt gtacaacgcc      780
atcatcggcg gcttcgtgac agagagcggc gagaagatca agggcctgaa cgagtacatc      840
aacctctaca accagaaaac gaagcagaag ctgcccaagt tcaagcccct gtacaaacag      900
gtgctgagcg acagagagag cctgtccttt tacggcgagg gctataccag cgacgaagag      960
gtgctggaag tgttcagaaa caccctgaac aagaacagcg agatcttcag ctccatcaag     1020
aagctcgaaa agctgtttaa gaacttcgac gagtacagca gcgccggcat cttcgtgaag     1080
aatggccctg ccatcagcac catctccaag gacatcttcg gcgagtggaa cgtgatccgg     1140
gacaagtgga acgccgagta cgacgacatc cacctgaaga aaaaggccgt ggtcaccgag     1200
aagtacgagg acgacagaag aaagagcttc aagaagatcg gcagcttcag cctggaacag     1260
ctgcaagagt acgccgacgc cgatctgagc gtggtggaaa agctgaaaga gattatcatc     1320
cagaaggtcg acgagatcta caaggtgtac ggcagcagcg agaagctgtt cgacgccgac     1380
tttgtgctgg aaaagagcct caaaaagaac gacgccgtgg tggccatcat gaaggacctg     1440
ctggatagcg tgaagtcctt cgagaactat attaaggcct tctttggcga gggcaaagag     1500
acaaaccggg acgagagctt ctacggcgat ttcgtgctgg cctacgacat cctgctgaaa     1560
gtggaccaca tctacgacgc catccggaac tacgtgaccc agaagcctta cagcaaggac     1620
aagtttaagc tgtacttcca gaatccgcag ttcatgggcg gctgggacaa agacaaagaa     1680
accgactacc gggccaccat cctgagatac ggctccaagt actatctggc cattatggac     1740
aagaaatacg ccaagtgcct gcagaagatc gataaggacg acgtgaacgg caactacgag     1800
aagattaact acaagctgct gcccggacct aacaagatgc tgcctaaggt gttctttagc     1860
aagaaatgga tggcctacta caacccccagc gaggatatcc agaaaatcta caagaacggc     1920
accttcaaga aaggcgacat gttcaacctg aacgactgcc acaagctgat cgatttcttc     1980
aaggacagca tcagcagata ccccaagtgg tccaacgcct acgacttcaa tttcagcgag     2040
acagagaagt ataaggatat cgccgggttc taccgcgagg tggaagaaca gggctataag     2100
gtgtcctttg agagcgccag caagaaagag gtggacaagc tggtcgaaga gggcaagctg     2160
tacatgttcc agatctataa caaggacttc tccgacaaga gccacggcac ccctaacctg     2220
cacaccatgt actttaagct gctgttcgat gagaacaacc acggccagat cagactgtct     2280
ggcggagccg agctgtttat gagaagggcc agcctgaaaa agaggaact ggtcgttcac      2340 cccgccaact ctccaatcgc caacaagaac cccgacaatc ccaagaaaac caccacactg     2400
agctacgacg tgtacaagga taagcggttc tccgaggacc agtacgagct gcacatccct     2460
atcgccatca cacagtgccc caagaatatc ttcaagatca caccgaagt gcgggtgctg      2520 ctgaagcacg acgacaaccc ttacgtgatc ggcatcgatc ggggcgagag aaacctgctg     2580
tatatcgtgg tggtggacgg caaggcaat atcgtggaac agtactccct gaatgagatc      2640
atcaacaact tcaatggcat ccggatcaag acggactacc acagcctgct ggacaaaaaa     2700
```

-continued

```
gagaaagaac gcttcgaggc ccggcagaac tggaccagca tcgagaacat caaagaactg   2760
aaggccggct acatctccca ggtggtgcac aagatctgcg agctggttga gaagtatgac   2820
gccgtgattg ccctggaaga tctgaatagc ggctttaaga acagccgcgt gaaggtcgag   2880
aaacaggtgt accagaaatt cgagaagatg ctgatcgaca agctgaacta catggtcgac   2940
aagaagtcta accctgcgc cacaggcgga gccctgaagg gatatcagat caccaacaag    3000
ttcgagtcct tcaagagcat gagcacccag aatggcttca tcttctacat ccccgcctgg   3060
ctgaccagca agatcgatcc tagcaccgga ttcgtgaacc tgctcaagac caagtacacc   3120
agcattgccg acagcaagaa gttcatctcc agcttcgacc ggattatgta cgtgcccgaa   3180
gaggacctgt tcgaattcgc cctggattac aagaacttca gccggaccga tgccgactat   3240
atcaagaagt ggaagctgta tagctacggc aaccgcatcc gcatcttcag aaacccgaag   3300
aaaaacaacg tgttcgactg ggaagaagtg tgcctgacca gcgcctacaa agaactcttc   3360
aacaaatacg gcatcaacta ccagcaggc gacatcagag ccctgctgtg cgagcagagc    3420
gacaaggcct tttacagctc cttcatggcc ctgatgagcc tgatgctgca gatgcggaat   3480
agcatcaccg gcaggaccga cgtggacttc ctgatcagcc ctgtgaagaa ttccgacggg   3540
atcttctacg acagcagaaa ctacgaggct caagagaacg ccatcctgcc taagaacgcc   3600
gatgccaacg gcgcctataa tatcgccaga aaggtgctgt gggccatcgg ccagtttaag   3660
aaggccgagg acgagaaact ggacaaagtg aagatcgcca tctctaacaa agagtggctg   3720
gaatacgccc agaccagcgt gaagcacggc agatctagtg acgatgaggc caccgccgat   3780
agccagcatg cagcccctcc aaagaaaaag cggaaagtgc tggaacacca ccaccatcac   3840
cac                                                                 3843
```

<210> SEQ ID NO 22
<211> LENGTH: 1363
<212> TYPE: PRT
<213> ORGANISM: Artificial Sequence
<220> FEATURE:
<223> OTHER INFORMATION: Synthetic Amino Acid Sequence

<400> SEQUENCE: 22

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160
```

-continued

```
Ser Phe Asp Lys Phe Thr Thr Tyr Phe Ser Gly Phe Tyr Glu Asn Arg
            165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
            195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
                260                 265                 270

Lys Ile Lys Gly Leu Asn Glu Val Leu Asn Leu Ala Ile Gln Lys Asn
                275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
                515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575
```

-continued

```
Ala Leu Ser Phe Glu Pro Thr Glu Lys Thr Ser Glu Gly Phe Asp Lys
            580             585             590

Met Tyr Tyr Asp Tyr Phe Pro Asp Ala Ala Lys Met Ile Pro Lys Cys
        595             600             605

Ser Thr Gln Leu Lys Ala Val Thr Ala His Phe Gln Thr His Thr Thr
    610             615             620

Pro Ile Leu Leu Ser Asn Asn Phe Ile Glu Pro Leu Glu Ile Thr Lys
625             630             635             640

Glu Ile Tyr Asp Leu Asn Asn Pro Glu Lys Glu Pro Lys Lys Phe Gln
            645             650             655

Thr Ala Tyr Ala Lys Lys Thr Gly Asp Gln Lys Gly Tyr Arg Glu Ala
        660             665             670

Leu Cys Lys Trp Ile Asp Phe Thr Arg Asp Phe Leu Ser Lys Tyr Thr
    675             680             685

Lys Thr Thr Ser Ile Asp Leu Ser Ser Leu Arg Pro Ser Ser Gln Tyr
    690             695             700

Lys Asp Leu Gly Glu Tyr Tyr Ala Glu Leu Asn Pro Leu Leu Tyr His
705             710             715             720

Ile Ser Phe Gln Arg Ile Ala Glu Lys Glu Ile Met Asp Ala Val Glu
            725             730             735

Thr Gly Lys Leu Tyr Leu Phe Gln Ile Tyr Asn Lys Asp Phe Ala Lys
        740             745             750

Gly His His Gly Lys Pro Asn Leu His Thr Leu Tyr Trp Thr Gly Leu
        755             760             765

Phe Ser Pro Glu Asn Leu Ala Lys Thr Ser Ile Lys Leu Asn Gly Gln
    770             775             780

Ala Glu Leu Phe Tyr Arg Pro Lys Ser Arg Met Lys Arg Met Ala His
785             790             795             800

Arg Leu Gly Glu Lys Met Leu Asn Lys Lys Leu Lys Asp Gln Lys Thr
            805             810             815

Pro Ile Pro Asp Thr Leu Tyr Gln Glu Leu Tyr Asp Tyr Val Asn His
        820             825             830

Arg Leu Ser His Asp Leu Ser Asp Glu Ala Arg Ala Leu Leu Pro Asn
        835             840             845

Val Ile Thr Lys Glu Val Ser His Glu Ile Ile Lys Asp Arg Arg Phe
    850             855             860

Thr Ser Asp Lys Phe Phe Phe His Val Pro Ile Thr Leu Asn Tyr Gln
865             870             875             880

Ala Ala Asn Ser Pro Ser Lys Phe Asn Gln Arg Val Asn Ala Tyr Leu
            885             890             895

Lys Glu His Pro Glu Thr Pro Ile Ile Gly Ile Asp Arg Gly Glu Arg
        900             905             910

Asn Leu Ile Tyr Ile Thr Val Ile Asp Ser Thr Gly Lys Ile Leu Glu
        915             920             925

Gln Arg Ser Leu Asn Thr Ile Gln Gln Phe Asp Tyr Gln Lys Lys Leu
    930             935             940

Asp Asn Arg Glu Lys Glu Arg Val Ala Ala Arg Gln Ala Trp Ser Val
945             950             955             960

Val Gly Thr Ile Lys Asp Leu Lys Gln Gly Tyr Leu Ser Gln Val Ile
            965             970             975

His Glu Ile Val Asp Leu Met Ile His Tyr Gln Ala Val Val Val Leu
            980             985             990

Glu Asn Leu Asn Phe Gly Phe Lys  Ser Lys Arg Thr Gly  Ile Ala Glu
```

-continued

```
              995                1000                1005
Lys Ala  Val Tyr Gln Gln Phe  Glu Lys Met Leu Ile  Asp Lys Leu
    1010            1015            1020

Asn Cys  Leu Val Leu Lys Asp  Tyr Pro Ala Glu Lys  Val Gly Gly
    1025            1030            1035

Val Leu  Asn Pro Tyr Gln Leu  Thr Asp Gln Phe Thr  Ser Phe Ala
    1040            1045            1050

Lys Met  Gly Thr Gln Ser Gly  Phe Leu Phe Tyr Val  Pro Ala Pro
    1055            1060            1065

Tyr Thr  Ser Lys Ile Asp Pro  Leu Thr Gly Phe Val  Asp Pro Phe
    1070            1075            1080

Val Trp  Lys Thr Ile Lys Asn  His Glu Ser Arg Lys  His Phe Leu
    1085            1090            1095

Glu Gly  Phe Asp Phe Leu His  Tyr Asp Val Lys Thr  Gly Asp Phe
    1100            1105            1110

Ile Leu  His Phe Lys Met Asn  Arg Asn Leu Ser Phe  Gln Arg Gly
    1115            1120            1125

Leu Pro  Gly Phe Met Pro Ala  Trp Asp Ile Val Phe  Glu Lys Asn
    1130            1135            1140

Glu Thr  Gln Phe Asp Ala Lys  Gly Thr Pro Phe Ile  Ala Gly Lys
    1145            1150            1155

Arg Ile  Val Pro Val Ile Glu  Asn His Arg Phe Thr  Gly Arg Tyr
    1160            1165            1170

Arg Asp  Leu Tyr Pro Ala Asn  Glu Leu Ile Ala Leu  Leu Glu Glu
    1175            1180            1185

Lys Gly  Ile Val Phe Arg Asp  Gly Ser Asn Ile Leu  Pro Lys Leu
    1190            1195            1200

Leu Glu  Asn Asp Asp Ser His  Ala Ile Asp Thr Met  Val Ala Leu
    1205            1210            1215

Ile Arg  Ser Val Leu Gln Met  Arg Asn Ser Asn Ala  Ala Thr Gly
    1220            1225            1230

Glu Asp  Tyr Ile Asn Ser Pro  Val Arg Asp Leu Asn  Gly Val Cys
    1235            1240            1245

Phe Asp  Ser Arg Phe Gln Asn  Pro Glu Trp Pro Met  Asp Ala Asp
    1250            1255            1260

Ala Asn  Gly Ala Tyr His Ile  Ala Leu Lys Gly Gln  Leu Leu Leu
    1265            1270            1275

Asn His  Leu Lys Glu Ser Lys  Asp Leu Lys Leu Gln  Asn Gly Ile
    1280            1285            1290

Ser Asn  Gln Asp Trp Leu Ala  Tyr Ile Gln Glu Leu  Arg Asn Gly
    1295            1300            1305

Arg Ser  Ser Asp Asp Glu Ala  Thr Ala Asp Ser Gln  His Ala Ala
    1310            1315            1320

Pro Pro  Lys Lys Lys Arg Lys  Val Gly Gly Ser Gly  Gly Ser Gly
    1325            1330            1335

Gly Ser  Gly Gly Ser Gly Gly  Ser Gly Gly Ser Gly  Gly Ser Gly
    1340            1345            1350

Gly Ser  Leu Glu His His His  His His His
    1355            1360
```

<210> SEQ ID NO 23
<211> LENGTH: 3846
<212> TYPE: DNA
<213> ORGANISM: Artificial Sequence -continued
<220> FEATURE:
<223> OTHER INFORMATION: Synthetic DNA
<400> SEQUENCE: 23

```
atgggggatc cactgaaaaa cgtgggtatt gatcgtctgg atgttgaaaa aggtcgcaaa      60
aatatgagca aactggaaaa gttcaccaac tgttatagcc tgagcaaaac cctgcgtttt     120
aaagcaattc cggttggtaa aacccaagag aacattgata ataaacgcct gctggtcgaa     180
gatgaaaaac gcgctgaaga ttataaaggc gtgaaaaaac tgctggatcg ctattatctg     240
agcttcatta acgatgtgct gcacagcatt aaactgaaga acctgaacaa ctatatcagc     300
ctgtttcgta aaaaaacccg caccgaaaaa gaaacaaag agctggaaaa cctggaaatc      360
aatctgcgta agaaatcgc caaagcgttt aaaggtaacg agggttataa aagcctgttc      420
aagaaagaca tcatcgaaac cattctgccg gaatttctgg atgataaaga tgaaattgcc     480
ctggtgaata gctttaatgg ctttaccacc gcatttaccg gctttttga taatcgcgaa      540 aacatgttca gcgaagaagc aaaaagcacc agcattgcat ttcgctgcat taatgaaaat     600
ctgacccgct acattagcaa catggatatc tttgaaaaag tggacgcgat cttcgataaa     660
cacgaagtgc aagagatcaa agagaaaatc ctgaacagcg attatgacgt cgaagatttt     720
tttgaaggcg agttctttaa cttcgttctg acccaagaag gtatcgacgt ttataacgca     780
attattggtg gttttgttac cgaaagcggt gagaaaatca aaggcctgaa tgaatatatc     840
aacctgtata accagaaaac caaacagaaa ctgccgaaat tcaaaccgct gtataaacag     900
gttctgagcg atcgtgaaag cctgagcttt tatggtgaag gttataccag tgatgaagag     960
gttctggaag tttttcgtaa caccctgaat aaaaacagcg agatctttag cagcatcaaa    1020
aagcttgaga aactgttcaa aaactttgat gagtatagca gcgcaggcat ctttgttaaa    1080
aatggtccgg caattagcac catcagcaaa gatattttg gcgaatggaa tgtgatccgc     1140
gataaatgga atgccgaata tgatgatatc cacctgaaaa aaaaggccgt ggtgaccgag    1200
aaatatgaag atgatcgtcg taaaagcttc aagaaaattg gtagctttag cctggaacag    1260
ctgcaagaat atgcagatgc agatctgagc gttgtggaaa aactgaaaga aatcatcatt    1320
cagaaggtgg acgagatcta taaagtttat ggtagcagcg aaaaactgtt cgatgcagat    1380
tttgttctgg aaaaaagcct gaaaaagaat gatgccgttg tggccattat gaaagatctg    1440
ctggatagcg ttaagagctt cgagaattac atcaaagcct tttttggtga gggcaaagaa    1500
accaatcgtg atgaaagttt ctatggcgat tttgtgctgg cctatgatat tctgctgaaa    1560
gtggaccata tttatgatgc cattcgcaat tatgttaccc agaaaccgta tagcaaagac    1620
aagttcaaac tgtactttca gaacccgcag tttatgggtg ttgggataa agataaagaa     1680 accgattatc gtgccaccat cctgcgttat ggtagtaaat actatctggc catcatggac    1740
aaaaaatacg caaatgcct gcagaaaatc gacaagatg atgtgaatgg caactatgaa      1800
aaaatcaact acaaactgct gcctggtccg aataaaatgc tgccgaaagt gttctttagc    1860
aagaaatgga tggcctatta taacccgagc gaggatattc aaaagatcta caaaaatggc    1920
acctttaaaa agggcgacat gttcaatctg aacgattgcc acaaactgat cgatttcttc    1980
aaagattcaa tttcgcgtta tccgaaatgg tccaatgcct atgattttaa ctttagcgaa    2040
accgaaaaat acaaagacat tgccggtttt tatcgcgaag tggaagaaca gggctataaa    2100
gtgagctttg aaagcgcaag caaaaaagag gttgataagc tggttgaaga gggcaaactg    2160
tatatgttcc agatttacaa caaagatttt agcgacaaaa gccatggcac cccgaatctg    2220
```

-continued

```
cataccatgt actttaaact gctgttcgac gaaaataacc atggtcagat tcgtctgagc      2280
ggtggtgccg aactgtttat gcgtcgtgca agtctgaaaa aagaagaact ggttgttcat      2340
ccggcaaata gcccgattgc aaacaaaaat ccggacaatc cgaaaaaaac cacgacactg      2400
agctatgatg tgtataaaga caaacgtttt agcgaggatc agtatgaact gcatatcccg      2460
attgccatca ataaatgccc gaaaaacatc tttaagatca caccgaagt tcgcgtgctg       2520 ctgaaacatg atgataatcc gtatgtgatt ggcattgatc gtggtgaacg taacctgctg      2580
tatattgttg ttgttgatgg taaaggcaac atcgtggaac agtatagtct gaacgaaatt      2640
atcaacaact ttaacggcat ccgcatcaaa accgactatc atagcctgct ggacaagaaa      2700
gaaaaagaac gttttgaagc acgtcagaac tggaccagta ttgaaaacat caagaactg       2760 aaagccggtt atattagcca ggtggttcat aaaatctgtg agctggtaga aaaatacgat      2820
gcagttattg cactggaaga tctgaatagc ggtttcaaaa atagccgtgt gaaagtcgaa      2880
aaacaggtgt atcagaaatt cgagaaaatg ctgatcgaca aactgaacta catggtcgac      2940
aaaaaaagca atccgtgtgc aaccggtggt gcactgaaag gttatcagat taccaacaaa      3000
tttgaaagct ttaaaagcat gagcacccag aacggcttta tcttctatat tccggcatgg      3060
ctgaccagca aaattgatcc gagcaccggt tttgtgaacc tgctgaaaac aaaatatacc      3120
tccattgccg acagcaagaa gtttattagc agctttgatc gcattatgta tgttccggaa      3180
gaggacctgt ttgaattcgc actggattac aaaaaatttca gccgtaccga tgccgactac     3240
atcaaaaaat ggaaactgta cagctatggt aaccgcattc gcatttttcg caacccgaag      3300
aaaaacaatg tgttcgattg ggaagaagtt tgtctgacca gcgcatataa agaactttc      3360 aacaaatacg gcatcaacta tcagcagggt gatattcgtg cactgctgtg tgaacagagc      3420
gataaagcgt tttatagcag tttttatggca ctgatgagcc tgatgctgca gatgcgtaat     3480
agcattaccg gtcgcaccga tgtggatttt ctgattagtc cggtgaaaaa ttccgatggc      3540 atctttttatg atagccgcaa ttacgaagca caagaaaatg caattctgcc gaaaaacgca     3600
gatgcaaatg gtgcatataa cattgcacgt aaagttctgt gggcaattgg ccagtttaag      3660
aaagcagaag atgagaagct ggacaaagtg aaaattgcga tcagcaataa agagtggctg      3720
gaatacgcac agaccagcgt taaacatggt cgtagcagtg atgatgaagc aaccgcagat      3780
agccagcatg cagcaccgcc gaaaaaaaaa cgcaaagtgc tcgagcacca ccaccaccac      3840
cactga                                                                 3846
```

```
<210> SEQ ID NO 24
<211> LENGTH: 1278
<212> TYPE: PRT
<213> ORGANISM: Artificial Sequence
<220> FEATURE:
<223> OTHER INFORMATION: Synthetic Amino Acid Sequence

<400> SEQUENCE: 24

Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
            20                  25                  30

Lys Thr Leu Arg Phe Lys Ala Ile Pro Val Gly Lys Thr Gln Glu Asn
        35                  40                  45

Ile Asp Asn Lys Arg Leu Leu Val Glu Asp Glu Lys Arg Ala Glu Asp
    50                  55                  60

Tyr Lys Gly Val Lys Lys Leu Leu Asp Arg Tyr Tyr Leu Ser Phe Ile
```

-continued

```
65                    70                75                80

Asn Asp Val Leu His Ser Ile Lys Leu Lys Asn Leu Asn Asn Tyr Ile
                85                    90                95

Ser Leu Phe Arg Lys Lys Thr Arg Thr Glu Lys Glu Asn Lys Glu Leu
                100               105               110

Glu Asn Leu Glu Ile Asn Leu Arg Lys Glu Ile Ala Lys Ala Phe Lys
                115               120               125

Gly Asn Glu Gly Tyr Lys Ser Leu Phe Lys Lys Asp Ile Ile Glu Thr
        130               135               140

Ile Leu Pro Glu Phe Leu Asp Asp Lys Asp Glu Ile Ala Leu Val Asn
145               150               155               160

Ser Phe Asn Gly Phe Thr Thr Ala Phe Thr Gly Phe Phe Asp Asn Arg
                165               170               175

Glu Asn Met Phe Ser Glu Glu Ala Lys Ser Thr Ser Ile Ala Phe Arg
                180               185               190

Cys Ile Asn Glu Asn Leu Thr Arg Tyr Ile Ser Asn Met Asp Ile Phe
                195               200               205

Glu Lys Val Asp Ala Ile Phe Asp Lys His Glu Val Gln Glu Ile Lys
        210               215               220

Glu Lys Ile Leu Asn Ser Asp Tyr Asp Val Glu Asp Phe Phe Glu Gly
225               230               235               240

Glu Phe Phe Asn Phe Val Leu Thr Gln Glu Gly Ile Asp Val Tyr Asn
                245               250               255

Ala Ile Ile Gly Gly Phe Val Thr Glu Ser Gly Glu Lys Ile Lys Gly
                260               265               270

Leu Asn Glu Tyr Ile Asn Leu Tyr Asn Gln Lys Thr Lys Gln Lys Leu
        275               280               285

Pro Lys Phe Lys Pro Leu Tyr Lys Gln Val Leu Ser Asp Arg Glu Ser
        290               295               300

Leu Ser Phe Tyr Gly Glu Gly Tyr Thr Ser Asp Glu Glu Val Leu Glu
305               310               315               320

Val Phe Arg Asn Thr Leu Asn Lys Asn Ser Glu Ile Phe Ser Ser Ile
                325               330               335

Lys Lys Leu Glu Lys Leu Phe Lys Asn Phe Asp Glu Tyr Ser Ser Ala
                340               345               350

Gly Ile Phe Val Lys Asn Gly Pro Ala Ile Ser Thr Ile Ser Lys Asp
        355               360               365

Ile Phe Gly Glu Trp Asn Val Ile Arg Asp Lys Trp Asn Ala Glu Tyr
        370               375               380

Asp Asp Ile His Leu Lys Lys Lys Ala Val Val Thr Glu Lys Tyr Glu
385               390               395               400

Asp Asp Arg Arg Lys Ser Phe Lys Lys Ile Gly Ser Phe Ser Leu Glu
                405               410               415

Gln Leu Gln Glu Tyr Ala Asp Ala Asp Leu Ser Val Val Glu Lys Leu
                420               425               430

Lys Glu Ile Ile Ile Gln Lys Val Asp Glu Ile Tyr Lys Val Tyr Gly
        435               440               445

Ser Ser Glu Lys Leu Phe Asp Ala Asp Phe Val Leu Glu Lys Ser Leu
        450               455               460

Lys Lys Asn Asp Ala Val Val Ala Ile Met Lys Asp Leu Leu Asp Ser
465               470               475               480

Val Lys Ser Phe Glu Asn Tyr Ile Lys Ala Phe Phe Gly Glu Gly Lys
                485               490               495
```

-continued

```
Glu Thr Asn Arg Asp Glu Ser Phe Tyr Gly Asp Phe Val Leu Ala Tyr
            500                 505                 510

Asp Ile Leu Leu Lys Val Asp His Ile Tyr Asp Ala Ile Arg Asn Tyr
            515                 520                 525

Val Thr Gln Lys Pro Tyr Ser Lys Asp Lys Phe Lys Leu Tyr Phe Gln
            530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Tyr Leu Ala Ile Met
                565                 570                 575

Asp Lys Lys Tyr Ala Lys Cys Leu Gln Lys Ile Asp Lys Asp Asp Val
                580                 585                 590

Asn Gly Asn Tyr Glu Lys Ile Asn Tyr Lys Leu Leu Pro Gly Pro Asn
                595                 600                 605

Lys Met Leu Pro Lys Val Phe Phe Ser Lys Lys Trp Met Ala Tyr Tyr
            610                 615                 620

Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
                645                 650                 655

Phe Lys Asp Ser Ile Ser Arg Tyr Pro Lys Trp Ser Asn Ala Tyr Asp
                660                 665                 670

Phe Asn Phe Ser Glu Thr Glu Lys Tyr Lys Asp Ile Ala Gly Phe Tyr
                675                 680                 685

Arg Glu Val Glu Glu Gln Gly Tyr Lys Val Ser Phe Glu Ser Ala Ser
            690                 695                 700

Lys Lys Glu Val Asp Lys Leu Val Glu Glu Gly Lys Leu Tyr Met Phe
705                 710                 715                 720

Gln Ile Tyr Asn Lys Asp Phe Ser Asp Lys Ser His Gly Thr Pro Asn
                725                 730                 735

Leu His Thr Met Tyr Phe Lys Leu Leu Phe Asp Glu Asn Asn His Gly
                740                 745                 750

Gln Ile Arg Leu Ser Gly Gly Ala Glu Leu Phe Met Arg Arg Ala Ser
            755                 760                 765

Leu Lys Lys Glu Glu Leu Val Val His Pro Ala Asn Ser Pro Ile Ala
            770                 775                 780

Asn Lys Asn Pro Asp Asn Pro Lys Lys Thr Thr Thr Leu Ser Tyr Asp
785                 790                 795                 800

Val Tyr Lys Asp Lys Arg Phe Ser Glu Asp Gln Tyr Glu Leu His Ile
                805                 810                 815

Pro Ile Ala Ile Asn Lys Cys Pro Lys Asn Ile Phe Lys Ile Asn Thr
                820                 825                 830

Glu Val Arg Val Leu Leu Lys His Asp Asp Asn Pro Tyr Val Ile Gly
            835                 840                 845

Ile Asp Arg Gly Glu Arg Asn Leu Leu Tyr Ile Val Val Val Asp Gly
            850                 855                 860

Lys Gly Asn Ile Val Glu Gln Tyr Ser Leu Asn Glu Ile Ile Asn Asn
865                 870                 875                 880

Phe Asn Gly Ile Arg Ile Lys Thr Asp Tyr His Ser Leu Leu Asp Lys
                885                 890                 895

Lys Glu Lys Glu Arg Phe Glu Ala Arg Gln Asn Trp Thr Ser Ile Glu
            900                 905                 910
```

-continued

```
Asn Ile Lys Glu Leu Lys Ala Gly Tyr Ile Ser Gln Val Val His Lys
        915                 920                 925

Ile Cys Glu Leu Val Glu Lys Tyr Asp Ala Val Ile Ala Leu Glu Asp
    930                 935                 940

Leu Asn Ser Gly Phe Lys Asn Ser Arg Val Lys Val Glu Lys Gln Val
945                 950                 955                 960

Tyr Gln Lys Phe Glu Lys Met Leu Ile Asp Lys Leu Asn Tyr Met Val
                965                 970                 975

Asp Lys Lys Ser Asn Pro Cys Ala Thr Gly Gly Ala Leu Lys Gly Tyr
                980                 985                 990

Gln Ile Thr Asn Lys Phe Glu Ser  Phe Lys Ser Met Ser  Thr Gln Asn
        995                 1000                1005

Gly Phe  Ile Phe Tyr Ile Pro  Ala Trp Leu Thr Ser  Lys Ile Asp
    1010                1015                1020

Pro Ser  Thr Gly Phe Val Asn  Leu Leu Lys Thr Lys  Tyr Thr Ser
    1025                1030                1035

Ile Ala  Asp Ser Lys Lys Phe  Ile Ser Ser Phe Asp  Arg Ile Met
    1040                1045                1050

Tyr Val  Pro Glu Glu Asp Leu  Phe Glu Phe Ala Leu  Asp Tyr Lys
    1055                1060                1065

Asn Phe  Ser Arg Thr Asp Ala  Asp Tyr Ile Lys Lys  Trp Lys Leu
    1070                1075                1080

Tyr Ser  Tyr Gly Asn Arg Ile  Arg Ile Phe Arg Asn  Pro Lys Lys
    1085                1090                1095

Asn Asn  Val Phe Asp Trp Glu  Glu Val Cys Leu Thr  Ser Ala Tyr
    1100                1105                1110

Lys Glu  Leu Phe Asn Lys Tyr  Gly Ile Asn Tyr Gln  Gln Gly Asp
    1115                1120                1125

Ile Arg  Ala Leu Leu Cys Glu  Gln Ser Asp Lys Ala  Phe Tyr Ser
    1130                1135                1140

Ser Phe  Met Ala Leu Met Ser  Leu Met Leu Gln Met  Arg Asn Ser
    1145                1150                1155

Ile Thr  Gly Arg Thr Asp Val  Asp Phe Leu Ile Ser  Pro Val Lys
    1160                1165                1170

Asn Ser  Asp Gly Ile Phe Tyr  Asp Ser Arg Asn Tyr  Glu Ala Gln
    1175                1180                1185

Glu Asn  Ala Ile Leu Pro Lys  Asn Ala Asp Ala Asn  Gly Ala Tyr
    1190                1195                1200

Asn Ile  Ala Arg Lys Val Leu  Trp Ala Ile Gly Gln  Phe Lys Lys
    1205                1210                1215

Ala Glu  Asp Glu Lys Leu Asp  Lys Val Lys Ile Ala  Ile Ser Asn
    1220                1225                1230

Lys Glu  Trp Leu Glu Tyr Ala  Gln Thr Ser Val Lys  His Gly Arg
    1235                1240                1245

Ser Ser  Asp Asp Glu Ala Thr  Ala Asp Ser Gln His  Ala Ala Pro
    1250                1255                1260

Pro Lys  Lys Lys Arg Lys Val  Leu Glu His His His  His His His
    1265                1270                1275
```

<210> SEQ ID NO 25
<211> LENGTH: 21
<212> TYPE: DNA
<213> ORGANISM: Artificial Sequence
<220> FEATURE:
<223> OTHER INFORMATION: Synthetic DNA -continued

<400> SEQUENCE: 25
gtgtccaaga ccctgagatt c                                                          21

<210> SEQ ID NO 26
<211> LENGTH: 20
<212> TYPE: DNA
<213> ORGANISM: Artificial Sequence
<220> FEATURE:
<223> OTHER INFORMATION: Synthetic DNA

<400> SEQUENCE: 26
gggcttcagc tctttgtagt                                                           20

<210> SEQ ID NO 27
<211> LENGTH: 24
<212> TYPE: DNA
<213> ORGANISM: Artificial Sequence
<220> FEATURE:
<223> OTHER INFORMATION: Synthetic DNA

<400> SEQUENCE: 27
agggcaagac actgaagcac atcc                                                      24

<210> SEQ ID NO 28
<211> LENGTH: 20
<212> TYPE: DNA
<213> ORGANISM: Artificial Sequence
<220> FEATURE:
<223> OTHER INFORMATION: Synthetic DNA

<400> SEQUENCE: 28
cagaaactac gccaccaaga                                                           20

<210> SEQ ID NO 29
<211> LENGTH: 22
<212> TYPE: DNA
<213> ORGANISM: Artificial Sequence
<220> FEATURE:
<223> OTHER INFORMATION: Synthetic DNA

<400> SEQUENCE: 29
gccgttgttc ttctctttgt tc                                                        22

<210> SEQ ID NO 30
<211> LENGTH: 25
<212> TYPE: DNA
<213> ORGANISM: Artificial Sequence
<220> FEATURE:
<223> OTHER INFORMATION: Synthetic DNA

<400> SEQUENCE: 30
taagctgaac ttccagatgc ccacc                                                     25

<210> SEQ ID NO 31
<211> LENGTH: 22
<212> TYPE: DNA
<213> ORGANISM: Artificial Sequence
<220> FEATURE:
<223> OTHER INFORMATION: Synthetic DNA

<400> SEQUENCE: 31
gtggacctga tgatccacta tc                                                        22

<210> SEQ ID NO 32

-continued

```
<211> LENGTH: 18
<212> TYPE: DNA
<213> ORGANISM: Artificial Sequence
<220> FEATURE:
<223> OTHER INFORMATION: Synthetic DNA

<400> SEQUENCE: 32
gctggtacac ggctttct                                          18

<210> SEQ ID NO 33
<211> LENGTH: 24
<212> TYPE: DNA
<213> ORGANISM: Artificial Sequence
<220> FEATURE:
<223> OTHER INFORMATION: Synthetic DNA

<400> SEQUENCE: 33
acctgaactt cggcttcaag agca                                   24

<210> SEQ ID NO 34
<211> LENGTH: 22
<212> TYPE: DNA
<213> ORGANISM: Artificial Sequence
<220> FEATURE:
<223> OTHER INFORMATION: Synthetic DNA

<400> SEQUENCE: 34
tgctgaacca tctgaaagag ag                                     22

<210> SEQ ID NO 35
<211> LENGTH: 22
<212> TYPE: DNA
<213> ORGANISM: Artificial Sequence
<220> FEATURE:
<223> OTHER INFORMATION: Synthetic DNA

<400> SEQUENCE: 35
gttccgcagt tcctggatat ag                                     22

<210> SEQ ID NO 36
<211> LENGTH: 23
<212> TYPE: DNA
<213> ORGANISM: Artificial Sequence
<220> FEATURE:
<223> OTHER INFORMATION: Synthetic DNA

<400> SEQUENCE: 36
agtcctggtt ggagatgccg ttc                                    23

<210> SEQ ID NO 37
<211> LENGTH: 44
<212> TYPE: RNA
<213> ORGANISM: Artificial Sequence
<220> FEATURE:
<223> OTHER INFORMATION: Synthetic RNA

<400> SEQUENCE: 37
uaauuucuac ucuuguagau uaaacacugu uucauuucau ccgu             44

<210> SEQ ID NO 38
<211> LENGTH: 44
<212> TYPE: RNA
<213> ORGANISM: Artificial Sequence
<220> FEATURE:
<223> OTHER INFORMATION: Synthetic RNA

<400> SEQUENCE: 38
```
uaauuucuac ucuuguagau accagcaagc uguuaauuac aaaa                    44

<210> SEQ ID NO 39
<211> LENGTH: 44
<212> TYPE: RNA
<213> ORGANISM: Artificial Sequence
<220> FEATURE:
<223> OTHER INFORMATION: Synthetic RNA

<400> SEQUENCE: 39
uaauuucuac ucuuguagau accaucuuua accuaaaaga guuu                    44

<210> SEQ ID NO 40
<211> LENGTH: 44
<212> TYPE: RNA
<213> ORGANISM: Artificial Sequence
<220> FEATURE:
<223> OTHER INFORMATION: Synthetic RNA

<400> SEQUENCE: 40
uaauuucuac ucuuguagau gguuaaagau gguuaaauga uuga                    44

<210> SEQ ID NO 41
<211> LENGTH: 44
<212> TYPE: RNA
<213> ORGANISM: Artificial Sequence
<220> FEATURE:
<223> OTHER INFORMATION: Synthetic RNA

<400> SEQUENCE: 41
uaauuucuac ucuuguagau ugugaaaugg cuuauaauug cuua                    44

<210> SEQ ID NO 42
<211> LENGTH: 44
<212> TYPE: RNA
<213> ORGANISM: Artificial Sequence
<220> FEATURE:
<223> OTHER INFORMATION: Synthetic RNA

<400> SEQUENCE: 42
uaauuucuac ucuuguagau aauguaagua auugcuucuu uuuc                    44

<210> SEQ ID NO 43
<211> LENGTH: 43
<212> TYPE: RNA
<213> ORGANISM: Artificial Sequence
<220> FEATURE:
<223> OTHER INFORMATION: Synthetic RNA

<400> SEQUENCE: 43
aauuucuacu cuuguagauu aaacacuguu ucauuucauc cgu                     43

<210> SEQ ID NO 44
<211> LENGTH: 42
<212> TYPE: RNA
<213> ORGANISM: Artificial Sequence
<220> FEATURE:
<223> OTHER INFORMATION: Synthetic RNA

<400> SEQUENCE: 44
auuucuacuc uuguagauua aacacuguuu cauuucaucc gu                      42

<210> SEQ ID NO 45
<211> LENGTH: 41
<212> TYPE: RNA

-continued

```
<213> ORGANISM: Artificial Sequence
<220> FEATURE:
<223> OTHER INFORMATION: Synthetic RNA

<400> SEQUENCE: 45
uuucuacucu uguagauuaa acacuguuuc auuucauccg u                          41

<210> SEQ ID NO 46
<211> LENGTH: 43
<212> TYPE: RNA
<213> ORGANISM: Artificial Sequence
<220> FEATURE:
<223> OTHER INFORMATION: Synthetic RNA

<400> SEQUENCE: 46
aauuucuacu cuuguagaua ccagcaagcu guuaauuaca aaa                        43

<210> SEQ ID NO 47
<211> LENGTH: 42
<212> TYPE: RNA
<213> ORGANISM: Artificial Sequence
<220> FEATURE:
<223> OTHER INFORMATION: Synthetic RNA

<400> SEQUENCE: 47
auuucuacuc uuguagauac cagcaagcug uuaauuacaa aa                         42

<210> SEQ ID NO 48
<211> LENGTH: 41
<212> TYPE: RNA
<213> ORGANISM: Artificial Sequence
<220> FEATURE:
<223> OTHER INFORMATION: Synthetic RNA

<400> SEQUENCE: 48
uuucuacucu uguagauacc agcaagcugu uaauuacaaa a                          41

<210> SEQ ID NO 49
<211> LENGTH: 43
<212> TYPE: RNA
<213> ORGANISM: Artificial Sequence
<220> FEATURE:
<223> OTHER INFORMATION: Synthetic RNA

<400> SEQUENCE: 49
aauuucuacu cuuguagaua ccaucuuuaa ccuaaaagag uuu                        43

<210> SEQ ID NO 50
<211> LENGTH: 42
<212> TYPE: RNA
<213> ORGANISM: Artificial Sequence
<220> FEATURE:
<223> OTHER INFORMATION: Synthetic RNA

<400> SEQUENCE: 50
auuucuacuc uuguagauac caucuuuaac cuaaaagagu uu                         42

<210> SEQ ID NO 51
<211> LENGTH: 41
<212> TYPE: RNA
<213> ORGANISM: Artificial Sequence
<220> FEATURE:
<223> OTHER INFORMATION: Synthetic RNA

<400> SEQUENCE: 51
uuucuacucu uguagauacc aucuuuaacc uaaaagaguu u                          41
```

```
<210> SEQ ID NO 52
<211> LENGTH: 43
<212> TYPE: RNA
<213> ORGANISM: Artificial Sequence
<220> FEATURE:
<223> OTHER INFORMATION: Synthetic RNA

<400> SEQUENCE: 52
aauuucuacu cuuguagaug guuaaagaug guuaaaugau uga                    43

<210> SEQ ID NO 53
<211> LENGTH: 42
<212> TYPE: RNA
<213> ORGANISM: Artificial Sequence
<220> FEATURE:
<223> OTHER INFORMATION: Synthetic RNA

<400> SEQUENCE: 53
auuucuacuc uuguagaugg uuaaagaugg uuaaaugauu ga                     42

<210> SEQ ID NO 54
<211> LENGTH: 41
<212> TYPE: RNA
<213> ORGANISM: Artificial Sequence
<220> FEATURE:
<223> OTHER INFORMATION: Synthetic RNA

<400> SEQUENCE: 54
uuucuacucu uguagauggu uaaagauggu uaaaugauug a                      41

<210> SEQ ID NO 55
<211> LENGTH: 43
<212> TYPE: RNA
<213> ORGANISM: Artificial Sequence
<220> FEATURE:
<223> OTHER INFORMATION: Synthetic RNA

<400> SEQUENCE: 55
aauuucuacu cuuguagauu gugaaauggc uuauaauugc uua                    43

<210> SEQ ID NO 56
<211> LENGTH: 42
<212> TYPE: RNA
<213> ORGANISM: Artificial Sequence
<220> FEATURE:
<223> OTHER INFORMATION: Synthetic RNA

<400> SEQUENCE: 56
auuucuacuc uuguagauug ugaaauggcu uauaauugcu ua                     42

<210> SEQ ID NO 57
<211> LENGTH: 41
<212> TYPE: RNA
<213> ORGANISM: Artificial Sequence
<220> FEATURE:
<223> OTHER INFORMATION: Synthetic RNA

<400> SEQUENCE: 57
uuucuacucu uguagauugu gaaauggcuu auaauugcuu a                      41

<210> SEQ ID NO 58
<211> LENGTH: 43
<212> TYPE: RNA
<213> ORGANISM: Artificial Sequence
<220> FEATURE:
```

-continued

<223> OTHER INFORMATION: Synthetic RNA

<400> SEQUENCE: 58
aauuucuacu cuuguagaua auguaaguaa uugcuucuuu uuc                    43

<210> SEQ ID NO 59
<211> LENGTH: 42
<212> TYPE: RNA
<213> ORGANISM: Artificial Sequence
<220> FEATURE:
<223> OTHER INFORMATION: Synthetic RNA

<400> SEQUENCE: 59
auuucuacuc uuguagauaa uguaaguaau ugcuucuuuu uc                     42

<210> SEQ ID NO 60
<211> LENGTH: 41
<212> TYPE: RNA
<213> ORGANISM: Artificial Sequence
<220> FEATURE:
<223> OTHER INFORMATION: Synthetic RNA

<400> SEQUENCE: 60
uuucuacucu uguagauaau guaaguaauu gcuucuuuuu c                      41

<210> SEQ ID NO 61
<211> LENGTH: 41
<212> TYPE: RNA
<213> ORGANISM: Artificial Sequence
<220> FEATURE:
<223> OTHER INFORMATION: Synthetic RNA

<400> SEQUENCE: 61
uaauuucuac ucuuguagau aaacacugu uucauuucau c                       41

<210> SEQ ID NO 62
<211> LENGTH: 40
<212> TYPE: RNA
<213> ORGANISM: Artificial Sequence
<220> FEATURE:
<223> OTHER INFORMATION: Synthetic RNA

<400> SEQUENCE: 62
aauuucuacu cuuguagauu aaacacuguu ucauuucauc                        40

<210> SEQ ID NO 63
<211> LENGTH: 39
<212> TYPE: RNA
<213> ORGANISM: Artificial Sequence
<220> FEATURE:
<223> OTHER INFORMATION: Synthetic RNA

<400> SEQUENCE: 63
auuucuacuc uuguagauua aacacuguuu cauuucauc                         39

<210> SEQ ID NO 64
<211> LENGTH: 38
<212> TYPE: RNA
<213> ORGANISM: Artificial Sequence
<220> FEATURE:
<223> OTHER INFORMATION: Synthetic RNA

<400> SEQUENCE: 64
uuucuacucu uguagauuaa acacguuuc auuucauc                           38

-continued

```
<210> SEQ ID NO 65
<211> LENGTH: 41
<212> TYPE: RNA
<213> ORGANISM: Artificial Sequence
<220> FEATURE:
<223> OTHER INFORMATION: Synthetic RNA

<400> SEQUENCE: 65
uaauuucuac ucuuguagau accagcaagc uguuaauuac a                                41

<210> SEQ ID NO 66
<211> LENGTH: 40
<212> TYPE: RNA
<213> ORGANISM: Artificial Sequence
<220> FEATURE:
<223> OTHER INFORMATION: Synthetic RNA

<400> SEQUENCE: 66
aauuucuacu cuuguagaua ccagcaagcu guuaauuaca                                 40

<210> SEQ ID NO 67
<211> LENGTH: 39
<212> TYPE: RNA
<213> ORGANISM: Artificial Sequence
<220> FEATURE:
<223> OTHER INFORMATION: Synthetic RNA

<400> SEQUENCE: 67
auuucuacuc uuguagauac cagcaagcug uuaauuaca                                  39

<210> SEQ ID NO 68
<211> LENGTH: 38
<212> TYPE: RNA
<213> ORGANISM: Artificial Sequence
<220> FEATURE:
<223> OTHER INFORMATION: Synthetic RNA

<400> SEQUENCE: 68
uuucuacucu uguagauacc agcaagcugu uaauuaca                                   38

<210> SEQ ID NO 69
<211> LENGTH: 41
<212> TYPE: RNA
<213> ORGANISM: Artificial Sequence
<220> FEATURE:
<223> OTHER INFORMATION: Synthetic RNA

<400> SEQUENCE: 69
uaauuucuac ucuuguagau accacuuuua accuaaaaga g                                41

<210> SEQ ID NO 70
<211> LENGTH: 40
<212> TYPE: RNA
<213> ORGANISM: Artificial Sequence
<220> FEATURE:
<223> OTHER INFORMATION: Synthetic RNA

<400> SEQUENCE: 70
aauuucuacu cuuguagaua ccacuuuaa ccuaaaagag                                  40

<210> SEQ ID NO 71
<211> LENGTH: 39
<212> TYPE: RNA
<213> ORGANISM: Artificial Sequence
<220> FEATURE:
<223> OTHER INFORMATION: Synthetic RNA
```

-continued

<400> SEQUENCE: 71
auuucuacuc uuguagauac caucuuuaac cuaaaagag                              39

<210> SEQ ID NO 72
<211> LENGTH: 38
<212> TYPE: RNA
<213> ORGANISM: Artificial Sequence
<220> FEATURE:
<223> OTHER INFORMATION: Synthetic RNA

<400> SEQUENCE: 72
uuucuacucu uguagauacc aucuuuaacc uaaaagag                               38

<210> SEQ ID NO 73
<211> LENGTH: 41
<212> TYPE: RNA
<213> ORGANISM: Artificial Sequence
<220> FEATURE:
<223> OTHER INFORMATION: Synthetic RNA

<400> SEQUENCE: 73
uaauuucuac ucuuguagau gguuaaagau gguuaaauga u                           41

<210> SEQ ID NO 74
<211> LENGTH: 40
<212> TYPE: RNA
<213> ORGANISM: Artificial Sequence
<220> FEATURE:
<223> OTHER INFORMATION: Synthetic RNA

<400> SEQUENCE: 74
aauuucuacu cuuguagaug guuaaagaug guuaaaugau                             40

<210> SEQ ID NO 75
<211> LENGTH: 39
<212> TYPE: RNA
<213> ORGANISM: Artificial Sequence
<220> FEATURE:
<223> OTHER INFORMATION: Synthetic RNA

<400> SEQUENCE: 75
auuucuacuc uuguagaugg uuaaagaugg uuaaaugau                              39

<210> SEQ ID NO 76
<211> LENGTH: 38
<212> TYPE: RNA
<213> ORGANISM: Artificial Sequence
<220> FEATURE:
<223> OTHER INFORMATION: Synthetic RNA

<400> SEQUENCE: 76
uuucuacucu uguagauggu uaaagauggu uaaaugau                               38

<210> SEQ ID NO 77
<211> LENGTH: 41
<212> TYPE: RNA
<213> ORGANISM: Artificial Sequence
<220> FEATURE:
<223> OTHER INFORMATION: Synthetic RNA

<400> SEQUENCE: 77
uaauuucuac ucuuguagau ugugaaaugg cuuauaauug c                           41

<210> SEQ ID NO 78
<211> LENGTH: 40

-continued

```
<212> TYPE: RNA
<213> ORGANISM: Artificial Sequence
<220> FEATURE:
<223> OTHER INFORMATION: Synthetic RNA

<400> SEQUENCE: 78
aauuucuacu cuuguagauu gugaaauggc uuauaauugc                              40

<210> SEQ ID NO 79
<211> LENGTH: 39
<212> TYPE: RNA
<213> ORGANISM: Artificial Sequence
<220> FEATURE:
<223> OTHER INFORMATION: Synthetic RNA

<400> SEQUENCE: 79
auuucuacuc uuguagauug ugaaauggcu uauaauugc                               39

<210> SEQ ID NO 80
<211> LENGTH: 38
<212> TYPE: RNA
<213> ORGANISM: Artificial Sequence
<220> FEATURE:
<223> OTHER INFORMATION: Synthetic RNA

<400> SEQUENCE: 80
uuucuacucu uguagauugu gaaauggcuu auaauugc                                38

<210> SEQ ID NO 81
<211> LENGTH: 41
<212> TYPE: RNA
<213> ORGANISM: Artificial Sequence
<220> FEATURE:
<223> OTHER INFORMATION: Synthetic RNA

<400> SEQUENCE: 81
uaauuucuac ucuuguagau aauguaagua auugcuucuu u                            41

<210> SEQ ID NO 82
<211> LENGTH: 40
<212> TYPE: RNA
<213> ORGANISM: Artificial Sequence
<220> FEATURE:
<223> OTHER INFORMATION: Synthetic RNA

<400> SEQUENCE: 82
aauuucuacu cuuguagaua auguaaguaa uugcuucuuu                              40

<210> SEQ ID NO 83
<211> LENGTH: 39
<212> TYPE: RNA
<213> ORGANISM: Artificial Sequence
<220> FEATURE:
<223> OTHER INFORMATION: Synthetic RNA

<400> SEQUENCE: 83
auuucuacuc uuguagauaa uguaaguaau ugcuucuuu                               39

<210> SEQ ID NO 84
<211> LENGTH: 38
<212> TYPE: RNA
<213> ORGANISM: Artificial Sequence
<220> FEATURE:
<223> OTHER INFORMATION: Synthetic RNA

<400> SEQUENCE: 84
```
uuucuacucu uguagauaau guaaguaauu gcuucuuu                                                 38

<210> SEQ ID NO 85
<211> LENGTH: 39
<212> TYPE: RNA
<213> ORGANISM: Artificial Sequence
<220> FEATURE:
<223> OTHER INFORMATION: Synthetic RNA

<400> SEQUENCE: 85
uaauuucuac ucuuguagau uaaacacugu uucauuuca                                                39

<210> SEQ ID NO 86
<211> LENGTH: 38
<212> TYPE: RNA
<213> ORGANISM: Artificial Sequence
<220> FEATURE:
<223> OTHER INFORMATION: Synthetic RNA

<400> SEQUENCE: 86
uaauuucuac ucuuguagau uaaacacugu uucauuuc                                                 38

<210> SEQ ID NO 87
<211> LENGTH: 37
<212> TYPE: RNA
<213> ORGANISM: Artificial Sequence
<220> FEATURE:
<223> OTHER INFORMATION: Synthetic RNA

<400> SEQUENCE: 87
uaauuucuac ucuuguagau uaaacacugu uucauu                                                   37

<210> SEQ ID NO 88
<211> LENGTH: 39
<212> TYPE: RNA
<213> ORGANISM: Artificial Sequence
<220> FEATURE:
<223> OTHER INFORMATION: Synthetic RNA

<400> SEQUENCE: 88
uaauuucuac ucuuguagau accagcaagc uguuaauua                                                39

<210> SEQ ID NO 89
<211> LENGTH: 38
<212> TYPE: RNA
<213> ORGANISM: Artificial Sequence
<220> FEATURE:
<223> OTHER INFORMATION: Synthetic RNA

<400> SEQUENCE: 89
uaauuucuac ucuuguagau accagcaagc uguuaauu                                                 38

<210> SEQ ID NO 90
<211> LENGTH: 37
<212> TYPE: RNA
<213> ORGANISM: Artificial Sequence
<220> FEATURE:
<223> OTHER INFORMATION: Synthetic RNA

<400> SEQUENCE: 90
uaauuucuac ucuuguagau accagcaagc uguuaau                                                  37

<210> SEQ ID NO 91
<211> LENGTH: 39
<212> TYPE: RNA
<213> ORGANISM: Artificial Sequence
<220> FEATURE:
<223> OTHER INFORMATION: Synthetic RNA

<400> SEQUENCE: 91
uaauuucuac ucuuguagau accaucuuua accuaaaag                              39

<210> SEQ ID NO 92
<211> LENGTH: 38
<212> TYPE: RNA
<213> ORGANISM: Artificial Sequence
<220> FEATURE:
<223> OTHER INFORMATION: Synthetic RNA

<400> SEQUENCE: 92
uaauuucuac ucuuguagau accaucuuua accuaaaa                               38

<210> SEQ ID NO 93
<211> LENGTH: 37
<212> TYPE: RNA
<213> ORGANISM: Artificial Sequence
<220> FEATURE:
<223> OTHER INFORMATION: Synthetic RNA

<400> SEQUENCE: 93
uaauuucuac ucuuguagau accaucuuua accuaaa                                37

<210> SEQ ID NO 94
<211> LENGTH: 39
<212> TYPE: RNA
<213> ORGANISM: Artificial Sequence
<220> FEATURE:
<223> OTHER INFORMATION: Synthetic RNA

<400> SEQUENCE: 94
uaauuucuac ucuuguagau gguuaaagau gguuaaaug                              39

<210> SEQ ID NO 95
<211> LENGTH: 38
<212> TYPE: RNA
<213> ORGANISM: Artificial Sequence
<220> FEATURE:
<223> OTHER INFORMATION: Synthetic RNA

<400> SEQUENCE: 95
uaauuucuac ucuuguagau gguuaaagau gguuaaau                               38

<210> SEQ ID NO 96
<211> LENGTH: 37
<212> TYPE: RNA
<213> ORGANISM: Artificial Sequence
<220> FEATURE:
<223> OTHER INFORMATION: Synthetic RNA

<400> SEQUENCE: 96
uaauuucuac ucuuguagau gguuaaagau gguuaaa                                37

<210> SEQ ID NO 97
<211> LENGTH: 39
<212> TYPE: RNA
<213> ORGANISM: Artificial Sequence
<220> FEATURE:
<223> OTHER INFORMATION: Synthetic RNA

<400> SEQUENCE: 97
uaauuucuac ucuuguagau ugugaaaugg cuuauaauu                              39

-continued

```
<210> SEQ ID NO 98
<211> LENGTH: 38
<212> TYPE: RNA
<213> ORGANISM: Artificial Sequence
<220> FEATURE:
<223> OTHER INFORMATION: Synthetic RNA

<400> SEQUENCE: 98
uaauuucuac ucuuguagau ugugaaaugg cuuauaau                              38

<210> SEQ ID NO 99
<211> LENGTH: 37
<212> TYPE: RNA
<213> ORGANISM: Artificial Sequence
<220> FEATURE:
<223> OTHER INFORMATION: Synthetic RNA

<400> SEQUENCE: 99
uaauuucuac ucuuguagau ugugaaaugg cuuauaa                               37

<210> SEQ ID NO 100
<211> LENGTH: 39
<212> TYPE: RNA
<213> ORGANISM: Artificial Sequence
<220> FEATURE:
<223> OTHER INFORMATION: Synthetic RNA

<400> SEQUENCE: 100
uaauuucuac ucuuguagau aauguaagua auugcuucu                             39

<210> SEQ ID NO 101
<211> LENGTH: 38
<212> TYPE: RNA
<213> ORGANISM: Artificial Sequence
<220> FEATURE:
<223> OTHER INFORMATION: Synthetic RNA

<400> SEQUENCE: 101
uaauuucuac ucuuguagau aauguaagua auugcuuc                              38

<210> SEQ ID NO 102
<211> LENGTH: 37
<212> TYPE: RNA
<213> ORGANISM: Artificial Sequence
<220> FEATURE:
<223> OTHER INFORMATION: Synthetic RNA

<400> SEQUENCE: 102
uaauuucuac ucuuguagau aauguaagua auugcuu                               37

<210> SEQ ID NO 103
<211> LENGTH: 44
<212> TYPE: RNA
<213> ORGANISM: Artificial Sequence
<220> FEATURE:
<223> OTHER INFORMATION: Synthetic RNA

<400> SEQUENCE: 103
uaauuucuac ucuuguagau ugugaaaugg cuuauaauug cuua                       44

<210> SEQ ID NO 104
<211> LENGTH: 44
<212> TYPE: RNA
<213> ORGANISM: Artificial Sequence
<220> FEATURE:
<223> OTHER INFORMATION: Synthetic RNA
```

-continued

<400> SEQUENCE: 104
uaauuucuac ucuuguagau ugugaaaugg cuuauaauug cuua                          44

<210> SEQ ID NO 105
<211> LENGTH: 44
<212> TYPE: RNA
<213> ORGANISM: Artificial Sequence
<220> FEATURE:
<223> OTHER INFORMATION: Synthetic RNA

<400> SEQUENCE: 105
uaauuucuac ucuuguagau ugugaaaugg cuuauaauug cuua                          44

<210> SEQ ID NO 106
<211> LENGTH: 44
<212> TYPE: RNA
<213> ORGANISM: Artificial Sequence
<220> FEATURE:
<223> OTHER INFORMATION: Synthetic RNA

<400> SEQUENCE: 106
uaauuucuac ucuuguagau ugugaaaugg cuuauaauug cuua                          44

<210> SEQ ID NO 107
<211> LENGTH: 44
<212> TYPE: RNA
<213> ORGANISM: Artificial Sequence
<220> FEATURE:
<223> OTHER INFORMATION: Synthetic RNA

<400> SEQUENCE: 107
uaauuucuac ucuuguagau ugugaaaugg cuuauaauug cuua                          44

<210> SEQ ID NO 108
<211> LENGTH: 44
<212> TYPE: RNA
<213> ORGANISM: Artificial Sequence
<220> FEATURE:
<223> OTHER INFORMATION: Synthetic RNA

<400> SEQUENCE: 108
uaauuucuac ucuuguagau ugugaaaugg cuuauaauug cuua                          44

<210> SEQ ID NO 109
<211> LENGTH: 44
<212> TYPE: RNA
<213> ORGANISM: Artificial Sequence
<220> FEATURE:
<223> OTHER INFORMATION: Synthetic RNA

<400> SEQUENCE: 109
uaauuucuac ucuuguagau ugugaaaugg cuuauaauug cuua                          44

<210> SEQ ID NO 110
<211> LENGTH: 44
<212> TYPE: RNA
<213> ORGANISM: Artificial Sequence
<220> FEATURE:
<223> OTHER INFORMATION: Synthetic RNA

<400> SEQUENCE: 110
uaauuucuac ucuuguagau ugugaaaugg cuuauaauug cuua                          44

<210> SEQ ID NO 111

-continued

```
<211> LENGTH: 44
<212> TYPE: RNA
<213> ORGANISM: Artificial Sequence
<220> FEATURE:
<223> OTHER INFORMATION: Synthetic RNA

<400> SEQUENCE: 111
uaauuucuac ucuuguagau ugugaaaugg cuuauaauug cuua                        44

<210> SEQ ID NO 112
<211> LENGTH: 44
<212> TYPE: RNA
<213> ORGANISM: Artificial Sequence
<220> FEATURE:
<223> OTHER INFORMATION: Synthetic RNA

<400> SEQUENCE: 112
uaauuucuac ucuuguagau ugugaaaugg cuuauaauug cuua                        44

<210> SEQ ID NO 113
<211> LENGTH: 44
<212> TYPE: RNA
<213> ORGANISM: Artificial Sequence
<220> FEATURE:
<223> OTHER INFORMATION: Synthetic RNA

<400> SEQUENCE: 113
uaauuucuac ucuuguagau ugugaaaugg cuuauaauug cuua                        44

<210> SEQ ID NO 114
<211> LENGTH: 44
<212> TYPE: RNA
<213> ORGANISM: Artificial Sequence
<220> FEATURE:
<223> OTHER INFORMATION: Synthetic RNA

<400> SEQUENCE: 114
uaauuucuac ucuuguagau ugugaaaugg cuuauaauug cuua                        44

<210> SEQ ID NO 115
<211> LENGTH: 44
<212> TYPE: RNA
<213> ORGANISM: Artificial Sequence
<220> FEATURE:
<223> OTHER INFORMATION: Synthetic RNA

<400> SEQUENCE: 115
uaauuucuac ucuuguagau ugugaaaugg cuuauaauug cuua                        44

<210> SEQ ID NO 116
<211> LENGTH: 44
<212> TYPE: RNA
<213> ORGANISM: Artificial Sequence
<220> FEATURE:
<223> OTHER INFORMATION: Synthetic RNA

<400> SEQUENCE: 116
uaauuucuac ucuuguagau ugugaaaugg cuuauaauug cuua                        44

<210> SEQ ID NO 117
<211> LENGTH: 44
<212> TYPE: RNA
<213> ORGANISM: Artificial Sequence
<220> FEATURE:
<223> OTHER INFORMATION: Synthetic RNA

<400> SEQUENCE: 117
```

-continued uaauuucuac ucuuguagau ugugaaaugg cuuauaauug cuua                          44

<210> SEQ ID NO 118
<211> LENGTH: 44
<212> TYPE: RNA
<213> ORGANISM: Artificial Sequence
<220> FEATURE:
<223> OTHER INFORMATION: Synthetic RNA

<400> SEQUENCE: 118
uaauuucuac ucuuguagau ugugaaaugg cuuauaauug cuua                          44

<210> SEQ ID NO 119
<211> LENGTH: 44
<212> TYPE: RNA
<213> ORGANISM: Artificial Sequence
<220> FEATURE:
<223> OTHER INFORMATION: Synthetic RNA

<400> SEQUENCE: 119
uaauuucuac ucuuguagau ugugaaaugg cuuauaauug cuua                          44

<210> SEQ ID NO 120
<211> LENGTH: 44
<212> TYPE: RNA
<213> ORGANISM: Artificial Sequence
<220> FEATURE:
<223> OTHER INFORMATION: Synthetic RNA

<400> SEQUENCE: 120
uaauuucuac ucuuguagau ugugaaaugg cuuauaauug cuua                          44

<210> SEQ ID NO 121
<211> LENGTH: 44
<212> TYPE: RNA
<213> ORGANISM: Artificial Sequence
<220> FEATURE:
<223> OTHER INFORMATION: Synthetic RNA

<400> SEQUENCE: 121
uaauuucuac ucuuguagau ugugaaaugg cuuauaauug cuua                          44

<210> SEQ ID NO 122
<211> LENGTH: 44
<212> TYPE: RNA
<213> ORGANISM: Artificial Sequence
<220> FEATURE:
<223> OTHER INFORMATION: Synthetic RNA

<400> SEQUENCE: 122
uaauuucuac ucuuguagau ugugaaaugg cuuauaauug cuua                          44

<210> SEQ ID NO 123
<211> LENGTH: 44
<212> TYPE: RNA
<213> ORGANISM: Artificial Sequence
<220> FEATURE:
<223> OTHER INFORMATION: Synthetic RNA

<400> SEQUENCE: 123
uaauuucuac ucuuguagau ugugaaaugg cuuauaauug cuua                          44

<210> SEQ ID NO 124
<211> LENGTH: 44
<212> TYPE: RNA

<213> ORGANISM: Artificial Sequence
<220> FEATURE:
<223> OTHER INFORMATION: Synthetic RNA

<400> SEQUENCE: 124
uaauuucuac ucuuguagau ugugaaaugg cuuauaauug cuua                    44

<210> SEQ ID NO 125
<211> LENGTH: 44
<212> TYPE: RNA
<213> ORGANISM: Artificial Sequence
<220> FEATURE:
<223> OTHER INFORMATION: Synthetic RNA

<400> SEQUENCE: 125
uaauuucuac ucuuguagau ugugaaaugg cuuauaauug cuua                    44

<210> SEQ ID NO 126
<211> LENGTH: 44
<212> TYPE: RNA
<213> ORGANISM: Artificial Sequence
<220> FEATURE:
<223> OTHER INFORMATION: Synthetic RNA

<400> SEQUENCE: 126
uaauuucuac ucuuguagau ugugaaaugg cuuauaauug cuua                    44

<210> SEQ ID NO 127
<211> LENGTH: 44
<212> TYPE: RNA
<213> ORGANISM: Artificial Sequence
<220> FEATURE:
<223> OTHER INFORMATION: Synthetic RNA

<400> SEQUENCE: 127
uaauuucuac ucuuguagau ugugaaaugg cuuauaauug cuua                    44

<210> SEQ ID NO 128
<211> LENGTH: 44
<212> TYPE: RNA
<213> ORGANISM: Artificial Sequence
<220> FEATURE:
<223> OTHER INFORMATION: Synthetic RNA

<400> SEQUENCE: 128
uaauuucuac ucuuguagau ugugaaaugg cuuauaauug cuua                    44

<210> SEQ ID NO 129
<211> LENGTH: 44
<212> TYPE: RNA
<213> ORGANISM: Artificial Sequence
<220> FEATURE:
<223> OTHER INFORMATION: Synthetic RNA

<400> SEQUENCE: 129
uaauuucuac ucuuguagau ugugaaaugg cuuauaauug cuua                    44

<210> SEQ ID NO 130
<211> LENGTH: 44
<212> TYPE: RNA
<213> ORGANISM: Artificial Sequence
<220> FEATURE:
<223> OTHER INFORMATION: Synthetic RNA

<400> SEQUENCE: 130
uaauuucuac ucuuguagau ugugaaaugg cuuauaauug cuua                    44

-continued

```
<210> SEQ ID NO 131
<211> LENGTH: 44
<212> TYPE: RNA
<213> ORGANISM: Artificial Sequence
<220> FEATURE:
<223> OTHER INFORMATION: Synthetic RNA

<400> SEQUENCE: 131
uaauuucuac ucuuguagau ugugaaaugg cuuauaauug cuua                       44

<210> SEQ ID NO 132
<211> LENGTH: 44
<212> TYPE: RNA
<213> ORGANISM: Artificial Sequence
<220> FEATURE:
<223> OTHER INFORMATION: Synthetic RNA

<400> SEQUENCE: 132
uaauuucuac ucuuguagau ugugaaaugg cuuauaauug cuua                       44

<210> SEQ ID NO 133
<211> LENGTH: 44
<212> TYPE: RNA
<213> ORGANISM: Artificial Sequence
<220> FEATURE:
<223> OTHER INFORMATION: Synthetic RNA

<400> SEQUENCE: 133
uaauuucuac ucuuguagau ugugaaaugg cuuauaauug cuua                       44

<210> SEQ ID NO 134
<211> LENGTH: 44
<212> TYPE: RNA
<213> ORGANISM: Artificial Sequence
<220> FEATURE:
<223> OTHER INFORMATION: Synthetic RNA

<400> SEQUENCE: 134
uaauuucuac ucuuguagau ugugaaaugg cuuauaauug cuua                       44

<210> SEQ ID NO 135
<211> LENGTH: 44
<212> TYPE: RNA
<213> ORGANISM: Artificial Sequence
<220> FEATURE:
<223> OTHER INFORMATION: Synthetic RNA

<400> SEQUENCE: 135
uaauuucuac ucuuguagau ugugaaaugg cuuauaauug cuua                       44

<210> SEQ ID NO 136
<211> LENGTH: 44
<212> TYPE: RNA
<213> ORGANISM: Artificial Sequence
<220> FEATURE:
<223> OTHER INFORMATION: Synthetic RNA

<400> SEQUENCE: 136
uaauuucuac ucuuguagau ugugaaaugg cuuauaauug cuua                       44

<210> SEQ ID NO 137
<211> LENGTH: 44
<212> TYPE: RNA
<213> ORGANISM: Artificial Sequence
<220> FEATURE:
```

-continued

<223> OTHER INFORMATION: Synthetic RNA

<400> SEQUENCE: 137
uaauuucuac ucuuguagau ugugaaaugg cuuauaauug cuua                          44

<210> SEQ ID NO 138
<211> LENGTH: 44
<212> TYPE: RNA
<213> ORGANISM: Artificial Sequence
<220> FEATURE:
<223> OTHER INFORMATION: Synthetic RNA

<400> SEQUENCE: 138
uaauuucuac ucuuguagau ugugaaaugg cuuauaauug cuua                          44

<210> SEQ ID NO 139
<211> LENGTH: 44
<212> TYPE: RNA
<213> ORGANISM: Artificial Sequence
<220> FEATURE:
<223> OTHER INFORMATION: Synthetic RNA

<400> SEQUENCE: 139
uaauuucuac ucuuguagau ugugaaaugg cuuauaauug cuua                          44

<210> SEQ ID NO 140
<211> LENGTH: 44
<212> TYPE: RNA
<213> ORGANISM: Artificial Sequence
<220> FEATURE:
<223> OTHER INFORMATION: Synthetic RNA

<400> SEQUENCE: 140
uaauuucuac ucuuguagau ugugaaaugg cuuauaauug cuua                          44

<210> SEQ ID NO 141
<211> LENGTH: 44
<212> TYPE: RNA
<213> ORGANISM: Artificial Sequence
<220> FEATURE:
<223> OTHER INFORMATION: Synthetic RNA

<400> SEQUENCE: 141
uaauuucuac ucuuguagau ugugaaaugg cuuauaauug cuua                          44

<210> SEQ ID NO 142
<211> LENGTH: 44
<212> TYPE: RNA
<213> ORGANISM: Artificial Sequence
<220> FEATURE:
<223> OTHER INFORMATION: Synthetic RNA

<400> SEQUENCE: 142
uaauuucuac ucuuguagau ugugaaaugg cuuauaauug cuua                          44

<210> SEQ ID NO 143
<211> LENGTH: 44
<212> TYPE: RNA
<213> ORGANISM: Artificial Sequence
<220> FEATURE:
<223> OTHER INFORMATION: Synthetic RNA

<400> SEQUENCE: 143
uaauuucuac ucuuguagau ugugaaaugg cuuauaauug cuua                          44

-continued

```
<210> SEQ ID NO 144
<211> LENGTH: 44
<212> TYPE: RNA
<213> ORGANISM: Artificial Sequence
<220> FEATURE:
<223> OTHER INFORMATION: Synthetic RNA

<400> SEQUENCE: 144
uaauuucuac ucuuguagau ugugaaaugg cuuauaauug cuua                        44

<210> SEQ ID NO 145
<211> LENGTH: 44
<212> TYPE: RNA
<213> ORGANISM: Artificial Sequence
<220> FEATURE:
<223> OTHER INFORMATION: Synthetic RNA

<400> SEQUENCE: 145
uaauuucuac ucuuguagau ugugaaaugg cuuauaauug cuua                        44

<210> SEQ ID NO 146
<211> LENGTH: 44
<212> TYPE: RNA
<213> ORGANISM: Artificial Sequence
<220> FEATURE:
<223> OTHER INFORMATION: Synthetic RNA

<400> SEQUENCE: 146
uaauuucuac ucuuguagau ugugaaaugg cuuauaauug cuua                        44

<210> SEQ ID NO 147
<211> LENGTH: 44
<212> TYPE: RNA
<213> ORGANISM: Artificial Sequence
<220> FEATURE:
<223> OTHER INFORMATION: Synthetic RNA

<400> SEQUENCE: 147
uaauuucuac ucuuguagau ugugaaaugg cuuauaauug cuua                        44

<210> SEQ ID NO 148
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 148
uaauuucuac ucuuguagau ugugaaaugg cuuauaauug c                           41

<210> SEQ ID NO 149
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 149
uaauuucuac ucuuguagau ugugaaaugg cuuauaauug c                           41

<210> SEQ ID NO 150
<211> LENGTH: 41
<212> TYPE: RNA
<213> ORGANISM: Artificial Sequence
<220> FEATURE:
<223> OTHER INFORMATION: SYNTHETIC RNA
```

-continued

```
<400> SEQUENCE: 150
uaauuucuac ucuuguagau ugugaaaugg cuuauaauug c                    41

<210> SEQ ID NO 151
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 151
uaauuucuac ucuuguagau ugugaaaugg cuuauaauug c                    41

<210> SEQ ID NO 152
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 152
uaauuucuac ucuuguagau ugugaaaugg cuuauaauug c                    41

<210> SEQ ID NO 153
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 153
uaauuucuac ucuuguagau ugugaaaugg cuuauaauug c                    41

<210> SEQ ID NO 154
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 154
uaauuucuac ucuuguagau ugugaaaugg cuuauaauug c                    41

<210> SEQ ID NO 155
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 155
uaauuucuac ucuuguagau ugugaaaugg cuuauaauug c                    41

<210> SEQ ID NO 156
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 156
uaauuucuac ucuuguagau ugugaaaugg cuuauaauug c                    41

<210> SEQ ID NO 157
<211> LENGTH: 41
```

-continued

```
<212> TYPE: RNA
<213> ORGANISM: Artificial Sequence
<220> FEATURE:
<223> OTHER INFORMATION: SYNTHETIC RNA

<400> SEQUENCE: 157
uaauuucuac ucuuguagau ugugaaaugg cuuauaauug c                            41

<210> SEQ ID NO 158
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 158
uaauuucuac ucuuguagau ugugaaaugg cuuauaauug c                            41

<210> SEQ ID NO 159
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 159
uaauuucuac ucuuguagau ugugaaaugg cuuauaauug c                            41

<210> SEQ ID NO 160
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 160
uaauuucuac ucuuguagau ugugaaaugg cuuauaauug c                            41

<210> SEQ ID NO 161
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 161
uaauuucuac ucuuguagau ugugaaaugg cuuauaauug c                            41

<210> SEQ ID NO 162
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 162
uaauuucuac ucuuguagau ugugaaaugg cuuauaauug c                            41

<210> SEQ ID NO 163
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 163
```

-continued uaauuucuac ucuuguagau ugugaaaugg cuuauaauug c                                    41

<210> SEQ ID NO 164
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 164
uaauuucuac ucuuguagau ugugaaaugg cuuauaauug c                                    41

<210> SEQ ID NO 165
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 165
uaauuucuac ucuuguagau ugugaaaugg cuuauaauug c                                    41

<210> SEQ ID NO 166
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 166
uaauuucuac ucuuguagau ugugaaaugg cuuauaauug c                                    41

<210> SEQ ID NO 167
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 167
uaauuucuac ucuuguagau ugugaaaugg cuuauaauug c                                    41

<210> SEQ ID NO 168
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 168
uaauuucuac ucuuguagau ugugaaaugg cuuauaauug c                                    41

<210> SEQ ID NO 169
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 169
uaauuucuac ucuuguagau ugugaaaugg cuuauaauug c                                    41

<210> SEQ ID NO 170
<211> LENGTH: 41
<212> TYPE: RNA
<213> ORGANISM: Artificial Sequence 269                                  270

-continued

```
<220> FEATURE:
<223> OTHER INFORMATION: SYNTHETIC RNA

<400> SEQUENCE: 170
uaauuucuac ucuuguagau ugugaaaugg cuuauaauug c                    41

<210> SEQ ID NO 171
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 171
uaauuucuac ucuuguagau ugugaaaugg cuuauaauug c                    41

<210> SEQ ID NO 172
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 172
uaauuucuac ucuuguagau ugugaaaugg cuuauaauug c                    41

<210> SEQ ID NO 173
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 173
uaauuucuac ucuuguagau ugugaaaugg cuuauaauug c                    41

<210> SEQ ID NO 174
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 174
uaauuucuac ucuuguagau ugugaaaugg cuuauaauug c                    41

<210> SEQ ID NO 175
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 175
uaauuucuac ucuuguagau ugugaaaugg cuuauaauug c                    41

<210> SEQ ID NO 176
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 176
uaauuucuac ucuuguagau ugugaaaugg cuuauaauug c                    41
```

-continued

```
<210> SEQ ID NO 177
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 177
uaauuucuac ucuuguagau ugugaaaugg cuuauaauug c                            41

<210> SEQ ID NO 178
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 178
uaauuucuac ucuuguagau ugugaaaugg cuuauaauug c                            41

<210> SEQ ID NO 179
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 179
uaauuucuac ucuuguagau ugugaaaugg cuuauaauug c                            41

<210> SEQ ID NO 180
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 180
uaauuucuac ucuuguagau ugugaaaugg cuuauaauug c                            41

<210> SEQ ID NO 181
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 181
uaauuucuac ucuuguagau ugugaaaugg cuuauaauug c                            41

<210> SEQ ID NO 182
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 182
uaauuucuac ucuuguagau ugugaaaugg cuuauaauug c                            41

<210> SEQ ID NO 183
<211> LENGTH: 41
<212> TYPE: RNA
<213> ORGANISM: Artificial Sequence
<220> FEATURE:
<223> OTHER INFORMATION: SYNTHETIC RNA
```

-continued

```
<400> SEQUENCE: 183
uaauuucuac ucuuguagau ugugaaaugg cuuauaauug c                    41

<210> SEQ ID NO 184
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 184
uaauuucuac ucuuguagau ugugaaaugg cuuauaauug c                    41

<210> SEQ ID NO 185
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 185
uaauuucuac ucuuguagau ugugaaaugg cuuauaauug c                    41

<210> SEQ ID NO 186
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 186
uaauuucuac ucuuguagau ugugaaaugg cuuauaauug c                    41

<210> SEQ ID NO 187
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 187
uaauuucuac ucuuguagau ugugaaaugg cuuauaauug c                    41

<210> SEQ ID NO 188
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 188
uaauuucuac ucuuguagau ugugaaaugg cuuauaauug c                    41

<210> SEQ ID NO 189
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 189
uaauuucuac ucuuguagau ggaaagagaa uuguuuucuc cuuc                44

<210> SEQ ID NO 190
```

```
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 190
uaauuucuac ucuuguagau ggaaagagaa uuguuuucuc cuuc                        44

<210> SEQ ID NO 191
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 191
uaauuucuac ucuuguagau ggaaagagaa uuguuuucuc cuuc                        44

<210> SEQ ID NO 192
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 192
uaauuucuac ucuuguagau ggaaagagaa uuguuuucuc cuuc                        44

<210> SEQ ID NO 193
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 193
uaauuucuac ucuuguagau ggaaagagaa uuguuuucuc cuuc                        44

<210> SEQ ID NO 194
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 194
uaauuucuac ucuuguagau ggaaagagaa uuguuuucuc cuuc                        44

<210> SEQ ID NO 195
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 195
uaauuucuac ucuuguagau ggaaagagaa uuguuuucuc cuuc                        44

<210> SEQ ID NO 196
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 196
```
uaauuucuac ucuuguagau ggaaagagaa uuguuuucuc cuuc                    44

<210> SEQ ID NO 197
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 197
uaauuucuac ucuuguagau ggaaagagaa uuguuuucuc cuuc                    44

<210> SEQ ID NO 198
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 198
uaauuucuac ucuuguagau ggaaagagaa uuguuuucuc cuuc                    44

<210> SEQ ID NO 199
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 199
uaauuucuac ucuuguagau ggaaagagaa uuguuuucuc cuuc                    44

<210> SEQ ID NO 200
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 200
uaauuucuac ucuuguagau ggaaagagaa uuguuuucuc cuuc                    44

<210> SEQ ID NO 201
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 201
uaauuucuac ucuuguagau ggaaagagaa uuguuuucuc cuuc                    44

<210> SEQ ID NO 202
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 202
uaauuucuac ucuuguagau ggaaagagaa uuguuuucuc cuuc                    44

<210> SEQ ID NO 203
<211> LENGTH: 44
<212> TYPE: RNA

-continued

```
<213> ORGANISM: Artificial Sequence
<220> FEATURE:
<223> OTHER INFORMATION: SYNTHETIC RNA

<400> SEQUENCE: 203
uaauuucuac ucuuguagau ggaaagagaa uuguuucuc cuuc                          44

<210> SEQ ID NO 204
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 204
uaauuucuac ucuuguagau ggaaagagaa uuguuucuc cuuc                          44

<210> SEQ ID NO 205
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 205
uaauuucuac ucuuguagau ggaaagagaa uuguuucuc cuuc                          44

<210> SEQ ID NO 206
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 206
uaauuucuac ucuuguagau ggaaagagaa uuguuucuc cuuc                          44

<210> SEQ ID NO 207
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 207
uaauuucuac ucuuguagau ggaaagagaa uuguuucuc cuuc                          44

<210> SEQ ID NO 208
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 208
uaauuucuac ucuuguagau ggaaagagaa uuguuucuc cuuc                          44

<210> SEQ ID NO 209
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 209
uaauuucuac ucuuguagau ggaaagagaa uuguuucuc cuuc                          44
```

-continued

```
<210> SEQ ID NO 210
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 210
uaauuucuac ucuuguagau ggaaagagaa uuguuuucuc cuuc                    44

<210> SEQ ID NO 211
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 211
uaauuucuac ucuuguagau ggaaagagaa uuguuuucuc cuuc                    44

<210> SEQ ID NO 212
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 212
uaauuucuac ucuuguagau ggaaagagaa uuguuuucuc cuuc                    44

<210> SEQ ID NO 213
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 213
uaauuucuac ucuuguagau ggaaagagaa uuguuuucuc cuuc                    44

<210> SEQ ID NO 214
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 214
uaauuucuac ucuuguagau ggaaagagaa uuguuuucuc cuuc                    44

<210> SEQ ID NO 215
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 215
uaauuucuac ucuuguagau ggaaagagaa uuguuuucuc cuuc                    44

<210> SEQ ID NO 216
<211> LENGTH: 44
<212> TYPE: RNA
<213> ORGANISM: Artificial Sequence
<220> FEATURE:
```

```
<223> OTHER INFORMATION: SYNTHETIC RNA

<400> SEQUENCE: 216
uaauuucuac ucuuguagau ggaaagagaa uuguuuucuc cuuc                44

<210> SEQ ID NO 217
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 217
uaauuucuac ucuuguagau ggaaagagaa uuguuuucuc cuuc                44

<210> SEQ ID NO 218
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 218
uaauuucuac ucuuguagau ggaaagagaa uuguuuucuc cuuc                44

<210> SEQ ID NO 219
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 219
uaauuucuac ucuuguagau ggaaagagaa uuguuuucuc cuuc                44

<210> SEQ ID NO 220
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 220
uaauuucuac ucuuguagau ggaaagagaa uuguuuucuc cuuc                44

<210> SEQ ID NO 221
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 221
uaauuucuac ucuuguagau ggaaagagaa uuguuuucuc cuuc                44

<210> SEQ ID NO 222
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 222
uaauuucuac ucuuguagau ggaaagagaa uuguuuucuc cuuc                44
```

-continued

<210> SEQ ID NO 223
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 223
uaauuucuac ucuuguagau ggaaagagaa uuguuuucuc cuuc                          44

<210> SEQ ID NO 224
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 224
uaauuucuac ucuuguagau ggaaagagaa uuguuuucuc cuuc                          44

<210> SEQ ID NO 225
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 225
uaauuucuac ucuuguagau ggaaagagaa uuguuuucuc cuuc                          44

<210> SEQ ID NO 226
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 226
uaauuucuac ucuuguagau ggaaagagaa uuguuuucuc cuuc                          44

<210> SEQ ID NO 227
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 227
uaauuucuac ucuuguagau ggaaagagaa uuguuuucuc cuuc                          44

<210> SEQ ID NO 228
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 228
uaauuucuac ucuuguagau ggaaagagaa uuguuuucuc cuuc                          44

<210> SEQ ID NO 229
<211> LENGTH: 44
<212> TYPE: RNA
<213> ORGANISM: Artificial Sequence
<220> FEATURE:
<223> OTHER INFORMATION: SYNTHETIC RNA -continued

<400> SEQUENCE: 229
uaauuucuac ucuuguagau ggaaagagaa uuguuuucuc cuuc                    44

<210> SEQ ID NO 230
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 230
uaauuucuac ucuuguagau ggaaagagaa uuguuuucuc cuuc                    44

<210> SEQ ID NO 231
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 231
uaauuucuac ucuuguagau ggaaagagaa uuguuuucuc cuuc                    44

<210> SEQ ID NO 232
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 232
uaauuucuac ucuuguagau ggaaagagaa uuguuuucuc cuuc                    44

<210> SEQ ID NO 233
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 233
uaauuucuac ucuuguagau ggaaagagaa uuguuuucuc cuuc                    44

<210> SEQ ID NO 234
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 234
uaauuucuac ucuuguagau ggaaagagaa uuguuuucuc c                       41

<210> SEQ ID NO 235
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 235
uaauuucuac ucuuguagau ggaaagagaa uuguuuucuc c                       41

<210> SEQ ID NO 236
<211> LENGTH: 41

```
<212> TYPE: RNA
<213> ORGANISM: Artificial Sequence
<220> FEATURE:
<223> OTHER INFORMATION: SYNTHETIC RNA

<400> SEQUENCE: 236
uaauuucuac ucuuguagau ggaaagagaa uuguuuucuc c                              41

<210> SEQ ID NO 237
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 237
uaauuucuac ucuuguagau ggaaagagaa uuguuuucuc c                              41

<210> SEQ ID NO 238
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 238
uaauuucuac ucuuguagau ggaaagagaa uuguuuucuc c                              41

<210> SEQ ID NO 239
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 239
uaauuucuac ucuuguagau ggaaagagaa uuguuuucuc c                              41

<210> SEQ ID NO 240
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 240
uaauuucuac ucuuguagau ggaaagagaa uuguuuucuc c                              41

<210> SEQ ID NO 241
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 241
uaauuucuac ucuuguagau ggaaagagaa uuguuuucuc c                              41

<210> SEQ ID NO 242
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 242
```
uaauuucuac ucuuguagau ggaaagagaa uuguuucuc c                    41

<210> SEQ ID NO 243
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 243
uaauuucuac ucuuguagau ggaaagagaa uuguuucuc c                    41

<210> SEQ ID NO 244
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 244
uaauuucuac ucuuguagau ggaaagagaa uuguuucuc c                    41

<210> SEQ ID NO 245
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 245
uaauuucuac ucuuguagau ggaaagagaa uuguuucuc c                    41

<210> SEQ ID NO 246
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 246
uaauuucuac ucuuguagau ggaaagagaa uuguuucuc c                    41

<210> SEQ ID NO 247
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 247
uaauuucuac ucuuguagau ggaaagagaa uuguuucuc c                    41

<210> SEQ ID NO 248
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 248
uaauuucuac ucuuguagau ggaaagagaa uuguuucuc c                    41

<210> SEQ ID NO 249
<211> LENGTH: 41
<212> TYPE: RNA
<213> ORGANISM: Artificial Sequence -continued

```
<220> FEATURE:
<223> OTHER INFORMATION: SYNTHETIC RNA

<400> SEQUENCE: 249
uaauuucuac ucuuguagau ggaaagagaa uuguuuucuc c                            41

<210> SEQ ID NO 250
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 250
uaauuucuac ucuuguagau ggaaagagaa uuguuuucuc c                            41

<210> SEQ ID NO 251
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 251
uaauuucuac ucuuguagau ggaaagagaa uuguuuucuc c                            41

<210> SEQ ID NO 252
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 252
uaauuucuac ucuuguagau ggaaagagaa uuguuuucuc c                            41

<210> SEQ ID NO 253
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 253
uaauuucuac ucuuguagau ggaaagagaa uuguuuucuc c                            41

<210> SEQ ID NO 254
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 254
uaauuucuac ucuuguagau ggaaagagaa uuguuuucuc c                            41

<210> SEQ ID NO 255
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 255
uaauuucuac ucuuguagau ggaaagagaa uuguuuucuc c                            41
```

```
<210> SEQ ID NO 256
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 256
uaauuucuac ucuuguagau ggaaagagaa uuguuuucuc c                    41

<210> SEQ ID NO 257
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 257
uaauuucuac ucuuguagau ggaaagagaa uuguuuucuc c                    41

<210> SEQ ID NO 258
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 258
uaauuucuac ucuuguagau ggaaagagaa uuguuuucuc c                    41

<210> SEQ ID NO 259
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 259
uaauuucuac ucuuguagau ggaaagagaa uuguuuucuc c                    41

<210> SEQ ID NO 260
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 260
uaauuucuac ucuuguagau ggaaagagaa uuguuuucuc c                    41

<210> SEQ ID NO 261
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 261
uaauuucuac ucuuguagau ggaaagagaa uuguuuucuc c                    41

<210> SEQ ID NO 262
<211> LENGTH: 41
<212> TYPE: RNA
<213> ORGANISM: Artificial Sequence
<220> FEATURE:
<223> OTHER INFORMATION: SYNTHETIC RNA
```

<400> SEQUENCE: 262
uaauuucuac ucuuguagau ggaaagagaa uuguuucuc c                              41

<210> SEQ ID NO 263
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 263
uaauuucuac ucuuguagau ggaaagagaa uuguuucuc c                              41

<210> SEQ ID NO 264
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 264
uaauuucuac ucuuguagau ggaaagagaa uuguuucuc c                              41

<210> SEQ ID NO 265
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 265
uaauuucuac ucuuguagau ggaaagagaa uuguuucuc c                              41

<210> SEQ ID NO 266
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 266
uaauuucuac ucuuguagau ggaaagagaa uuguuucuc c                              41

<210> SEQ ID NO 267
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 267
uaauuucuac ucuuguagau ggaaagagaa uuguuucuc c                              41

<210> SEQ ID NO 268
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 268
uaauuucuac ucuuguagau ggaaagagaa uuguuucuc c                              41

<210> SEQ ID NO 269

-continued

```
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 269
uaauuucuac ucuuguagau ggaaagagaa uuguuuucuc c                            41

<210> SEQ ID NO 270
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 270
uaauuucuac ucuuguagau ggaaagagaa uuguuuucuc c                            41

<210> SEQ ID NO 271
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 271
uaauuucuac ucuuguagau ggaaagagaa uuguuuucuc c                            41

<210> SEQ ID NO 272
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 272
uaauuucuac ucuuguagau ggaaagagaa uuguuuucuc c                            41

<210> SEQ ID NO 273
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 273
uaauuucuac ucuuguagau ggaaagagaa uuguuuucuc c                            41

<210> SEQ ID NO 274
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 274
uaauuucuac ucuuguagau ggaaagagaa uuguuuucuc c                            41

<210> SEQ ID NO 275
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 275
```
uaauuucuac ucuuguagau ggaaagagaa uuguuuucuc c                                          41

<210> SEQ ID NO 276
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 276
uaauuucuac ucuuguagau ugugaaaugg cuuauaauug cuua                                       44

<210> SEQ ID NO 277
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 277
uaauuucuac ucuuguagau ugugaaaugg cuuauaauug cuua                                       44

<210> SEQ ID NO 278
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 278
uaauuucuac ucuuguagau ugugaaaugg cuuauaauug cuua                                       44

<210> SEQ ID NO 279
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 279
uaauuucuac ucuuguagau ugugaaaugg cuuauaauug c                                          41

<210> SEQ ID NO 280
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 280
uaauuucuac ucuuguagau ugugaaaugg cuuauaauug c                                          41

<210> SEQ ID NO 281
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 281
uaauuucuac ucuuguagau ugugaaaugg cuuauaauug c                                          41

<210> SEQ ID NO 282
<211> LENGTH: 44
<212> TYPE: RNA

-continued

<213> ORGANISM: Artificial Sequence
<220> FEATURE:
<223> OTHER INFORMATION: SYNTHETIC RNA

<400> SEQUENCE: 282
uaauuucuac ucuuguagau ggaaagagaa uuguuuucuc cuuc                          44

<210> SEQ ID NO 283
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 283
uaauuucuac ucuuguagau ggaaagagaa uuguuuucuc cuuc                          44

<210> SEQ ID NO 284
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 284
uaauuucuac ucuuguagau ggaaagagaa uuguuuucuc cuuc                          44

<210> SEQ ID NO 285
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 285
uaauuucuac ucuuguagau ggaaagagaa uuguuuucuc c                            41

<210> SEQ ID NO 286
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 286
uaauuucuac ucuuguagau ggaaagagaa uuguuuucuc c                            41

<210> SEQ ID NO 287
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 287
uaauuucuac ucuuguagau ggaaagagaa uuguuuucuc c                            41

<210> SEQ ID NO 288
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 288
uaauuucuac ucuuguagau ggaaagagaa uuguuuucuc c                            41

-continued

```
<210> SEQ ID NO 289
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 289
uaauuucuac ucuuguagau ggaaagagaa uuguuucuc c                       41

<210> SEQ ID NO 290
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 290
uaauuucuac ucuuguagau ggaaagagaa uuguuucuc c                       41

<210> SEQ ID NO 291
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 291
uaauuucuac ucuuguagau ggaaagagaa uuguuucuc c                       41

<210> SEQ ID NO 292
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 292
uaauuucuac ucuuguagau ggaaagagaa uuguuucuc c                       41

<210> SEQ ID NO 293
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 293
uaauuucuac ucuuguagau ggaaagagaa uuguuucuc c                       41

<210> SEQ ID NO 294
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 294
uaauuucuac ucuuguagau ggaaagagaa uuguuucuc c                       41

<210> SEQ ID NO 295
<211> LENGTH: 41
<212> TYPE: RNA
<213> ORGANISM: Artificial Sequence
<220> FEATURE:
```

-continued

<223> OTHER INFORMATION: SYNTHETIC RNA

<400> SEQUENCE: 295
uaauuucuac ucuuguagau ggaaagagaa uuguuuucuc c                                    41

<210> SEQ ID NO 296
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 296
uaauuucuac ucuuguagau ggaaagagaa uuguuuucuc c                                    41

<210> SEQ ID NO 297
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 297
uaauuucuac ucuuguagau ggaaagagaa uuguuuucuc c                                    41

<210> SEQ ID NO 298
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 298
uaauuucuac ucuuguagau ggaaagagaa uuguuuucuc c                                    41

<210> SEQ ID NO 299
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 299
uaauuucuac ucuuguagau ggaaagagaa uuguuuucuc c                                    41

<210> SEQ ID NO 300
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 300
uaauuucuac ucuuguagau ggaaagagaa uuguuuucuc c                                    41

<210> SEQ ID NO 301
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 301
uaauuucuac ucuuguagau ggaaagagaa uuguuuucuc c                                    41

```
<210> SEQ ID NO 302
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 302
uaauuucuac ucuuguagau ggaaagagaa uuguuuucuc c                          41

<210> SEQ ID NO 303
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 303
uaauuucuac ucuuguagau ggaaagagaa uuguuuucuc c                          41

<210> SEQ ID NO 304
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 304
uaauuucuac ucuuguagau ggaaagagaa uuguuuucuc c                          41

<210> SEQ ID NO 305
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 305
uaauuucuac ucuuguagau ggaaagagaa uuguuuucuc c                          41

<210> SEQ ID NO 306
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 306
uaauuucuac ucuuguagau ggaaagagaa uuguuuucuc c                          41

<210> SEQ ID NO 307
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 307
uaauuucuac ucuuguagau ggaaagagaa uuguuuucuc c                          41

<210> SEQ ID NO 308
<211> LENGTH: 41
<212> TYPE: RNA
<213> ORGANISM: Artificial Sequence
<220> FEATURE:
<223> OTHER INFORMATION: SYNTHETIC RNA
```

-continued

```
<400> SEQUENCE: 308
uaauuucuac ucuuguagau ggaaagagaa uuguuuucuc c                        41

<210> SEQ ID NO 309
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 309
uaauuucuac ucuuguagau ggaaagagaa uuguuuucuc c                        41

<210> SEQ ID NO 310
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 310
uaauuucuac ucuuguagau ggaaagagaa uuguuuucuc c                        41

<210> SEQ ID NO 311
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 311
uaauuucuac ucuuguagau ggaaagagaa uuguuuucuc c                        41

<210> SEQ ID NO 312
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 312
uaauuucuac ucuuguagau ggaaagagaa uuguuuucuc c                        41

<210> SEQ ID NO 313
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 313
uaauuucuac ucuuguagau ggaaagagaa uuguuuucuc c                        41

<210> SEQ ID NO 314
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 314
uaauuucuac ucuuguagau ggaaagagaa uuguuuucuc c                        41

<210> SEQ ID NO 315
<211> LENGTH: 41
```

-continued

```
<212> TYPE: RNA
<213> ORGANISM: Artificial Sequence
<220> FEATURE:
<223> OTHER INFORMATION: SYNTHETIC RNA

<400> SEQUENCE: 315
uaauuucuac ucuuguagau ggaaagagaa uuguuuucuc c                            41

<210> SEQ ID NO 316
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 316
uaauuucuac ucuuguagau ggaaagagaa uuguuuucuc c                            41

<210> SEQ ID NO 317
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 317
uaauuucuac ucuuguagau ggaaagagaa uuguuuucuc c                            41

<210> SEQ ID NO 318
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 318
uaauuucuac ucuuguagau ggaaagagaa uuguuuucuc c                            41

<210> SEQ ID NO 319
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 319
uaauuucuac ucuuguagau ggaaagagaa uuguuuucuc c                            41

<210> SEQ ID NO 320
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 320
uaauuucuac ucuuguagau ggaaagagaa uuguuuucuc c                            41

<210> SEQ ID NO 321
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 321
```
uaauuucuac ucuuguagau ggaaagagaa uuguuucuc c                        41

<210> SEQ ID NO 322
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 322
uaauuucuac ucuuguagau ggaaagagaa uuguuucuc c                        41

<210> SEQ ID NO 323
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 323
uaauuucuac ucuuguagau ggaaagagaa uuguuucuc c                        41

<210> SEQ ID NO 324
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 324
uaauuucuac ucuuguagau ggaaagagaa uuguuucuc c                        41

<210> SEQ ID NO 325
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 325
uaauuucuac ucuuguagau ggaaagagaa uuguuucuc c                        41

<210> SEQ ID NO 326
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 326
uaauuucuac ucuuguagau ggaaagagaa uuguuucuc c                        41

<210> SEQ ID NO 327
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 327
uaauuucuac ucuuguagau ggaaagagaa uuguuucuc c                        41

<210> SEQ ID NO 328
<211> LENGTH: 41
<212> TYPE: RNA
<213> ORGANISM: Artificial Sequence -continued

```
<220> FEATURE:
<223> OTHER INFORMATION: SYNTHETIC RNA

<400> SEQUENCE: 328
uaauuucuac ucuuguagau ggaaagagaa uuguuucuc c                              41

<210> SEQ ID NO 329
<211> LENGTH: 41
<212> TYPE: DNA
<213> ORGANISM: Artificial Sequence
<220> FEATURE:
<223> OTHER INFORMATION: SYNTHETIC RNA-DNA

<400> SEQUENCE: 329
taauuucuac ucuuguagau ggaaagagaa uuguuucuc c                              41

<210> SEQ ID NO 330
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 330
uaauuucuac ucuuguagau ggaaagagaa uuguuucuc c                              41

<210> SEQ ID NO 331
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 331
uaauuucuac ucuuguagau ggaaagagaa uuguuucuc c                              41

<210> SEQ ID NO 332
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 332
uaauuucuac ucuuguagau ggaaagagaa uuguuucuc c                              41

<210> SEQ ID NO 333
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 333
uaauuucuac ucuuguagau ggaaagagaa uuguuucuc c                              41

<210> SEQ ID NO 334
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 334
uaauuucuac ucuuguagau ggaaagagaa uuguuucuc c                              41
```

-continued

<210> SEQ ID NO 335
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 335
uaauuucuac ucuuguagau ggaaagagaa uuguuuucuc c                              41

<210> SEQ ID NO 336
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 336
uaauuucuac ucuuguagau ggaaagagaa uuguuuucuc c                              41

<210> SEQ ID NO 337
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 337
uaauuucuac ucuuguagau ggaaagagaa uuguuuucuc c                              41

<210> SEQ ID NO 338
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 338
uaauuucuac ucuuguagau cuugggugug uuaaaaguga c                              41

<210> SEQ ID NO 339
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 339
uaauuucuac ucuuguagau cuugggugug uuaaaaguga c                              41

<210> SEQ ID NO 340
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 340
uaauuucuac ucuuguagau cuugggugug uuaaaaguga c                              41

<210> SEQ ID NO 341
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 341
uaauuucuac ucuuguagau cuggggugug uuaaaaguga c                        41

<210> SEQ ID NO 342
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 342
uaauuucuac ucuuguagau cuggggugug uuaaaaguga c                        41

<210> SEQ ID NO 343
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 343
uaauuucuac ucuuguagau acauaaaacu cuuuuagguu a                        41

<210> SEQ ID NO 344
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 344
uaauuucuac ucuuguagau acauaaaacu cuuuuagguu a                        41

<210> SEQ ID NO 345
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 345
uaauuucuac ucuuguagau acauaaaacu cuuuuagguu a                        41

<210> SEQ ID NO 346
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 346
uaauuucuac ucuuguagau acauaaaacu cuuuuagguu a                        41

<210> SEQ ID NO 347
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 347
uaauuucuac ucuuguagau acauaaaacu cuuuuagguu a                        41

<210> SEQ ID NO 348

```
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 348
uaauuucuac ucuuguagau acauaaaacu cuuuuagguu a                          41

<210> SEQ ID NO 349
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 349
uaauuucuac ucuuguagau acauaaaacu cuuuuagguu a                          41

<210> SEQ ID NO 350
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 350
uaauuucuac ucuuguagau acauaaaacu cuuuuagguu a                          41

<210> SEQ ID NO 351
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 351
uaauuucuac ucuuguagau acauaaaacu cuuuuagguu a                          41

<210> SEQ ID NO 352
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 352
uaauuucuac ucuuguagau acauaaaacu cuuuuagguu a                          41

<210> SEQ ID NO 353
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 353
uaauuucuac ucuuguagau acauaaaacu cuuuuagguu a                          41

<210> SEQ ID NO 354
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 354
```

-continued

```
uaauuucuac ucuuguagau acauaaaacu cuuuuagguu a                        41

<210> SEQ ID NO 355
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 355
uaauuucuac ucuuguagau acauaaaacu cuuuuagguu a                        41

<210> SEQ ID NO 356
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 356
uaauuucuac ucuuguagau acauaaaacu cuuuuagguu a                        41

<210> SEQ ID NO 357
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 357
uaauuucuac ucuuguagau auagucuuuc cuugggugug u                        41

<210> SEQ ID NO 358
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 358
uaauuucuac uaaguguaga uauagucuuu ccuugggugu gu                       42

<210> SEQ ID NO 359
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 359
uaauuucuac uaaguguaga uauagucuuu ccuugggugu guua                     44

<210> SEQ ID NO 360
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 360
uaauuucuac ucuuguagau cuugggugug uuaaaaguga c                        41

<210> SEQ ID NO 361
<211> LENGTH: 42
<212> TYPE: RNA
```

-continued

<213> ORGANISM: Artificial Sequence
<220> FEATURE:
<223> OTHER INFORMATION: SYNTHETIC RNA

<400> SEQUENCE: 361
uaauuucuac uaaguguaga ucuugggugu guuaaaagug ac                        42

<210> SEQ ID NO 362
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 362
uaauuucuac uaaguguaga ucuugggugu guuaaaagug acca                      44

<210> SEQ ID NO 363
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 363
uaauuucuac uaaguguaga ucuugggugu guuaaaagug acca                      44

<210> SEQ ID NO 364
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 364
uaauuucuac uaaguguaga uacacaccca aggaaagacu au                        42

<210> SEQ ID NO 365
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 365
uaauuucuac uaaguguaga uacacaccca aggaaagacu auga                      44

<210> SEQ ID NO 366
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 366
uaauuucuac ucuuguagau auccgugcug aguguaccau g                         41

<210> SEQ ID NO 367
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 367
uaauuucuac uaaguguaga uauccgugcu gaguguacca ug                        42

-continued

```
<210> SEQ ID NO 368
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 368
uaauuucuac uaaguguaga uauccgugcu gaguguacca ugca              44

<210> SEQ ID NO 369
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 369
uaauuucuac ucuuguagau uaaacacugu uucauuucau c               41

<210> SEQ ID NO 370
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 370
uaauuucuac uaaguguaga uuaaacacug uuucauuuca uc              42

<210> SEQ ID NO 371
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 371
uaauuucuac uaaguguaga uuaaacacug uuucauuuca uccg            44

<210> SEQ ID NO 372
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 372
uaauuucuac ucuuguagau gaaacgucag ucuucucuuu u               41

<210> SEQ ID NO 373
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 373
uaauuucuac uaaguguaga ugaaacguca gucuucucuu uu             42

<210> SEQ ID NO 374
<211> LENGTH: 44
<212> TYPE: RNA
<213> ORGANISM: Artificial Sequence
<220> FEATURE:
```

-continued

```
<223> OTHER INFORMATION: SYNTHETIC RNA

<400> SEQUENCE: 374
uaauuucuac uaaguguaga ugaaacguca gucuucucuu uugu                    44

<210> SEQ ID NO 375
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 375
uaauuucuac ucuuguagau uaaugcccug uagucucucu g                       41

<210> SEQ ID NO 376
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 376
uaauuucuac uaaguguaga uuaaugcccu guagucucuc ug                      42

<210> SEQ ID NO 377
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 377
uaauuucuac uaaguguaga uuaaugcccu guagucucuc ugua                    44

<210> SEQ ID NO 378
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 378
uaauuucuac ucuuguagau uaauuaacag cuugcuggug a                       41

<210> SEQ ID NO 379
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 379
uaauuucuac uaaguguaga uuaauuaaca gcuugcuggu ga                      42

<210> SEQ ID NO 380
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 380
uaauuucuac uaaguguaga uuaauuaaca gcuugcuggu gaaa                    44
```

-continued

```
<210> SEQ ID NO 381
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 381
uaauuucuac ucuuguagau gguuaaagau gguuaaauga u                             41

<210> SEQ ID NO 382
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 382
uaauuucuac uaaguguaga ugguuaaaga ugguuaaaug au                            42

<210> SEQ ID NO 383
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 383
uaauuucuac uaaguguaga ugguuaaaga ugguuaaaug auug                          44

<210> SEQ ID NO 384
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 384
uaauuucuac ucuuguagau ugugaaaugg cuuauaauug c                             41

<210> SEQ ID NO 385
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 385
uaauuucuac uaaguguaga uugugaaaug gcuuauaauu gc                            42

<210> SEQ ID NO 386
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 386
uaauuucuac uaaguguaga uugugaaaug gcuuauaauu gcuu                          44

<210> SEQ ID NO 387
<211> LENGTH: 41
<212> TYPE: RNA
<213> ORGANISM: Artificial Sequence
<220> FEATURE:
<223> OTHER INFORMATION: SYNTHETIC RNA
```

<400> SEQUENCE: 387
uaauuucuac ucuuguagau guuguuggau uugaaauucc a                          41

<210> SEQ ID NO 388
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 388
uaauuucuac uaaguguaga uguuguugga uuugaaauuc ca                         42

<210> SEQ ID NO 389
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 389
uaauuucuac uaaguguaga uguuguugga uuugaaauuc caga                       44

<210> SEQ ID NO 390
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 390
uaauuucuac ucuuguagau uuguaggaua ugcccuugac u                          41

<210> SEQ ID NO 391
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 391
uaauuucuac uaaguguaga uuuguaggau augcccuuga cu                         42

<210> SEQ ID NO 392
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 392
uaauuucuac uaaguguaga uuuguaggau augcccuuga cuau                       44

<210> SEQ ID NO 393
<211> LENGTH: 27
<212> TYPE: DNA
<213> ORGANISM: Artificial Sequence
<220> FEATURE:
<223> OTHER INFORMATION: SYNTHETIC DNA

<400> SEQUENCE: 393
aagaatgttg tgataaaagg tgatgct                                          27

<210> SEQ ID NO 394
<211> LENGTH: 24

-continued

```
<212> TYPE: DNA
<213> ORGANISM: Artificial Sequence
<220> FEATURE:
<223> OTHER INFORMATION: SYNTHETIC DNA

<400> SEQUENCE: 394
acacatccat gggacttctg cctc                                              24

<210> SEQ ID NO 395
<211> LENGTH: 3834
<212> TYPE: DNA
<213> ORGANISM: Artificial Sequence
<220> FEATURE:
<223> OTHER INFORMATION: SYNTHETIC DNA

<400> SEQUENCE: 395
atgctgaaga acgtgggcat cgaccggctg gacgtggaaa agggcagaaa gaacatgagc      60
aagctcgaga agttcaccaa ctgctacagc ctgagcaaga ccctgcggtt caaggccatt     120
cctgtgggca agacccaaga gaacatcgac aacaagcggc tgctggtgga agatgagaag     180
agagccgagg actacaaggg cgtgaagaag ctgctggacc ggtactacct gagcttcatc     240
aacgacgtgc tgcacagcat caagctcaag aacctgaaca actacatcag cctgttccgg     300
aagaaaaccc ggaccgagaa agagaacaaa gagctggaaa acctcgagat caacctgcgg     360
aaagagatcg ccaaggcctt caagggcaac gagggctaca gagcctgtt caagaaggac     420 atcatcgaga caatcctgcc tgagttcctg gacgacaagg acgagatcgc cctggtcaac     480
agcttcaacg gcttcacaac cgccttcacc ggcttttttcg acaaccgcga gaatatgttc     540
agcgaggaag ccaagagcac ctctatcgcc ttccggtgca tcaacgagaa tctgacccgg     600
tacatcagca acatggatat cttcgagaag gtggacgcca tcttcgacaa gcacgaggtg     660
caagagatca agaaaagat cctgaacagc gactacgacg tcgaggactt cttcgagggc     720
gagttcttca acttcgtgct gacacaagag ggcatcgatg tgtacaacgc catcatcggc     780
ggcttcgtga cagagagcgg cgagaagatc aagggcctga cgagtacat caacctctac     840 aaccagaaaa cgaagcagaa gctgcccaag ttcaagcccc tgtacaaaca ggtgctgagc     900
gacagagaga gcctgtcctt ttacggcgag ggctatacca gcgacgaaga ggtgctggaa     960
gtgttcagaa acaccctgaa caagaacagc gagatcttca gctccatcaa gaagctcgaa    1020 aagctgtttta agaacttcga cgagtacagc agcgccggca tcttcgtgaa gaatggccct    1080
gccatcagca ccatctccaa ggacatcttc ggcgagtgga acgtgatccg ggacaagtgg    1140
aacgccgagt acgacgacat ccacctgaag aaaaaggccg tggtcaccga gaagtacgag    1200
gacgacagaa gaaagagctt caagaagatc ggcagcttca gcctggaaca gctgcaagag    1260
tacgccgacg ccgatctgag cgtggtggaa aagctgaaag agattatcat ccagaaggtc    1320
gacgagatct acaaggtgta cggcagcagc gagaagctgt tcgacgccga ctttgtgctg    1380
gaaaagagcc tcaaaaagaa cgacgccgtg gtggccatca tgaaggacct gctggatagc    1440
gtgaagtcct tcgagaacta tattaaggcc ttctttggcg agggcaaaga gacaaaccgg    1500
gacgagagct ctacggcga tttcgtgctg gcctacgaca tcctgctgaa agtggaccac    1560
atctacgacg ccatccggaa ctacgtgacc cagaagcctt acagcaagga caagtttaag    1620
ctgtacttcc agaatccgca gttcatgggc ggctgggaca agacaaaga aaccgactac    1680 cgggccacca tcctgagata cggctccaag tactatctgg ccattatgga caagaaatac    1740
gccaagtgcc tgcagaagat cgataaggac gacgtgaacg gcaactacga gaagattaac    1800
```

-continued

```
tacaagctgc tgcccggacc taacaagatg ctgcctaagg tgttctttag caagaaatgg   1860
atggcctact acaaccccag cgaggatatc cagaaaatct acaagaacgg caccttcaag   1920
aaaggcgaca tgttcaacct gaacgactgc cacaagctga tcgatttctt caaggacagc   1980
atcagcagat accccaagtg gtccaacgcc tacgacttca atttcagcga gacagagaag   2040
tataaggata tcgccgggtt ctaccgcgag gtggaagaac agggctataa ggtgtccttt   2100
gagagcgcca gcaagaaaga ggtggacaag ctggtcgaag agggcaagct gtacatgttc   2160
cagatctata acaaggactt ctccgacaag agccacggca cccctaacct gcacaccatg   2220
tactttaagc tgctgttcga tgagaacaac cacggccaga tcagactgtc tggcggagcc   2280
gagctgttta tgagaagggc cagcctgaaa aaagaggaac tggtcgttca ccccgccaac   2340
tctccaatcg ccaacaagaa ccccgacaat cccaagaaaa ccaccacact gagctacgac   2400
gtgtacaagg ataagcggtt ctccgaggac cagtacgagc tgcacatccc tatcgccatc   2460
aacaagtgcc ccaagaatat cttcaagatc aacaccgaag tgcgggtgct gctgaagcac   2520
gacgacaacc cttacgtgat cggcatcgac agaggcgagc ggaacctgct gtatatcgtg   2580
gtggtggacg gcaagggcaa tatcgtggaa cagtactccc tgaatgagat catcaacaac   2640
ttcaatggca tccggatcaa gacggactac cacagcctgc tggacaaaaa agagaaagaa   2700
cgcttcgagg cccggcagaa ctggaccagc atcgagaaca tcaaagaact gaaggccggc   2760
tacatctccc aggtggtgca caagatctgc gagctggttg agaagtatga cgccgtgatt   2820
gccctggaag atctgaatag cggctttaag aacagccgcg tgaaggtcga gaaacaggtg   2880
taccagaaat tcgagaagat gctgatcgac aagctgaact acatggtcga caagaagtct   2940
aacccctgcg ccacaggcgg agccctgaag ggatatcaga tcaccaacaa gttcgagtcc   3000
ttcaagagca tgagcaccca gaatggcttc atcttctaca tccccgcctg gctgaccagc   3060
aagatcgatc ctagcaccgg attcgtgaac ctgctcaaga ccaagtacac cagcattgcc   3120
gacagcaaga agttcatctc cagcttcgac cggattatgt acgtgcccga agaggacctg   3180
ttcgaattcg ccctggatta caagaacttc agccggaccg atgccgacta tatcaagaag   3240
tggaagctgt atagctacgg caaccgcatc cgcatcttca gaaacccgaa gaaaaacaac   3300
gtgttcgact gggaagaagt gtgcctgacc agcgcctaca aagaactctt caacaaatac   3360
ggcatcaact accagcaggg cgacatcaga gccctgctgt gcgagcagag cgacaaggcc   3420
ttttacagct ccttcatggc cctgatgtcc ctgatgctgc agatgcggaa tagcatcacc   3480
ggcaggaccg acgtggactt cctgatcagc cctgtgaaga attccgacgg gatcttctac   3540
gacagcagaa actacgaggc tcaagagaac gccatcctgc ctaagaacgc cgatgccaac   3600
ggcgcctata atatcgccag aaaggtgctg tgggccatcg gccagtttaa gaaggccgag   3660
gacgagaaac tggacaaagt gaagatcgcc atctctaaca aagagtggct ggaatacgcc   3720
cagaccagcg tgaagcacgg cagatctagt gacgatgagg ccaccgccga tagccagcat   3780
gcagcccctc caaagaaaaa gcggaaagtg ctggaacacc accaccatca ccac         3834
```